US008084498B2

(12) United States Patent
Dasseux et al.

(10) Patent No.: US 8,084,498 B2
(45) Date of Patent: Dec. 27, 2011

(54) KETONE COMPOUNDS AND COMPOSITIONS FOR CHOLESTEROL MANAGEMENT AND RELATED USES

(75) Inventors: Jean-Louis Henri Dasseux, Brighton, MI (US); Daniela Carmen Oniciu, Ann Arbor, MI (US)

(73) Assignee: Esperion Therapeutics, Inc., Plymouth, MI (US)

( * ) Notice: Subject to any disclaimer, the term of this patent is extended or adjusted under 35 U.S.C. 154(b) by 0 days.

(21) Appl. No.: 12/492,597

(22) Filed: Jun. 26, 2009

(65) Prior Publication Data

US 2010/0137444 A1      Jun. 3, 2010

Related U.S. Application Data

(63) Continuation of application No. 10/596,047, filed as application No. PCT/US03/41448 on Dec. 24, 2003, now Pat. No. 7,705,177.

(51) Int. Cl.
*A61K 31/19* (2006.01)
(52) U.S. Cl. ...................................................... 514/531
(58) Field of Classification Search .................. 514/574, 514/531, 572; 562/578
See application file for complete search history.

(56) References Cited

U.S. PATENT DOCUMENTS

| | | |
|---|---|---|
| 3,441,605 A | 4/1969 | Blake |
| 3,773,946 A | 11/1973 | Creger |
| 3,930,024 A | 12/1975 | Creger |
| 4,287,200 A | 9/1981 | Kawamatsu |
| 4,584,321 A | 4/1986 | Manqhisi et al. |
| 4,613,593 A | 9/1986 | Yamatsu et al. |
| 4,634,719 A | 1/1987 | Takaishi et al. |
| 4,689,344 A | 8/1987 | Bar-Tana |
| 4,711,896 A | 12/1987 | Bar-Tana et al. |
| 5,502,198 A | 3/1996 | Picard et al. |
| 5,504,073 A | 4/1996 | Homan |
| 5,578,639 A | 11/1996 | Homan |
| 5,633,287 A | 5/1997 | Lee et al. |
| 5,648,387 A | 7/1997 | Bisgaier et al. |
| 5,750,569 A | 5/1998 | Bisgaier et al. |
| 5,756,344 A | 5/1998 | Onda et al. |
| 5,756,544 A | 5/1998 | Bisgaier et al. |
| 5,783,600 A | 7/1998 | Bisgaier et al. |
| 5,968,963 A | 10/1999 | Homan |
| 5,981,595 A | 11/1999 | Picard et al. |
| 6,017,905 A | 1/2000 | Roark et al. |
| 6,093,719 A | 7/2000 | Bocan |
| 6,093,744 A | 7/2000 | Lee et al. |
| 6,124,309 A | 9/2000 | Bocan |
| 6,143,755 A | 11/2000 | Bocan |
| 6,699,910 B2 | 3/2004 | Dasseux et al. |
| 2003/0078239 A1 | 4/2003 | Dasseux et al. |
| 2004/0198814 A1 | 10/2004 | Dasseux |

FOREIGN PATENT DOCUMENTS

| | | |
|---|---|---|
| WO | 9630328 | 10/1996 |
| WO | 9830530 | 7/1998 |
| WO | 9900116 | 1/1999 |
| WO | 0064911 | 11/2000 |
| WO | 0146110 | 6/2001 |
| WO | 0230860 | 4/2002 |

OTHER PUBLICATIONS

Acton et al., 1996, "Identification of Scavenger Receptor SR-BI as a high density lipoprotein receptor", Science 271 :518-520.
Badimon et al., 1992, "Role of high density lipoproteins in the regression of atherosclerosis", Circulation 86(Suppl. 111):86-94.
Barrans et al., 1996 "Pre-beta HDL: structure and metabolism", Biochem. Biophys Acta 1300:73-85.
Bisgaier et al., 1998, "A novel compound that elevates high density lipoprotein and activates the peroxisome proliferator activated receptor", J. Lipid Res. 39:17-30; (1998).
Brown and Goldstein, 1990, "Drugs used in the treatment of hyperlipoproteinemias", In: The Pharmacological Basis of Therapeutics, 8th Ed., Goodman & Gilman, eds., Pergamon Press, Ch. 36 pp. 874-896.
Bruce et al., 1998, "Plasma lipid transfer proteins, high-density lipoproteins, and reverse cholesterol transport" Annu. Rev. Nutr. 18:297-330.
Dansky and Fisher, 1999, "High-density lipoprotein and plaque regression: the good cholesterol gets even better" Circulation 100:1762-1763.
Decossin et al., 1997, Subclasses of LpA-I in coronary artery disease: distribution and cholesterol efflux ability, Eur. J. Clin. Invest. 27:299-307.
Fielding and Fielding, 1995, "Molecular physiology of reverse cholesterol transport", J. Lipid Res. 36:211-228.
Gearing et al., 1993, "Interaction of the peroxisome-prolifertor-activated receptor and retinoid X receptor", Proc. Natl. Acad. Sci. USA 90:1440-1444.
Harris and Kletzien, 1994, "Localization of pioglitazone response element in the adipocyte fatty acid-binding protein gene", Mol. Pharmacol. 45:439-445.
Heyman et al., 1992, "Affinity purification of the hepatic high-density lipoprotein receptor identifies two acidic glycoprotins and enables further characterization of their binding properties", Biochem. J. 284:161-167.
Hidaka and Fedge, 1992, "Affinity purification of the hepatic high-density lipoprotein receptor identifies two acidic glycoproteins and enables further characterization of their binding properties", Biochem. J. 284:161-167.

(Continued)

*Primary Examiner* — Taofiq A Solola
(74) *Attorney, Agent, or Firm* — Brinks Hofer Gilson & Lione

(57) ABSTRACT

The present invention relates to novel ketone compounds, compositions comprising ketone compounds, and methods useful for treating and preventing cardiovascular diseases, dyslipidemias, dysproteinemias, and glucose metabolism disorders comprising administering a composition comprising a ketone compound. The compounds, compositions, and methods of the invention are also useful for treating and preventing Alzheimer's disease, Syndrome X, peroxisome proliferator activated receptor-related disorders, septicemia, thrombotic disorders, obesity, pancreatitis, hypertension, renal disease, cancer, inflammation, and impotence. In certain embodiments, the compounds, compositions, and methods of the invention are useful in combination therapy with other therapeutics, such as hypocholesterolemic and hypoglycemic agents.

14 Claims, 5 Drawing Sheets

OTHER PUBLICATIONS

Hirano et al., 1997, "Genetic cholesterol ester transfer protein deficiency is extremely frequent in the Omagari area of Japan. Marked hyperalphalipoproteinemia caused by CETP gene mutation is not associated with longevity", Aarterioscler, Thromb. Vasc. Biol. 17:1053-1059.

Issemann and Green, 1990, "Activation of a member of the steroid hormone receptor superfamily by peroxisome proliferators", Nature 347:645-650.

Keller and Wahli, 1993, "Peroxisome proliferator-activated receptors—a link between endocrinoloov and nutrition" TEM 4:291-296.

Keller et al., 1993, "Fatty acids and retinoids control lipid metabolism through activation of peroxisome proliferator-activated receptor-retinoid X receptor heterodimers", Proc. Natl. Acad. Sci. A 90:2160-2164.

Kliewer et al., 1992, "Convergence of 9-cis retinoic acid and peroxisome proliferator signaling oathwavs through heterodimer formation of their receptors", Nature 358:771-774.

Kurata et al., 1998, "A candidate high density lipoprotein (HDL) receptor, HB2, with possible multiple functions shows sequence homology with adhesion molecules", J. Atheroscler. and Thromb. 4:112-117.

Lagrost et al., 1996, "Opposite effects of cholesterol ester transfer protein and phospholipid transfer protein on the size distribution of plasma high density lipoproteins. Physiological relevance in alcoholic patients", J. Biol. Chem. 271:19058-19065.

Landschulz et al., 1996, "Regulation of scavenger receptor, class B, type I, a high density lipoprotein receptor, in liver and steroidoqenic tissues of the rat", J. Clin. Invest. 98:984-995.

Lazarow and Fujiki, 1985, "Biooenesis of peroxisornes", Annu. Rev. Cell Biol. 1:489-530.

Levin et al., 1992, "9-cis retinoic acid stereoisomer binds and activates the nuclear receptor RXRo", Nature 355:359-361.

Nemali et al., 1988, "Comparison of constitutive and inducible levels of expression of peroxisomal p-oxidation and catalase genes in liver and extrahepatic tissues of rat", Cancer Res. 48:5316-5324.

Parra et al., 1992, "A case-control study of lipoprotein particles in two populations at contrasting risk for coronary heart disease. The ECTIM Study", Arterioscler. Thromb. 707.

Reaven, 1993, "Role of insulin resistance in human disease (syndrome X): an expanded definition", Annu. Rev. Med. 44:121-131.

Reddy and Lalwai, 1983, "Carcinogenesis by hepatic peroxisome proliferators: evaluation of the risk of hypolipidemic drugs and industrial plasticizers to humans", Crit. Rev. Toxicol. 12:1-58.

Rigotti et al., 1996, "Regulation by adrenocorticotropic hormone of the in vivo expression of scavenger receptor class B type I (SR-BI), a high density lipoprotein receptor, in steroidogenic cells of the murine adrenal gland", J. Biol. Chem. 271:33545-33549.

Robins and Fasulo, 1997, "High density lipoproteins, but not other lipoprotens, provide a vehicle for sterol transport to bile", J. Clin. Invest. 99:380-384.

Staels and Auwerx, 1998, "Regulation of apo A-I gene expression by fibrates", Atherosclerosis 137 (Suppl.):S19-S23.

Tontonoz et al., 1994, "Adipocyte-specific transcription factor ARF6 is a heterodimeric complex of two nuclear hormone receptors, PPARy and RXRα", Nucl. Acids Res. 22:5628-5634.

Vamecq and Draye, 1989, "Pathophysiology of peroxisomal β-oxidation", Essays Biochem. 24:115-225.

Nan F. et al. "Dual Function Glutamate-Related Ligands: Discovery of a Novel, Potent Inhibitor of Glutamate Carboxypeptidase II Possessing mGluR3 Agonist Activity" Journal of Medicinal Chemistry 2000, 43:pp. 772-774.

International Search Report for PCT/US/03/41448 (mailed Aug. 31, 2004).

Effect of One Week of Daily Oral Gavage Treatment with Compound B on Lipoprotein Total Cholesterol in Chow-Fed Male Sprague-Dawly Rats Effect of One Week of Daily Oral Gavage Treatment with Compound B on Serum Lipids in Chow-Fed Male Sprague-Dawly Rats Effect of Two Weeks of Daily Oral Gavage Treatment with Compound B on Lipoprotein
Total Cholesterol in Chow Fed Obese Female Zucker Rats

Figure 4

Effect of Two Weeks of Daily Oral Gavage Treatment with Compound B
in Chow-Fed Obese Female Zucker Rats

| Variable | Units | Control n=3 | | | Compound B n=4 97/mg/kg/day | | |
|---|---|---|---|---|---|---|---|
| | | Pre | 1 Week | 2 Week | Pre | 1 Week | 2 Week |
| 14 Day Percent Weight Gain | Percent | 0 | | 13.6 | 0 | | 14.6 |
| Liver/Body Weight | Percent | | | 4.09 | | | 5.70 |
| Blood Glucose | mg/dL | 122 | 98 | 130 | 108 | 116 | 120 |
| Insulin | ng/mL | 12.2 | 8.7 | 6.2 | 10.0 | 8.7 | 8.7 |
| Non-Esterified Fatty Acids | mmol/L | 1.95 | 1.27 | 1.21 | 2.13 | 0.60 | 0.57 |
| β-hydroxy butyrate | mg/dL | 2.29 | 1.62 | 2.90 | 1.44 | 2.56 | 3.97 |
| Total Cholesterol | mg/dL | 62 | 56 | 68 | 59 | 93 | 112 |
| Percent HDL Cholesterol (Gain/Loss) | Percent | 0 | -10 | 10 | 0 | 58 | 90 |
| VLDL plus LDL Cholesterol | mg/dL | 21 | 26 | 27 | 21 | 17 | 19 |
| HDL Cholesterol | mg/dL | 42 | 30 | 41 | 38 | 76 | 93 |
| Percent HDL Cholesterol (Gain/Loss) | Percent | 0 | -28 | 0 | 0 | 99 | 143 |
| HDL / (VLDL plus LDL) | Ratio | 2.32 | 1.30 | 1.77 | 1.97 | 4.85 | 5.47 |
| Triglycerides | mg/dL | 999 | 984 | 887 | 861 | 299 | 324 |
| Triglycerides (Gain/Loss) | Percent | 0 | -2 | -11 | 0 | -65 | .82 |

KETONE COMPOUNDS AND COMPOSITIONS FOR CHOLESTEROL MANAGEMENT AND RELATED USES

CROSS REFERENCE TO RELATED APPLICATIONS

This application is a continuation application of U.S. patent application Ser. No. 10/596,047, now allowed, which is a 371 application of PCT/US2003/041448, filed Dec. 24, 2003.

1. FIELD OF THE INVENTION

The invention encompasses ketone compounds and pharmaceutically acceptable salts, hydrates, solvates, and mixtures thereof; compositions comprising urea and thiourea compounds and pharmaceutically acceptable salts, hydrates, solvates, and mixtures thereof; and methods for treating or preventing a disease or disorder such as, but not limited to, aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, or enhancing bile production, or enhancing reverse lipid transport, which method comprise administering a ketone compound or composition of the invention to a patient in need thereof. The compounds of the invention can also treat or prevent inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism.

2. BACKGROUND OF THE INVENTION

Obesity, hyperlipidemia, and diabetes have been shown to play a causal role in atherosclerotic cardiovascular diseases, which currently account for a considerable proportion of morbidity in Western society. Further, one human disease, termed "Syndrome X" or "Metabolic Syndrome", is manifested by defective glucose metabolism (insulin resistance), elevated blood pressure (hypertension), and a blood lipid imbalance (dyslipidemia). See e.g. Reaven, 1993, *Annu. Rev. Med.* 44:121-131.

The evidence linking elevated serum cholesterol to coronary heart disease is overwhelming. Circulating cholesterol is carried by plasma lipoproteins, which are particles of complex lipid and protein composition that transport lipids in the blood. Low density lipoprotein (LDL) and high density lipoprotein (HDL) are the major cholesterol-carrier proteins. LDL is believed to be responsible for the delivery of cholesterol from the liver, where it is synthesized or obtained from dietary sources, to extrahepatic tissues in the body. The term "reverse cholesterol transport" describes the transport of cholesterol from extrahepatic tissues to the liver, where it is catabolized and eliminated. It is believed that plasma HDL particles play a major role in the reverse transport process, acting as scavengers of tissue cholesterol. HDL is also responsible for the removal of non-cholesterol lipid, oxidized cholesterol and other oxidized products from the bloodstream.

Atherosclerosis, for example, is a slowly progressive disease characterized by the accumulation of cholesterol within the arterial wall. Compelling evidence supports the belief that lipids deposited in atherosclerotic lesions are derived primarily from plasma apolipoprotein B (apo B)-containing lipoproteins, which include chylomicrons, CLDL, intermediate-density lipoproteins (IDL), and LDL. The apo B-containing lipoprotein, and in particular LDL, has popularly become known as the "bad" cholesterol. In contrast, HDL serum levels correlate inversely with coronary heart disease. Indeed, high serum levels of HDL are regarded as a negative risk factor. It is hypothesized that high levels of plasma HDL are not only protective against coronary artery disease, but may actually induce regression of atherosclerotic plaque (e.g., see Badimon et al., 1992, *Circulation* 86:(Suppl. 11)86-94; Dansky and Fisher, 1999, *Circulation* 100:1762 3.). Thus, HDL has popularly become known as the "good" cholesterol.

2.1. Cholesterol Transport

The fat-transport system can be divided into two pathways: an exogenous one for cholesterol and triglycerides absorbed from the intestine and an endogenous one for cholesterol and triglycerides entering the bloodstream from the liver and other non-hepatic tissue.

In the exogenous pathway, dietary fats are packaged into lipoprotein particles called chylomicrons, which enter the bloodstream and deliver their triglycerides to adipose tissue for storage and to muscle for oxidation to supply energy. The remnant of the chylomicron, which contains cholesteryl esters, is removed from the circulation by a specific receptor found only on liver cells. This cholesterol then becomes available again for cellular metabolism or for recycling to extrahepatic tissues as plasma lipoproteins.

In the endogenous pathway, the liver secretes a large, very-low-density lipoprotein particle (VLDL) into the bloodstream. The core of VLDL consists mostly of triglycerides synthesized in the liver, with a smaller amount of cholesteryl esters either synthesized in the liver or recycled from chylomicrons. Two predominant proteins are displayed on the surface of VLDL, apolipoprotein B-100 (apo B-100) and apolipoprotein E (apo E), although other apolipoproteins are present, such as apolipoprotein CIII (apo CIII) and apolipoprotein CII (apo CII). When VLDL reaches the capillaries of adipose tissue or of muscle, its triglyceride is extracted. This results in the formation of a new kind of particle called intermediate-density lipoprotein (IDL) or VLDL remnant, decreased in size and enriched in cholesteryl esters relative to a VLDL, but retaining its two apoproteins.

In human beings, about half of the IDL particles are removed from the circulation quickly, generally within two to six hours of their formation. This is because IDL particles bind tightly to liver cells, which extract IDL cholesterol to make new VLDL and bile acids. The IDL not taken up by the liver is catabolized by the hepatic lipase, an enzyme bound to the proteoglycan on liver cells. Apo E dissociates from IDL as it is transformed to LDL. Apo B-100 is the sole protein of LDL.

Primarily, the liver takes up and degrades circulating cholesterol to bile acids, which are the end products of cholesterol metabolism. The uptake of cholesterol-containing particles is mediated by LDL receptors, which are present in high concentrations on hepatocytes. The LDL receptor binds both apo E and apo B-100 and is responsible for binding and removing both IDL and LDL from the circulation. In addition, remnant receptors are responsible for clearing chylomicrons and VLDL remnants (i.e., IDL). However, the affinity of apo E for the LDL receptor is greater than that of apo B-100. As a result, the LDL particles have a much longer circulating life span than IDL particles; LDL circulates for an average of two and a half days before binding to the LDL receptors in the liver and other tissues. High serum levels of LDL, the "bad" cholesterol, are positively associated with coronary heart disease. For example, in atherosclerosis, cholesterol derived from circulating LDL accumulates in the walls of arteries. This accumulation forms bulky plaques that inhibit the flow of blood until a clot eventually forms, obstructing an artery and causing a heart attack or stroke.

Ultimately, the amount of intracellular cholesterol liberated from the LDL controls cellular cholesterol metabolism. The accumulation of cellular cholesterol derived from VLDL and LDL controls three processes. First, it reduces the ability of the cell to make its own cholesterol by turning off the synthesis of HMGCoA reductase, a key enzyme in the cholesterol biosynthetic pathway. Second, the incoming LDL-derived cholesterol promotes storage of cholesterol by the action of cholesterol acyltransferase ("ACAT"), the cellular enzyme that converts cholesterol into cholesteryl esters that are deposited in storage droplets. Third, the accumulation of cholesterol within the cell drives a feedback mechanism that inhibits cellular synthesis of new LDL receptors. Cells, therefore, adjust their complement of LDL receptors so that enough cholesterol is brought in to meet their metabolic needs, without overloading (for a review, see Brown & Goldstein, in *The Pharmacological Basis Of Therapeutics,* 8th Ed., Goodman & Gilman, Pergamon Press, New York, 1990, Ch. 36, pp. 874-896).

High levels of apo B-containing lipoproteins can be trapped in the subendothelial space of an artery and undergo oxidation. The oxidized lipoprotein is recognized by scavenger receptors on macrophages. Binding of oxidized lipoprotein to the scavenger receptors can enrich the macrophages with cholesterol and cholesteryl esters independently of the LDL receptor. Macrophages can also produce cholesteryl esters by the action of ACAT. LDL can also be complexed to a high molecular weight glycoprotein called apolipoprotein (a), also known as apo(a), through a disulfide bridge. The LDL-apo(a) complex is known as Lipoprotein(a) or Lp(a). Elevated levels of Lp(a) are detrimental, having been associated with atherosclerosis, coronary heart disease, myocardial infarction, stroke, cerebral infarction, and restenosis following angioplasty.

2.2. Reverse Cholesterol Transport

Peripheral (non-hepatic) cells predominantly obtain their cholesterol from a combination of local synthesis and uptake of preformed sterol from VLDL and LDL. Cells expressing scavenger receptors, such as macrophages and smooth muscle cells, can also obtain cholesterol from oxidized apo B-containing lipoproteins. In contrast, reverse cholesterol transport (RCT) is the pathway by which peripheral cell cholesterol can be returned to the liver for recycling to extrahepatic tissues, hepatic storage, or excretion into the intestine in bile. The RCT pathway represents the only means of eliminating cholesterol from most extrahepatic tissues and is crucial to the maintenance of the structure and function of most cells in the body.

The enzyme in blood involved in the RCT pathway, lecithin:cholesterol acyltransferase (LCAT), converts cell-derived cholesterol to cholesteryl esters, which are sequestered in HDL destined for removal. LCAT is produced mainly in the liver and circulates in plasma associated with the HDL fraction. Cholesterol ester transfer protein (CETP) and another lipid transfer protein, phospholipid transfer protein (PLTP), contribute to further remodeling the circulating HDL population (see for example Bruce et al., 1998, *Annu. Rev. Nutr.* 18:297 330). PLTP supplies lecithin to HDL, and CETP can move cholesteryl esters made by LCAT to other lipoproteins, particularly apoB-containing lipoproteins, such as VLDL. HDL triglycerides can be catabolized by the extracellular hepatic triglyceride lipase, and lipoprotein cholesterol is removed by the liver via several mechanisms.

Each HDL particle contains at least one molecule, and usually two to four molecules, of apolipoprotein A I (apo A I). Apo A I is synthesized by the liver and small intestine as preproapolipoprotein, which is secreted as a proprotein that is rapidly cleaved to generate a mature polypeptide having 243 amino acid residues. Apo A I consists mainly of a 22 amino acid repeating segment, spaced with helix-breaking proline residues. Apo A I forms three types of stable structures with lipids: small, lipid-poor complexes referred to as pre-beta-1 HDL; flattened discoidal particles, referred to as pre-beta-2 HDL, which contain only polar lipids (e.g., phospholipid and cholesterol); and spherical particles containing both polar and nonpolar lipids, referred to as spherical or mature HDL (HDL3 and HDL2). Most HDL in the circulating population contains both apo A I and apo A II, a second major HDL protein. This apo A I- and apo A II-containing fraction is referred to herein as the AI/AII-HDL fraction of HDL. But the fraction of HDL containing only apo A I, referred to herein as the AI HDL fraction, appears to be more effective in RCT. Certain epidemiologic studies support the hypothesis that the AI-HDL fraction is antiartherogenic (Parra et al., 1992, *Arterioscler. Thromb.* 12:701-707; Decossin et al., 1997, *Eur. J. Clin. Invest.* 27:299-307).

Although the mechanism for cholesterol transfer from the cell surface is unknown, it is believed that the lipid-poor complex, pre-beta-1 HDL, is the preferred acceptor for cholesterol transferred from peripheral tissue involved in RCT. Cholesterol newly transferred to pre-beta-1 HDL from the cell surface rapidly appears in the discoidal pre-beta-2 HDL. PLTP may increase the rate of disc formation (Lagrost et al., 1996, *J. Biol. Chem.* 271:19058-19065), but data indicating a role for PLTP in RCT is lacking. LCAT reacts preferentially with discoidal and spherical HDL, transferring the 2-acyl group of lecithin or phosphatidylethanolamine to the free hydroxyl residue of fatty alcohols, particularly cholesterol, to generate cholesteryl esters (retained in the HDL) and lysolecithin. The LCAT reaction requires an apolipoprotein such as apo A I or apo A-IV as an activator. ApoA-I is one of the natural cofactors for LCAT. The conversion of cholesterol to its HDL-sequestered ester prevents re-entry of cholesterol into the cell, resulting in the ultimate removal of cellular cholesterol. Cholesteryl esters in the mature HDL particles of the AI-HDL fraction are removed by the liver and processed into bile more effectively than those derived from the AI/AII-HDL fraction. This may be due, in part, to the more effective binding of AI-HDL to the hepatocyte membrane. Several HDL receptors have been identified, the most well characterized of which is the scavenger receptor class B, type I (SR BI) (Acton et al., 1996, *Science* 271:518-520). The SR-BI is expressed most abundantly in steroidogenic tissues (e.g., the adrenals), and in the liver (Landshulz et al., 1996, *J. Clin. Invest.* 98:984-995; Rigotti et al., 1996, *J. Biol. Chem.* 271: 33545-33549). Other proposed HDL receptors include HB1 and HB2 (Hidaka and Fidge, 1992, *Biochem J.* 15:161 7; Kurata et al., 1998, *J. Atherosclerosis and Thrombosis* 4:112 7).

While there is a consensus that CETP is involved in the metabolism of VLDL- and LDL-derived lipids, its role in RCT remains controversial. However, changes in CETP activity or its acceptors, VLDL and LDL, play a role in "remodeling" the HDL population. For example, in the absence of CETP, the HDL becomes enlarged particles that are poorly removed from the circulation (for reviews on RCT and HDL, See Fielding & Fielding, 1995, *J. Lipid Res.* 36:211-228; Barrans et al., 1996, *Biochem. Biophys. Acta.* 1300:73-85; Hirano et al., 1997, *Arterioscler. Thromb. Vasc. Biol.* 17:1053-1059).

2.3. Reverse Transport of Other Lipids

HDL is not only involved in the reverse transport of cholesterol, but also plays a role in the reverse transport of other lipids, i.e., the transport of lipids from cells, organs, and tissues to the liver for catabolism and excretion. Such lipids include sphingomyelin, oxidized lipids, and lysophophatidylcholine. For example, Robins and Fasulo (1997, *J. Clin. Invest.* 99:380 384) have shown that HDL stimulates the transport of plant sterol by the liver into bile secretions.

2.4. Peroxisome Proliferator Activated Receptor Pathway

Peroxisome proliferators are a structurally diverse group of compounds that, when administered to rodents, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, 1985, *Ann. Rev. Cell Biol.* 1:489 530; Vamecq and Draye, 1989, *Essays Biochem.* 24:1115 225; and Nelali et al., 1988, *Cancer Res.* 48:5316 5324). Chemicals included in this group are the fibrate class of hypolipidemic drugs, herbicides, and phthalate plasticizers (Reddy and Lalwani, 1983, *Crit. Rev. Toxicol.* 12:1 58). Peroxisome proliferation can also be elicited by dietary or physiological factors, such as a high fat diet and cold acclimatization.

Insight into the mechanism whereby peroxisome proliferators exert their pleiotropic effects was provided by the identification of a member of the nuclear hormone receptor superfamily activated by these chemicals (Isseman and Green, 1990, *Nature* 347:645 650). This receptor, termed peroxisome proliferator activated receptor α (PPARα), was subsequently shown to be activated by a variety of medium and long chain fatty acids. PPARα activates transcription by binding to DNA sequence elements, termed peroxisome proliferator response elements (PPRE), in the form of a heterodimer with the retinoid X receptor (RXR). RXR is activated by 9-cis retinoic acid (see Kliewer et al., 1992, *Nature* 358:771 774; Gearing et al., 1993, *Proc. Natl. Acad. Sci. USA* 90:1440 1444, Keller et al., 1993, *Proc. Natl. Acad. Sci. USA* 90:2160 2164; Heyman et al., 1992, *Cell* 68:397 406, and Levin et al., 1992, *Nature* 355:359 361). Since the discovery of PPARα, additional isoforms of PPAR have been identified, e.g., PPARβ, PPARγ and PPARδ, which have similar functions and are similarly regulated.

PPARs have been identified in the enhancers of a number of gene-encoding proteins that regulate lipid metabolism. These proteins include the three enzymes required for peroxisomal t-oxidation of fatty acids; apolipoprotein A-I; medium chain acyl-CoA dehydrogenase, a key enzyme in mitochondrial β-oxidation; and aP2, a lipid binding protein expressed exclusively in adipocytes (reviewed in Keller and Whali, 1993, *TEM*, 4:291 296; see also Staels and Auwerx, 1998, *Atherosclerosis* 137 Suppl:S19 23). The nature of the PPAR target genes coupled with the activation of PPARs by fatty acids and hypolipidemic drugs suggests a physiological role for the PPARs in lipid homeostasis.

Pioglitazone, an antidiabetic compound of the thiazolidinedione class, was reported to stimulate expression of a chimeric gene containing the enhancer/promoter of the lipid binding protein aP2 upstream of the chloroamphenicol acetyl transferase reporter gene (Harris and Kletzien, 1994, *Mol. Pharmacol.* 45:439 445). Deletion analysis led to the identification of an approximately 30 bp region accounting for pioglitazone responsiveness. In an independent study, this 30 bp fragment was shown to contain a PPRE (Tontonoz et al., 1994, *Nucleic Acids Res.* 22:5628 5634). Taken together, these studies suggested the possibility that the thiazolidinediones modulate gene expression at the transcriptional level through interactions with a PPAR and reinforce the concept of the interrelatedness of glucose and lipid metabolism.

2.5. Current Cholesterol Management Therapies

In the past two decades or so, the segregation of cholesterolemic compounds into HDL and LDL regulators and recognition of the desirability of decreasing blood levels of the latter has led to the development of a number of drugs. However, many of these drugs have undesirable side effects and/or are contraindicated in certain patients, particularly when administered in combination with other drugs.

Bile-acid-binding resins are a class of drugs that interrupt the recycling of bile acids from the intestine to the liver. Examples of bile-acid-binding resins are cholestyramine (QUESTRAN LIGHT, Bristol-Myers Squibb), and colestipol hydrochloride (COLESTID, Pharmacia & Upjohn Company). When taken orally, these positively charged resins bind to negatively charged bile acids in the intestine. Because the resins cannot be absorbed from the intestine, they are excreted, carrying the bile acids with them. The use of such resins, however, at best only lowers serum cholesterol levels by about 20%. Moreover, their use is associated with gastrointestinal side-effects, including constipation and certain vitamin deficiencies. Moreover, since the resins bind to drugs, other oral medications must be taken at least one hour before or four to six hours subsequent to ingestion of the resin, complicating heart patients' drug regimens.

The statins are inhibitors of cholesterol synthesis. Sometimes, the statins are used in combination therapy with bile-acid-binding resins. Lovastatin (MEVACOR, Merck & Co., Inc.), a natural product derived from a strain of *Aspergillus*; pravastatin (PRAVACHOL, Bristol-Myers Squibb Co.); and atorvastatin (LIPITOR, Warner Lambert) block cholesterol synthesis by inhibiting HMGCoA reductase, the key enzyme involved in the cholesterol biosynthetic pathway. Lovastatin significantly reduces serum cholesterol and LDL-serum levels. However, serum HDL levels are only slightly increased following lovastatin administration. The mechanism of the LDL-lowering effect may involve both reduction of VLDL concentration and induction of cellular expression of LDL-receptor, leading to reduced production and/or increased catabolism of LDL. Side effects, including liver and kidney dysfunction are associated with the use of these drugs.

Nicotinic acid, also known as niacin, is a water-soluble vitamin B-complex used as a dietary supplement and antihyperlipidemic agent. Niacin diminishes the production of VLDL and is effective at lowering LDL. It is used in combination with bile-acid-binding resins. Niacin can increase HDL when administered at therapeutically effective doses; however, its usefulness is limited by serious side effects.

Fibrates are a class of lipid-lowering drugs used to treat various forms of hyperlipidemia, elevated serum triglycerides, which may also be associated with hypercholesterolemia. Fibrates appear to reduce the VLDL fraction and modestly increase HDL; however, the effects of these drugs on serum cholesterol is variable. In the United States, fibrates have been approved for use as antilipidemic drugs, but have not received approval as hypercholesterolemia agents. For example, clofibrate (ATROMID-S, Wyeth-Ayerst Laboratories) is an antilipidemic agent that acts to lower serum triglycerides by reducing the VLDL fraction. Although ATROMID-S may reduce serum cholesterol levels in certain patient subpopulations, the biochemical response to the drug is variable, and is not always possible to predict which patients will obtain favorable results. ATROMID-S has not been shown to be effective for prevention of coronary heart disease. The chemically and pharmacologically related drug, gemfibrozil (LOPID, Parke-Davis), is a lipid regulating agent which moderately decreases serum triglycerides and VLDL cholesterol. LOPID also increases HDL cholesterol, particularly the HDL2 and HDL3 subfractions, as well as both the AI/AII-HDL fractions. However, the lipid response to LOPID is heterogeneous, especially among different patient populations. Moreover, while prevention of coronary heart disease was observed in male patients between the ages of 40 and 55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates, including toxicity; malignancy, particularly malignancy of gastrointestinal cancer, gallbladder disease; and an increased incidence in non-coronary mortality. These drugs are not indicated for the treatment of patients with high LDL or low HDL as their only lipid abnormality.

Oral estrogen replacement therapy may be considered for moderate hypercholesterolemia in post-menopausal women. However, increases in HDL may be accompanied with an increase in triglycerides. Estrogen treatment is, of course, limited to a specific patient population, postmenopausal women, and is associated with serious side effects, including induction of malignant neoplasms; gall bladder disease; thromboembolic disease; hepatic adenoma; elevated blood pressure; glucose intolerance; and hypercalcemia.

Long chain carboxylic acids, particularly long chain $\alpha,\omega$-dicarboxylic acids with distinctive substitution patterns, and their simple derivatives and salts, have been disclosed for treating atherosclerosis, obesity, and diabetes (See, e.g., Bisgaier et al., 1998, *J. Lipid Res.* 39:17-30, and references cited therein; International Patent Publication WO 98/30530; U.S. Pat. No. 4,689,344; International Patent Publication WO 99/00116; and U.S. Pat. No. 5,756,344). However, some of these compounds, for example the $\alpha,\omega$-dicarboxylic acids substituted at their $\alpha,\alpha'$-carbons (U.S. Pat. No. 3,773,946), while having serum triglyceride and serum cholesterol-lowering activities, have no value for treatment of obesity and hypercholesterolemia (U.S. Pat. No. 4,689,344).

U.S. Pat. No. 4,689,344 discloses $\beta,\beta,\beta',\beta'$-tetrasubstituted-$\alpha,\omega$-alkanedioic acids that are optionally substituted at their $\alpha,\alpha,\alpha',\alpha'$-positions, and alleges that they are useful for treating obesity, hyperlipidemia, and diabetes. According to this reference, both triglycerides and cholesterol are lowered significantly by compounds such as 3,3,14,14-tetramethyl-hexadecane-1,16-dioic acid. U.S. Pat. No. 4,689,344 further discloses that the $\beta,\beta,\beta',\beta'$-tetramethyl-alkanediols of U.S. Pat. No. 3,930,024 also are not useful for treating hypercholesterolemia or obesity.

Other compounds are disclosed in U.S. Pat. No. 4,711,896. In U.S. Pat. No. 5,756,544, $\alpha,\omega$-dicarboxylic acid-terminated dialkane ethers are disclosed to have activity in lowering certain plasma lipids, including Lp(a), triglycerides, VLDL-cholesterol, and LDL-cholesterol, in animals, and elevating others, such as HDL-cholesterol. The compounds are also stated to increase insulin sensitivity. In U.S. Pat. No. 4,613,593, phosphates of dolichol, a polyprenol isolated from swine liver, are stated to be useful in regenerating liver tissue, and in treating hyperuricuria, hyperlipemia, diabetes, and hepatic diseases in general.

U.S. Pat. No. 4,287,200 discloses azolidinedione derivatives with anti-diabetic, hypolipidemic, and anti-hypertensive properties. However, the administration of these compounds to patients can produce side effects such as bone marrow depression, and both liver and cardiac cytotoxicity. Further, the compounds disclosed by U.S. Pat. No. 4,287,200 stimulate weight gain in obese patients.

It is clear that none of the commercially available cholesterol management drugs has a general utility in regulating lipid, lipoprotein, insulin and glucose levels in the blood. Thus, compounds that have one or more of these utilities are clearly needed. Further, there is a clear need to develop safer drugs that are efficacious at lowering serum cholesterol, increasing HDL serum levels, preventing coronary heart disease, and/or treating existing disease such as atherosclerosis, obesity, diabetes, and other diseases that are affected by lipid metabolism and/or lipid levels. There is also a clear need to develop drugs that may be used with other lipid-altering treatment regimens in a synergistic manner. There is still a further need to provide useful therapeutic agents whose solubility and Hydrophile/Lipophile Balance (HLB) can be readily varied.

The recitation of any reference in Section 2 of this application is not an admission that the reference is available as prior art to this application.

3. SUMMARY OF THE INVENTION

In one embodiment, the invention encompasses compounds of formula I:

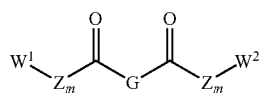

or a pharmaceutically acceptable salt, hydrate, solvate, or a mixture thereof, wherein
(a) each occurrence of Z is independently $CH_2$, CH=CH, or phenyl, wherein each occurrence of m is independently an integer ranging from 1 to 9, but when Z is phenyl then its associated m is 1;
(b) G is $(CH_2)_x$, $CH_2CH=CHCH_2$, CH=CH, $CH_2$-phenyl-$CH_2$, or phenyl, wherein x is 2, 3, or 4;
(c) $W^1$ and $W^2$ are independently L, V, $C(R^1)(R^2)$—$(CH_2)_c$—$C(R^3)(R^4)$—$(CH_2)_n$—Y, or $C(R^1)(R^2)$—$(CH_2)_c$—V, wherein c is 1 or 2 and n is an independent integer ranging from 0 to 4;
(d) $R^1$ and $R^2$ are independently $(C_1$-$C_6)$alkyl, $(C_2$-$C_6)$alkenyl, $(C_2$-$C_6)$alkynyl, phenyl, or benzyl or when $W^1$ or $W^2$ is C(R¹)(R²)—(CH₂)_c—C(R³)(R⁴)—Y, then R¹ and R² can both be H, or R¹ and R² and the carbon to which they are both attached are taken together to form a (C₃-C₇)cycloakyl group;

(e) R³ and R⁴ are independently H, OH, (C₁-C₆)alkyl, (C₂-C₆)alkenyl, (C₂-C₆)alkynyl, (C₁-C₆)alkoxy, phenyl, benzyl, Cl, Br, CN, NO₂, or CF₃, with the proviso that when R¹ and R² are both H, then one of R³ or R⁴ is not H or R³ and R⁴ and the carbon to which they are both attached are taken together to form a (C₃-C₇)cycloakyl group;

(f) L is C(R¹)(R²)—(CH₂)_n—Y;

(g) V is

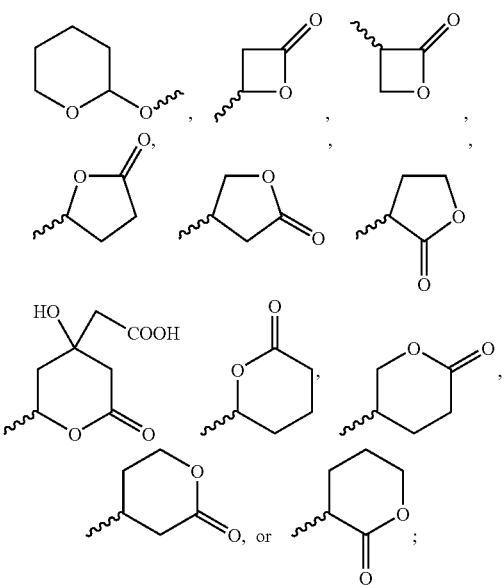

(h) Y is (C₁-C₆)alkyl, OH, COOH, CHO, COOR⁵, SO₃H,

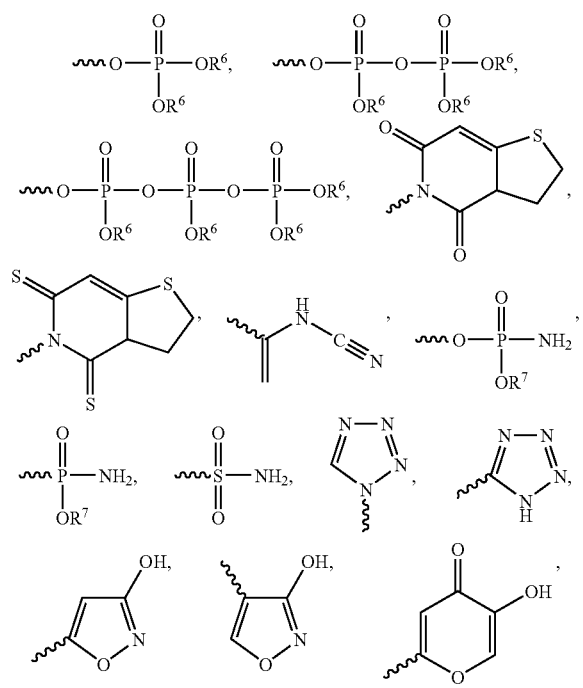

-continued

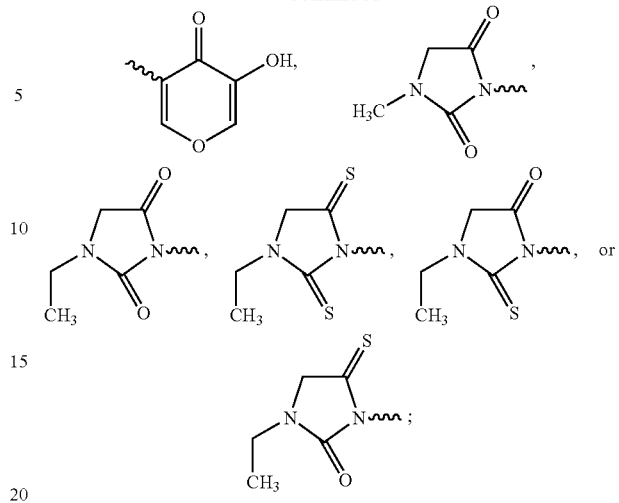

where
(I) R⁵ is (C₁-C₆)alkyl, (C₂-C₆)alkenyl, (C₂-C₆)alkynyl, phenyl, or benzyl and is unsubstituted or substituted with one or more halo, OH, (C₁-C₆)alkoxy, or phenyl groups,
(ii) each occurrence of R⁶ is independently H, (C₁-C₆)alkyl, (C₂-C₆)alkenyl, or (C₂-C₆)alkynyl and is unsubstituted or substituted with one or two halo, OH, C₁-C₆alkoxy, or phenyl groups; and
(iii) each occurrence of R⁷ is independently H, (C₁-C₆)alkyl, (C₂-C₆)alkenyl, or (C₂-C₆)alkynyl.

Preferred compounds of formula I are those wherein:
(a) W¹ and W² are independently L, V, or C(R¹)(R²)—(CH₂)_c—V, where c is 1 or 2; and
(b) R¹ and R² are independently (C₁-C₆)alkyl, (C₂-C₆)alkenyl, (C₂-C₆)alkynyl, phenyl, or benzyl.

Other preferred compounds of formula I are those wherein W¹ is L.

Other preferred compounds of formula I are those wherein W¹ is V.

Other preferred compounds of formula I are those wherein W¹ is C(R¹)(R²)—(CH₂)_c—C(R³)(R⁴)—(CH₂)_n—Y.

Other preferred compounds of formula I are those wherein W¹ is C(R¹)(R²)—(CH₂)_c—V.

Other preferred compounds of formula I are those wherein W¹ and W² are independent L groups.

Other preferred compounds of formula I are those wherein each occurrence of Y is independently OH, COOR⁵, or COOH.

In another embodiment, the invention encompasses compounds of formula Ia:

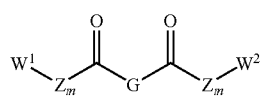

Ia or a pharmaceutically acceptable salt, hydrate, solvate, or a mixture thereof, wherein
(a) each occurrence of Z is independently CH₂ or CH=CH, wherein each occurrence of m is independently an integer ranging from 1 to 9;
(b) G is (CH₂)_x, CH₂CH=CHCH₂, or CH=CH, where x is 2, 3, or 4;

(c) $W^1$ and $W^2$ are independently L, V, or $C(R^1)(R^2)$—$(CH_2)_c$—V, where c is 1 or 2;

(d) each occurrence of $R^1$ and $R^2$ is independently $(C_1-C_6)$alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloakyl group;

(e) L is $C(R^1)(R^2)$—$(CH_2)_n$—Y, where n is an independent integer ranging from 0 to 4;

(f) V is

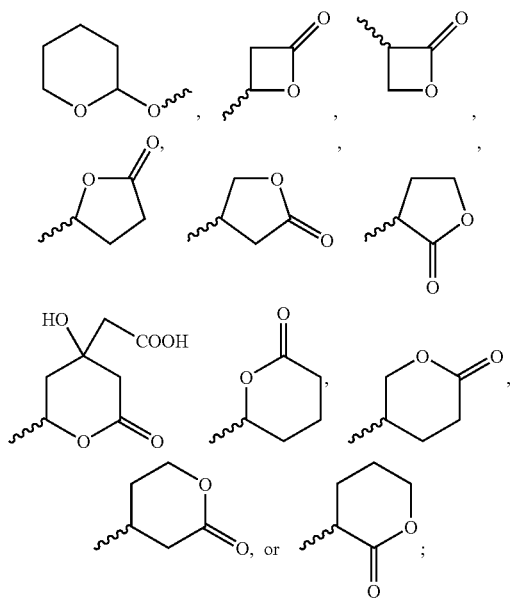

(g) each occurrence of Y is independently $(C_1-C_6)$alkyl, OH, COOH, CHO, $(CH_2)_n COOR^3$, $SO_3H$,

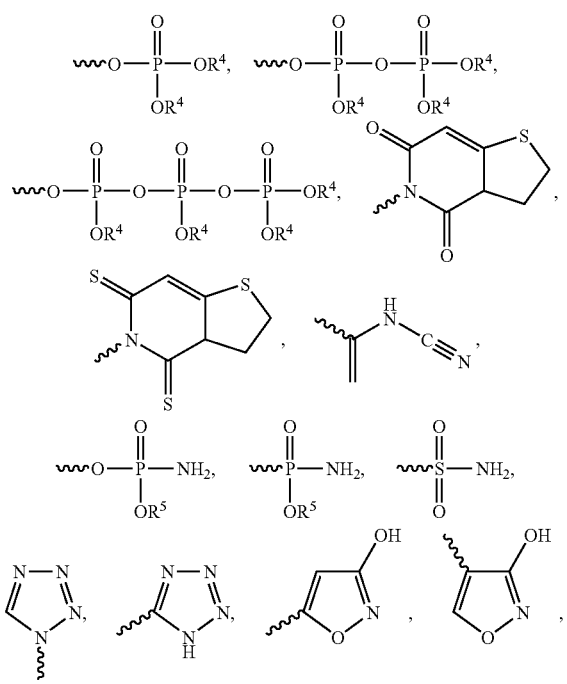

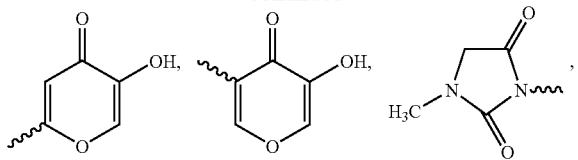

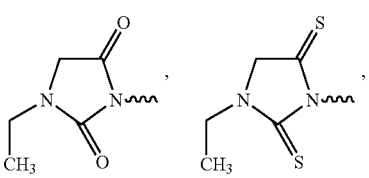

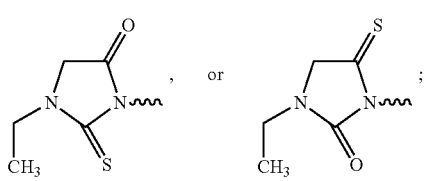

where (I) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups, (ii) each occurrence of $R^4$ is independently H, $(C_1-C_6)$alkyl, $(C_2-C_6)$alkenyl, or $(C_2-C_6)$alkynyl and is unsubstituted or substituted with one or two halo, OH, $C_1-C_6$ alkoxy, or phenyl groups; and (iii) each occurrence of $R^5$ is independently H, $(C_1-C_6)$alkyl, $(C_2-C_6)$alkenyl, or $(C_2-C_6)$alkynyl.

Preferably, in formula Ia each occurrence of Y is independently $(C_1-C_6)$alkyl, OH, $COOR^3$, or COOH.

In yet another embodiment, the invention encompasses compounds formula Ib

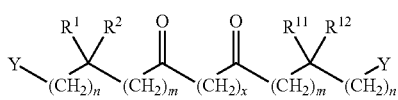

Ib or a pharmaceutically acceptable salt, hydrate, solvate, or a mixture thereof, wherein:

(a) each occurrence of m is independently an integer ranging from 1 to 9;

(b) x is 2, 3, or 4;

(c) n is an independent integer ranging from 0 to 4;

(d) each occurrence of $R^1$ and $R^2$ is independently $(C_1-C_6)$alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloakyl group;

(e) each occurrence of $R^{11}$ and $R^{12}$ is independently H, $(C_1$-$C_6)$alkyl, $(C_2$-$C_6)$alkenyl, $(C_2$-$C_6)$alkynyl, phenyl, benzyl, or $R^{11}$ and $R^{12}$ and the carbon to which they are both attached are taken together to form a $(C_3$-$C_7)$cycloakyl group;

(f) each occurrence of Y is independently $(C_1$-$C_6)$alkyl, OH, COOH, CHO, COOR$^3$, SO$_3$H,

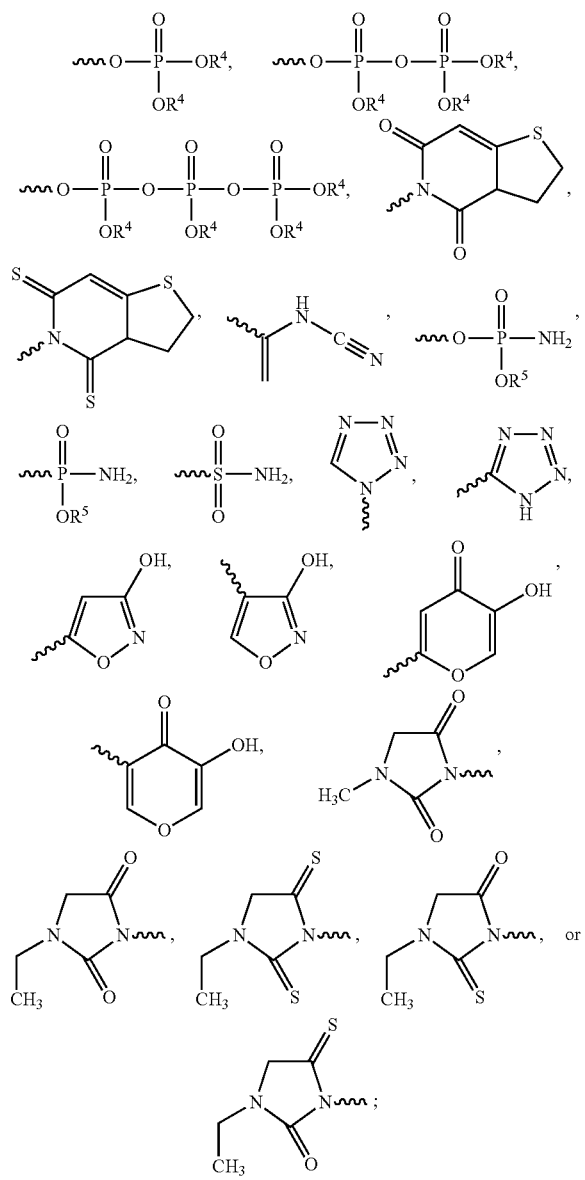

where
(I) $R^3$ is $(C_1$-$C_6)$alkyl, $(C_2$-$C_6)$alkenyl, $(C_2$-$C_6)$alkynyl, phenyl, or benzyl and is unsubstituted or substituted with one or more halo, OH, $(C_1$-$C_6)$alkoxy, or phenyl groups, (ii) each occurrence of $R^4$ is independently H, $(C_1$-$C_6)$ alkyl, $(C_2$-$C_6)$alkenyl, or $(C_2$-$C_6)$alkynyl and is unsubstituted or substituted with one or two halo, OH, $C_1$-$C_6$ alkoxy, or phenyl groups; and (iii) each occurrence of $R^5$ is independently H, $(C_1$-$C_6)$ alkyl, $(C_2$-$C_6)$alkenyl, or $(C_2$-$C_6)$alkynyl.

Preferably in formula Ib, each occurrence of Y is independently OH, COOR$^3$, or COOH.

In still another embodiment, the invention encompasses compounds of formula Ic

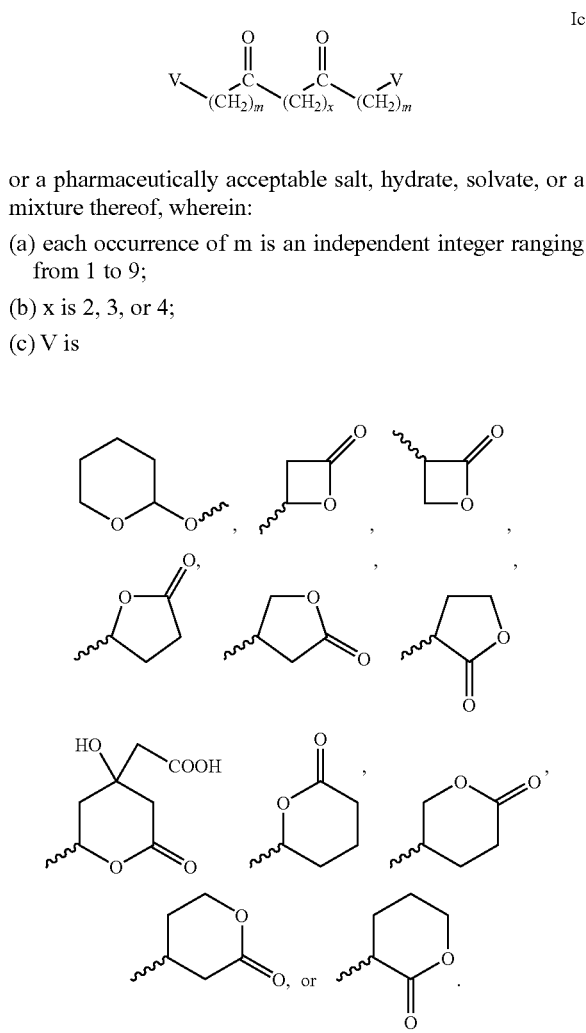

or a pharmaceutically acceptable salt, hydrate, solvate, or a mixture thereof, wherein:

(a) each occurrence of m is an independent integer ranging from 1 to 9;

(b) x is 2, 3, or 4;

(c) V is

In another embodiment, the invention encompasses compounds of formula II:

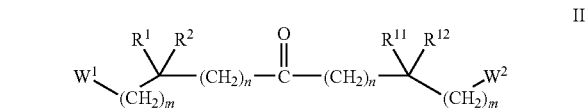

or a pharmaceutically acceptable salt, hydrate, solvate, or a mixture thereof, wherein (a) $R^1$ and $R^2$ are independently $(C_1$-$C_6)$alkyl, $(C_2$-$C_6)$alkenyl, $(C_2$-$C_6)$alkynyl, phenyl, or benzyl; or $R^1$, $R^2$, and the carbon to which they are both attached are taken together to form a $(C_3$-$C_7)$cycloalkyl group;

(b) $R^{11}$ and $R^{12}$ are independently $(C_1$-$C_6)$alkyl, $(C_2$-$C_6)$alkenyl, $(C_2$-$C_6)$alkynyl, phenyl, or benzyl; or $R^{11}$, $R^{12}$, and the carbon to which they are both attached are taken together to form a $(C_3$-$C_7)$cycloalkyl group;

(c) n is an integer ranging from 1 to 5;

(d) each occurrence of m is independently an integer ranging from 0 to 4;

(e) $W^1$ and $W^2$ are independently $(C_1-C_6)$alkyl, $CH_2OH$, $C(O)OH$, $CHO$, $OC(O)R^3$, $C(O)OR^3$, $SO_3H$,

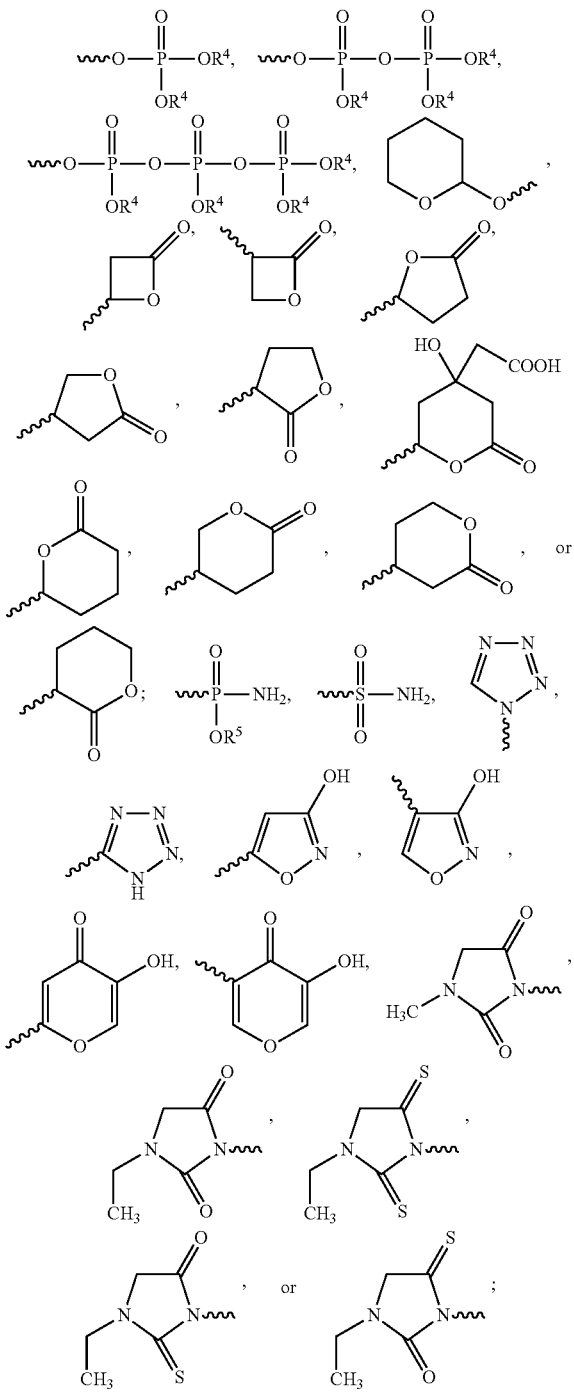

where
(I) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups, (ii) each occurrence of $R^4$ is independently H, $(C_1-C_6)$ alkyl, $(C_2-C_6)$alkenyl, or $(C_2-C_6)$alkynyl and is unsubstituted or substituted with one or two halo, OH, $C_1-C_6$ alkoxy, or phenyl groups; and (iii) each occurrence of $R^5$ is independently H, $(C_1-C_6)$ alkyl, $(C_2-C_6)$alkenyl, or $(C_2-C_6)$alkynyl.

Preferred compounds of formula II are those wherein each occurrence of W is independently OH, $COOR^3$, or COOH.

Other preferred compounds of formula II are those wherein $R^1$ and $R^2$ are independent $(C_1-C_6)$alkyl groups.

Other preferred compounds of formula II are those wherein m is 0.

Other preferred compounds of formula I are those wherein m is 1.

Other preferred compounds of formula II are those wherein $R^1$ and $R^2$ are each independently $(C_1-C_6)$ alkyl.

Other preferred compounds of formula II are those wherein $R^1$ and $R^2$ are each methyl.

Other preferred compounds of formula II are those wherein $W^1$ and/or $W^2$ is C(O)OH or $CH_2OH$.

In another embodiment, the invention encompasses compounds of formula IIa:

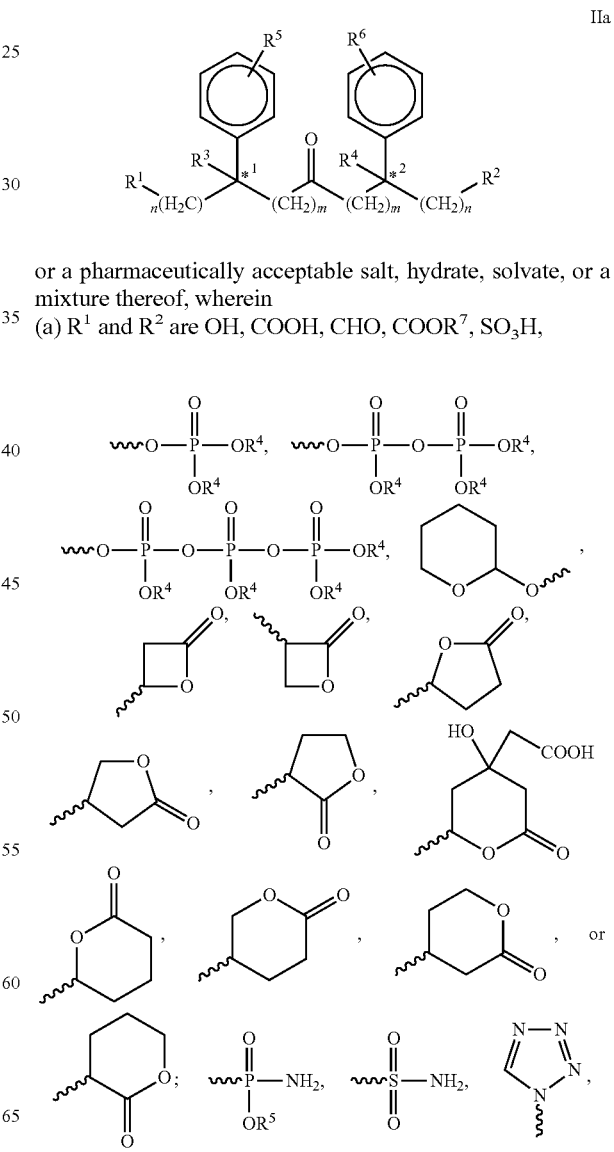

or a pharmaceutically acceptable salt, hydrate, solvate, or a mixture thereof, wherein
(a) $R^1$ and $R^2$ are OH, COOH, CHO, $COOR^7$, $SO_3H$,

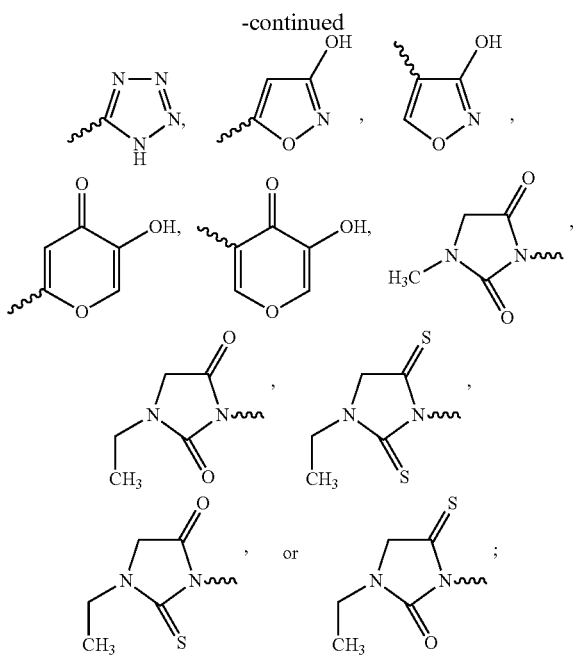

where
(I) $R^7$ is $(C_1$-$C_6)$alkyl, $(C_2$-$C_6)$alkenyl, $(C_2$-$C_6)$alkynyl, phenyl, or benzyl and is unsubstituted or substituted with one or more halo, OH, $(C_1$-$C_6)$alkoxy, or phenyl groups,
(ii) each occurrence of $R^8$ is independently H, $(C_1$-$C_6)$alkyl, $(C_2$-$C_6)$alkenyl, or $(C_2$-$C_6)$alkynyl and is unsubstituted or substituted with one or two halo, OH, $C_1$-$C_6$ alkoxy, or phenyl groups,
(iii) each occurrence of $R^9$ is independently H, $(C_1$-$C_6)$alkyl, $(C_2$-$C_6)$alkenyl, or $(C_2$-$C_6)$alkynyl;
(b) $R^3$ and $R^4$ are $(C_1$-$C_6)$alkyl, $(C_2$-$C_6)$alkenyl, $(C_2$-$C_6)$alkynyl, phenyl, or benzyl;
(c) $R^5$ and $R^6$ are hydrogen, halogen, $(C_1$-$C_4)$alkyl, $(C_1$-$C_4)$alkoxy, (C6)aryloxy, CN, or $NO_2$, $N(R^5)_2$ where $R^5$ is H, $(C_1$-$C_4)$ alkyl, phenyl, or benzyl;
(d) each occurrence of m is independently an integer ranging from 1 to 5;
(e) each occurrence of n is independently an integer ranging from 0 to 4; and
(f) *$^1$ and *$^2$ represent independent chiral-carbon centers, wherein each center may independently be R or S.

Preferred compounds of formula IIa are those wherein each occurrence of $R^1$ and $R^2$ is independently OH, $COOR^7$, or COOH.

Other preferred compounds of formula IIa are those wherein m is 0.

Other preferred compounds of formula IIa are those wherein m is 1.

Other preferred compounds of formula IIa are those wherein $R^1$ and/or $R^2$ is C(O)OH or $CH_2OH$.

Other preferred compounds of formula IIa are those wherein $R^3$ and $R^4$ are each independently $(C_1$-$C_6)$ alkyl.

Other preferred compounds of formula IIa are those wherein $R^3$ and $R^4$ are each methyl.

Other preferred compounds of formula IIa are those wherein *$^1$ is of the stereochemical configuration R or substantially R.

Other preferred compounds of formula IIa are those wherein *$^1$ is of the stereochemical configuration S or substantially S.

Other preferred compounds of formula IIa are those wherein *$^2$ is of the stereochemical configuration R or substantially R.

Other preferred compounds of formula IIa are those wherein *$^2$ is of the stereochemical configuration S or substantially S.

In a particular embodiment, compounds of formula IIa are those wherein *$^1$ *$^2$ are of the stereochemical configuration $(S^1,S^2)$ or substantially $(S^1,S^2)$.

In another particular embodiment, compounds of formula IIa are those wherein *$^1$ *$^2$ are of the stereochemical configuration $(S^1,R^2)$ or substantially $(S^1,R^2)$.

In another particular embodiment, compounds of formula IIa are those wherein *$^1$ *$^2$ are of the stereochemical configuration $(R^1,R^2)$ or substantially $(R^1,R^2)$.

In another particular embodiment, compounds of formula IIa are those wherein *$^1$ *$^2$ are of the stereochemical configuration $(R^1,S^2)$ or substantially $(R^1,S^2)$.

In still another embodiment, the invention encompasses compounds of formula III:

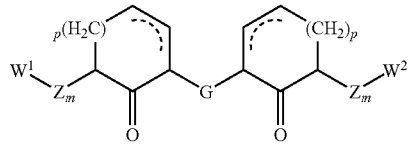

III or a pharmaceutically acceptable salt, hydrate, solvate, or a mixture thereof, wherein (a) each occurrence of Z is independently $CH_2$, CH=CH, or phenyl, where each occurrence of m is independently an integer ranging from 1 to 5, but when Z is phenyl then its associated m is 1;
(b) G is $(CH_2)_x$, $CH_2CH$=$CHCH_2$, CH=CH, $CH_2$ phenyl-$CH_2$, or phenyl, where x is an integer ranging from 1 to 4;
(c) $W^1$ and $W^2$ are independently $C(R^1)(R^2)$—$(CH_2)_n$—Y where n is an integer ranging from 0 to 4;
(d) $R^1$ and $R^2$ are independently $(C_1$-$C_6)$alkyl, $(C_2$-$C_6)$alkenyl, $(C_2$-$C_6)$alkynyl, phenyl, or benzyl or $R^1$ and $R^2$ are both H, or $R^1$, $R^1$, and the carbon to which they are both attached are taken together to form a $(C_3$-$C_7)$cycloalkyl group;
(e) Y is $(C_1$-$C_6)$alkyl, $(CH_2)_n$OH, $(CH_2)_n$COOH, $(CH_2)_n$CHO, $(CH_2)_n$COOR$^3$, $SO_3H$,

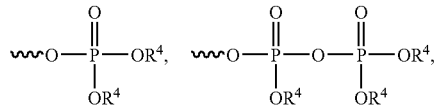

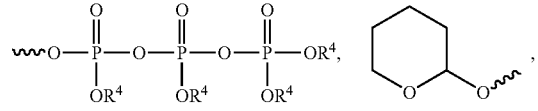

-continued

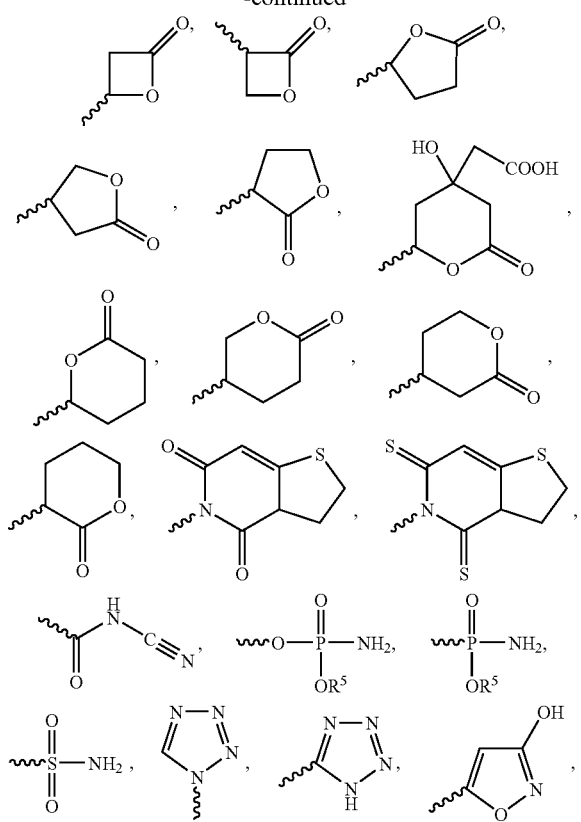

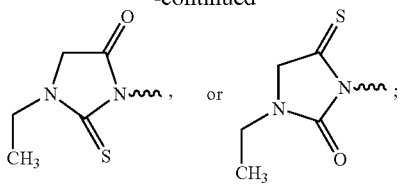

where
(I) $R^3$ is $(C_1\text{-}C_6)$alkyl, $(C_2\text{-}C_6)$alkenyl, $(C_2\text{-}C_6)$alkynyl, phenyl, or benzyl and is unsubstituted or substituted with one or more halo, OH, $(C_1\text{-}C_6)$alkoxy, or phenyl groups, (ii) each occurrence of $R^4$ is independently H, $(C_1\text{-}C_6)$ alkyl, $(C_2\text{-}C_6)$alkenyl, or $(C_2\text{-}C_6)$alkynyl and is unsubstituted or substituted with one or two halo, OH, $C_1\text{-}C_6$ alkoxy, or phenyl groups, (iii) each occurrence of $R^5$ is independently H, $(C_1\text{-}C_6)$ alkyl, $(C_2\text{-}C_6)$alkenyl, or $(C_2\text{-}C_6)$alkynyl; and (f) each occurrence of p is independently 2 or 3 where the broken line represents an optional presence of one or more additional carbon-carbon bonds that when present complete one or more carbon-carbon double bonds.

Preferred compounds of formula III are those wherein each occurrence of Y is independently OH, $COOR^3$, or COOH.

Other preferred compounds of formula III are those wherein p is 2.

Other preferred compounds of formula III are those wherein p is 3.

In yet another embodiment, the invention encompasses compounds of formula IIIa:

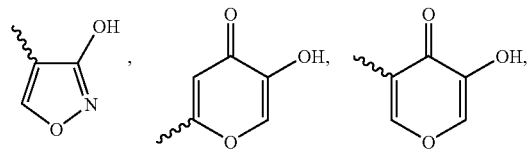

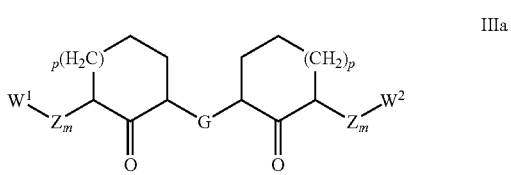

IIIa or a pharmaceutically acceptable salt, hydrate, solvate, thereof, wherein $W^1$, $W^2$ and $Z_m$ are the same as compound III. Preferably in compound IIIa, $W^1$ and $W^2$ are independent $C(R^1)(R^2)$—Y groups and each occurrence of Y is independently OH, $COOR^3$, or COOH. Illustrative compounds are illustrated below in Table 1.

TABLE 1

Compounds of the Invention

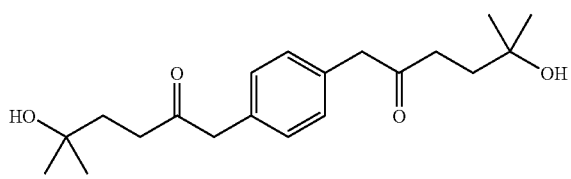

I-1

5-Hydroxy-1-[4-(5-hydroxy-5-methyl-2-oxo-hexyl)-phenyl]-5-methyl-hexan-2-one

TABLE 1-continued

Compounds of the Invention

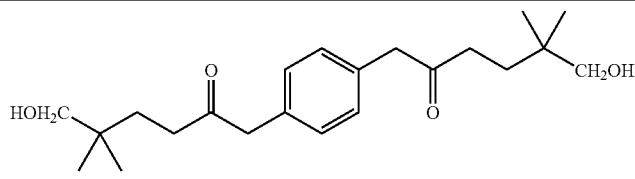

I-2

6-Hydroxy-1-[4-(6-hydroxy-5,5-dimethyl-2-oxo-hexyl)-phenyl]-5,5-dimethyl-hexan-2-one

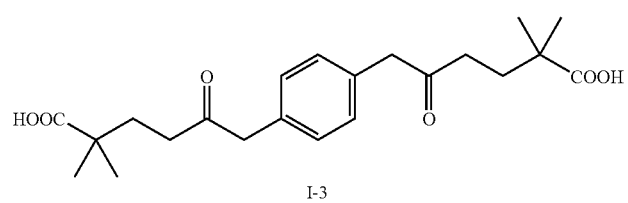

I-3

6-4-(5-Carboxy-5-methyl-2-oxo-hexyl)-phenyl]-2,2-dimethyl-5-oxo-hexanoic acid

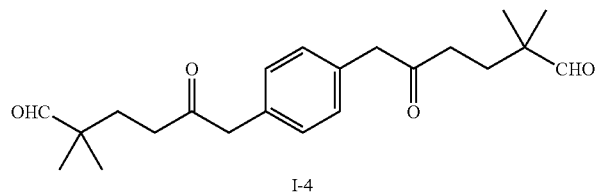

I-4

6-[4-(5,5-Dimethyl-2,6-dioxo-hexyl)-phenyl]-2,2-dimethyl-5-oxo-hexanal

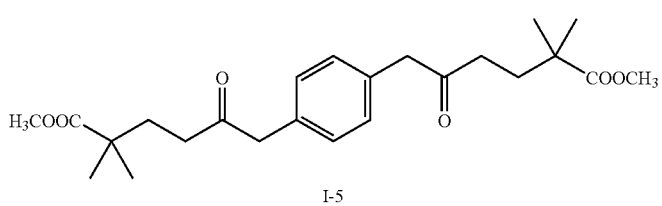

I-5

6-[4-(5-Methoxycarbonyl-5-methyl-2-oxo-hexyl)-phenyl]-2,2-dimethyl-5-oxo-hexanoic acid methyl ester

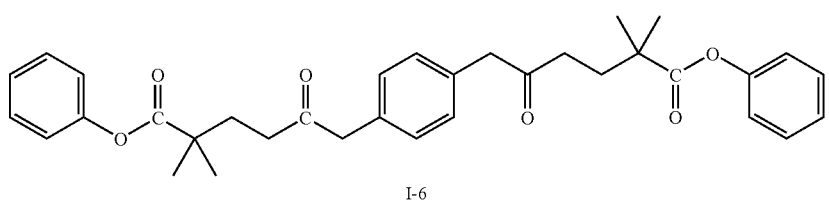

I-6

2,2-Dimethyl-6-[4-(5-methyl-2-oxo-5-phenoxycarbonyl-hexyl)-phenyl]-5-oxo-hexanoic acid phenyl ester

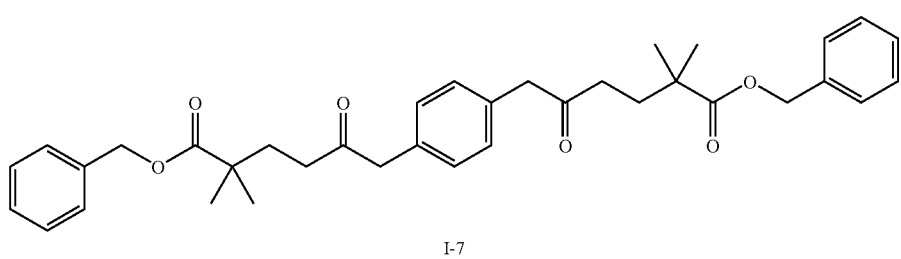

I-7

6-[4-(5-Benzyloxycarbonyl-5-methyl-2-oxo-hexyl)-phenyl]-2,2-dimethyl-5-oxo-hexanoic acid benzyl ester TABLE 1-continued Compounds of the Invention

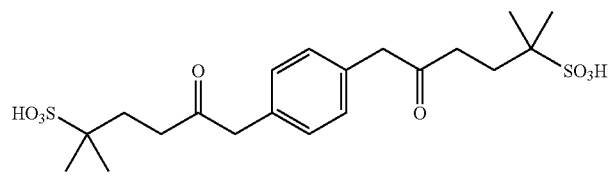

I-8
2-Methyl-6-[4-(5-methyl-2-oxo-5-sulfo-hexyl)-phenyl]-5-oxo-hexane-2-sulfonic acid

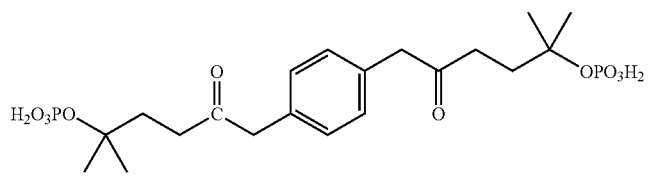

I-9
Phosphoric acid mono-{1,1-dimethyl-5-[4-(5-methyl-2-oxo-5-phosphonooxy-hexyl)-phenyl]-4-oxo-pentyl} ester

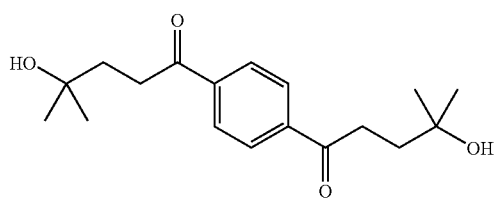

I-10
4-Hydroxy-1-[4-(4-hydroxy-4-methyl-pentanoyl)-phenyl]-4-methyl-pentan-1-one

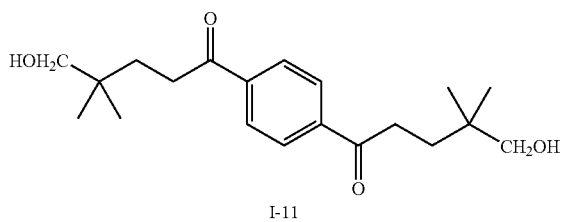

I-11
5-Hydroxy-1-[4-(5-hydroxy-4,4-dimethyl-pentanoyl)-phenyl]-4,4-dimethyl-pentan-1-one

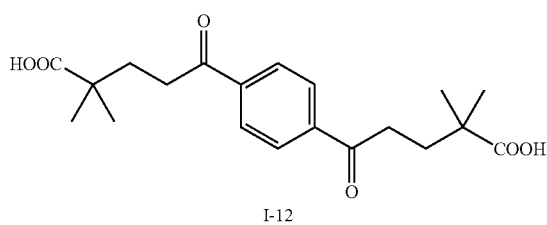

I-12
5-[4-(4-Carboxy-4-methyl-pentanoyl)-phenyl]-2,2-dimethyl-5-oxo-pentanoic acid

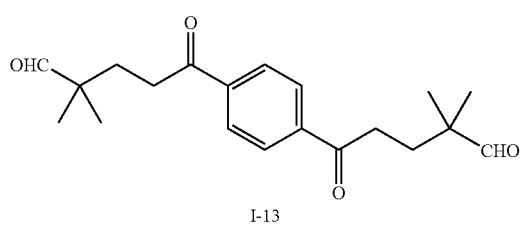

I-13
5-[4-(4,4-Dimethyl-5-oxo-pentanoyl)-phenyl]-2,2-dimethyl-5-oxo-pentanal

TABLE 1-continued

Compounds of the Invention

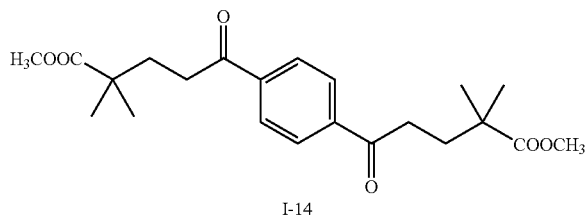

I-14

5-[4-(4-Methoxycarbonyl-4-methyl-pentanoyl)-phenyl]-2,2-dimethyl-5-oxo-pentanoic acid
methyl ester

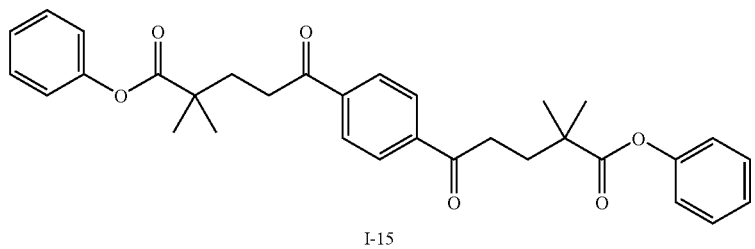

I-15

2,2-Dimethyl-6-[4-(5-methyl-2-oxo-5-phenoxycarbonyl-hexyl)-phenyl]-5-oxo-hexanoic
acid phenyl ester

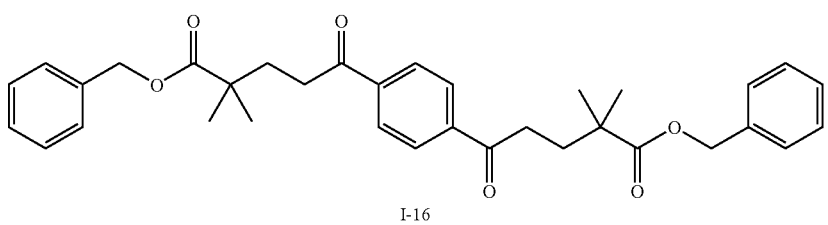

I-16

5-[4-(4-Benzyloxycarbonyl-4-methyl-pentanoyl)-phenyl]-2,2-dimethyl-5-oxo-pentanoic
acid benzyl ester

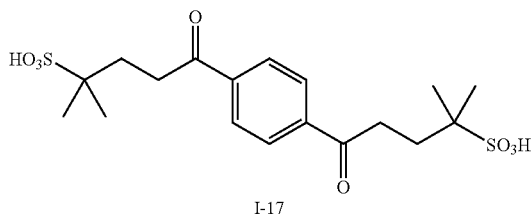

I-17

2-Methyl-5-[4-(4-methyl-4-sulfo-pentanoyl)-phenyl]-5-oxo-pentane-2-sulfonic acid

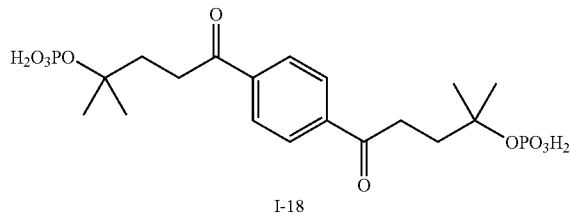

I-18

Phosphoric acid mono-{1,1-dimethyl-4-[4-(4-methyl-4-phosphonooxy-pentanoyl)-phenyl]-
4-oxo-butyl}ester

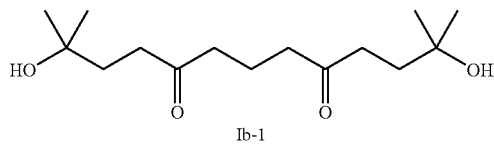

Ib-1

2,12-Dihydroxy-2,12-dimethyl-tridecane-5,9-dione

TABLE 1-continued

Compounds of the Invention

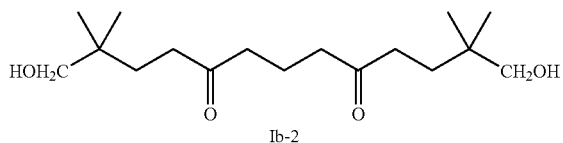

1,13-Dihydroxy-2,2,12,12-tetramethyl-tridecane-5,9-dione

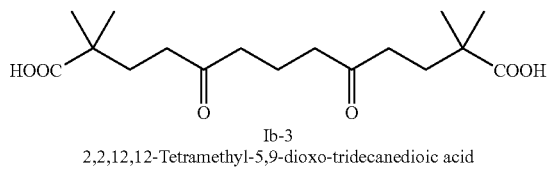

2,2,12,12-Tetramethyl-5,9-dioxo-tridecanedioic acid

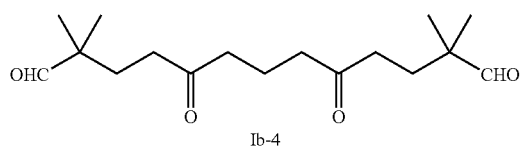

2,2,12,12-Tetramethyl-5,9-dioxo-tridecanedial

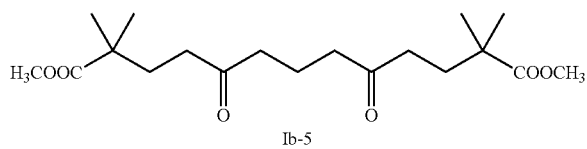

2,2,12,12-Tetramethyl-5,9-dioxo-tridecanedioic acid dimethyl ester

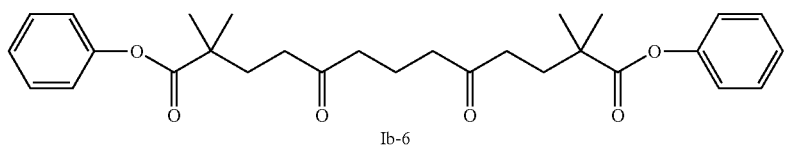

2,2,12,12-Tetramethyl-5,9-dioxo-tridecanedioic acid diphenyl ester

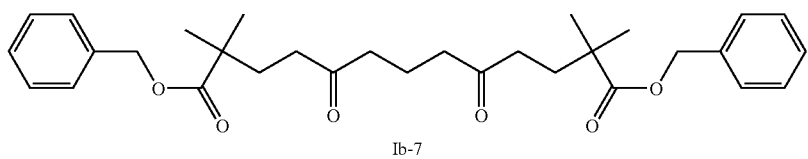

2,2,12,12-Tetramethyl-5,9-dioxo-tridecanedioic acid dibenzyl ester

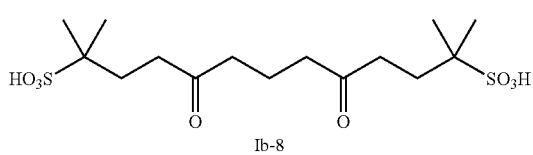

2,12-Dimethyl-5,9-dioxo-tridecane-2,12-disulfonic acid

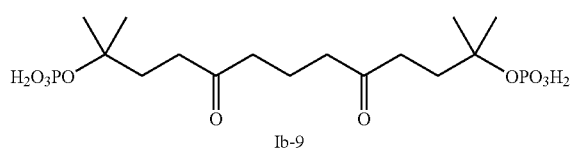

Phosphoric acid mono-(1,1,11-trimethyl-4,8-dioxo-11-phosphonooxy-dodecyl) ester

TABLE 1-continued

Compounds of the Invention

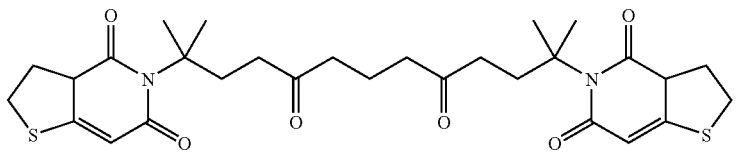
Ib-10

2,12-Bis-(4,6-dioxo-2,3,3a,6-tetrahydro-4H-thieno[3,2-c]pyridin-5-yl)-2,12-dimethyl-tridecane-5,9-dione

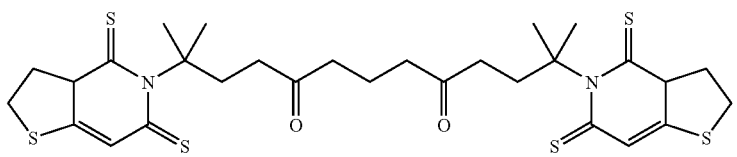
Ib-11

2,12-Bis-(4,6-dithioxo-2,3,3a,6-tetrahydro-4H-thieno[3,2-c]pyridin-5-yl)-2,12-dimethyl-tridecane-5,9-dione

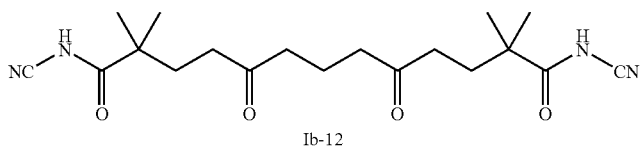
Ib-12

2,2,12,12-Tetramethyl-5,9-dioxo-tridecanedioic acid dicyanimide

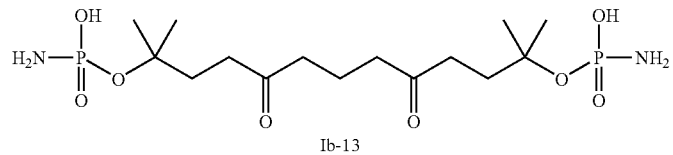
Ib-13

Phosphoramidic acid mono-[11-(amino-hydroxy-phosphoryloxy)-1,1,11-trimethyl-4,8-dioxo-dodecyl] ester

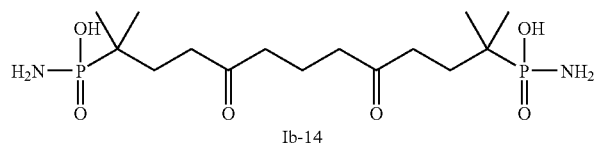
Ib-14

2,12-Dimethyl-2,12-bis-(amino-hydroxy-phosphoryloxy)-tridecane-5,9-dione

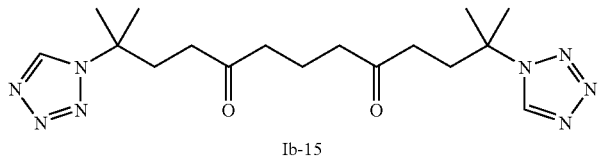
Ib-15

2,12-Dimethyl-2,12-bis-tetrazol-1-yl-tridecane-5,9-dione

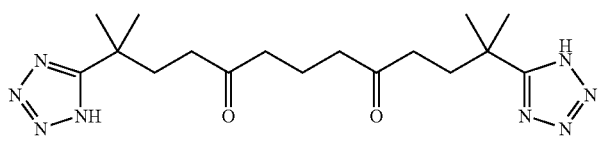
Ib-16

2,12-Dimethyl-2,12-bis-(1H-tetrazol-5-yl)-tridecane-5,9-dione

TABLE 1-continued

Compounds of the Invention

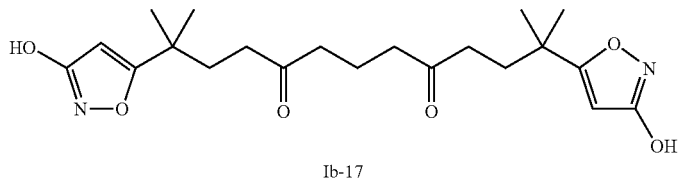

Ib-17

2,12-Bis-(3-hydroxy-isoxazol-5-yl)-2,12-dimethyl-tridecane-5,9-dione

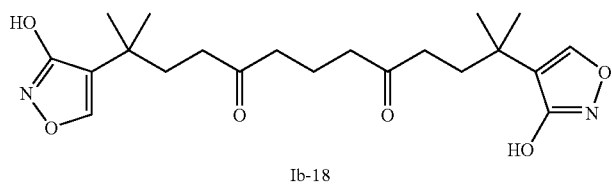

Ib-18

2,12-Bis-(3-hydroxy-isoxazol-4-yl)-2,12-dimethyl-tridecane-5,9-dione

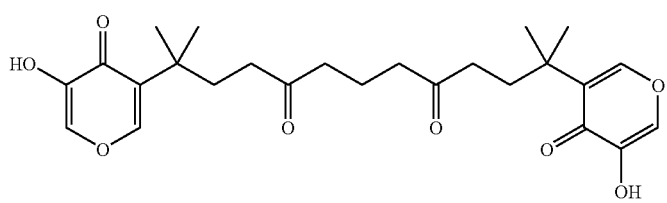

Ib-19

2,12-Bis-(5-hydroxy-4-oxo-4H-pyran-3-yl)-2,12-dimethyl-tridecane-5,9-dione

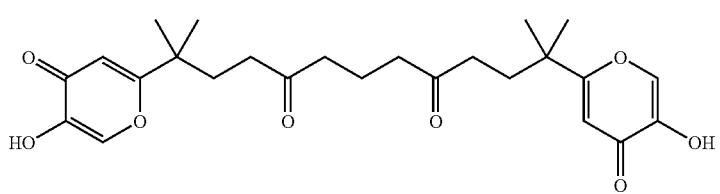

Ib-20

2,12-Bis-(5-hydroxy-4-oxo-4H-pyran-2-yl)-2,12-dimethyl-tridecane-5,9-dione

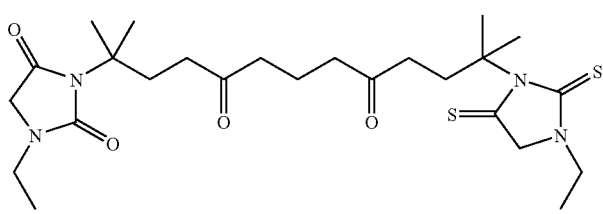

Ib-21

1-Ethyl-3-[11-(3-ethyl-2,5-dithioxo-imidazolidin-1-yl)-1,1,11-trimethyl-48-dioxo-
dodecyl]-imidazolidine-2,4-dione

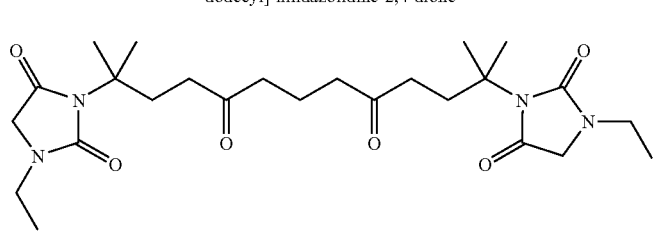

Ib-22

2,12-Bis-(3-ethyl-2,5-dioxo-imidazolidin-1-yl)-2,12-dimethyl-tridecane-5,9-dione TABLE 1-continued Compounds of the Invention

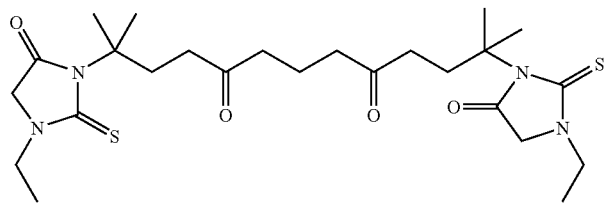

Ib-23

2,12-Bis-(3-ethyl-5-oxo-2-thioxo-imidazolidin-1-yl)-2,12-dimethyl-tridecane-5,9-dione

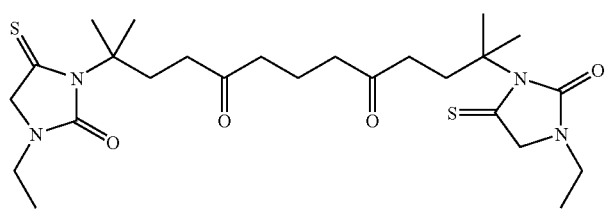

Ib-24

2,12-Bis-(3-ethyl-2-oxo-5-thioxo-imidazolidin-1-yl)-2,12-dimethyl-tridecane-5,9-dione

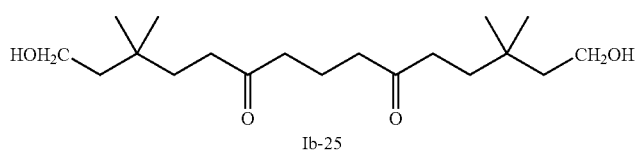

Ib-25

1,15-Dihydroxy-3,3,13,13-tetramethyl-pentadecane-6,10-dione

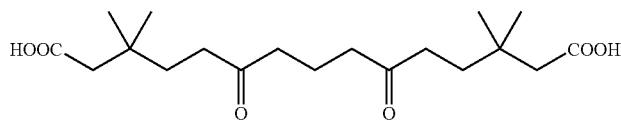

Ib-26

3,3,13,13-Tetramethyl-6,10-dioxo-pentadecanedioic acid

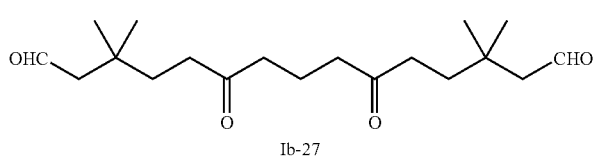

Ib-27

3,3,13,13-Tetramethyl-6,10-dioxo-pentadecanedial

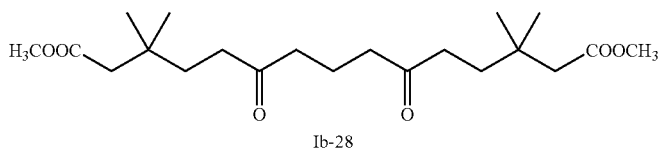

Ib-28

3,3,13,13-Tetramethyl-6,10-dioxo-pentadecanedioic acid dimethyl ester

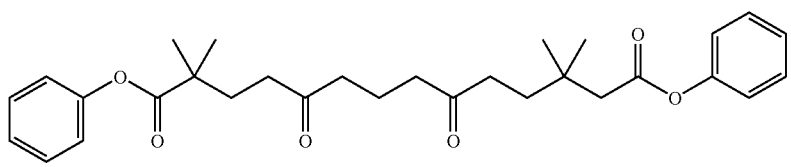

Ib-29

2,2,12,12-Tetramethyl-5,9-dioxo-tetradecanedioic acid diphenyl ester

TABLE 1-continued

Compounds of the Invention

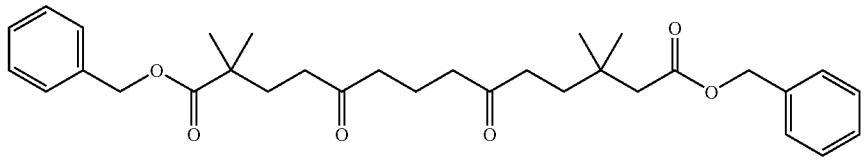
Ib-30

3,3,13,13-Tetramethyl-6,10,14-trioxo-16-phenyl-hexadecanoic acid benzyl ester

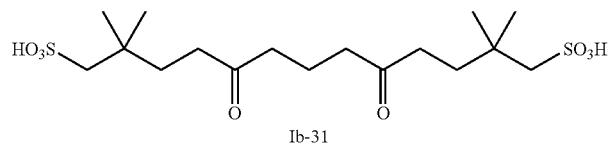
Ib-31

2,2,12,12-Tetramethyl-5,9-dioxo-tridecane-1,13-disulfonic acid

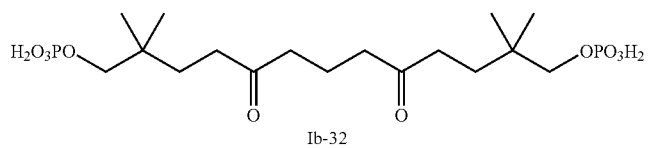
Ib-32

Phosphoric acid mono-(2,2,12,12-tetramethyl-5,9-dioxo-13-phosphonooxy-tridecyl) ester

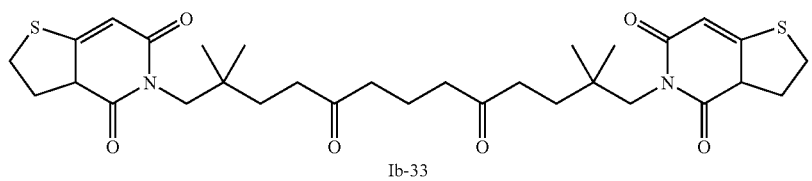
Ib-33

1,13-Bis-(4,6-dioxo-2,3,3a,6-tetrahydro-4H-thieno[3,2-c]pyridin-5-yl)-2,2,12,12-
tetramethyl-tridecane-5,9-dione

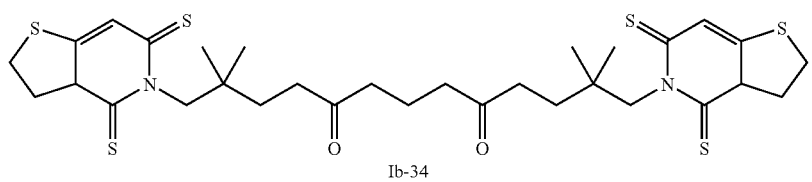
Ib-34

1,13-Bis-(4,6-dithioxo-2,3,3a,6-tetrahydro-4H-thieno[3,2-c]pyridin-5-yl)-2,2,12,12-
tetramethyl-tridecane-5,9-dione

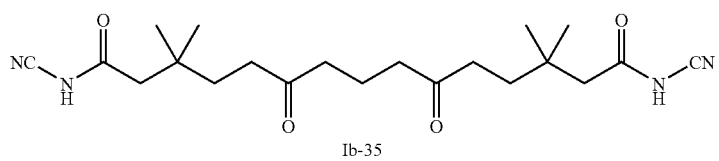
Ib-35

3,3,13,13-Tetramethyl-6,10-dioxo-pentadecanedioic acid dicyanimide

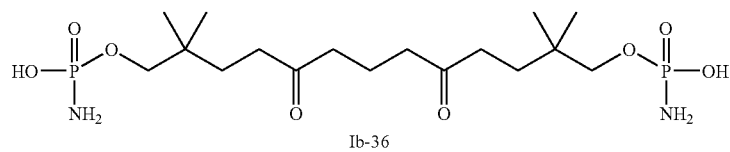
Ib-36

Phosphoramidic acid mono-[13-(amino-hydroxy-phosphoryloxy)-2,2,12,12-tetramethyl-6,9-
dioxo-tridecyl] ester TABLE 1-continued Compounds of the Invention

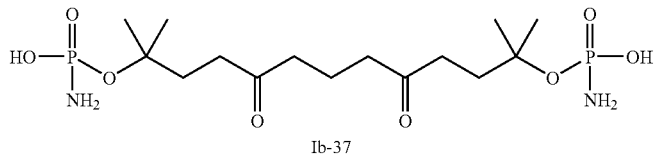

Ib-37

Phosphoramidic acid
mono-[11-(amino-hydroxy-phosphoryloxy)-1,1,11-trimethyl-4,8-dioxo-dodecyl] ester

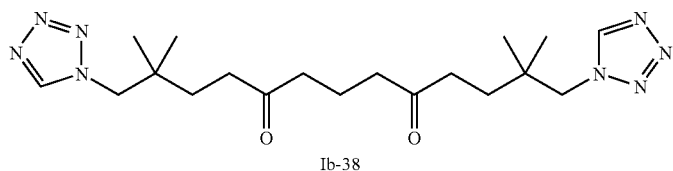

Ib-38

2,2,12,12-Tetramethyl-1,13-bis-tetrazol-1-yl-tridecane-5,9-dione

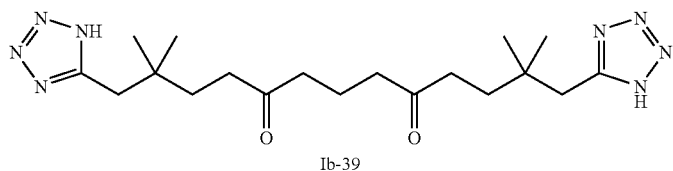

Ib-39

1,13-Bis-(3-hydroxy-isoxazol-5-yl)-2,2,12,12-tetrarnethyl-tridecane-5,9-dione

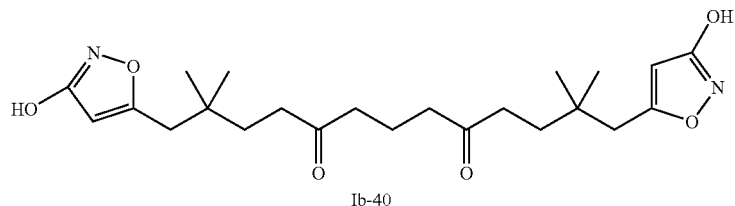

Ib-40

1,13-Bis-(3-hydroxy-isoxazol-5-yl)-2,2,12,12-tetramethyl-tridecane-5,9-dione

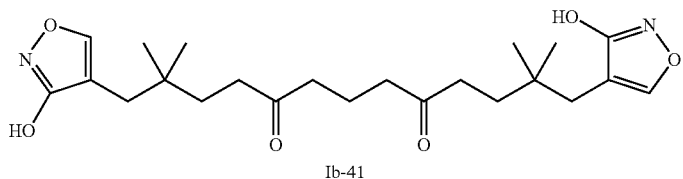

Ib-41

1,13-Bis-(3-hydroxy-isoxazol-4-yl)-2,2,12,12-tetramethyl-tridecane-5,9-dione

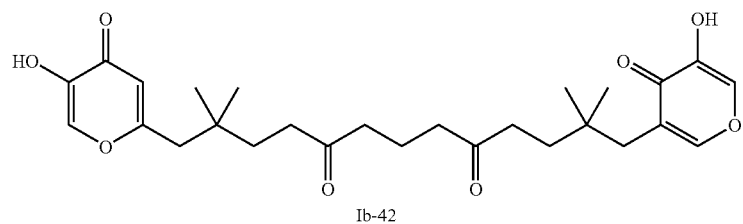

Ib-42

1-(5-Hydroxy-4-oxo-4H-pyran-3-yl)-13-(5-hydroxy-4-oxo-4H-pyran-2-yl)-2,2,12,12-
tetramethyl-tridecane-5,9-dione

TABLE 1-continued

Compounds of the Invention

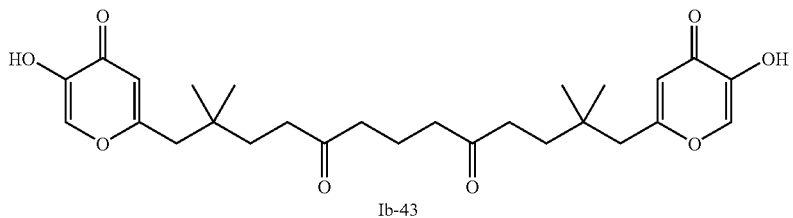

Ib-43

1,13-Bis-(5-hydroxy-4-oxo-4H-pyran-2-yl)-2,2,12,12-tetramethyl-tridecane-5,9-dione

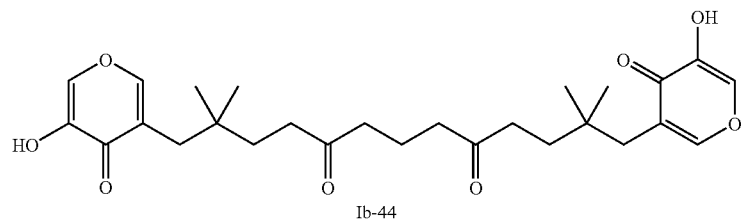

Ib-44

1,13-Bis-(5-hydroxy-4-oxo-4H-pyran-3-yl)-2,2,12,12-tetramethyl-tridecane-5,9-dione

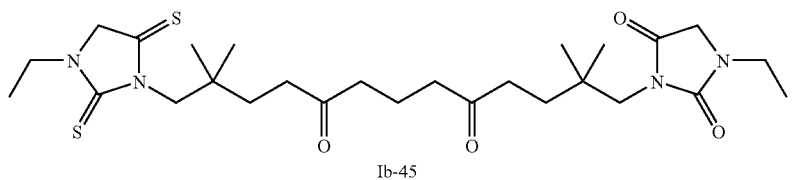

Ib-45

1-Ethyl-3-[13-(3-ethyl-2,5-dithioxo-imidazolidin-1-yl)-2,2,12,12-tetramethyl-5,9-dioxo-tridecyl]-imidazolidine-2,4-dione

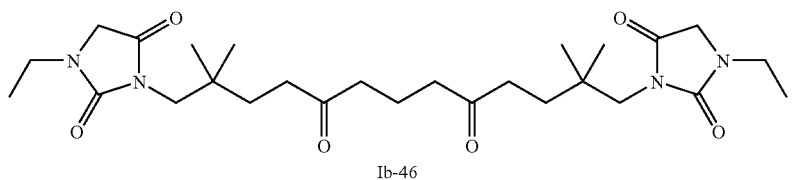

Ib-46

1,13-Bis-(3-ethyl-2,5-dioxo-imidazolidin-1-yl)-2,2,12,12-tetramethyl-tridecane-5,9-dione

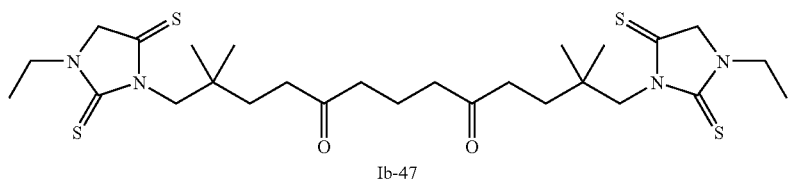

Ib-47

1,13-Bis-(3-ethyl-2,5-dithioxo-imidazolidin-1-yl)-2,2,12,12-tetramethyl-tridecane-5,9-dione

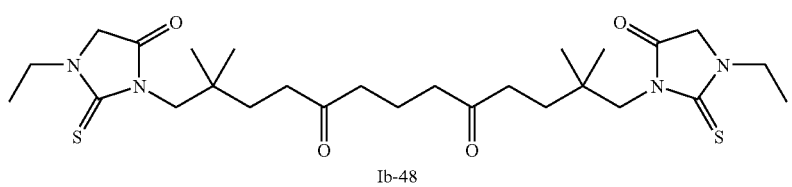

Ib-48

1,13-Bis-(3-ethyl-5-oxo-2-thioxo-imidazolidin-1-yl)-2,2,12,12-tetramethyl-tridecane-5,9-dione TABLE 1-continued Compounds of the Invention

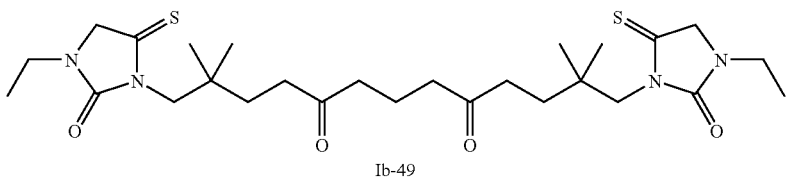
Ib-49

1,13-Bis-(3-ethyl-2-oxo-5-thioxo-imidazolidin-1-yl)-2,2,12,12-tetramethyl-tridecane-5,9-dione

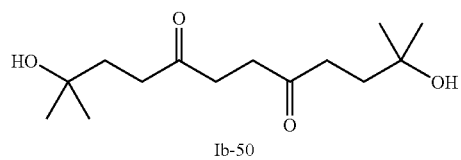
Ib-50

2,11-Dihydroxy-2,11-dimethyl-dodecane-5,8-dione

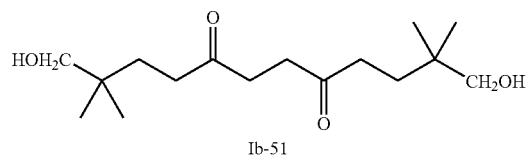
Ib-51

1,12-Dihydroxy-2,2,11,11-tetramethyl-dodecane-5,8-dione

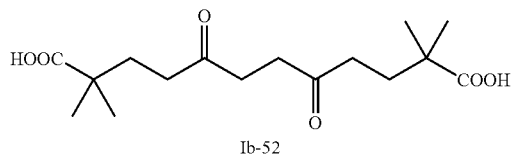
Ib-52

2,2,11,11-Tetramethyl-5,8-dioxo-dodecanedioic acid

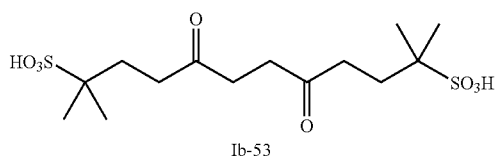
Ib-53

2,11-Dimethyl-5,8-dioxo-dodecane-2,11-disulfonic acid

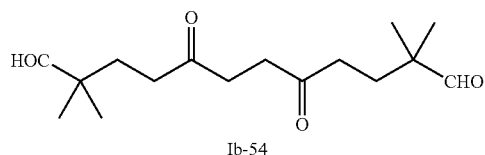
Ib-54

2,2,11,11-Tetramethyl-5,8-dioxo-dodecanedial

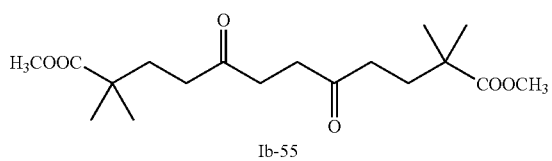
Ib-55

2,2,11,11-Tetramethyl-5,8-dioxo-dodecanedioic acid dimethyl ester

TABLE 1-continued

Compounds of the Invention

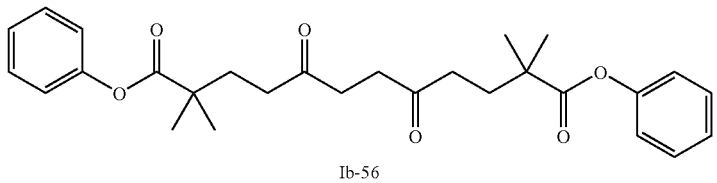

Ib-56

2,2,11,11-Tetramethyl-5,8-dioxo-dodecanedioic acid diphenyl ester

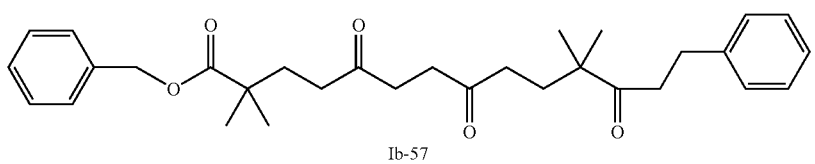

Ib-57

2,2,11,11-Tetramethyl-5,8-dioxo-dodecanedioic acid dibenzyl ester

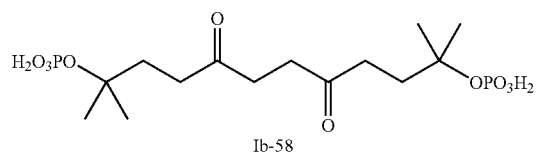

Ib-58

Phosphoric acid mono-(1,1,10-trimethyl-4,7-dioxo-10-phosphonooxy-undecyl) ester

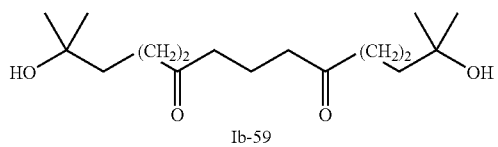

Ib-59

2,14-Dihydroxy-2,14-dimethyl-pentadecane-6,10-dione

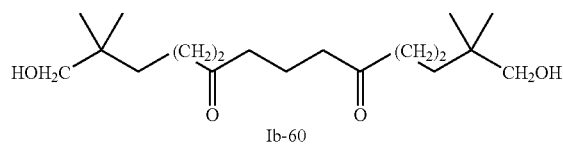

Ib-60

1,15-Dihydroxy-2,2,14,14-tetramethyl-pentadecane-6,10-dione

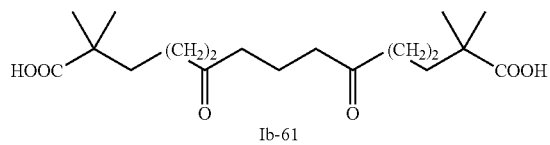

Ib-61

2,2,14,14-Tetramethyl-6,10-dioxo-pentadecanedioic acid

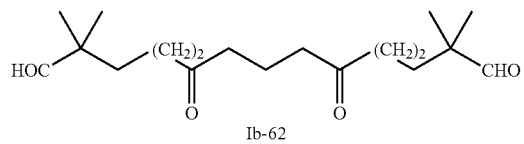

Ib-62

2,2,14,14-Tetramethyl-6,10-dioxo-pentadecanedial

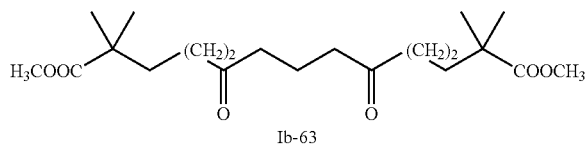

Ib-63

2,2,14,14-Tetramethyl-6,10-dioxo-pentadecanedioic acid dimethyl ester

TABLE 1-continued

Compounds of the Invention

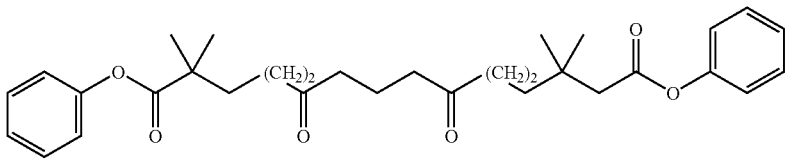

Ib-64

2,2,14,14-Tetramethyl-6,10-dioxo-hexadecanedioic acid diphenyl ester

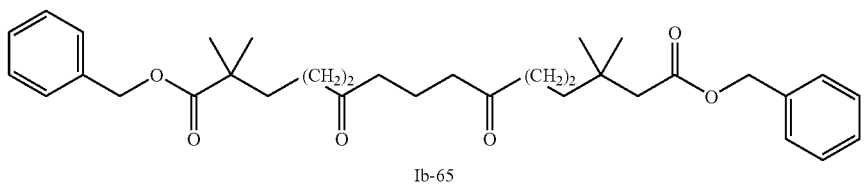

Ib-65

2,2,14,14-Tetramethyl-6,10-dioxo-hexadecanedioic acid dibenzyl ester

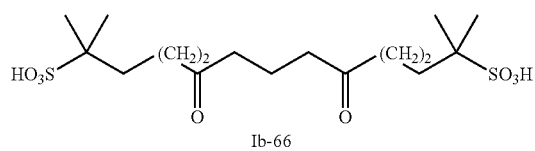

Ib-66

2,14-Dimetliyl-6,10-dioxo-pentadecane-2,14-disulfonic acid

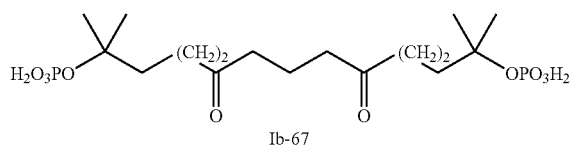

Ib-67

Phosphoric acid mono-(1,1,13-trimethyl-5,9-dioxo-13-phosphonooxy-tetradecyl) ester

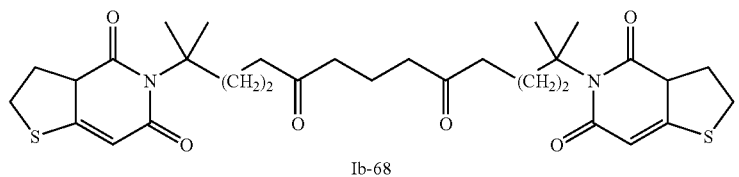

Ib-68

2,14-Bis-(4,6-dioxo-2,3,3a,6-tetrahydro-4H-thieno[3,2-c]pyridin-5-yl)-2,14-dimethyl-pentadecane-6,10-dione

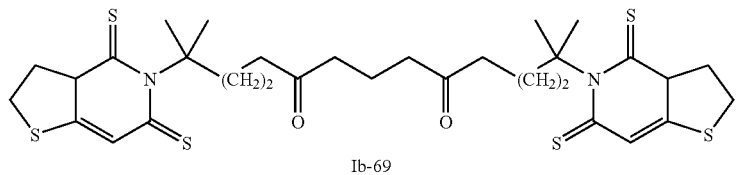

Ib-69

2,14-Bis-(4,6-dithioxo-2,3,3a,6-tetrahydro-4H-thieno[3,2-c]pyridin-5-yl)-2,14-dimethyl-pentadecane-6,10-dione

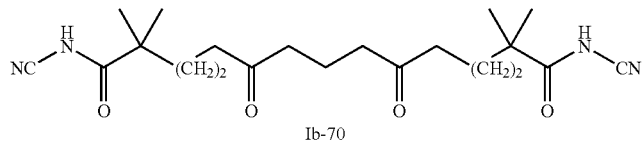

Ib-70

2,2,14,14-Tetramethyl-6,10-dioxo-pentadecanedioic acid dicyanimide

TABLE 1-continued

Compounds of the Invention

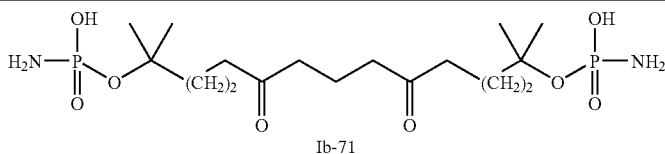

Ib-71

Phosphoramidic acid mono-[13-(amino-hydroxy-phosphoryloxy)-1,1,13-trimethyl-5,9-dioxo-tetradecyl] ester

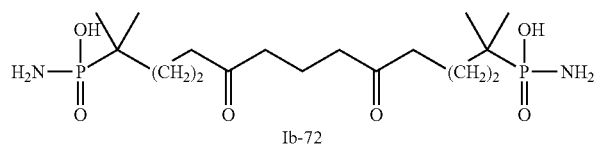

Ib-72

2,14-Dimethyl-2,14-bis-(amino-hydroxy-phosphoryloxy)-pentadecane-6,10-dione

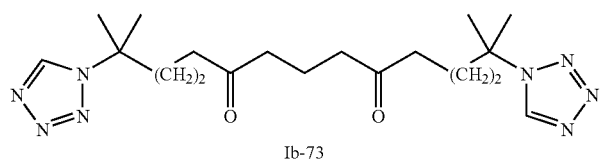

Ib-73

2,14-Dimethyl-2,14-bis-tetrazal-1-yl-pentadecane-6,10-dione

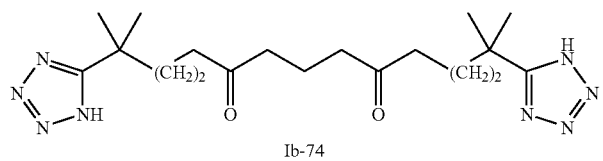

Ib-74

2,14-Dimethyl-2,14-bis-(1H-tetrazol-5-yl)-pentadecane-6,10-dione

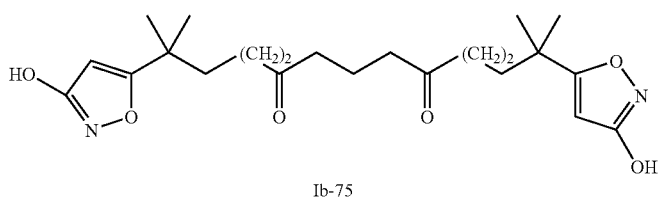

Ib-75

2,14-Bis-(3-hydroxy-isoxazol-5-yl)-2,14-dimethyl-pentadecane-6,10-dione

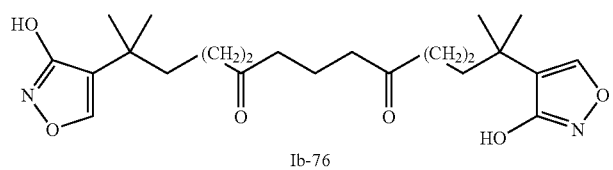

Ib-76

2,14-Bis-(3-hydroxy-isoxazol-4-yl)-2,14-dimethyl-pentadecane-6,10-dione

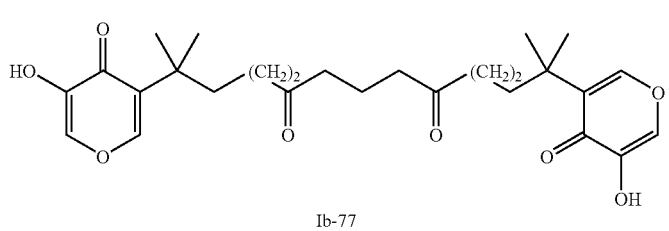

Ib-77

2,14-Bis-(5-hydroxy-4-oxo-4H-pyran-3-yl)-2,14-dimethyl-pentadecane-6,10-dione

TABLE 1-continued

Compounds of the Invention

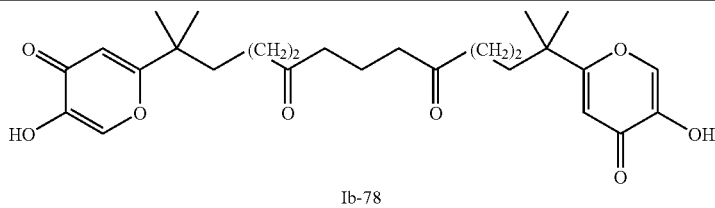

Ib-78

2-(5-Hydroxy-4-oxo-4H-pyran-2-yl)-2,14-dimethyl-14-(5-methyl-4-oxo-4H-pyran-2-yl)-pentadecane-6,10-dione

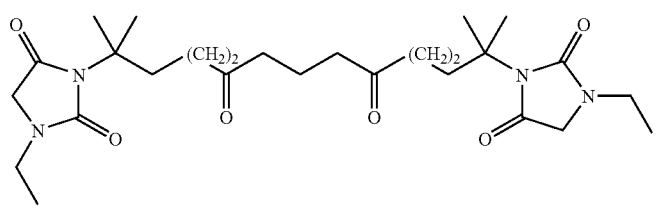

Ib-79

2,14-Bis-(3-ethyl-2,5-dioxo-imidazalidin-1-yl)-2,14-dimethyl-pentadecane-6,10-dione

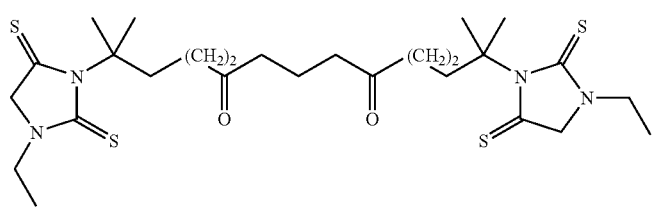

Ib-80

2,14-Bis-(3-ethyl-2,5-dithioxo-imidazolidin-1-yl)-2,14-dimethyl-pentadecane-6,10-dione

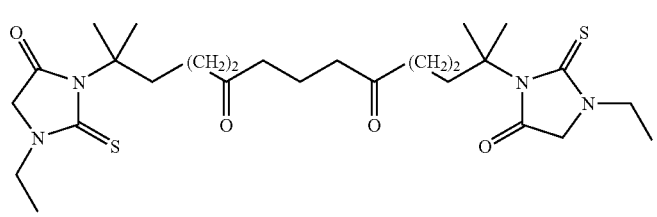

Ib-81

2,14-Bis-(3-ethyl-5-oxo-2-thioxo-imidazolidin-1-yl)-2,14-dimethyl-pentadecane-6,10-dione

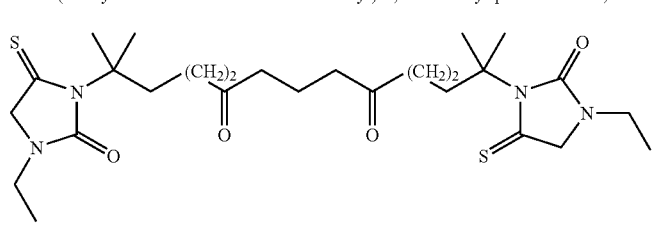

Ib-82

2,14-Bis-(3-ethyl-2-oxo-5-thioxo-imidazolidin-1-yl)-2,14-dimethyl-pentadecane-6,10-dione

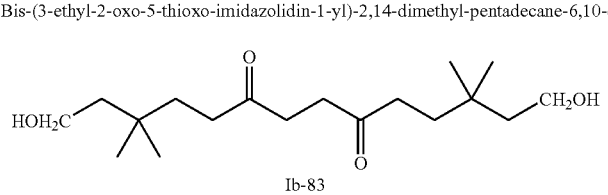

Ib-83

1,14-Dihydroxy-3,3,12 12-tetramethyl-tetradecane-6,9-dione

TABLE 1-continued

Compounds of the Invention

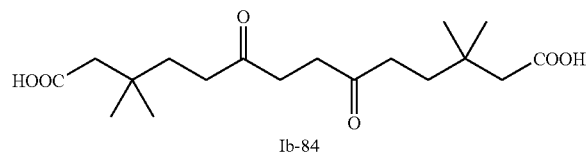
Ib-84

3,3,12,12-Tetramethyl-6,9-dioxo-tetradecanedioic acid

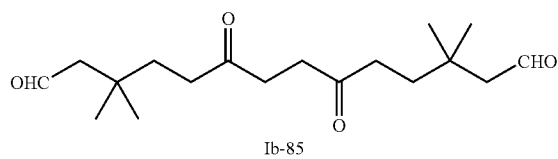
Ib-85

3,3,12,12-Tetramethyl-6,9-dioxo-tetradecanedial

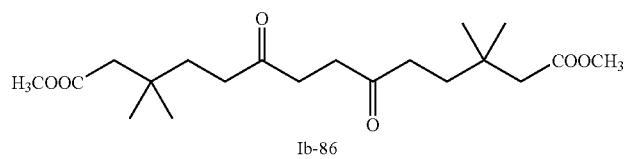
Ib-86

3,3,12,12-Tetramethyl-6,9-dioxo-tetradecanedioic acid dimethyl ester

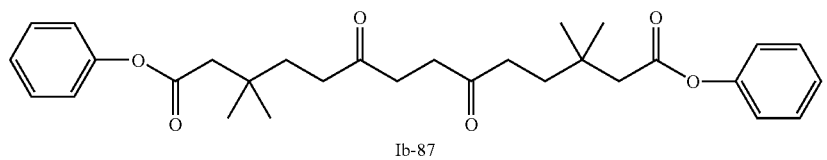
Ib-87

3,3,12,12-Tetramethyl-6,9-dioxo-tetradecanedioic acid diphenyl ester

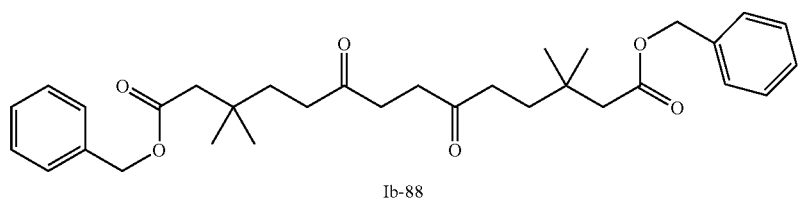
Ib-88

3,3,12,12-Tetramethyl-6,9-dioxo-tetradecanedioic acid dibenzyl ester

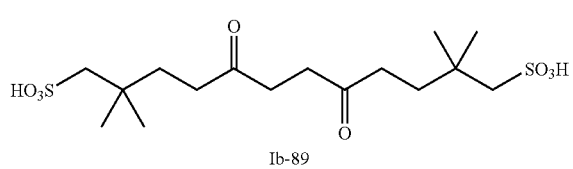
Ib-89

2,2,11,11-Tetramethyl-5,8-dioxo-dodecane-1,12-disulfonic acid

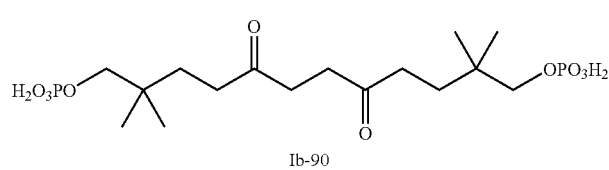
Ib-90

Phosphoric acid mono-(2,2,11,11-tetramethyl-5,8-dioxo-12-phosphonooxy-dodecyl) ester TABLE 1-continued Compounds of the Invention

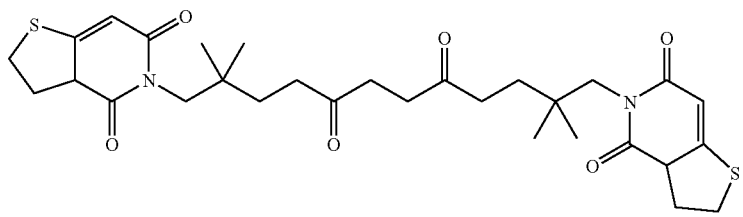

Ib-91

1,12-Bis-(4,6-dithioxo-2-3,3a,6-tetrahydro-4H-thieno[3,2-c]pyridin-5-yl)-2,2,11,11-tetramethyl-dodecane-5,8-dione

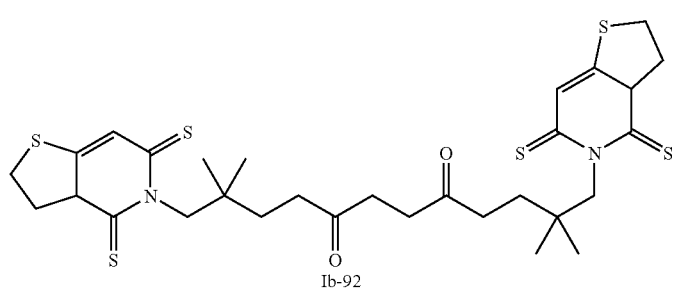

Ib-92

1,12-Bis-(4,6-dithioxo-2,3,3a,6-tetrahydro-4H-thieno[3,2-c]pyridin-5-yl)-2,2,11,11-tetramethyl-dodecane-5,8-dithione

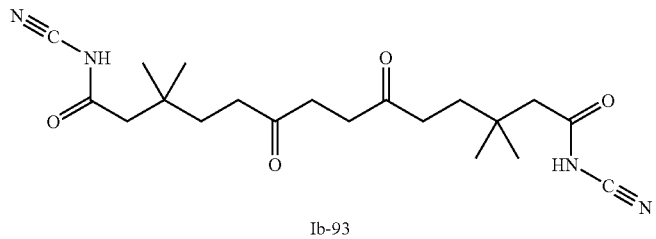

Ib-93

3,3,12,12-Tetramethyl-6,9-dioxo-tetradecanedioic acid dicyanimide

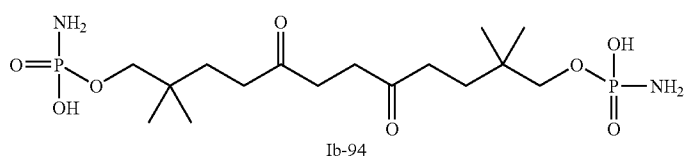

Ib-94

Phosphoramidic acid mono-[12-(amino-hydroxy-phosphoryloxy)-2,2,11,11-tetramethyl-5,8-dioxo-dodecyl] ester

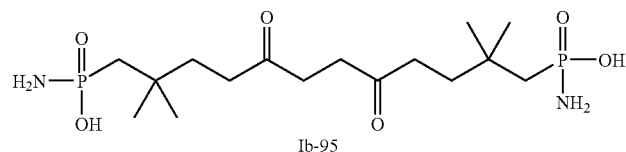

Ib-95

2,2,11,11-Tetramethyl-1,12-bis-(aminohydroxyphosphoryloxy)-dodecane-5,8-dione

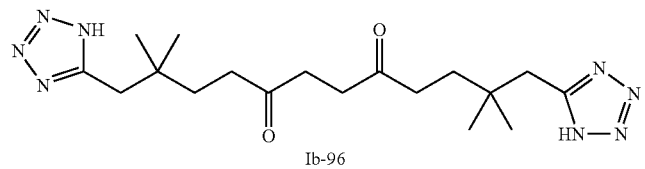

Ib-96

2,2,11,11-Tetramethyl-1,12-bis-(1H-tetrazol-5-yl)-dodecane-5,8-dione

TABLE 1-continued
Compounds of the Invention
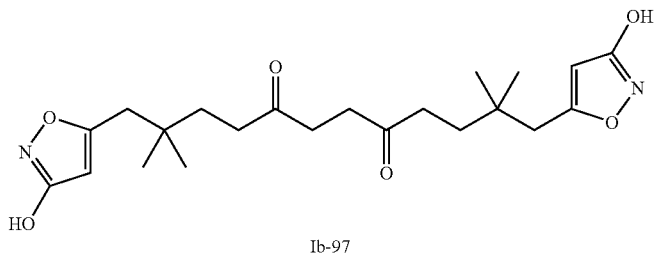
Ib-97
1,12-Bis-(3-hydroxy-isoxazol-5-yl)-2,2,11,11-tetramethyl-dodecane-5,8-dione
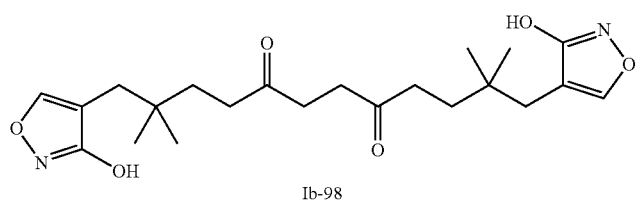
Ib-98
1,12-Bis-(3-hydroxy-isoxazol-4-yl)-2,2,11,11-tetramethyl-dodecane-5,8-dione
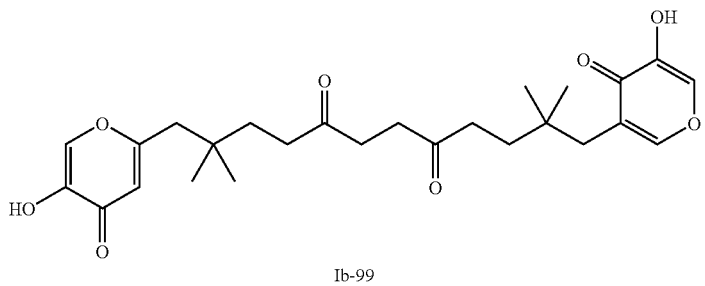
Ib-99
1-(5-Hydroxy-4-oxo-4H-pyran-3-yl)-12-(5-hydroxy-4-oxo-4H-pyran-2-yl)-2,2,11,11-tetramethyl-dodecane-5,8-dione
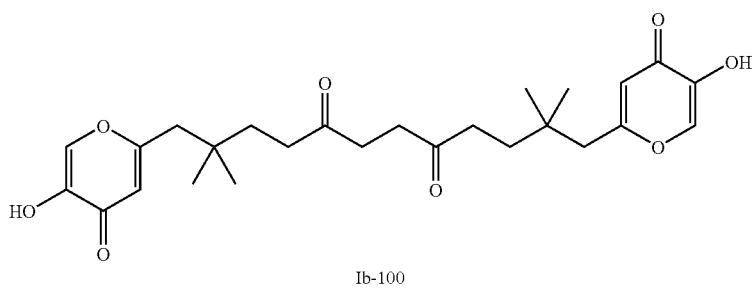
Ib-100
1,12-Bis-(5-hydroxy-4-oxo-4H-pyran-3-yl)-2,2,11,11-tetramethyl-dodecane-5,8-dione
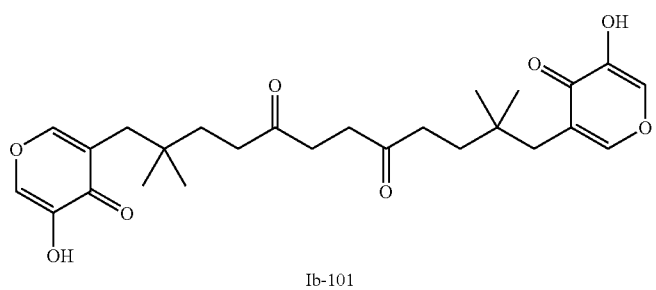
Ib-101
1,12-Bis-(5-hydroxy-4-oxo-4H-pyran-3-yl)-2,2,11,11-tetramethyl-dodecane-5,8-dione TABLE 1-continued Compounds of the Invention

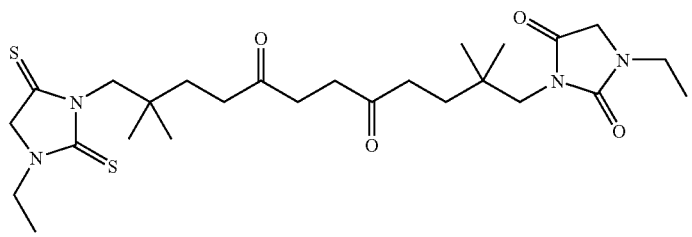

Ib-102

1-Ethyl-3-[12-(3-ethyl-2,5-dithioxo-imidazolidin-1-yl)-2,2,11,11-tetramethyl-5,8-dioxo-dodecyl]-imidazolidine-2,4-dione

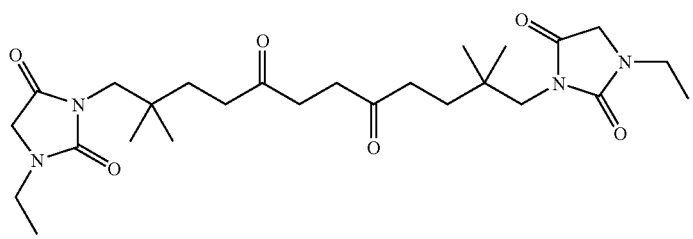

Ib-103

1-Ethyl-3-[12-(3-ethyl-2,5-dioxo-imidazolidin-1-yl)-2,2,11,11-tetramethyl-5,8-dioxo-dodecyl]-imidazolidine-2,4-dione

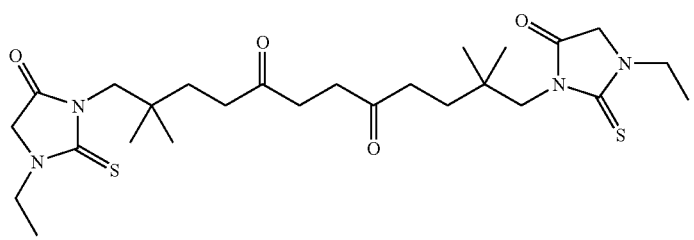

Ib-104

1,12-Bis-(3-ethyl-5-oxo-2-thioxo-imidazolidin-1-yl)-2,2,11,11-tetramethyl-dodecane-5,8-dione

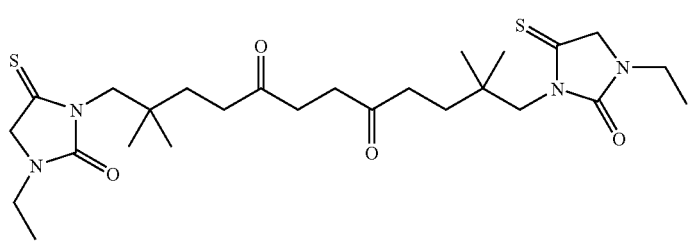

Ib-105

1,12-Bis-(3-ethyl-2-oxo-5-thioxo-imidazolidin-1-yl)-2,2,11,11-tetramethyl-dodecane-5,8-dione

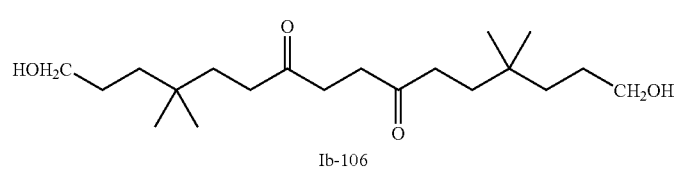

Ib-106

1,16-Dihydroxy-4,4,13,13-tetramethyl-hexadecane-7,10-dione

TABLE 1-continued

Compounds of the Invention

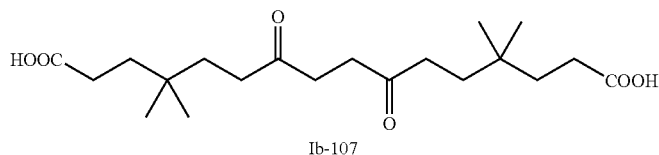

Ib-107

4,4,13,13-Tetramethyl-7,10-dioxo-hexadecanedioic acid

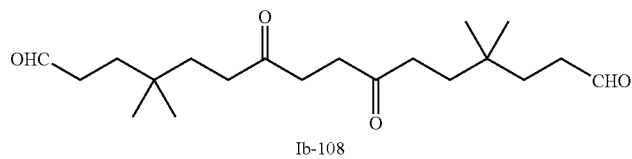

Ib-108

4,4,13,13-Tetramethyl-7,10-dioxo-hexadecanedial

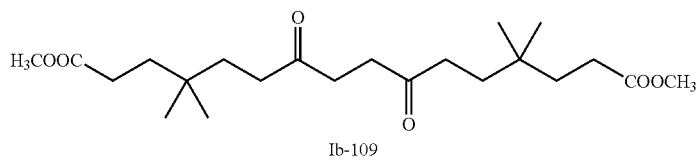

Ib-109

4,4,13,13-Tetramethyl-7,10-dioxo-hexadecanedioic acid dimethyl ester

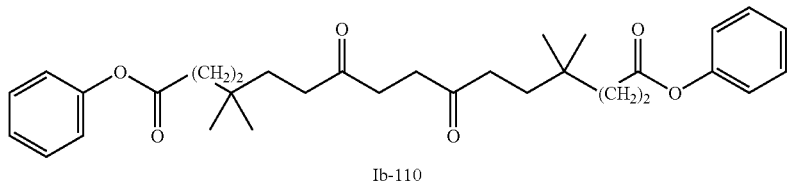

Ib-110

4,4,13,13-Tetramethyl-7,10-dioxo-hexadecanedioic acid diphenyl ester

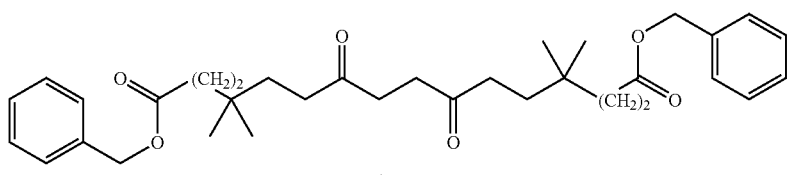

Ib-111

4,4,13,13-Tetramethyl-7,10-dioxo-hexadecanedioic acid dibenzyl ester

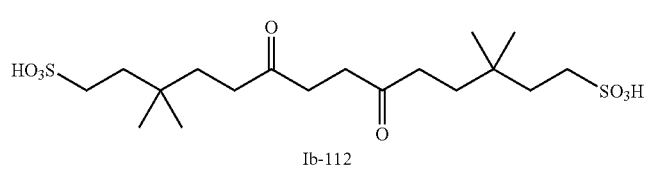

Ib-112

3,3,12,12-Tetramethyl-6,9-dioxo-tetradecane-1,14-disulfonic acid

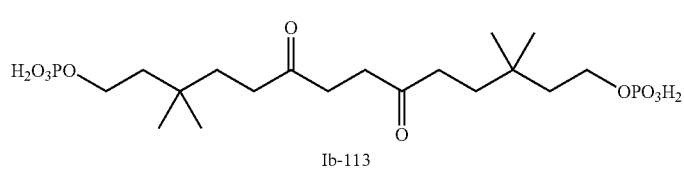

Ib-113

Phosphoric acid mono-(3,3,12,12-tetramethyl-6,9-dioxo-14-phosphonooxy-tetradecyl) ester

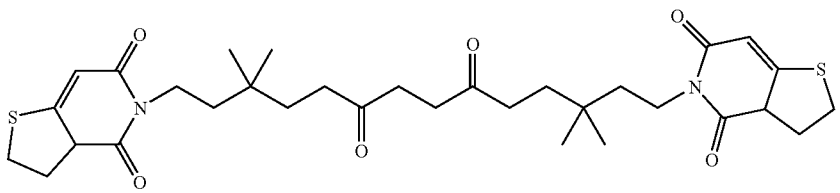

Ib-114

1,14-Bis-(4,6-dioxo-2,3,3a,6-tetrahydro-4H-thieno[3,2-c]pyridin-5-yl)-3,3,12,12-tetramethyl-tetradecane-6,9-dione

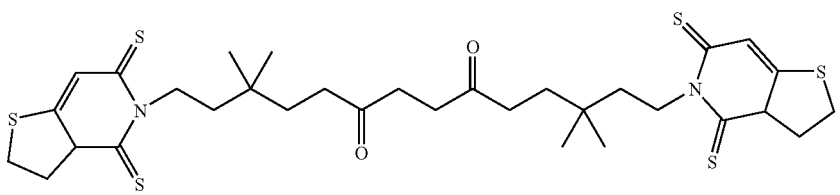

Ib-115

1,14-Bis-(4,6-dithioxo-2,3,3a,6-tetrahydro-4H-thieno[3,2-c]pyridin-5-yl)-3,3,12-12-tetramethyl-tetradecane-6,9-dione

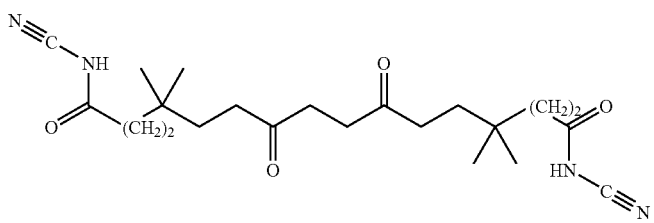

Ib-116

4,4,13,13-Tetramethyl-7,10-dioxo-hexadecanedioic acid dicyanimide

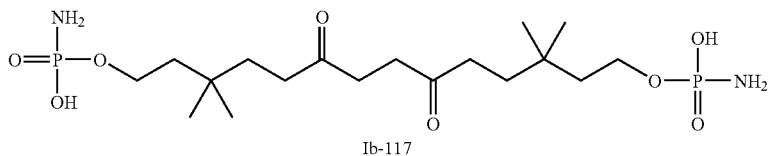

Ib-117

Phosphoramidic acid mono-[14-(amino-hydroxy-phospholyloxy)-3,3,12,12-tetramethyl-6,9-dioxo-tetradecyl] ester

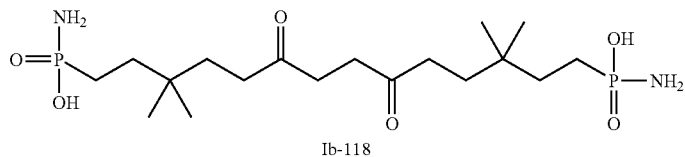

Ib-118

3,3,12,12-Tetramethyl-1,14-bis-(amino-hydroxy-phosphoryloxy)-tetradecane-6,9-dione

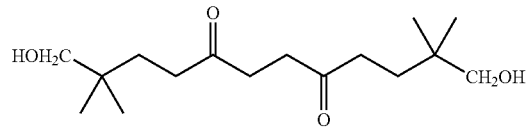

Ib-119

1,12-Dihydroxy-2,2,11,11-tetramethyl-dodecane-5,8-dione

TABLE 1-continued

Compounds of the Invention

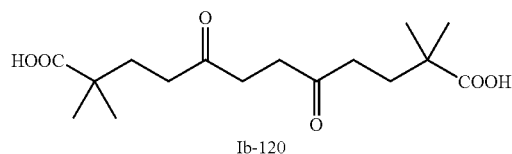
Ib-120

2,2,11,11-Tetramethyl-5,8-dioxo-dodecanedioic acid

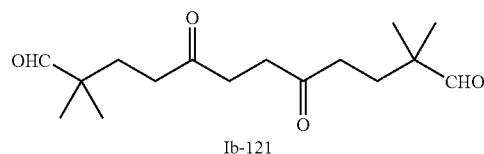
Ib-121

2,2,11,11-Tetramethyl-5,8-dioxo-dodecanedial

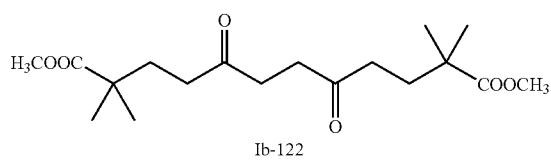
Ib-122

2,2,11,11-Tetramethyl-5,8-dioxo-dodecanedioic acid dimethyl ester

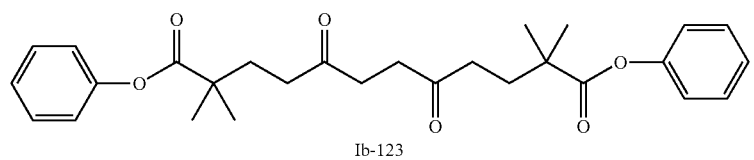
Ib-123

2,2,11,11-Tetramethyl-5,8-dioxo-dodecanedioic acid diphenyl ester

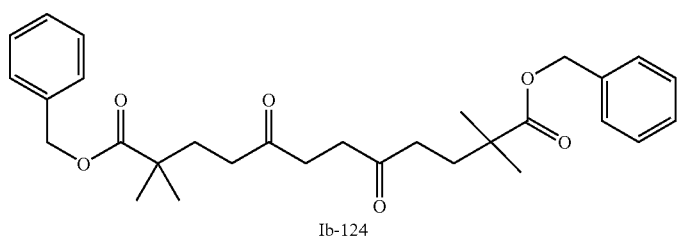
Ib-124

2,2,11,11-Tetramethyl-5,8-dioxo-dodecanedioic acid dibenzyl ester

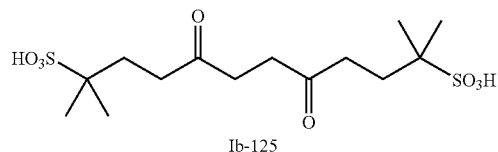
Ib-125

2,11-Dimethyl-5,8-dioxo-dodecane-2,11-disulfonic acid

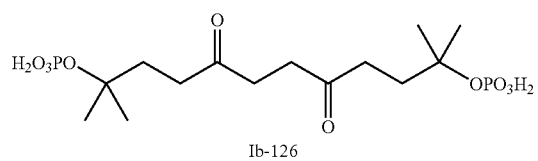
Ib-126

Phosphoric acid mono-(1,1,10-trimethyl-4,7-dioxo-10-phosphonooxy-undecyl) ester

TABLE 1-continued

Compounds of the Invention

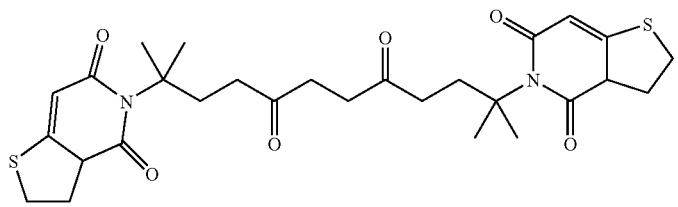

Ib-127

2,11-Bis-(4,6-dioxo-2,3,3a,6-tetrahydro-4H-thieno[3,2-c]pyridin-5-yl)-2,11-dimethyl-dodecane-5,8-dione

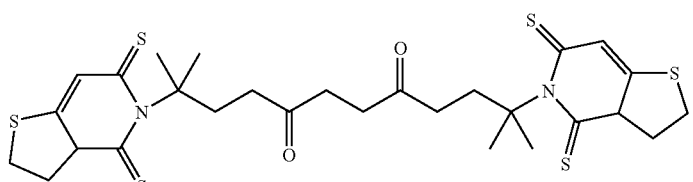

Ib-128

2,11-Bis-(4,6-dithioxo-2,3,3a,6-tetrahydro-4H-thieno[3,2-c]pyridin-5-yl)-2,11-dimethyl-dodecane-5,8-dione

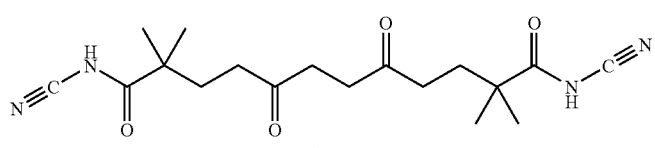

Ib-129

2,2,11,11-Tetramethyl-5,8-dioxo-dodecanedioic acid dicyanimide

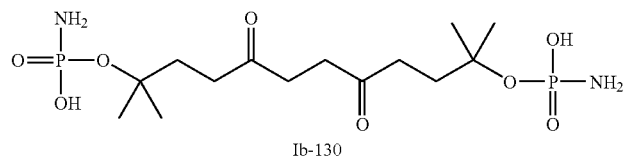

Ib-130

Phosphoramidic acid mono-[10-(amino-hydroxy-phosphoryloxy)-1,1,10-trimethyl-4,7-dioxo-undecyl] ester

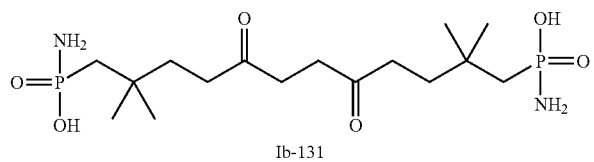

Ib-131

2,2,11,11-Tetramethyl-1,12-(amino-hydroxy-phosphoryloxy)-dodecane-5,8-dione

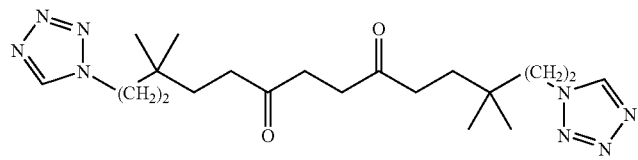

Ib-132

3,3,12,12-Tetramethyl-1,14-bis-tetrazol-1-yl-tetradecane-6,9-dione

TABLE 1-continued
Compounds of the Invention
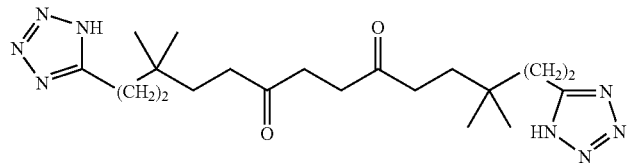
Ib-133
3,3,12,12-Tetramethyl-1,14-bis-(1H-tetrazol-5-yl)-tetradecane-6,9-dione
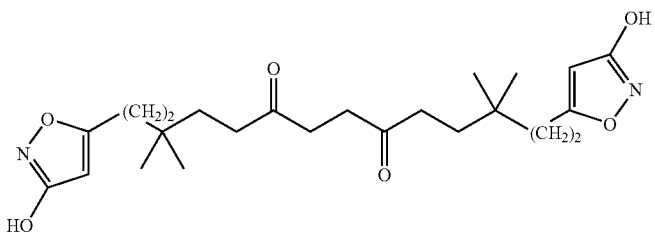
Ib-134
1,14-Bis-(3-hydroxy-isoxazol-5-yl)-3,3,12,12-tetramethyl-tetradecane-6,9-dione
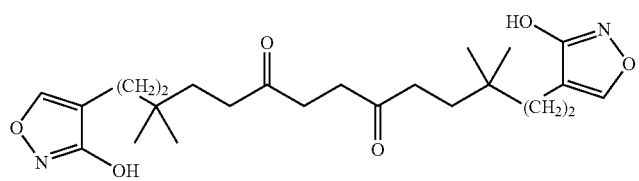
Ib-135
1,14-Bis-(3-hydroxy-isoxazol-4-yl)-3,3,12,12-tetramethyl-tetradecane-6,9-dione
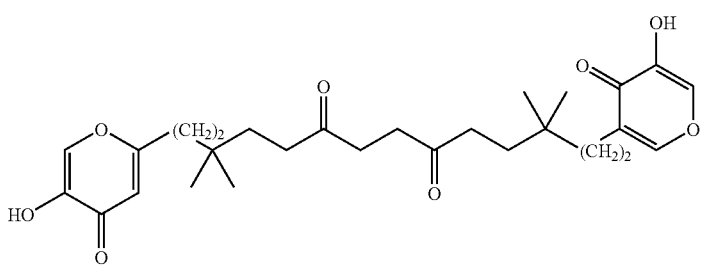
Ib-136
1-(5-Hydroxy-4-oxo-4H-pyran-2-yl)-14-(5-hydroxy-4-oxo-4H-pyran-3-yl)-3,3,12,12-tetramethyl-tetradecane-6,9-dione
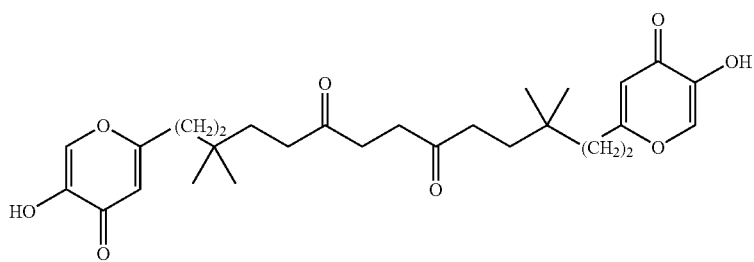
Ib-137
1,14-Bis-(5-hydroxy-4-oxo-4H-pyran-2-yl)-3,3,12,12-tetraniethyl-tetradecane-6,9-dione TABLE 1-continued Compounds of the Invention

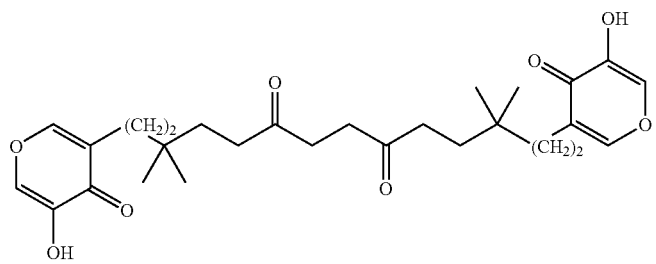

Ib-138
1,14-Bis-(5-hydroxy-3-oxo-4H-pyran-3-yl)-3,3,12,12-tetramethyl-tetradecane-6,9-dione

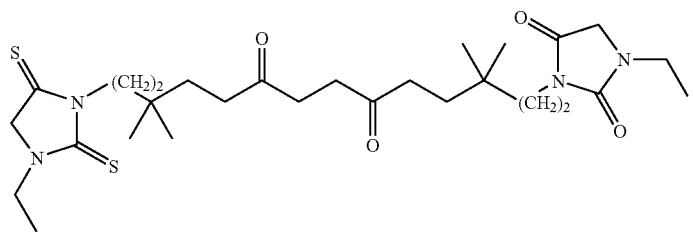

Ib-139
1-Ethyl-3-[14-(3-ethyl-2,5-dithioxo-imidazolidin-1-yl)-3,3,12,12-tetramethyl-6,9-dioxo-tetradecyl]-imidazolidine-2,4-dione

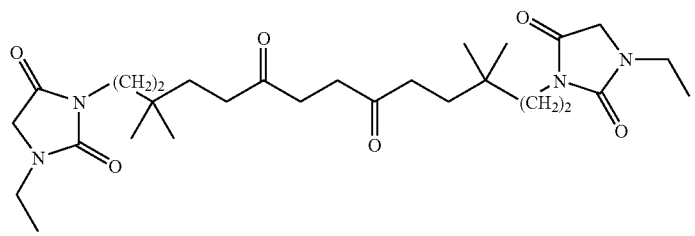

Ib-140
1-Ethyl-3-[14-(3-ethyl-2,5-dioxo-imidazolidin-1-yl)-3,3,12,12-tetramethyl-6,9-dioxo-tetradecyl]-imidazolidine-2,4-dione

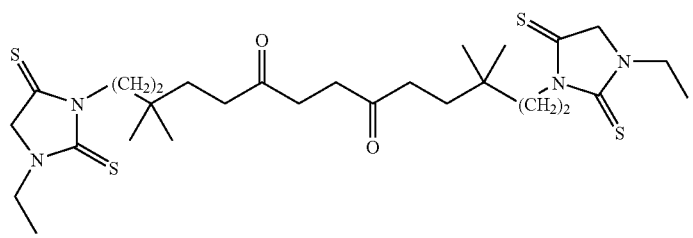

Ib-141
1-Ethyl-3-[14-(3-ethyl-2,5-dithioxo-iinidazolidin-1-yl)-3,3,12,12-tetramethyl-6,9-dioxo-tetradecyl]-imidazolidine-2,4-dithione

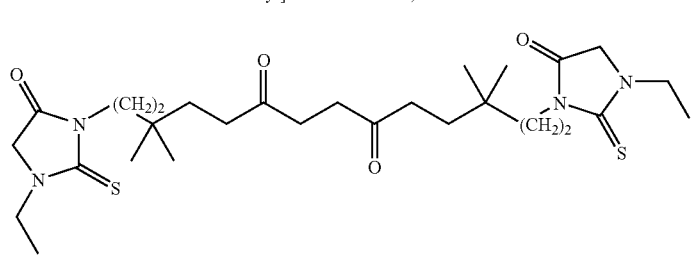

Ib-142
1,14-Bis-(3-ethyl-5-oxo-2-thioxo-imidazolidin-1-yl)-3,3,12,12-tetramethyl-tetradecane-6,9-dione TABLE 1-continued Compounds of the Invention

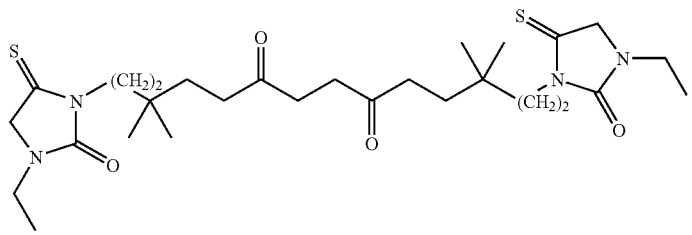

Ib-143

1,14-Bis-(3-ethyl-2-oxo-5-thioxo-imidazolidin-1-yl)-3,3,12,12-tetramethyl-tetradecane-6,9-dione

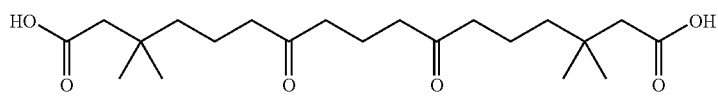

Ib-144

1,17-Dihydroxy-3,3,15,15-tetramethyl-heptadecane-7,11-dione

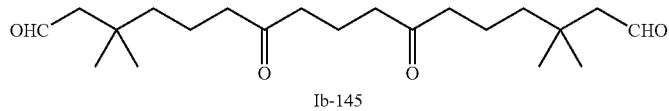

Ib-145

3,3,15,15-Tetramethyl-7,11-dioxo-heptadecanedial

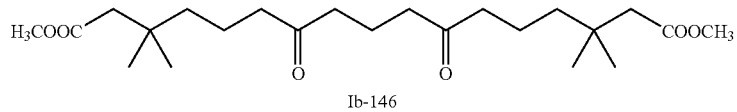

Ib-146

3,3,15,15-Tetramethyl-7,11-dioxo-heptadecanedioic acid dimethyl ester

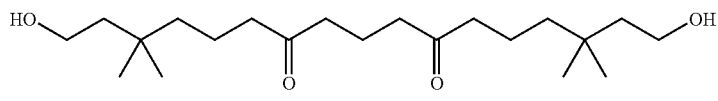

Ib-147

1,17-Dihydroxy-3,3,15,15-tetramethyl-heptadecane-7,11-dione

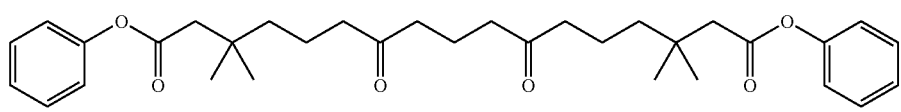

Ib-148

3,3,15,15-Tetramethyl-7,11-dioxo-heptadecanedioic acid diphenyl ester

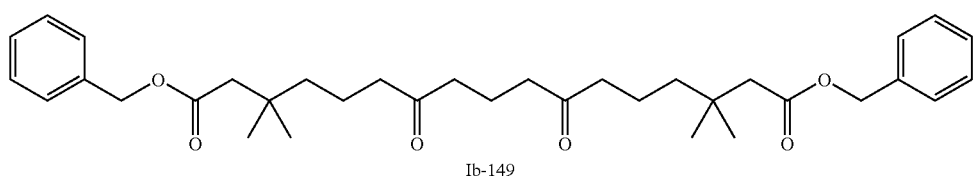

Ib-149

3,3,15,15-Tetramethyl-7,11-dioxo-heptadecanedioic acid dibenzyl ester

TABLE 1-continued

Compounds of the Invention

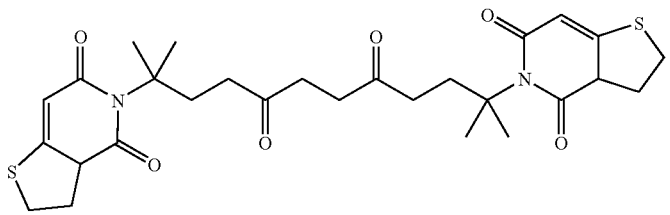

Ib-150

2,11-Bis-(4,6-dioxo-2,3,3a,6-tetrahydro-4H-thieno[3,2-c]pyiidin-5-yl)-2,11-dimethyl-dodecane-5,8-dione

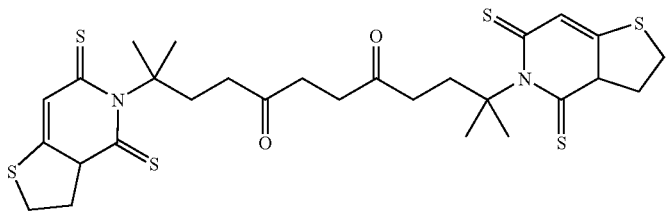

Ib-151

2,11-Dis-(4,6-dithioxo-2,3,3a,6-tetrahydro-4H-thieno[3,2-c]pyridin-5-yl)-2,11-dimethyl-dodecane-5,8-dione

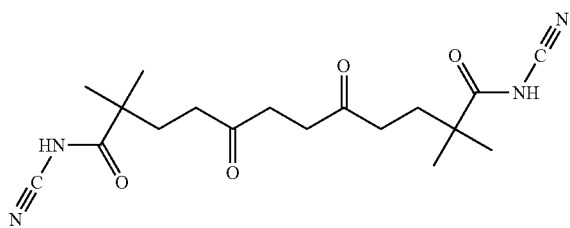

Ib-152

2,2,11-11-Tetramethyl-5,8-dioxo-dodecanedioic acid dicyanamide

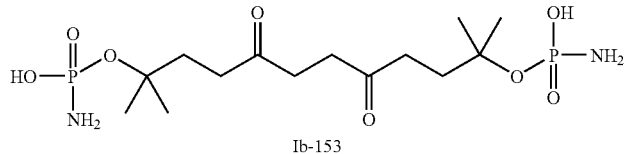

Ib-153

Phosphoramidic acid mono-(10-(amino-hydroxy-phosphoryloxy)-1,1,10-trimethyl-4,7-dioxo-undecyl] ester

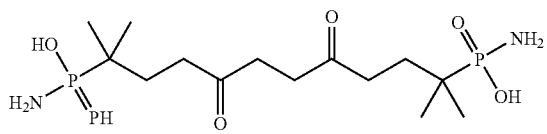

Ib-154

2,11-Dimethyl-2,11-bis-(amino-hydroxy-phosphoryloxy)-dodecane-5,8-dione

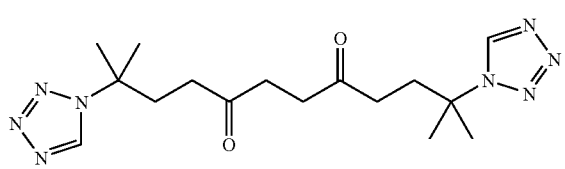

Ib-155

2,11-Dimethyl-2,11-bis-tetrazol-1-yl-dodecane-5,8-dione

TABLE 1-continued

Compounds of the Invention

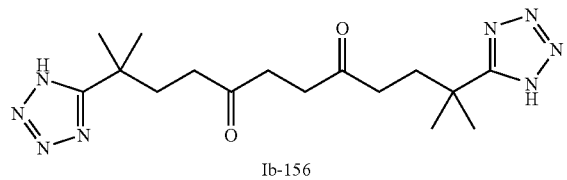

Ib-156

2,11-Dimethyl-2,11-bis-(1H-tetrazol-5-yl)-dodecane-5,8-dione

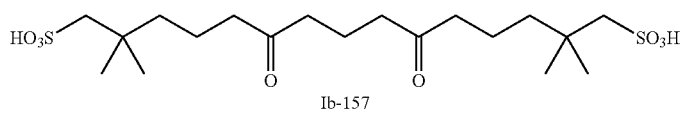

Ib-157

2,2,14,14-Tetramethyl-6,10-dioxo-pentadecane-1,15-disulfonic acid

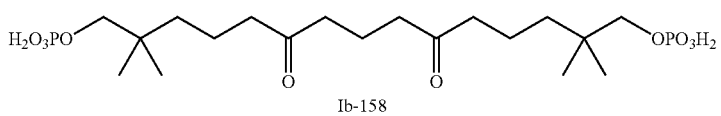

Ib-158

Phosphoric acid mono-(2,2,14,14-tetramethyl-6,10-dioxo-15-phosphonooxy-pentadecyl) ester

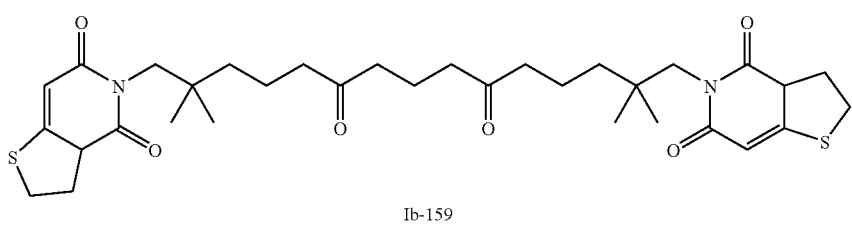

Ib-159

1,15-Bis-(4,6-dithioxo-2,3,3a,6-tetrahydro-4H-thieno[3,2-c]pyridin-5-yl)-2,2,14,14-tetramethyl-pentadecane-6,10-dione

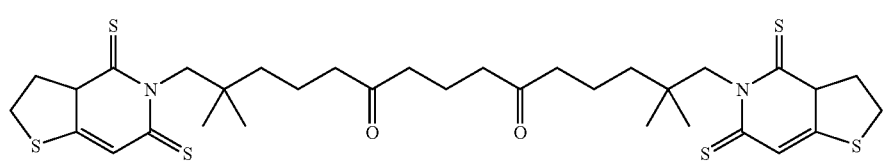

Ib-160

1,15-Bis-(4,6-dithioxo-2,3,3a,6-tetrahydro-4H-thieno[3,2-c]pyridin-5-yl)-2,2,14,14-tetramethyl-pentadecane-6,10-dione

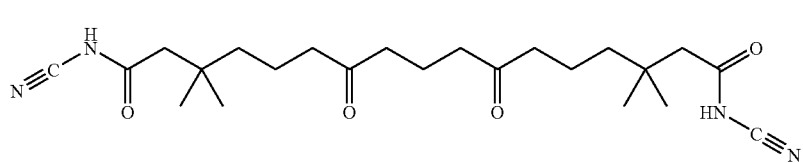

Ib-161

3,3,15,15-Tetramethyl-7,11-dioxo-heptadecanedioic acid dicyanamide

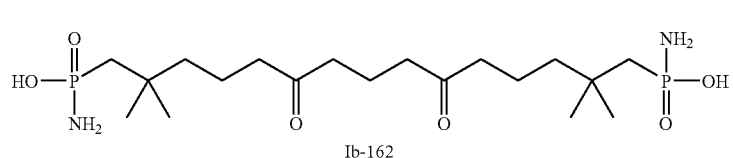

Ib-162

Phosphoramidic acid mono-[16-(amino-hydroxy-phosphoryloxy)-4,4,15,15-tetramethyl-7,11-dioxo-hexadecyl] ester TABLE 1-continued Compounds of the Invention

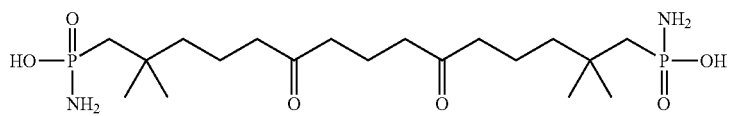
Ib-163

2,2,14,14-Tetramethyl-1,15-bis-(amino-hydroxy-phosphorylaxy)-pentadecane-6,10-dione

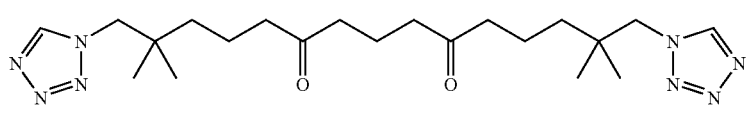
Ib-164

2,2,14,14-Tetramethyl-1,15-bis-tetrazol-1-yl-pentadecane-6,10-dione

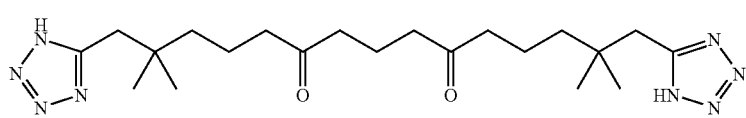
Ib-165

2,2,14,14-Tetramethyl-1,15-bis-(1H-tetrazol-5-yl)-pentadecane-6,10-dione

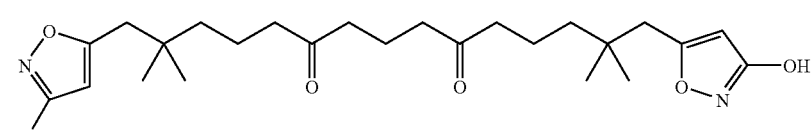
Ib-166

1,15-Bis-(3-hydroxy-isaxazal-5-yl)-2,2,14,14-tetramethyl-pentadecane-6,10-dione

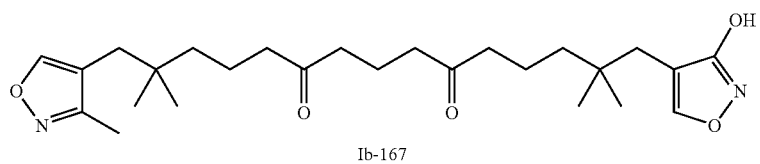
Ib-167

1,15-Bis-(3-hydroxy-isoxazol-4-yl)-2,2,14,14-tetramethyl-pentadecane-6,10-dione

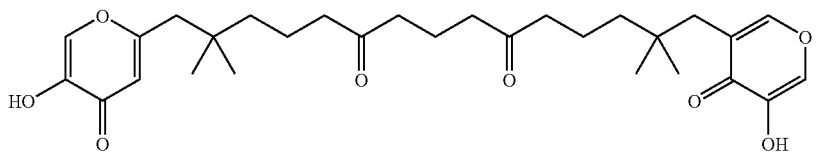
Ib-168

1-(5-Hydroxy-4-oxo-4H-pyran-3-yl)-15-(5-hydroxy-4-oxo-4H-pyran-2-yl)-2,2,14,14-tetramethyl-pentadecane-6,10-dione

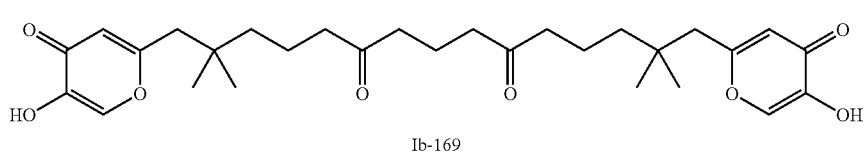
Ib-169

1,15-Bis-(5-hydroxy-4-oxo-4H-pyran-2-yl)-2,2,14,14-tetramethyl-pentadecane-6,10-dione TABLE 1-continued Compounds of the Invention

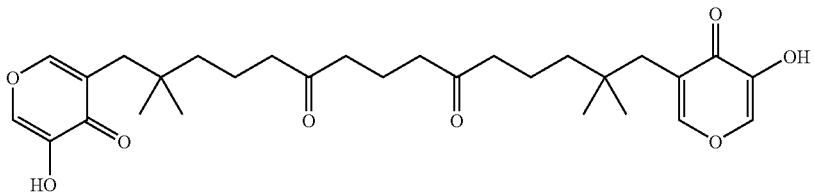

Ib-170

1,15-Bis-(5-hydroxy-4-oxo-4H-pyran-3-yl)-2,2,14,14-tetramethyl-pentadecane-6,10-dione

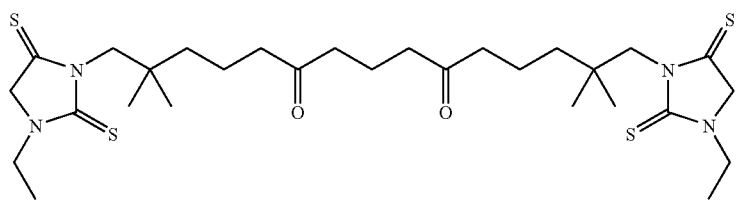

Ib-171

1,15-Bis-(3-ethyl-2,5-dithioxo-imidazolidin-1-yl)-2,2,14,14-tetramethyl-pentadecane-6,10-dione

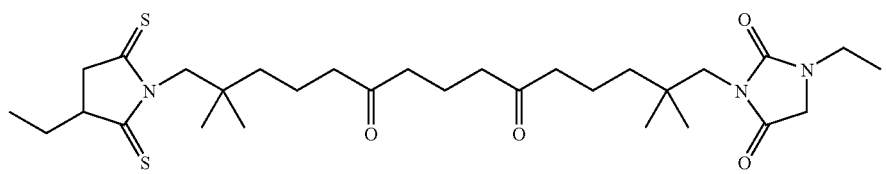

Ib-172

1-Ethyl-3-[15-(3-ethyl-2,5-dithioxo-imidazolidin-1-yl)-2,2-14,14-tetramethyl-6,10-dioxo pentadecyl]-imidazolidine-2,4-dione

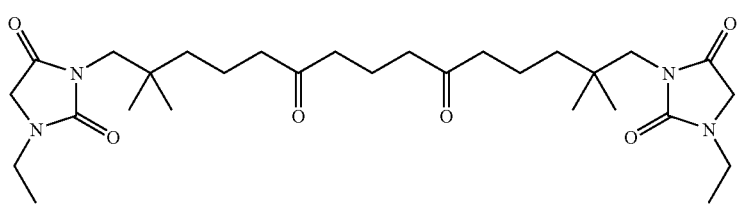

Ib-173

1,15-Bis-(3-ethyl-2,5-dioxo-imidazolidin-1-yl)-2,2,14,14-tetramethyl-pentadecane-6,10-dione

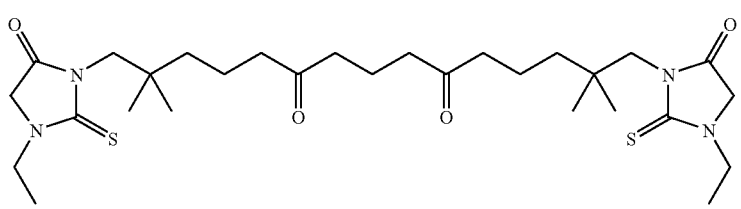

Ib-174

1,15-Bis-(3-ethyl-5-oxo-2-thioxo-imidazolidin-1-yl)-2,2,14,14-tetramethyl-pentadecane-6,10-dione TABLE 1-continued
Compounds of the Invention
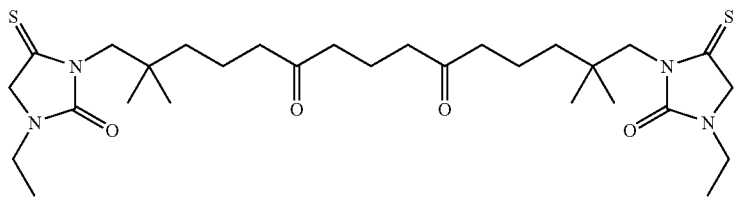
Ib-175
1,15-Bis-(3-ethyl-2-oxo-5-thioxo-imidazolidin-1-yl)-2,2,14,14-tetramethyl-pentadecane-6,10-dione
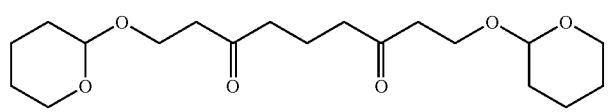
Ic-1
1,9-Bis-(tetrahydro-pyran-2-yloxy)-nonane-3,7-dione
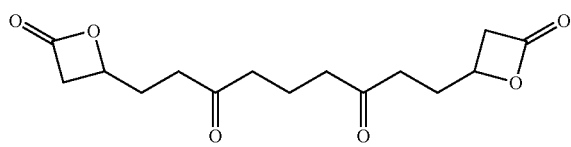
Ic-2
1,9-Bis-(4-oxo-oxetan-2-yl)-nonane-3,7-dione
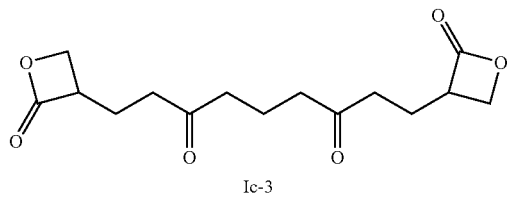
Ic-3
1,9-Bis-(2-oxo-oxetan-3-yl)-nonane-3,7-dione
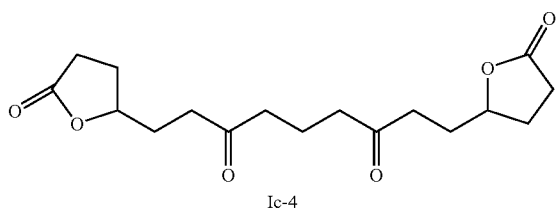
Ic-4
1,9-Bis-(5-oxo-tetrahydrofuran-2-yl)-nonane-3,7-dione
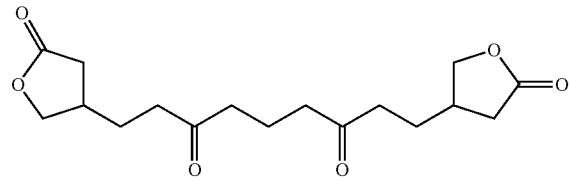
Ic-5
1,9-Bis-(5-oxo-tetrahydrofuran-3-yl)-nonane-3,7-dione TABLE 1-continued Compounds of the Invention

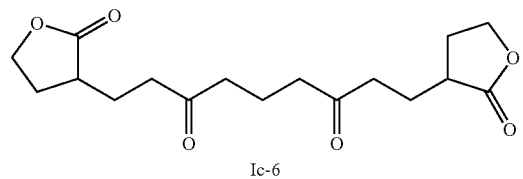

Ic-6

1,9-Bis-(2-oxo-tetrahydrofuran-3-yl)-nonane-3,7-dione

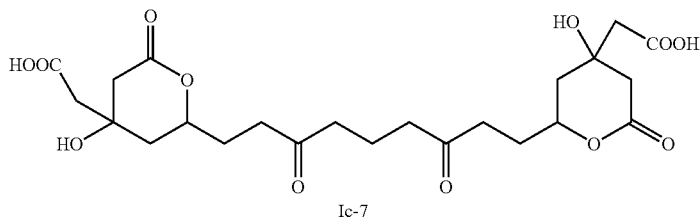

Ic-7

{2-[9-(4-Carboxymethyl-4-hydroxy-6-oxo-tetrahydro-pyran-2-yl)-3,7-dioxo-nonyl]-4-hydroxy-6-oxo-tetrahydropyran-4-yl}-acetic acid

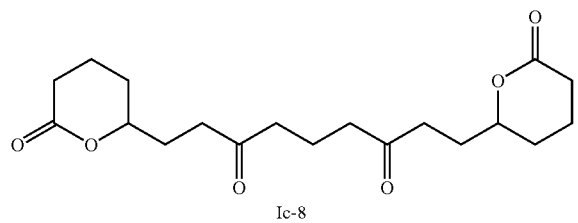

Ic-8

1,9-Bis-(6-oxo-tetrahydropyran-2-yl)-nonane-3,7-dione

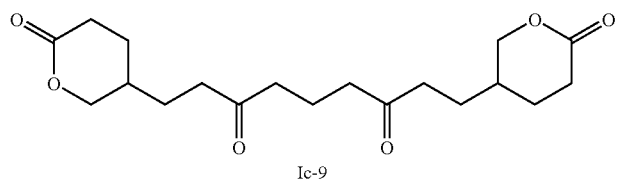

Ic-9

1,9-Bis-(6-oxo-tetrahydropyran-3-yl)-nonane-3,7-dione

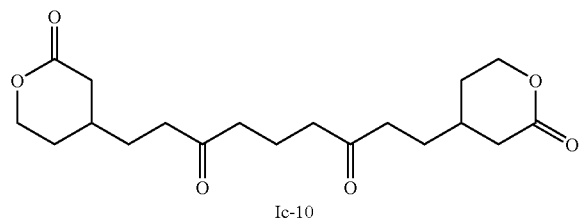

Ic-10

1,9-Bis-(2-oxo-tetrahydropyran-4-yl)-nonane-3,7-dione

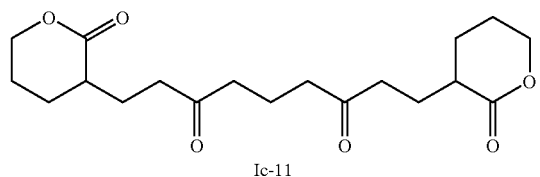

Ic-11

1,9-Bis-(2-oxo-tetrahydropyran-3-yl)-nonane-3,7-dione

TABLE 1-continued
Compounds of the Invention
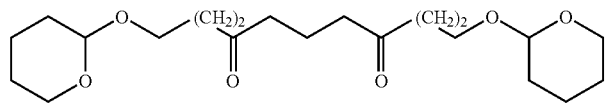
Ic-12
1,11-Bis-(tetrahydro-pyran-2-yloxy)-undecane-4,8-dione
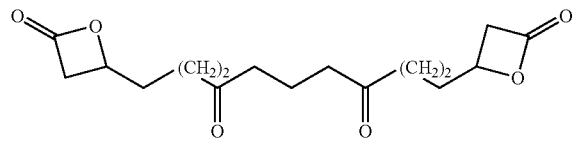
Ic-13
1,11-Bis-(2-oxo-oxetan-3-yl)-undecane-4,8-dione
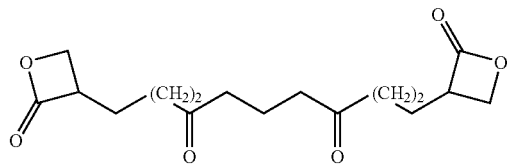
Ic-14
1,11-Bis-(2-oxo-oxetan-3-yl)-undecane-4,8-dione
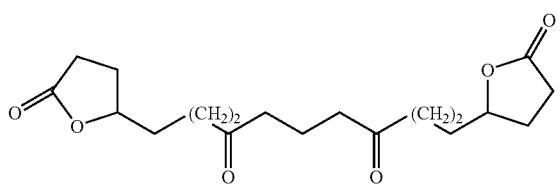
Ic-15
1,11-Bis-(5-oxo-tetrahydrofuran-2-yl)-undecane-4,8-dione
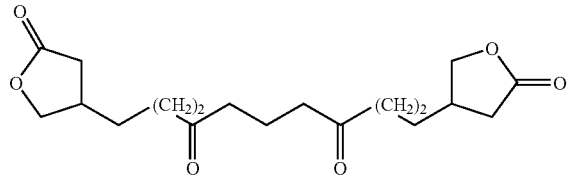
Ic-16
1,11-Bis-(5-oxo-tetrahydrofuran-3-yl)-undecane-4,8-dione
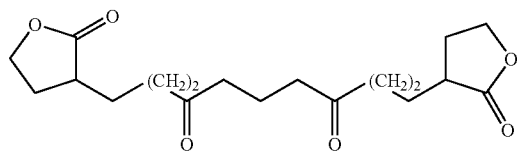
Ic-17
1,11-Bis-(2-oxo-tetrahydrofuran-3-yl)-undecane-4,8-dione TABLE 1-continued Compounds of the Invention

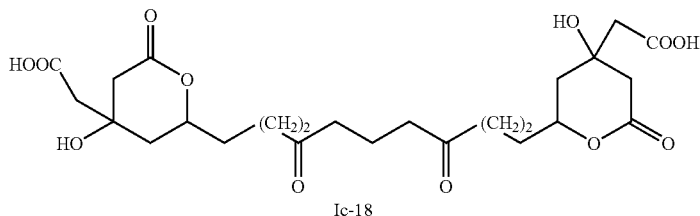

Ic-18

{2-(11-(4-Carboxymethyl-4-hydroxy-6-oxo-tetrahydro-pyran-2-yl)-4,8-dioxo-undecyl]-4-
hydroxy-6-oxo-tetrahydropyran-4-yl}-acetic acid

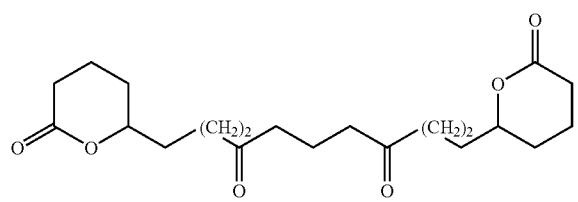

Ic-19

1,11-Bis-(6-oxo-tetrahydropyran-2-yl)-undecane-4,8-dione

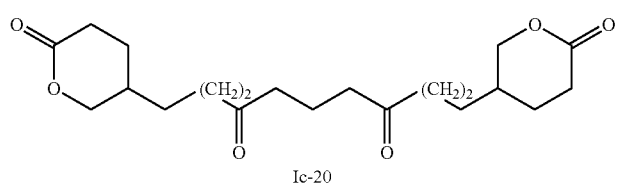

Ic-20

1,11-Bis-(6-oxo-tetrahydropyran-3-yl)-undecane-4,8-dione

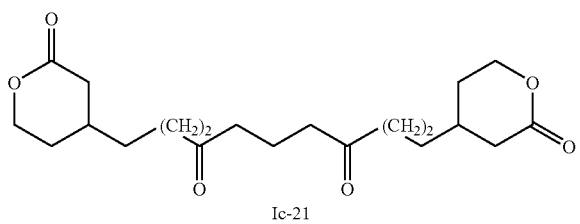

Ic-21

1,11-Bis-(2-oxo-tetrahydropyran-4-yl)-undecane-4,8-dione

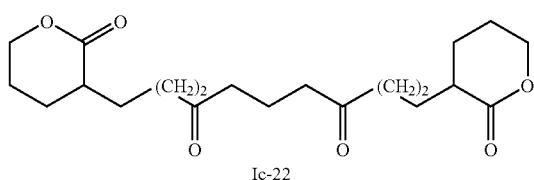

Ic-22

1,11-Bis-(2-axo-tetrahydropyran-3-yl)-undecane-4,8-dione

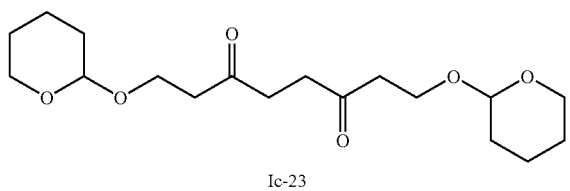

Ic-23

1,8-Bis-(tetrahydropyran-2-yloxy)-octane-3,6-dione

TABLE 1-continued
Compounds of the Invention
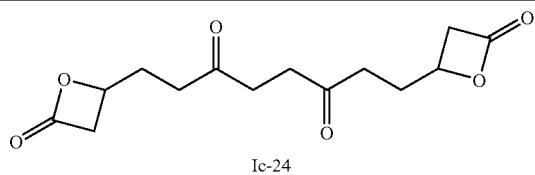
Ic-24
1,8-Bis-(4-axo-oxetan-2-yl)-octane-3,6-dione
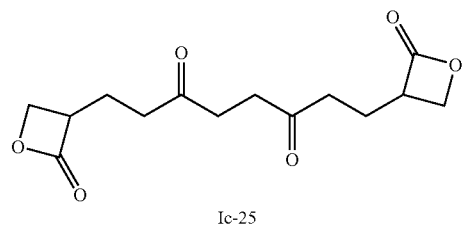
Ic-25
1,8-Bis-(2-oxo-oxetan-3-yl)-octane-3,6-dione
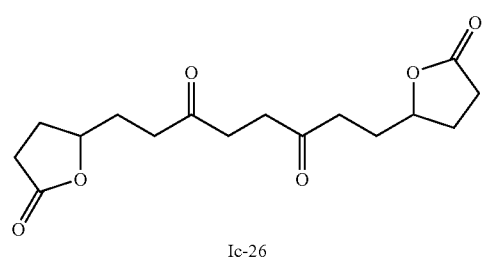
Ic-26
1,8-Bis-(5-oxo-tetrahydro-furan-2-yl)-octane-3,6-dione
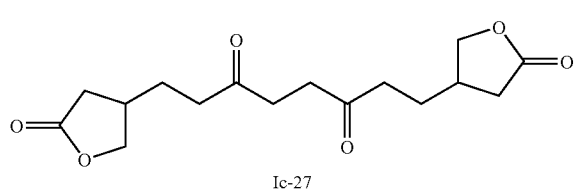
Ic-27
1,8-Bis-(5-oxo-tetrahydro-furan-3-yl)-octane-3,6-dione
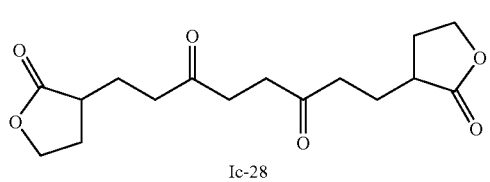
Ic-28
1,8-Bis-(2-oxo-tetrahydro-furan-3-yl)-octane-3,6-dione
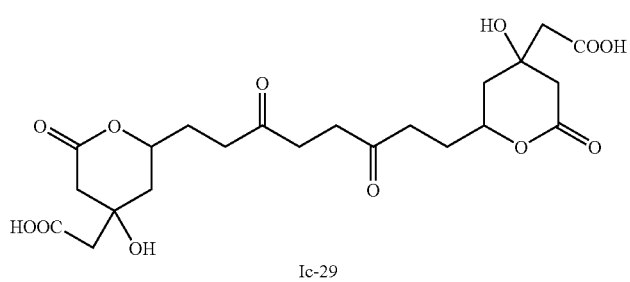
Ic-29
{2-(8-(4-Carboxymethyl-4-hydroxy-6-oxo-tetahydro-pyran-2-yl)-3,6-dioxo-octyl]-4-hydroxy-6-oxo-tetrahydro-pyran-4-yl}-acetic acid TABLE 1-continued Compounds of the Invention

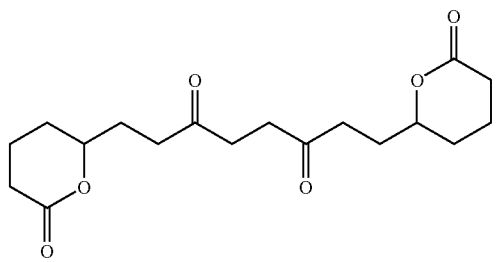

Ic-30

1,8-Bis-(6-oxo-tetrahydropyran-2-yl)-octane-3,6-dione

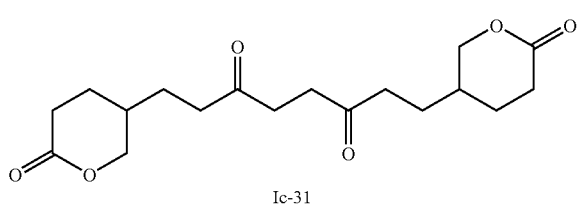

Ic-31

1,8-Bis-(6-oxo-tetrahydropyran-3-yl)-octane-3,6-dione

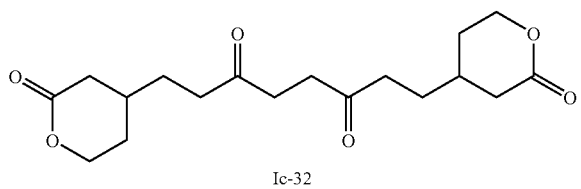

Ic-32

1,8-Bis-(2-oxo-tetrahydropyran-4-yl)-octane-3,6-dione

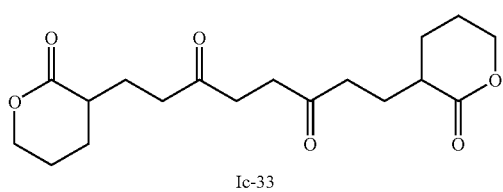

Ic-33

1,8-Bis-(2-oxo-tetrahydropyran-3-yl)-octane-3,6-dione

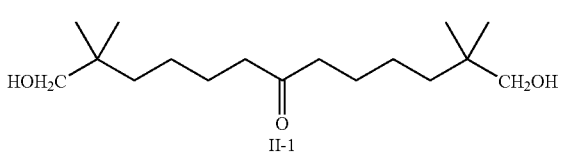

II-1

1,13-Dihydroxy-2,2,12,12-tetramethyl-tridecan-7-one

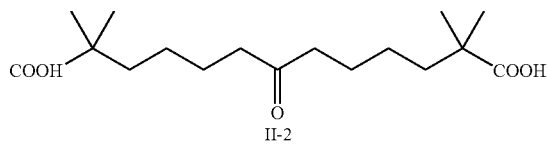

II-2

12-Hydroxy-2,2,12-trimethyl-7-oxo-tridecanoic acid; compound with formaldehyde

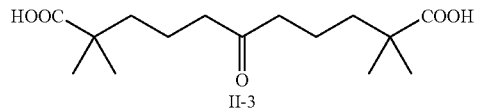

II-3

11-Hydroperoxy-2,2,10,10-tetramethyl-6-oxo-undecanoic acid

TABLE 1-continued

Compounds of the Invention

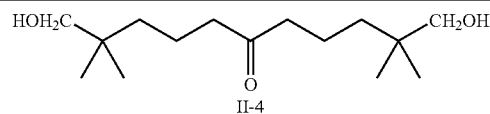
II-4

1,11-Dihydroxy-2,2.10,10-tetramethyl-undecan-6-one

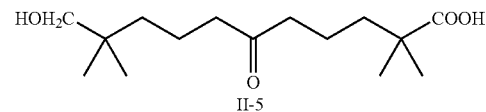
II-5

11-Hydroxy-2,2,10,10-tetramethyl-6-oxo-undecanoic acid

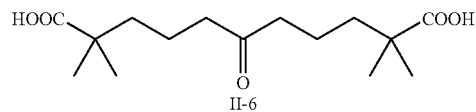
II-6

2,2,10,10-Tetramethyl-6-oxo-undecanedioic acid

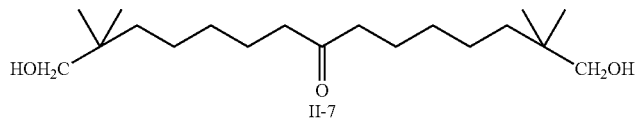
II-7

1,15-Dihydroxy-2,2,14,14-tetramethyl-pentadecan-8-one

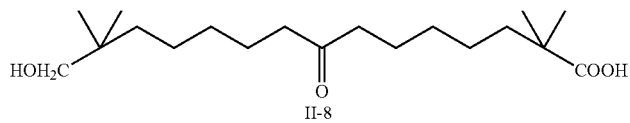
II-8

15-Hydroxy-2,2,14,14-tetramethyl-8-oxo-pentadecanoic acid

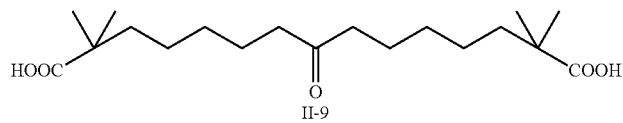
II-9

2,2,14,14-Tetramethyl-8-oxo-pentadecanedioic acid

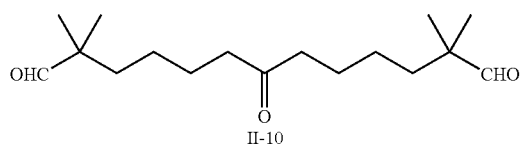
II-10

2,2,12,12-Tetramethyl-7-oxo-tridecanedial

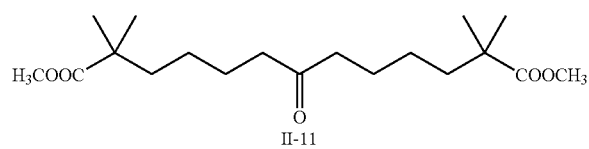
II-11

2,2,12,12-Tetramethyl-7-oxo-tridecanedioic acid dimethyl ester

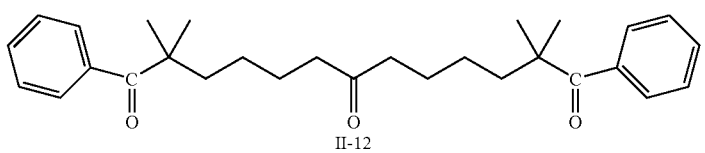
II-12

2,2,12,12-Tetramethyl-1,13-diphenyl-tridecane-1,7,13-trione

TABLE 1-continued

Compounds of the Invention

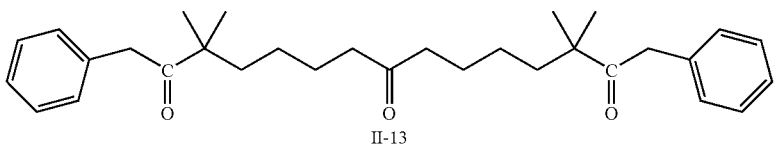

II-13

3,3,13,13-Tetramethyl-1,15-diphenyl-pentadecane-2,8,14-trione

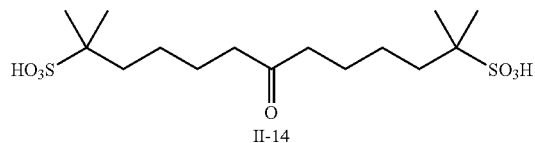

II-14

2,12-Dimethyl-7-oxo-tridecane-2,12-sulfonic acid

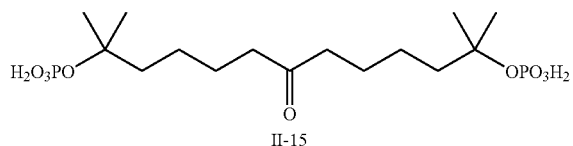

II-15

Phosphoric acid mono-(1,1,11-trimethyl-6-oxo-11-phosphonooxy-dodecyl) ester

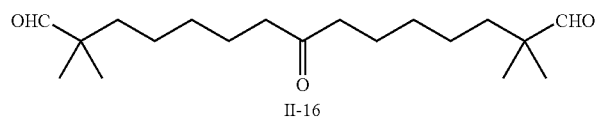

II-16

2,2,14,14-Tetramethyl-8-oxo-pentadecanedial

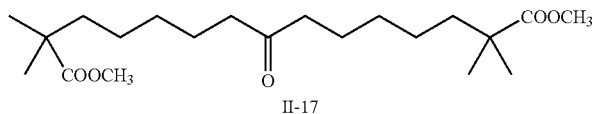

II-17

2,2,14,14-Tetramethyl-8-oxo-pentadecanedioic acid dimethyl ester

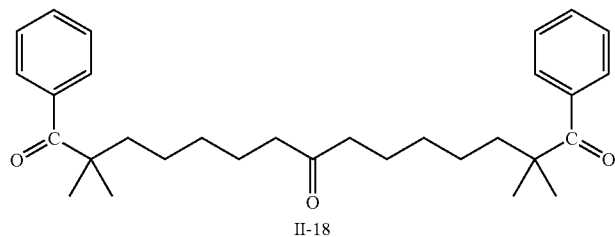

II-18

2,2,14,14-Tetramethyl-1,15-diphenyl-pentadecane-1,8,15-trione

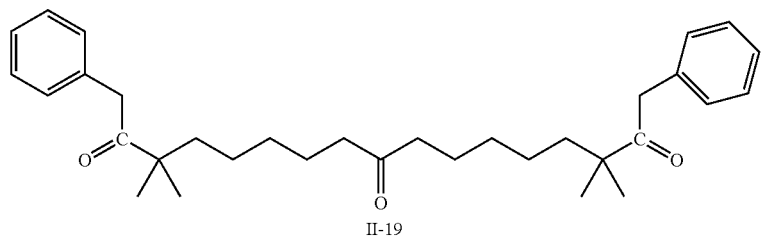

II-19

3,3,15,15-Tetramethyl-1,17-diphenyl-heptadecane-2,9,16-trione

TABLE 1-continued

Compounds of the Invention

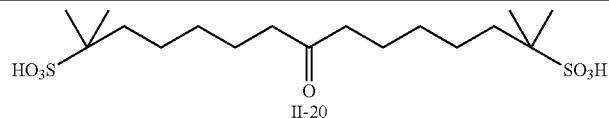
II-20

2,14-Dimethyl-8-oxo-pentadecane-2,14-disulfonic acid

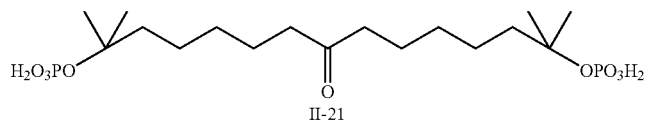
II-21

Phosphoric acid mono-(1,1,13-trimethyl-7-oxo-13-phosphonooxy-tetradecyl) ester

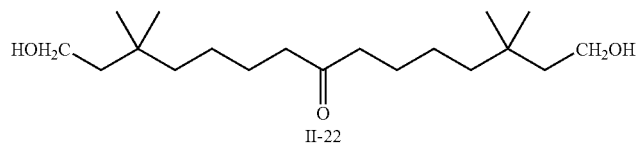
II-22

1,15-Dihydroxy-3,3,13,13-tetramethyl-pentadecan-8-one

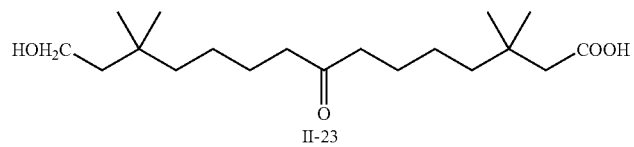
II-23

15-Hydroxy-3,3,13,13-tetramethyl-8-oxo-pentadecanoic acid

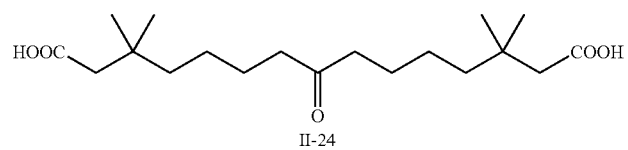
II-24

3,3,13,13-Tetramethyl-8-oxo-pentadec-edioic acid

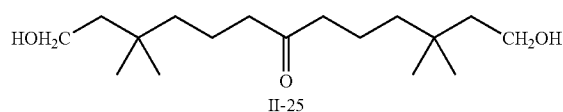
II-25

1,13-Dihydroxy-3,3,11,11-tetramethyl-tridecan-7one

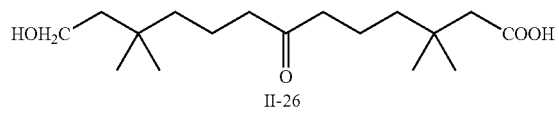
II-26

13-Hydroxy-3,3,11,11-tetramethyl-7-oxo-tridecanoic acid

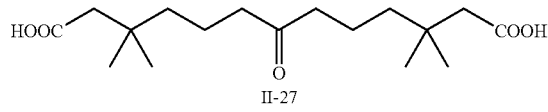
II-27

3,3,11,11-Tetramethyl-7-oxo-tridecanedioic acid

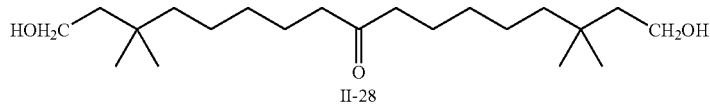
II-28

1,17-Dihydroxy-3,3,15,15-tetramethyl-heptadecan-9-one

TABLE 1-continued

Compounds of the Invention

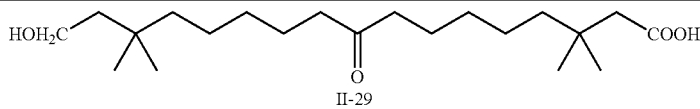

17-Hydroxy-3,3,15,15-tetramethyl-9-oxo-heptadecanoic acid

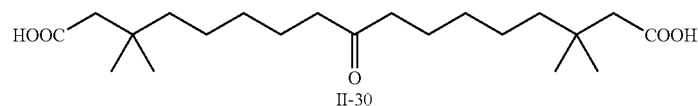

3,3,15,15-Tetramethyl-9-oxo-heptadecanedioic acid

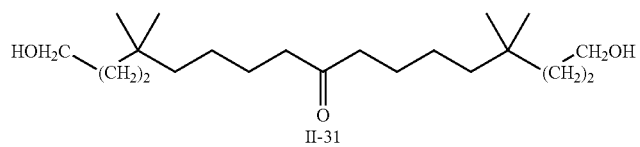

1,17-Dihydroxy-4,4,14,14-tetramethyl-heptadecan-9-one

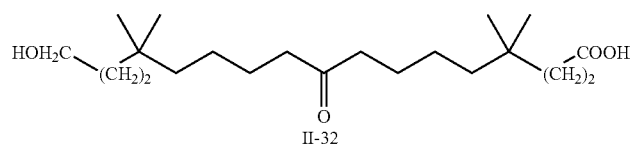

17-Hydroxy-4,4,14,14-tetramethyl-9-oxo-heptadecanoic acid

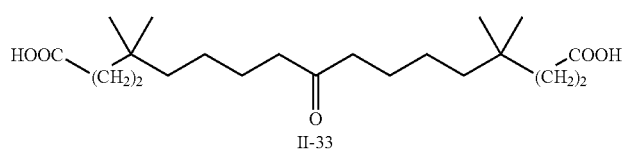

4,4,14,14-Tetramethyl-heptadecan-9-oxo-1,17-dicarboxylic acid

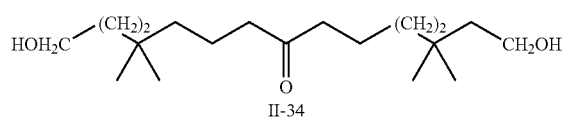

1,15-Dihydroxy-4,4,14,14-tetramethyl-pentadecan-8-one

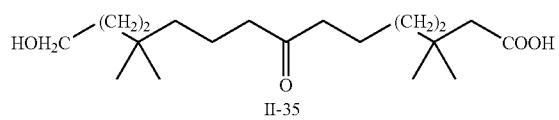

15-Hydroxy-4,4,12,12-tetramethyl-8-oxo-pentadecanoic acid

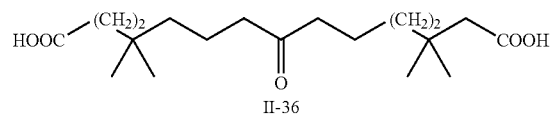

4,4,12,12-Tetramethyl-8-oxo-pentadecanedioic acid

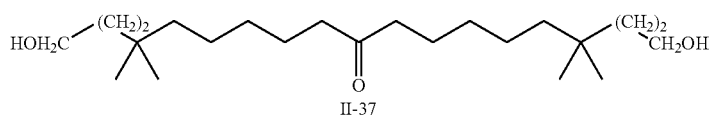

1,19-Dihydroxy-4,4,16,16-tetramethyl-nonadecan-10-one

TABLE 1-continued

Compounds of the Invention

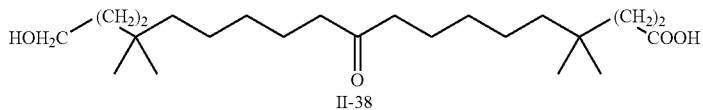

II-38

19-Hydroxy-4,4,16,16-tetramethyl-10-oxo-nonadecanoic acid

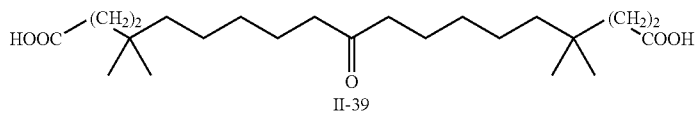

II-39

4,4,16,16-Tetramethyl-10-oxo-nonadecanedioic acid

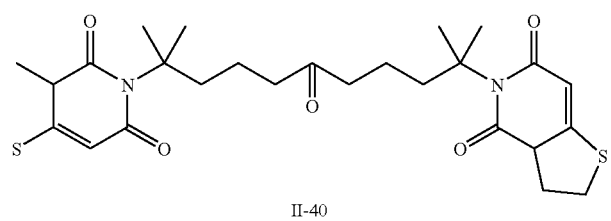

II-40

5-[9-(4-Mercapto-3-methyl-2,6-dioxo-3,6-dihydro-2H-pyridin-1-yl)-1,1,9-trimethyl-5-oxo-decyl]-3,3a-dihydro-2H-thieno[3,2-c]pyridine-4,6-dione

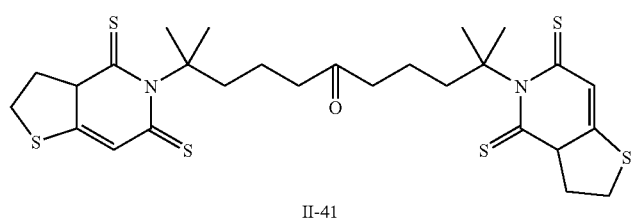

II-41

2,10-Bis-(4,6-dithioxo-2,3,3a,6-tetrahydro-4H-thieno[3,2-c]pyridin-5-yl)-2,10-dimethyl-undecan-6-one

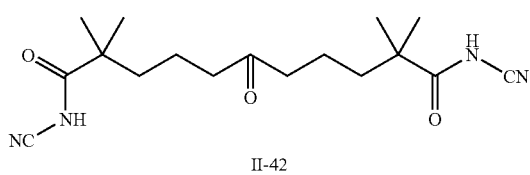

II-42

2,2,10,10-Tetramethyl-6-oxo-undecanedioic acid bis-cyanoamide

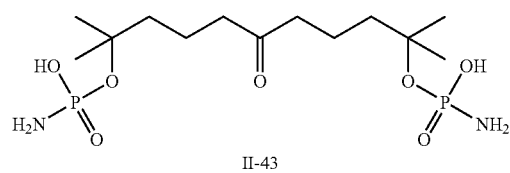

II-43

Phosphoramidic acid mono-[9-(amino-hydroxy-phosphoryloxy)-1,1,9-trimethyl-5-oxo-decyl] ester

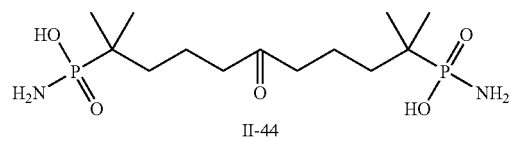

II-44

Phosphoramidic acid mono-[9-(amino-hydroxy-phosphoryloxy)-1,1,9-trimethyl-5-oxo-decyl] ester TABLE 1-continued Compounds of the Invention

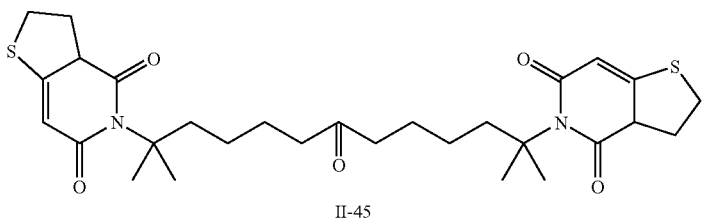

II-45

2,12-Bis-(4,6-dioxo-2,3,3a,6-tetrahydro-4H-thieno[3,2-c]pyridin-5-yl)-2,12-dimethyl-tridecan-7-one

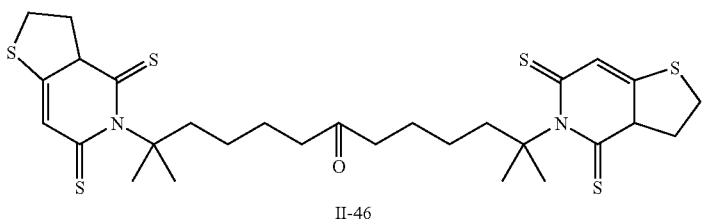

II-46

2,12-Bis-(4,6-dithioxo-2,3,3a,6-tetrahydro-4H-thieno[3,2-c]pyridi-5-yl)-2,12-dimehyl-tridecan-7-one

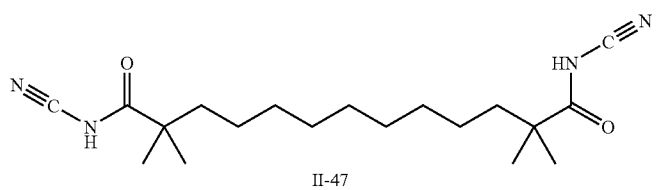

II-47

2,2,12,12-Tetramethyl-7-oxo-tridecanedioic acid bis-cyanoamide

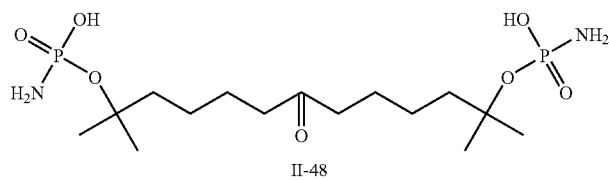

II-48

Phosphoramidic acid mono-[11-(amino-hydroxy-phosphoryloxy)-1,1,11-trimethyl-6-oxo-dodecyl] ester

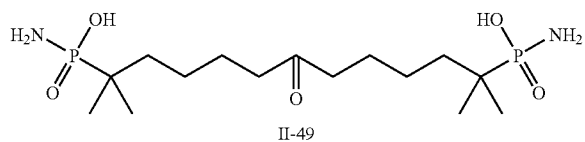

II-49

Phosphoramidic acid mono-[11(amino-hydroxy-phosphoryloxy)-1,1,11-trimethyl-6-oxo-dodecyl] ester

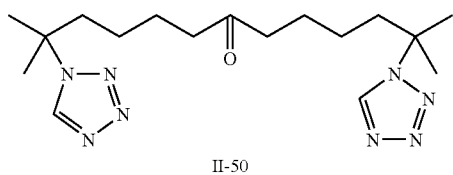

II-50

2,12-Dimethyl-2,12-bis-tetrazol-1-yl-tridecan-7-one

TABLE 1-continued

Compounds of the Invention

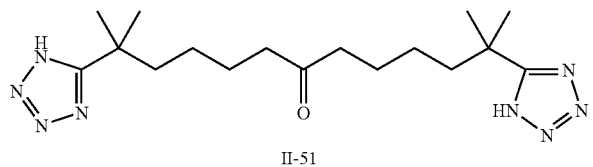

II-51

2,12-Dimethyl-2,12-bis-(1H-tetrazol-5-yl)-tridecan-7-one

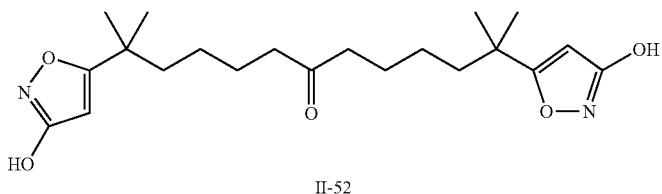

II-52

2,12-Bis-(3-hydroxy-isoxazol-5-yl)-2,12-dimethyl-tridecan-7-one

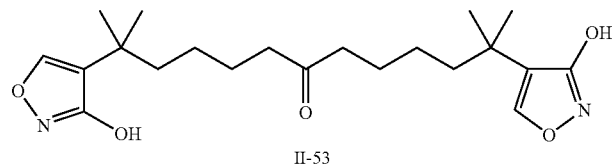

II-53

2,12-Bis-(3-hydroxy-isoxazol-4-yl)-2,12-dimethyl-tridecan-7-one

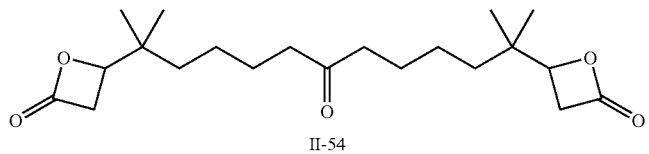

II-54

4-[11-(4-oxo-oxctan-2-yl)-1,1,11-Trimethyl-6-oxo-dodecyl]-oxetan-2-one

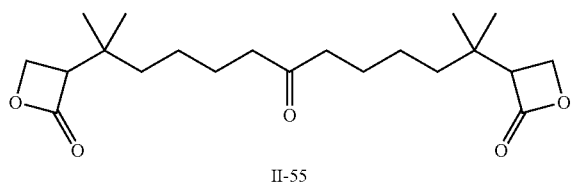

II-55

3-[11-(4-oxo-oxetan-2-yl)-1,1,11-Trimethyl-6-oxo-dodecyl]-oxetan-2-one

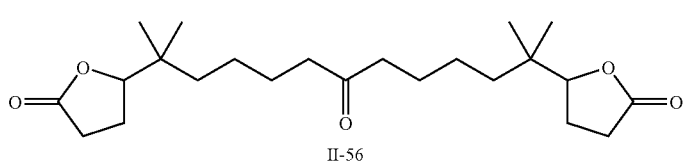

II-56

5-[11-(5-oxo-tetrahydro-furan-3-yl)-1,1,11-Trimethyl-6-oxo-dodecyl]-dihydro-furan-2-one

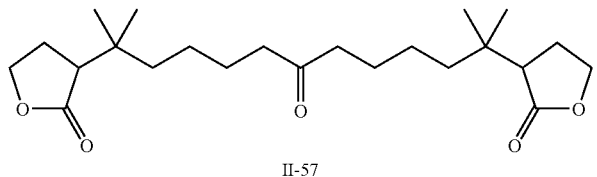

II-57

3-[11-(5-oxo-tetrahydro-furan-3-yl)-1,1,11-Trimethyl-6-oxo-dodecyl]-dihydro-furan-2-one TABLE 1-continued Compounds of the Invention

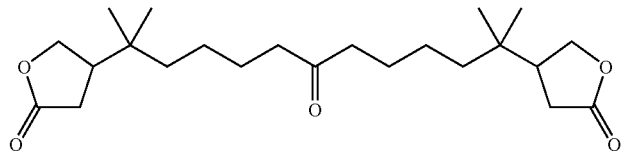

II-58

4-[11-(5-oxo-tetrahydro-furan-3-yl)-1,1,11-Trimethyl-6-oxo-dodecyl]-dihydro-furan-2-one

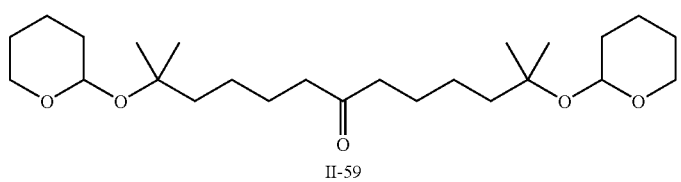

II-59

2,12-Dimethyl-2,12-bis-(tetrahydro-pyran-2-yloxy)-tridecan-7-one

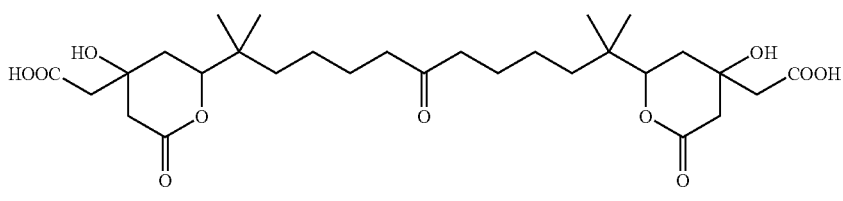

II-60

{2-(11-(4-Carboxymethyl-4-hydroxy-6-oxo-tetrahydro-pyran-2-yl)-1,1,11-
trimethyl-6-oxo-dodecyl]-4-hydroxy-
6-oxo-tetrahydro-pyran-4-yl}-acetic acid

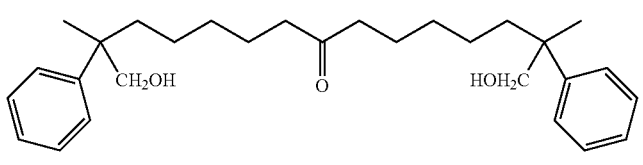

IIa-1

1,15-Dihydro-cy-2,14-dimethyl-2,14-diphenyl-pentadecan-8-one

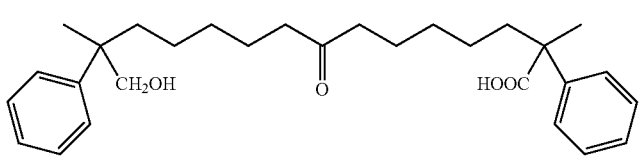

IIa-2

15-Hydroxy-2,14-dimethyl-8-oxo-2,14-diphenyl-pentadecanoic acid

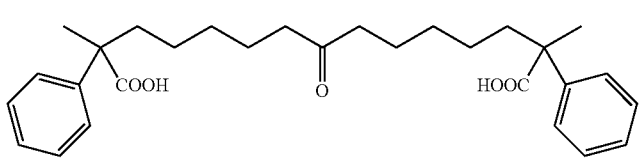

IIa-3

2,14-Dimethyl-8-oxo-2,14-diphenyl-pentadecanedioic acid

TABLE 1-continued
Compounds of the Invention
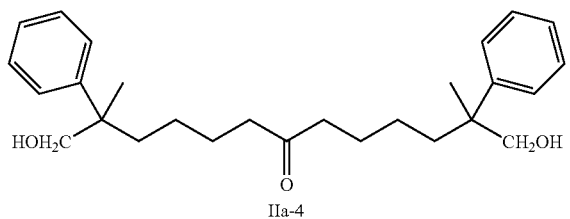
IIa-4
1,13-Dihydroxy-2,12-dimethyl-2,12-diphenyl-tridecan-7-one
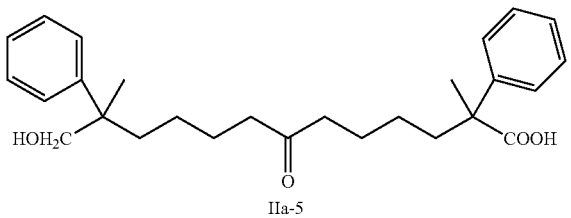
IIa-5
13-Hydroxy-2,12-dimethyl-7-oxo-2,12-diphenyl-tridecanoic acid
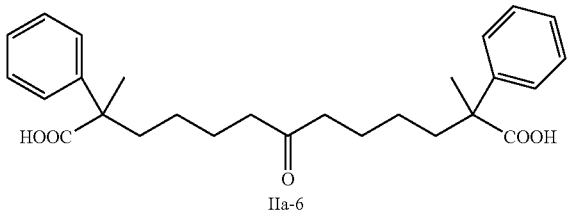
IIa-6
2,12-Dimethyl-7-oxo-2,12-diphenyl-tridecanedioic acid
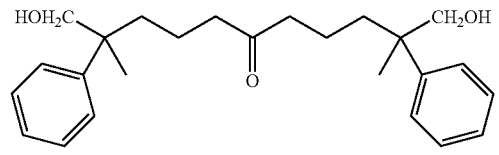
IIa-7
1,11-Dihydroxy-2,10-dimethyl-2,10-diphenyl-undecan-6-one
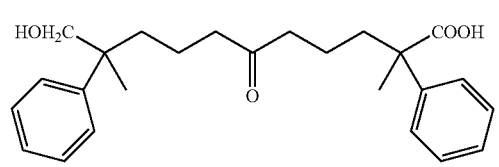
IIa-8
11-Hydroxy-2,10-dimethyl-6-oxo-2,10-diphenyl-undecanoic acid
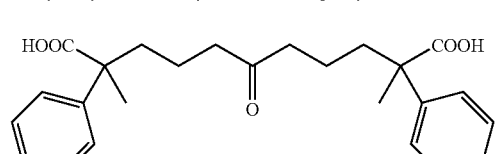
II-a9
2,10-Dimethyl-6-oxo-2,10-diphenyl-undecanedioic acid TABLE 1-continued Compounds of the Invention

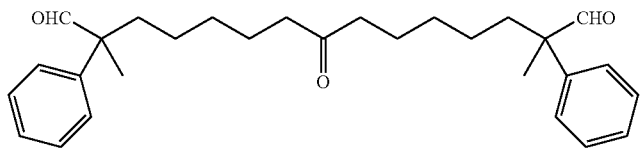

IIa-10

2,14-Dimethyl-8-oxo-2,14-diphenyl-pentadecanedial

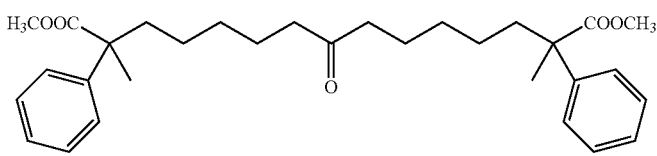

IIa-11

2,14-Dimethyl-8-oxo-2,14-diphenyl-pentadecanedioic acid dimethyl ester

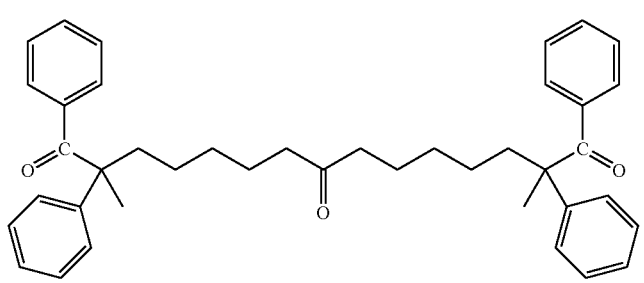

IIa-12

2,14-Dimethyl-1,2,14,15-tetraphenyl-pentadecane-1,8,15-trione

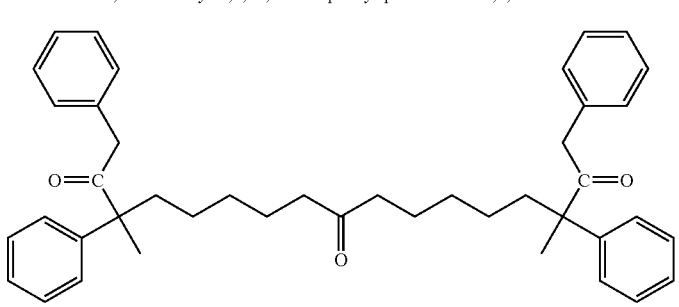

IIa-13

3,15-Dimethyl-1,3,15,17-tetraphenyl-heptadecane-2,9,16-trione

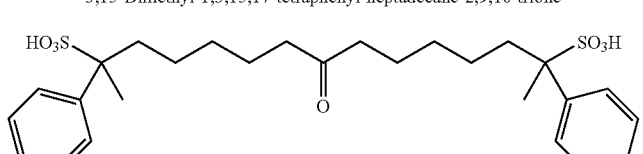

IIa-14

8-Oxo-2,14-diphenyl-pentadecane-2,14-disulfonic acid

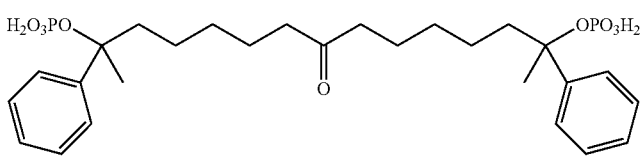

IIa-15

Phosphoric acid mono-(1-methyl-7-oxo-1,13-diphenyl-13-phosphonooxy-tetradecyl) ester TABLE 1-continued Compounds of the Invention

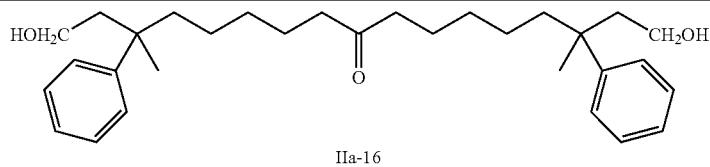

IIa-16

1,17-Dihydroxy-3,15-dimethyl-3,15-diphenyl-heptadecan-9-one

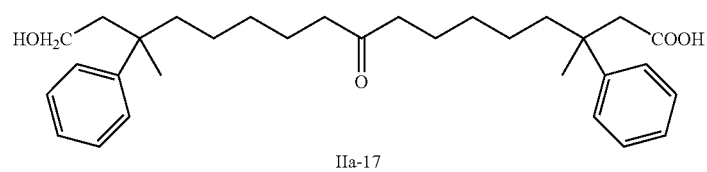

IIa-17

17-Hydroxy-3,15-dimethyl-9-oxo-3,15-diphenyl-heptadecanoic acid

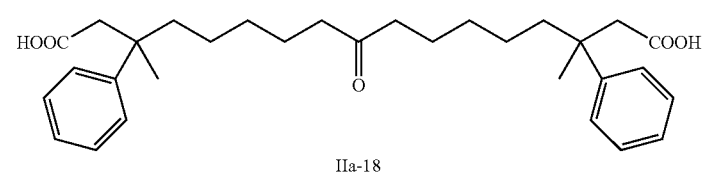

IIa-18

3,15-Dimethyl-9-oxo-3,15-diphenyl-heptadecanedioic acid

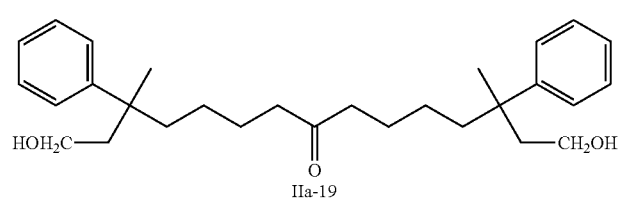

IIa-19

1,15-Dihydroxy-3,13-dimethyl-3,13-diphenyl-pentadecan-8-one

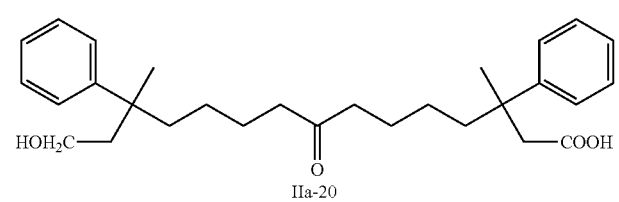

IIa-20

15-Hydroxy-3,13-dimethyl-8-oxo-3,13-diphenyl-pentadecanoic acid

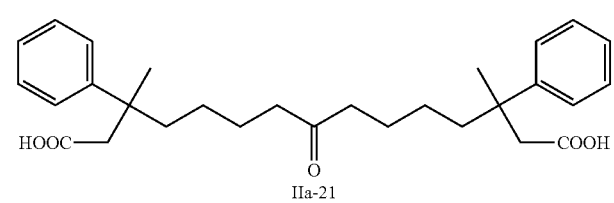

IIa-21

3,13-Dimethyl-8-oxo-3,13-diphenyl-pentadecanedioic acid

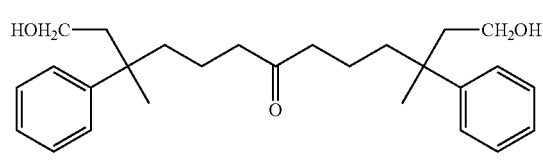

IIa-22

1,13-Dihydroxy-3,11-dimethyl-3,11-diphenyl-tridecan-7-one

TABLE 1-continued

Compounds of the Invention

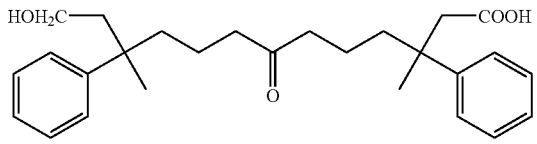

IIa-23

13-Hydroxy-3,11-dimethyl-7-oxo-3,11-diphenyl-tridecanoic acid

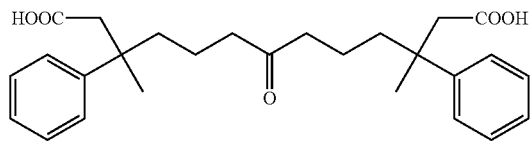

IIa-24

3,11-Dimethyl-7-oxo-3,11-diphenyl-tridecanedioic acid

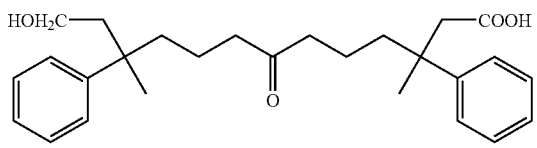

IIa-25

13-Hydroxy-3,11-dimethyl-7-oxo-3,11-diphenyl-tridecanoic acid

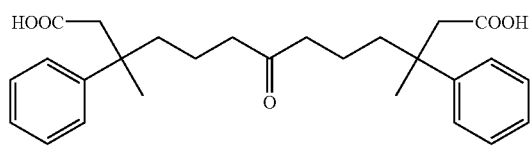

IIa-26

3,11-Dimethyl-7-oxo-3,11-diphenyl-tridecanedioic acid

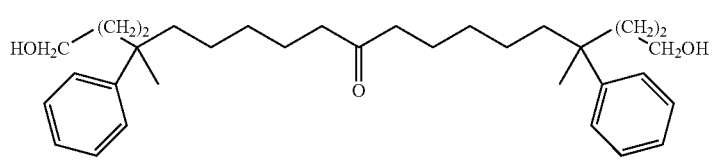

IIa-27

1,19-Dihydroxy-4,16-dimethyl-4,16-diphenyl-nonadecan-10-one

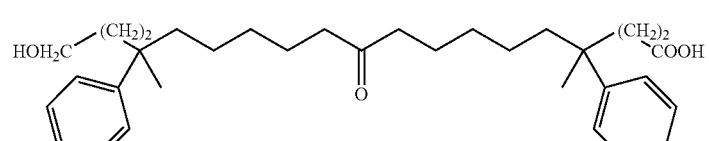

IIa-28

19-Hydroxy-4,16-dimethyl-10-oxo-4,16-diphenyl-nonadecanoic acid

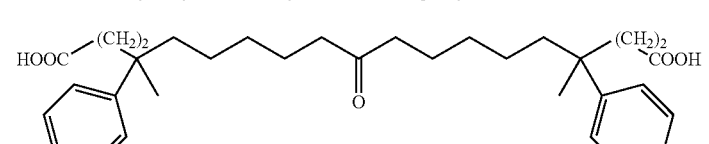

IIa-29

4,16-Dimethyl-10-oxo-4,16-diphenyl-nonadecanedioic acid

TABLE 1-continued
Compounds of the Invention
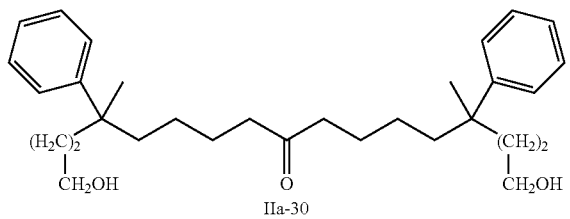
IIa-30
1,17-Dihydroxy-4,14-dimethyl-4,14-diphenyl-heptadecan-9-one
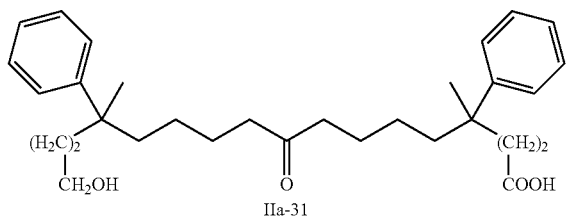
IIa-31
17-Hydroxy-4,14-dimethyl-9-oxo-4,14-diphenyl-heptadecanoic acid
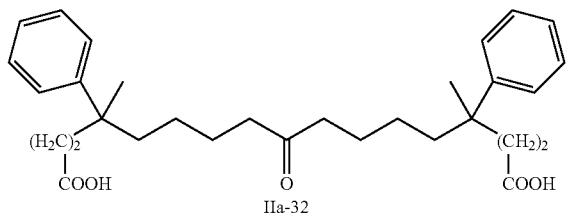
IIa-32
4,14-Dimethyl-9-oxo-4,14-diphenyl-heptadecanedioic acid
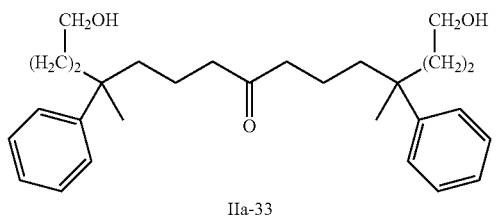
IIa-33
1,15-Dihydroxy-4,12-dimethyl-4,12-diphenyl-pentadecan-8-one
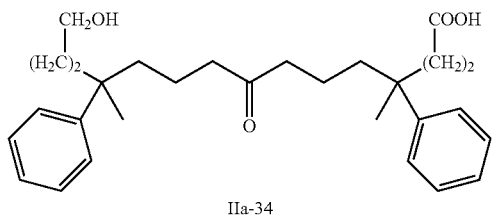
IIa-34
15-Hydroxy-4,12-dimethyl-8-oxo-4,12-diphenyl-pentadecanoic acid
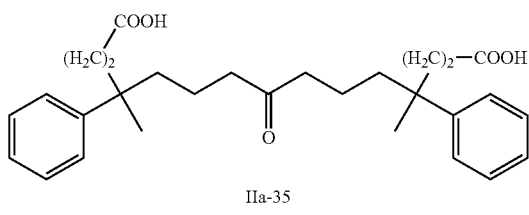
IIa-35
4,12-Dimethyl-8-oxo-4,12-diphenyl-pentadecanedioic acid TABLE 1-continued Compounds of the Invention

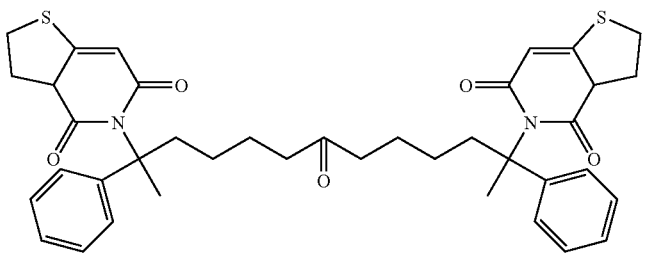

IIa-36

2,12-Bis-(4,6 dioxo-2,3,3a,6-tetrahydro-4H-thieno[3,2-c]pyridin-5-yl)-2,12-diphenyl-tridecan-7-one

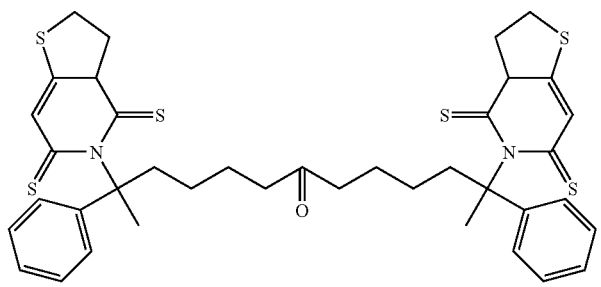

IIa-37

2,12-Bis-(4,6-dithioxo-2,3,3a,6-tehydro-4H-thieno[3,2-c]pyridn-5-yl)-2,12-diphenyl-tridecan-7-one

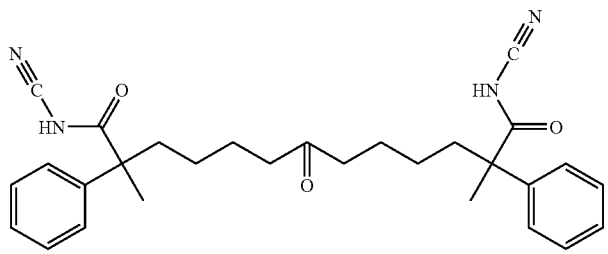

IIa-38

2,12-Dimethyl-2,12-diphenyl-7-oxo-tridecanedioic acid bis-cyanoamide

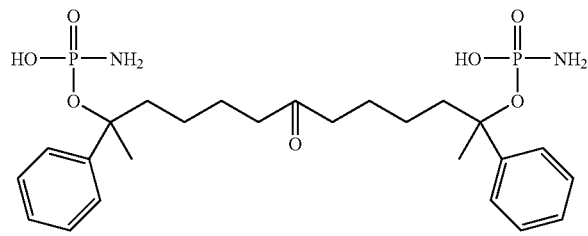

IIa-39

Phosphoramidic acid mono-[11-(amino-hydroxy-phosphorylaxy)-1-methyl-6-oxo-1,11-diphenyl-dodecyl] ester

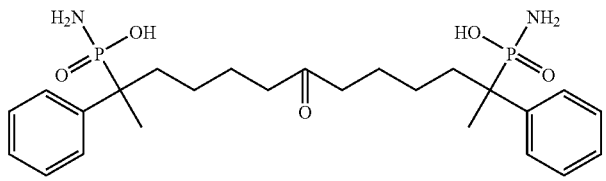

IIa-40

Phosphoramidic acid mono-[11(amino-hydroxy-phosphoryloxy)-1,11-dipehnyl-1-methyl-6-oxo-dodecyl] ester TABLE 1-continued
Compounds of the Invention
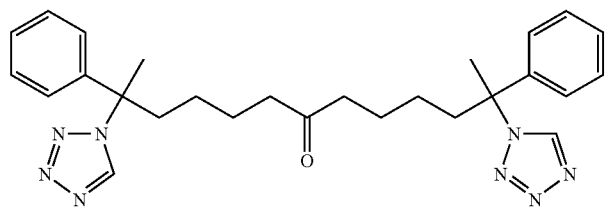
IIa-41
2,12-Diphenyl-2,12-bis-tetrazol-1-yl-tridecan-7-one
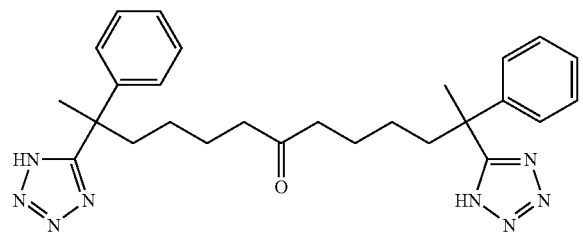
IIa-42
2,12-Diphenyl-2,12-bis-(1H-tetrazol-5-yl)-tridecan-7-one
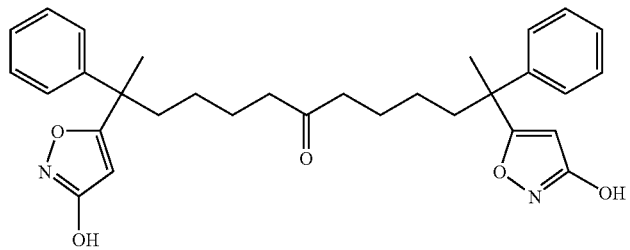
IIa-43
2,12-Bis-(3-hydroxy-isoxazol-5-yl)-2,12-diphenyl-tridecan-7-one
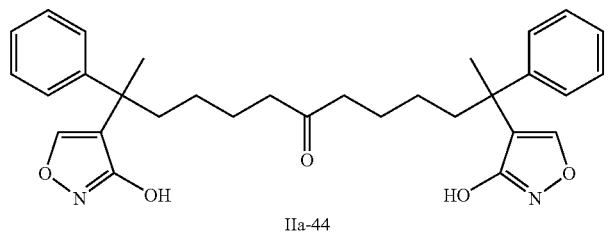
IIa-44
2,12-Bis-(3-hydroxy-isoxazol-4-yl)-2,12-diphenyl-tridecan-7-one
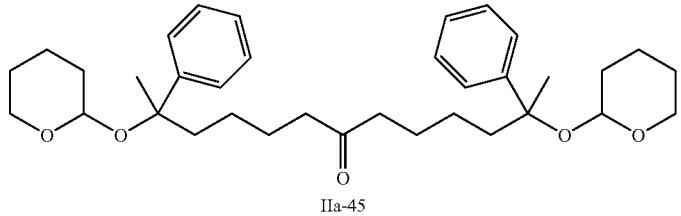
IIa-45
2,12-Diphenyl-2,12-bis-(tetrahydro-pyran-2-yloxy)-tridecan-7-one TABLE 1-continued Compounds of the Invention

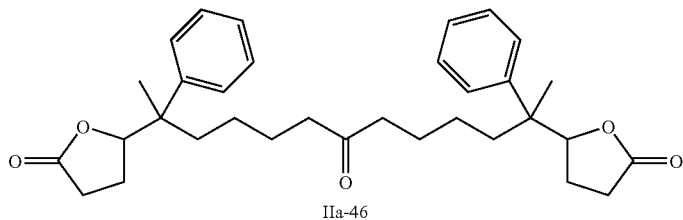

IIa-46

5-[11-(5-oxo-tetrahydro-furan-2-yl)-1,11-Diphenyl-1-methyl-6-oxo-dodecyl]-dihydro-furan-2-one

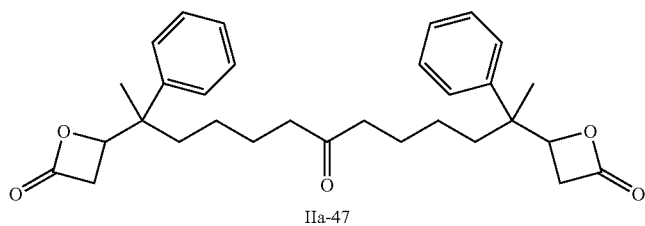

IIa-47

4[11-(4-oxo-oxetan-2-yl)-1,11-diphenyl-1-methyl-6-oxo-dodecyl]-oxetan-2-one

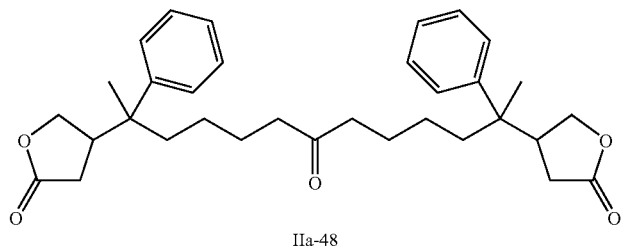

IIa-48

4-[11-(5-oxo-tetrahydro-furan-2-yl)-1,11-Diphenyl-1-methyl-6-oxo-dodecyl]-dihydro-furan-2-one

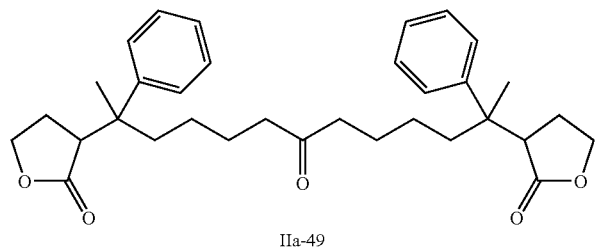

IIa-49

3-[11-(5-oxo-tetrahydro-furan-2-yl)-1,11-Diphenyl-1-methyl-6-oxo-dodecyl]-dihydro-furan-2-one

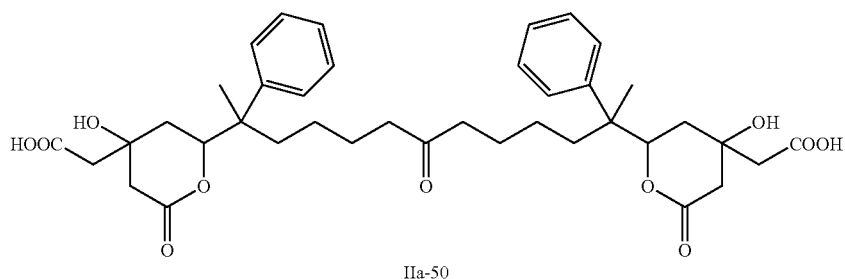

IIa-50

{2-[11-(4-Carboxymethyl-4-hydroxy-6-oxo-tetrahydro-pyran-2-yl)-1-methyl-6-oxo-1,11-diphenyl-dodecyl]-4-hydroxy-6-oxo-tetrahydro-pyran-4-yl}-acetic acid TABLE 1-continued Compounds of the Invention

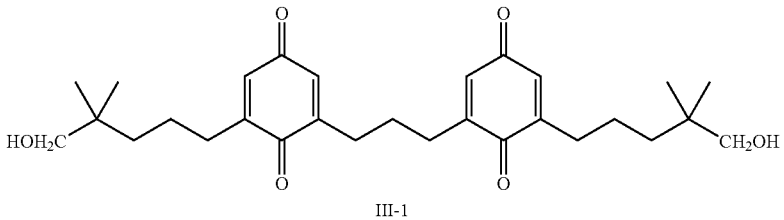

III-1

5-(6-(3-[6-(5-Hydroxy-4,4-dimethyl-pentyl)-1,4-dioxo-cyclohexadien-2-yl]-propyl}-1,4-
dioxo-cyclohexadien-2-yl)-2,2-dimethyl-pentan-1-ol

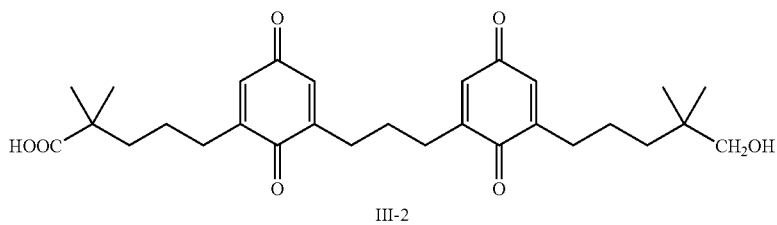

III-2

5-(6-{3-[6-(5-Hydroxy-4,4-dimethyl-pentyl)-1,4-dioxo-cyclohexadien-2-yl]-propyl)-1,4-
dioxo-cyclohexadien-2-yl)-2,2-dimethyl-pentanoic acid

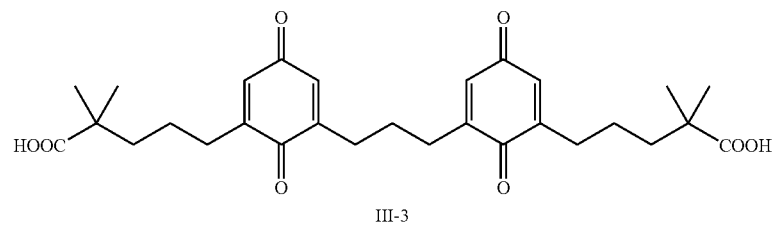

III-3

5-(6-{3-[6-(4-Carboxy-4-methyl-pentyl)-1,4-dioxo-cyclohexadien-2-yl]-propyl}-1,4-dioxo-
cyclohexadien-2-yl)-2,2-dimethyl-pentanoic acid

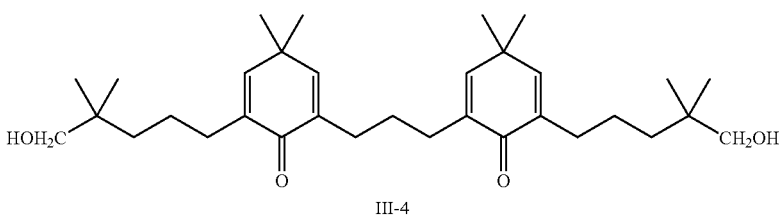

III-4

5-(6-{3-[6-(5-Hydroxy-4,4-dimethyl-pentyl)-4,4-dimethyl-1-oxo-cyclohexadien-2-yl]-
propyl}-4,4-dimethyl-1-oxo-cyclohexadien-2-yl)-2,2-dimethyl-pentan-1-ol

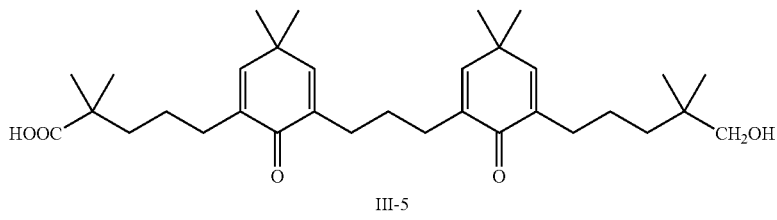

III-5

5-(6-{3-[6-(5-Hydroxy-4,4-dimethyl-pentyl)-4,4-dimethyl-1-oxo-cyclohexadien-2-yl]-
propyl}-4,4-dimethyl-1-oxo-cyclohexadien-2-yl)-2,2-dimethyl-pentanoic acid

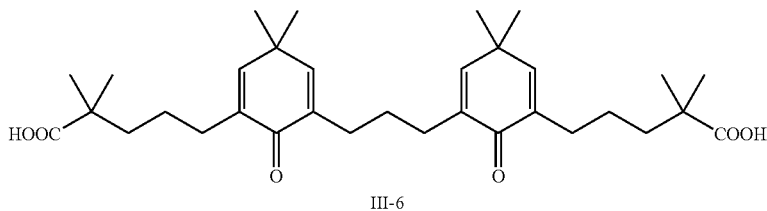

III-6

5-(6-{3-[6-(4-Carboxy-4-methyl-pentyl)-4,4-dimethyl-1-oxo-cyclohexadien-2-yl]-propyl}-
4,4-dimethyl-1-oxo-cyclohexadien-2-yl)-2,2-dimethyl-pentanoic acid

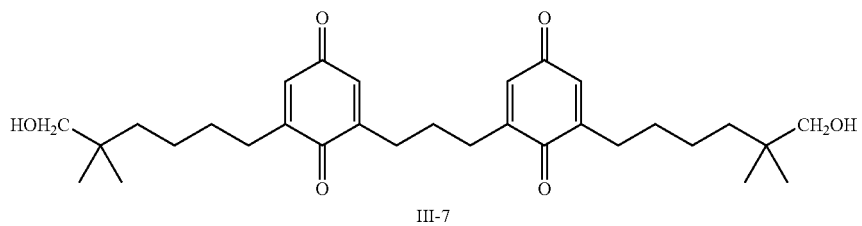

III-7

6-(6-{3-[6-(6-Hydroxy-5,5-dimethyl-hexyl)-1,4-dioxo-cyclohexadien-2-yl]-propyl}-1,4-
dioxo-cyclohexadien-2-yl)-2,2-dimethyl-hexan-1-ol

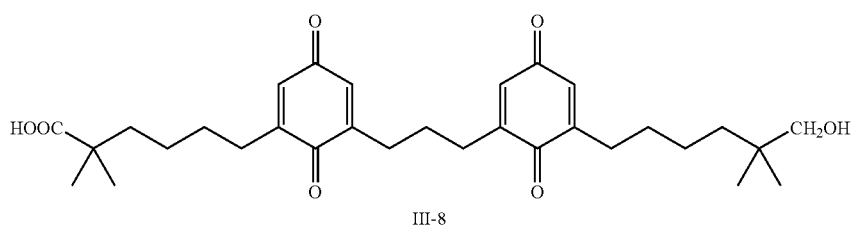

III-8

6-(6-{3-[6-(6-Hydroxy-5,5-dimethyl-hexyl)-1,4-dioxo-cyclohexadien-2-yl]-propyl}-1,4-
dioxo-cyclohexadien-2-yl)-2,2-dimethyl-hexanoic acid

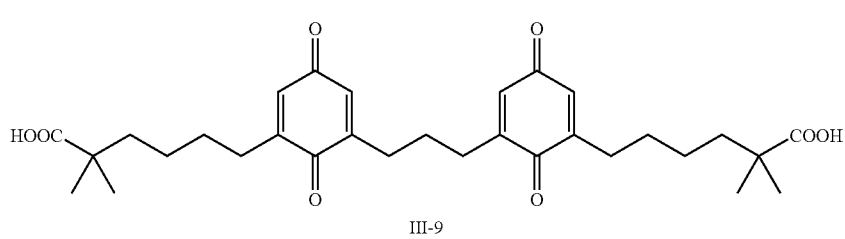

III-9

6-(6-{3-[6-(5-Carboxy-5-methyl-hexyl}-1,4-dioxo-cyclohexadien-2-yl]-propyl}-1,4-dioxo-
cyclohexadien-2-yl)-2,2-dimethyl-hexanoic acid

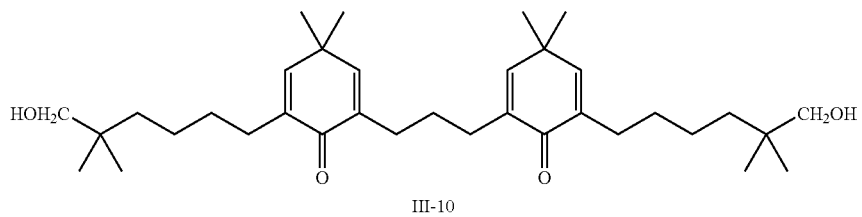

III-10

6-(6-{3-[6-(6-Hydroxy-5,5-dimethyl-hexyl)-4,4-dimethyl-1-oxo-cyclohexadien-2-yl]-
propyl}-4,4-dimethyl-1-oxo-cyclohexadien-2-yl)-2,2-dimethyl-hexan-1-ol TABLE 1-continued Compounds of the Invention

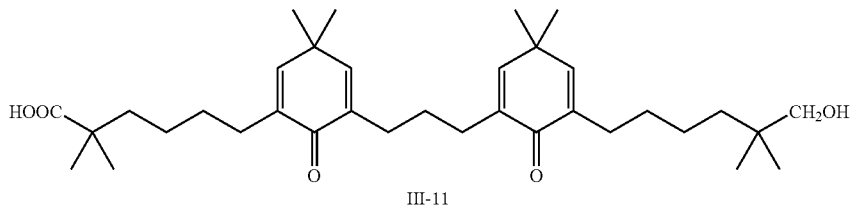

III-11

6-(6-{3-[6-(6-Hydroxy-5,5-dimethyl-hexyl)-4,4-dimethyl-1-oxo-cyclohexadien-2-yl]-propyl}-4,4-dimethyl-1-oxo-cyclohexadien-2-yl)-2,2-dimethyl-hexanoic acid

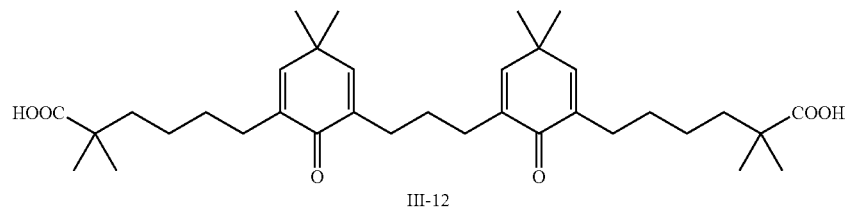

III-12

6-(6-{3-[6-(5-Carboxy-5-methyl-hexyl)-4,4-dimethyl-1-oxo-cyclohexadien-2-yl]-propyl}-4,4-dimethyl-1-oxo-cyclohexadien-2-yl)-2,2-dimethyl-hexanoic acid

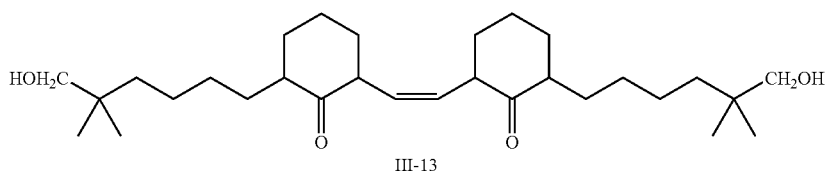

III-13

6-(6-{2-[6-(6-Hydroxy-5,5-dimethyl-hexyl)-1-oxo-cyclohexan-2-yl]-vinyl}-1-oxo-cyclohexan-2-yl)-2,2-dimethyl-hexan-1-ol

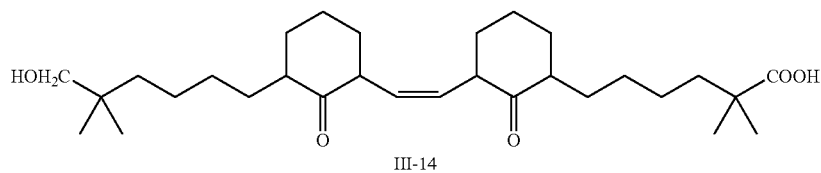

III-14

6-(6-{2-[6-(6-Hydroxy-5,5-dimethyl-hexyl)-1-oxo-cyclohexan-2-yl]-vinyl}-1-oxo-cyclohexan-2-yl)-2,2-dimethyl-hexanoic acid

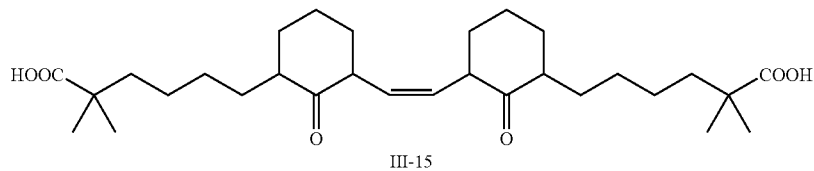

III-15

6-(6-{2-[6-(5-Carboxy-5-methyl-hexyl)-1-oxo-cyclohexan-2-yl]-vinyl}-1-oxo-cyclohexan-2-yl)-2,2-dimethyl-hexanoic acid

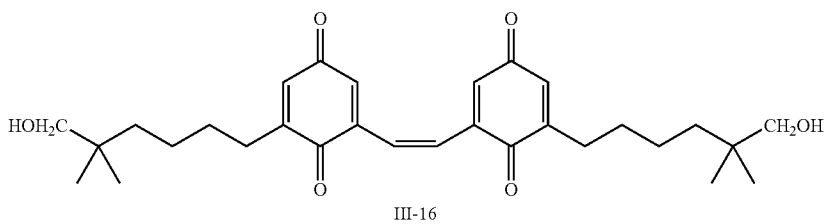

III-16

6-(6-{2-[6-(6-Hydroxy-5,5-dimethyl-hexyl)-1,4-dioxo-cyclohexadien-2-yl]-vinyl}-1,4-dioxo-cyclohexadien-2-yl)-2,2-dimethyl-hexan-1-ol TABLE 1-continued Compounds of the Invention

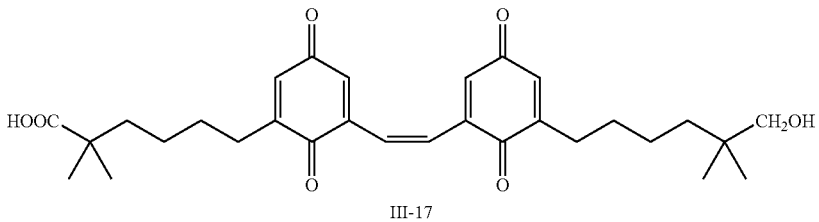

III-17

6-(6-{2-[6-(6-Hydroxy-5,5-dimethyl-hexyl)-1,4-dioxo-cyclohexadien-2-yl]-vinyl}-1,4-
dioxo-cyclohexadien-2-yl)-2,2-dimethyl-hexanoic acid

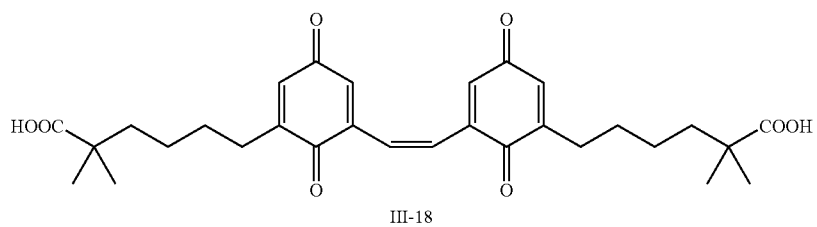

III-18

6-(6-{2-[6-(5-Carboxy-5-methyl-hexyl)-1,4-dioxo-cyclohexadien-2-yl]-vinyl}-1,4-dioxo-
cyclohexadien-2-yl)-2,2-dimethyl-hexanoic acid

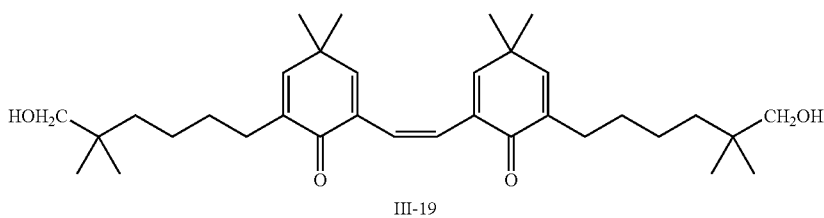

III-19

6-(6-{2-[6-(6-Hydroxy-5,5-dimethyl-hexyl)-4,4-dimethyl-1-oxo-cyclohexadien-2-yl]-
vinyl}-4,4-dimethyl-1-oxo-cyclohexadien-2-yl)-22-dimethyl-hexan-1-ol

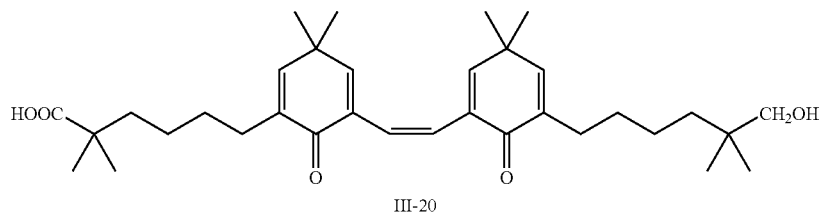

III-20

6-(6-{2-[6-(6-Hydroxy-5,5-dimethyl-hexyl)-4,4-dimethyl-1-oxo-cyclohexadien-2-yl]-
vinyl}-4,4-dimethyl-1-oxo-cyclohexadien-2-yl)-2,2-dimethyl-hexanoic acid

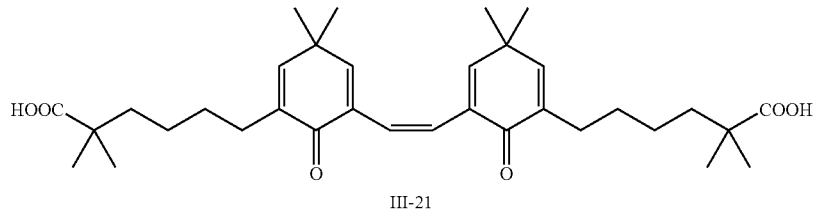

III-21

6-(6-{2-[6-(5-Carboxy-5-methyl-hexyl)-4,4-dimethyl-1-oxo-cyclohexadien-2-yl]-vinyl}-
4,4-dimethyl-1-oxo-cyclohexadien-2-yl)-2,2-dimethyl-hexanoic acid TABLE 1-continued Compounds of the Invention

III-22

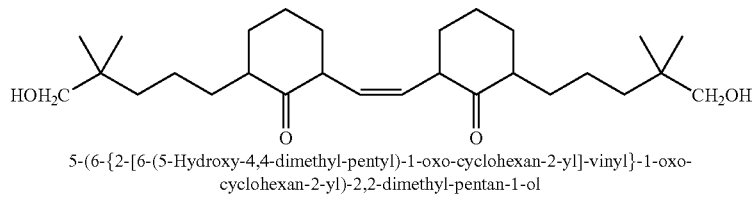

5-(6-{2-[6-(5-Hydroxy-4,4-dimethyl-pentyl)-1-oxo-cyclohexan-2-yl]-vinyl}-1-oxo-cyclohexan-2-yl)-2,2-dimethyl-pentan-1-ol

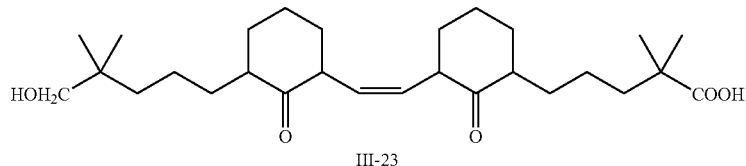

III-23

5-(6-{2-[6-(5-Hydroxy-4,4-dimethyl-pentyl)-1-oxo-cyclohexan-2-yl]-vinyl}-1-oxo-cyclohexan-2-yl)-2,2-dimethyl-pentanoic acid

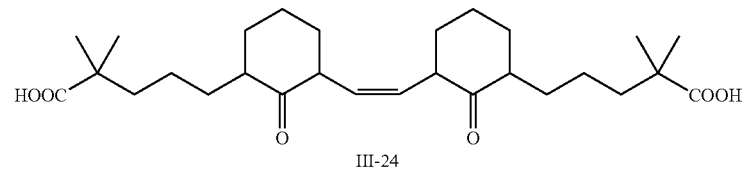

III-24

5-(6-{2-[6-(4-Carboxy-4-methyl-pentyl)-1-oxo-cyclohexan-2-yl]-vinyl}-1-oxo-cyclohexan-2-yl)-2,2-dimethyl-pentanoic acid

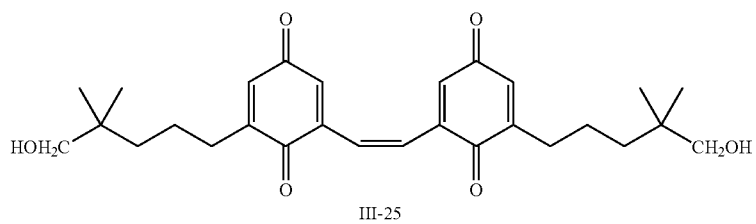

III-25

5-(6-{2-[6-(5-Hydroxy-4,4-dimethyl-pentyl)-1,4-dioxo-cyclohexadien-2-yl]-vinyl}-1,4-dioxo-cyclohexadien-2-yl)-2,2-dimethyl-pentan-1-ol

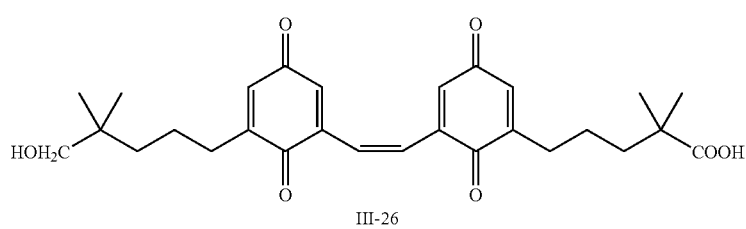

III-26

5-(6-{2-[6-(5-Hydroxy-4,4-dimethyl-pentyl)-1,4-dioxo-cyclohexadien-2-yl]-vinyl}-1,4-dioxo-cyclohexadien-2-yl)-2,2-dimethyl-pentanoic acid

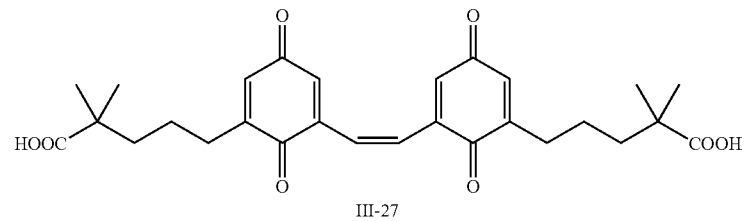

III-27

5-(6-{2-[6-(4-Carboxy-4-methyl-pentyl)-1,4-dioxo-cyclohexadien-2-yl]-vinyl}-1,4-dioxo-cyclohexadien-2-yl)-2,2-dimethyl-pentanoic acid TABLE 1-continued Compounds of the Invention

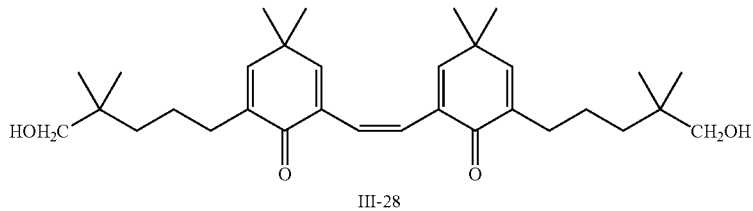

III-28

5-(6-{2-[6-(5-Hydroxy-4,4-dimethyl-pentyl)-4,4-dimethyl-1-oxo-cyclohexadien-2-yl]-
vinyl}-4,4-dimethyl-1-oxo-cyclohexadien-2-yl)-2,2-dimethyl-pentan-1-ol

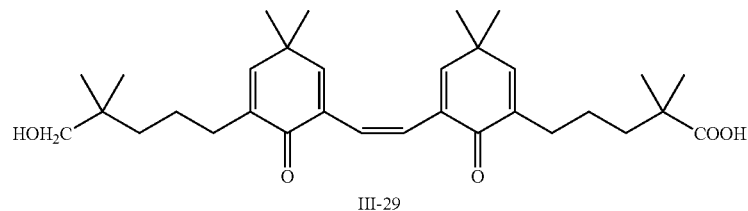

III-29

5-(6-{2-(6-(5-Hydroxy-4,4-dimethyl-pentyl)-4,4-dimethyl-1-oxo-cyclohexadien-2-yl]-
vinyl}-4,4-dimethyl-1-oxo-cyclohexadien-2-yl)-2,2-dimethyl-pentanoic acid

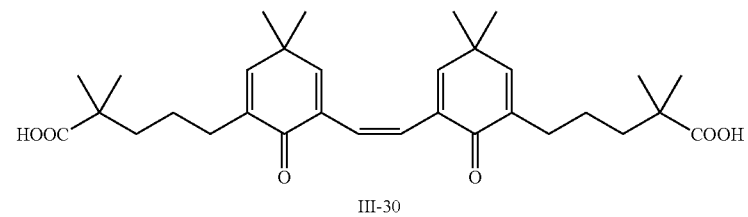

III-30

5-(6-{2-[6-(4-Carboxy-4-methyl-pentyl)-4,4-dimethyl-1-oxo-cyclohexadien-2-yl]-vinyl}-
4,4-dimethyl-1-oxo-cyclohexadien-2-yl)-2,2-dimethyl-pentanoic acid

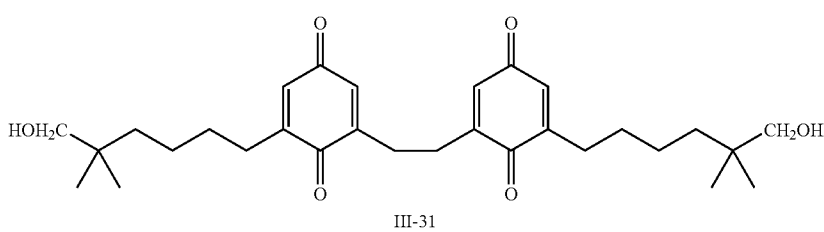

III-31

6-(6-{2-[6-(6-Hydroxy-5,5-dimethyl-hexyl)-1,4-dioxo-cyclohexadien-2-yl]-ethyl}-1,4-
dioxo-cyclohexadien-2-yl)-2,2-dimethyl-hexan-1-ol

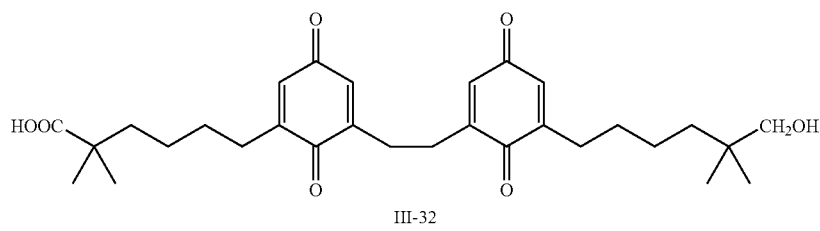

III-32

6-(6-{2-[6-(6-Hydroxy-5,5-dimethyl-hexyl)-1,4-dioxo-cyclohexadien-2-yl]-ethyl}-1,4-
dioxo-cyclohexadien-2-yl)-2,2-dimethyl-hexanoic acid TABLE 1-continued Compounds of the Invention

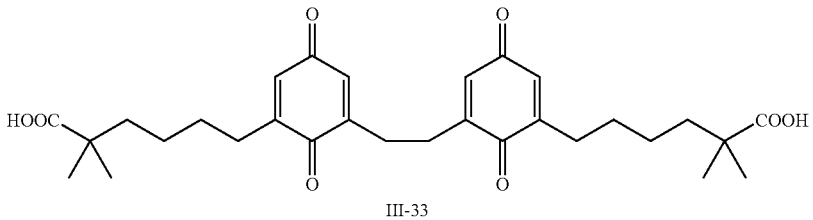

III-33

6-(6-{2-[6-(5-Carboxy-5-methyl-hexyl)-1,4-dioxo-cyclohexadien-2-yl]-ethyl}-1,4-dioxo-
cyclohexadien-2-yl)-2,2-dimethyl-hexanoic acid

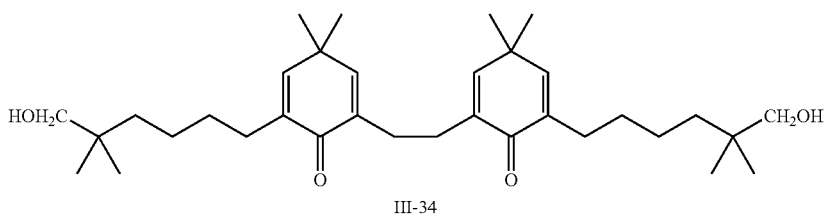

III-34

6-(6-{2-[6-(6-Hydroxy-5,5-dimethyl-hexyl)-4,4-dimehyl-1-oxo-cyclohexadien-2-yl]-ethyl}-
4,4-dimethyl-1-oxo-cyclohexadien-2-yl)-2,2-dimethyl-hexan-1-ol

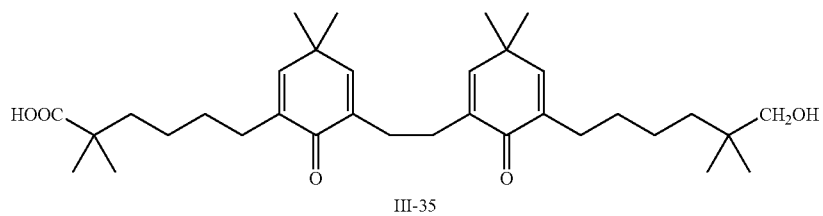

III-35

6-(6-{2-[6-(6-Hydroxy-5,5-dimethyl-hexyl)-4,4-dimethyl-1-oxo-cyclohexadien-2-yl]-ethyl}-
4,4-dimethyl-1-oxo-cyclohexadien-2-yl)-2,2-dimethyl-hexanoic acid

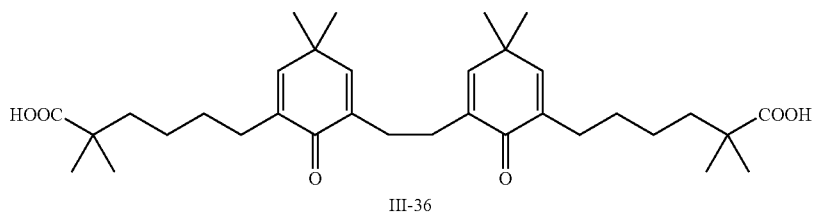

III-36

6-(6-{2-[6-(5-Carboxy-5-methyl-hexyl)-4,4-dimethyl-1-oxo-cyclohexadien-2-yl]-ethyl}-4,4-
dimethyl-1-oxo-cyclohexadien-2-yl)-2,2-dimethyl-hexanoic acid

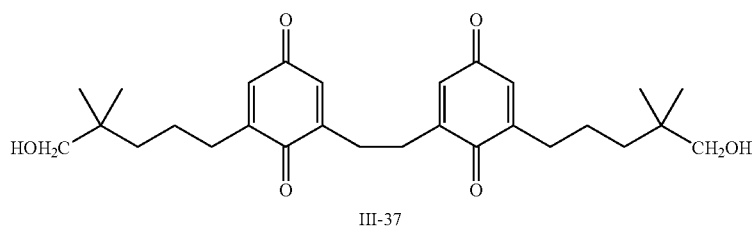

III-37

5-(6-{2-[6-(5-Hydroxy-4,4-dimethyl-pentyl)-1,4-dioxo-cyclohexadien-2-yl]-ethyl}-1,4-
dioxo-cyclohexadien-2-yl)-2,2-dimethyl-pentan-1-ol TABLE 1-continued Compounds of the Invention

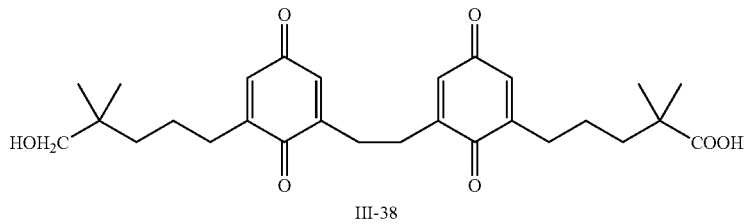

III-38

5-(6-{2-[6-(5-Hydroxy-4,4-dimethyl-pentyl)-1,4-dioxo-cyclohexadien-2-yl]-ethyl}-1,4-dioxo-cyclohexadien-2-yl)-2,2-dimethyl-pentanoic acid

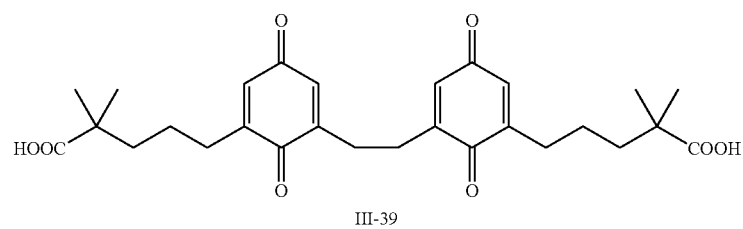

III-39

5-(6-{2-[6-(4-Carboxy-4-methyl-pentyl)-1,4-dioxo-cyclohexadien-2-yl]-ethyl}-1,4-dioxo-cyclohexadien-2-yl)-2,2-dimethyl-pentanoic acid

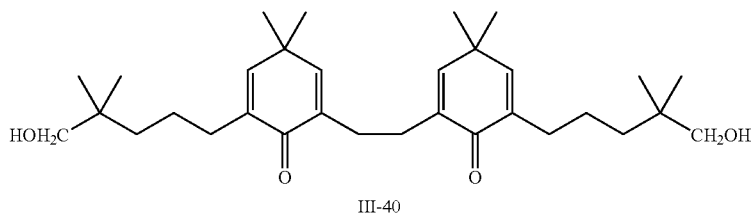

III-40

5-(6-{2-[6-(5-Hydroxy-4,4-dimethyl-pentyl)-4,4-dimethyl-1-oxo-cyclohexadien-2-yl]-ethyl}-4,4-dimethyl-1-oxo-cyclohexadien-2-yl)-2,2-dimethyl-pentan-1-ol

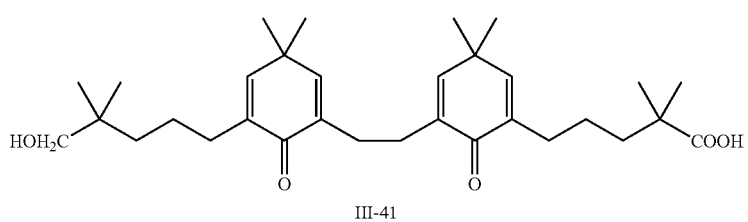

III-41

5-(6-{2-[6-(5-Hydroxy-4,4-dimethyl-pentyl)-4,4-dimethyl-1-oxo-cyclohexadien-2-yl]-ethyl}-4,4-dimethyl-1-oxo-cyclohexadien-2-yl)-2,2-dimethyl-pentanoic acid

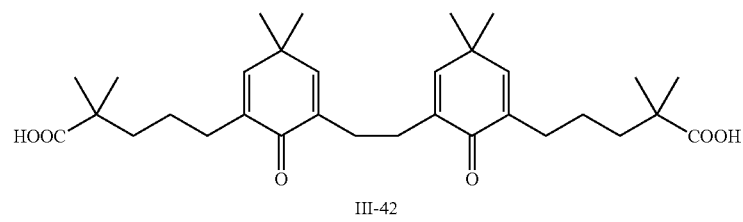

III-42

5-(6-{2-[6-(4-Carboxy-4-methyl-pentyl)-4,4-dimethyl-1-oxo-cyclohexadien-2-yl]ethyl}-4,4-dimethyl-1-oxo-cyclohexadien-2-yl)-2,2-dimethyl-pentanoic acid TABLE 1-continued Compounds of the Invention

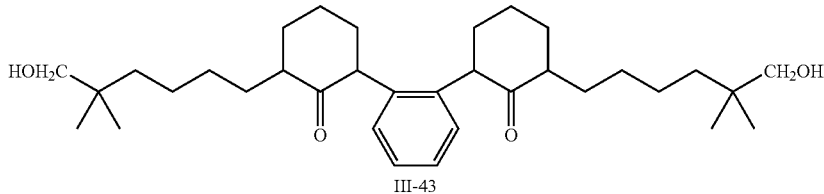

III-43

6-(6-{2-[6-(6-Hydroxy-5,5-dimethyl-hexyl)-1-oxo-cyclohexan-2-yl]-phenyl}-1-oxo-
cyclohexan-2-yl)-2,2-dimethyl-hexan-1-ol

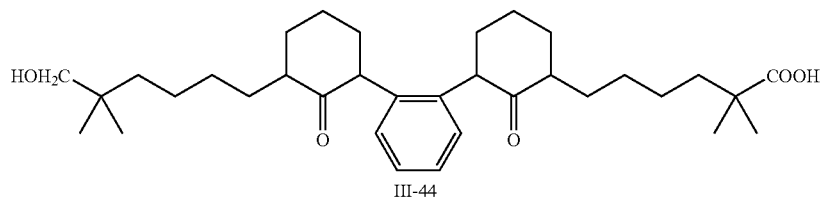

III-44

6-(6-{2-[6-(6-Hydroxy-5,5-dimethyl-hexyl)-1-oxo-cyclohexan-2-yl]-phenyl}-1-oxo
cyclohexan-2-yl)-2,2-dimethyl-hexanoic acid

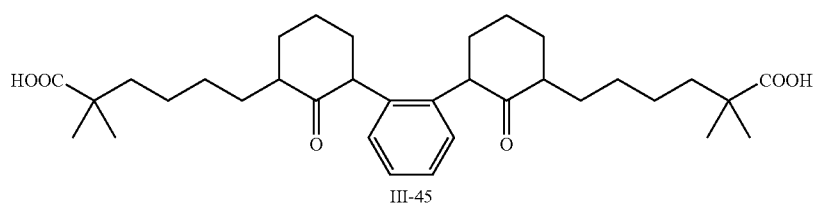

III-45

6-(6-{2-[6-(6-Carboxy-5,5-dimethyl-hexyl)-1-oxo-cyclohexan-2-yl]-phenyl}-1-oxo-
cyclohexan-2-yl)-2,2-dimethyl-hexanoic acid

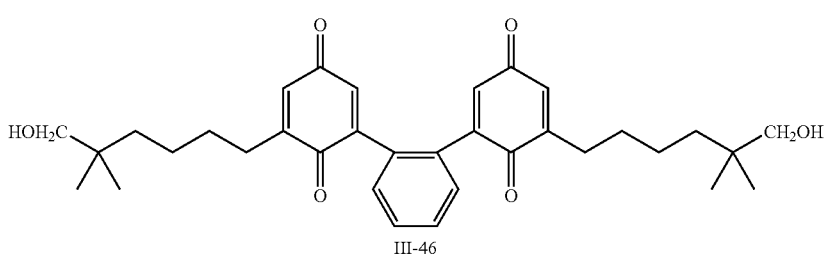

III-46

6-(6-{2-[6-(6-Hydroxy-5,5-dimethyl-hexyl)-1,4-dioxo-cyclohexadien-2-yl}-phenyl}-1-oxo-
cyclohexan-2-yl)-2,2-dimethyl-hexan-1-ol

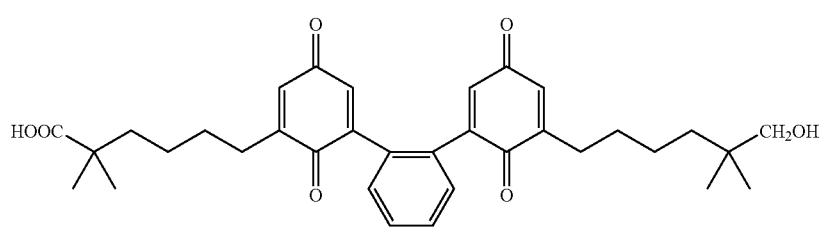

6-(6-{2-[6-(6-Hydroxy-5,5-dimethyl-hexyl)-1,4-dioxo-cyclohexadien-2-yl]-phenyl}-1-oxo-
cyclohexan-2-yl)-2,2-dimethyl-hexan-1-ol
III-47
6-(6-{2-[6-(6-Hydroxy-5,5-dimethyl-hexyl)-1,4-dioxocyclohexadien-2-yl]-phenyl}-1,4-dio TABLE 1-continued Compounds of the Invention

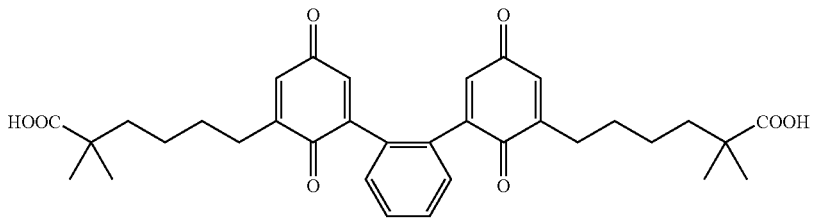

xo-cyclohexadien-2-yl)-2,2-dimethyl-hexanoic acid
III-48
6-(6-{2-[6-(5-Carboxy-5-methyl-hexyl)-1,4-dioxo-cyclohexadien-2-yl]-phenyl}-1,4-dioxo-c

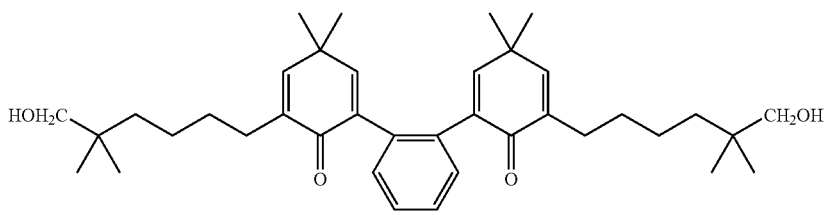

yclohexadien-2-yl)-2,2-dimethyl-hexanoic acid
III-49
6-(6-{2-[6-(6-Hydroxy-5,5-dimethyl-hexyl)-4,4-dimethyl-1-oxo-cyclohexadien-2-yl]-phenyl}-
4,4-dimethyl-1-oxo-cyclohexadien-2-yl)-2,2-dimethyl-hexan-1-ol

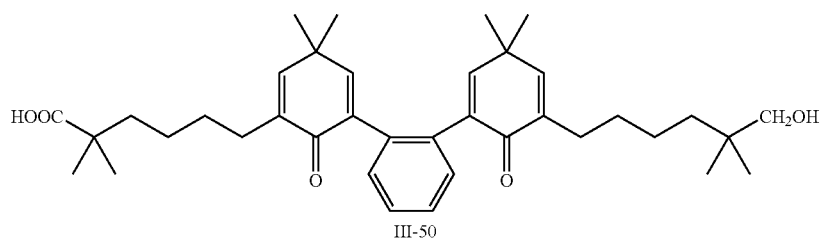

III-50

6-(6-{2-[6-(6-Hydroxy-5,5-dimethyl-hexyl)-4,4-dimethyl-1-oxo-cyclohexadien-2-yl]phenyl

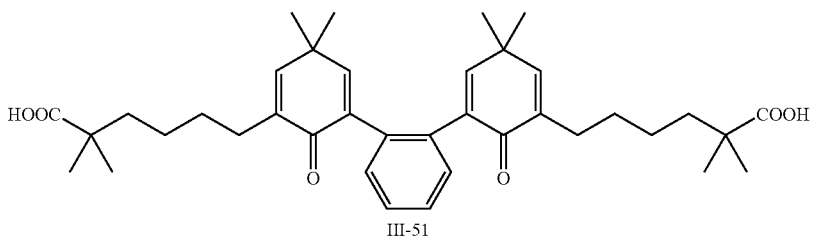

III-51

6-(6-{2-[6-(5-Carboxy-5-methyl-hexyl)-4,4-dimethyl-1-oxo-cyclohexadien-2-yl]-phenyl}-
4,4-dimethyl-1-oxo-cyclohexadien-2-yl)-2,2-dimethyl-hexanoic acid

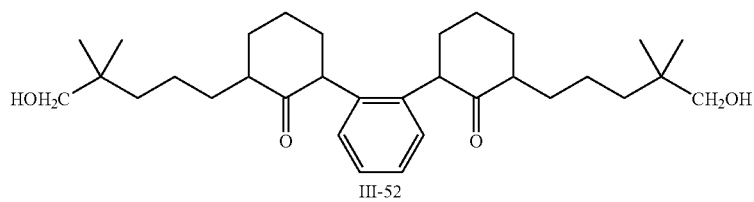

III-52

5-(6-{2-[6-(5-Hydroxy-4,4-dimethyl-pentyl)-1-oxo-cyclohexan-2-yl]-phenyl}-1-oxo-
cyclohexan-2-yl)-2,2-dimethyl-pentan-1-ol TABLE 1-continued Compounds of the Invention

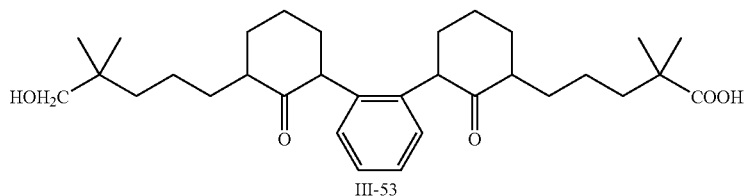

III-53

5-(6-{2-[6-(5-Hydroxy-4,4-dimethyl-pentyl)-1-oxo-cyclohexan-2-yl]-phenyl}-1-oxo-
cyclohexan-2-yl)-2,2-dimethyl-pentanoic acid

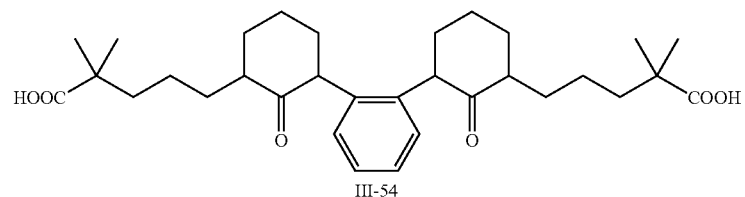

III-54

5-(6-{2-[6-(4-Carboxy-4-methyl-pentyl)-1-oxo-cyclohexan-2-yl]-phenyl}-1-oxo-
cyclohexan-2-yl)-2-2-dimethyl-pentanoic acid

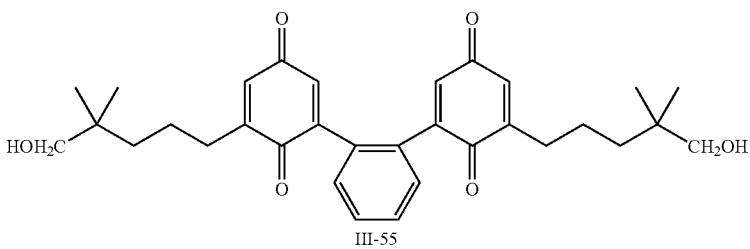

III-55

5-(6-{2-[6-(5-Hydroxy-4-methyl-pentyl)-1,4-dioxo-cyclohex-2-yl]-phenyl}-1,4-dioxo-
cyclohex-2-yl)-2,2-dimethyl-pentan-1-ol

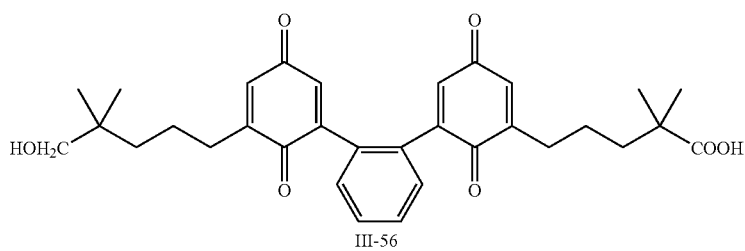

III-56

5-(6-{2-[6-(5-Hydroxy-4-methyl-pentyl)-1,4-dioxo-cyclohexadien-2-yl]-phenyl}-1,4-dioxo-
cyclohexadien-2-yl)-2,2-dimethyl-pentanoic acid

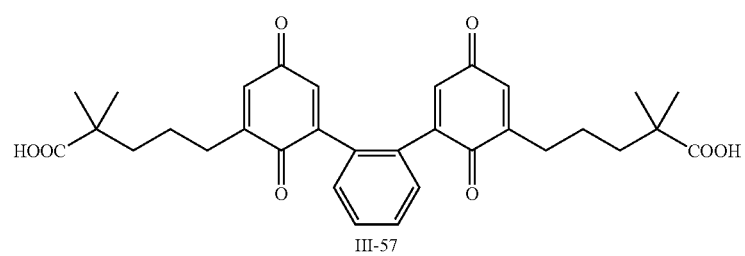

III-57

5-(6-{2-[6-(4-Carboxy-4-methyl-pentyl)-1,4-dioxo-cyclohexadien-2-yl]-phenyl}-1,4-dioxo-
cyclohexadien-2-yl)-2,2-dimethyl-pentanoic acid TABLE 1-continued Compounds of the Invention

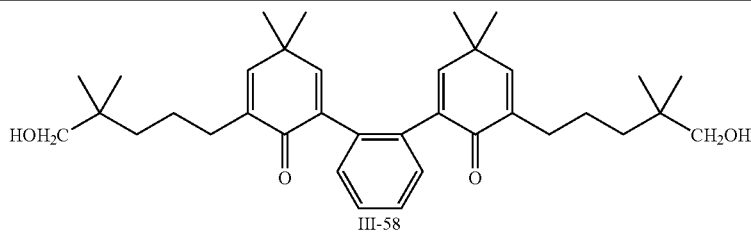

III-58

5-(6-{2-[6-(5-Hydroxy-4,4-dimethyl-pentyl)-4,4-dimehyl-1-oxo-cyclohexadien-2-yl]-
phenyl)-4,4-dimethyl-1-oxo-cyclohexadien-2-yl)-2,2-dimethyl-pentan-1-ol

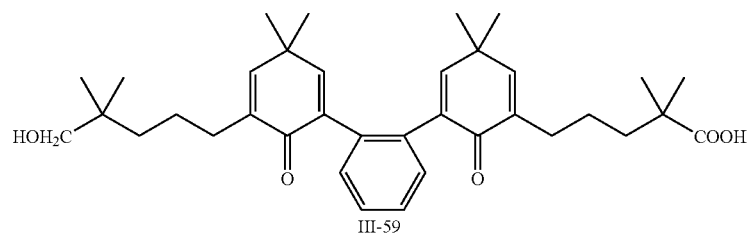

III-59

5-(6-{2-[6-(5-Hydroxy-4,4-dimethyl-pentyl)-4,4-dimethyl-1-oxo-cyclohexadien-2-yl]-
phenyl}-4,4-dimethyl-1-oxo-cyclohexadien-2-yl)-2,2-dimethyl-pentanoic acid

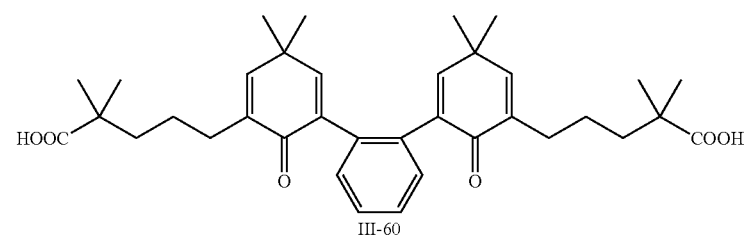

III-60

5-(6-{2-[6-(4-Carboxy-4-methyl-pentyl)-4,4-dimethyl-1-oxo-cyclohexadien-2-yl]-phenyl}-
4,4-dimethyl-1-oxo-cyclohexadien-2-yl)-2,2-dimethyl-pentanoic acid

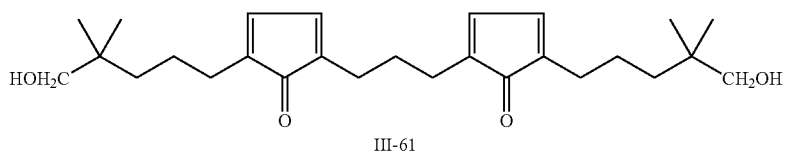

III-61

5-(5-{3-[5-(5-Hydroxy-4,4-dimethyl-pentyl)-1-oxo-cyclopentadien-2-yl]-propyl}-1-oxo-
cyclopentadien-2-yl)-2,2-dimethyl-pentan-1-ol

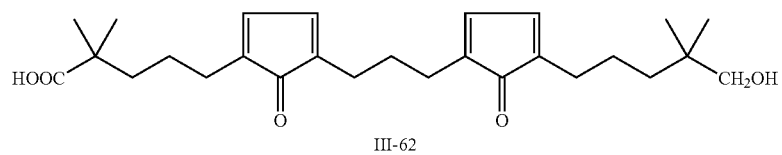

III-62

5-(5-{3-[5-(5-Hydroxy-4,4-dimethyl-pentyl)-1-oxo-cyclopentadien-2-yl]-propyl}-1-oxo-
cyclopentadien-2-yl)-2,2-dimethyl-pentanoic acid

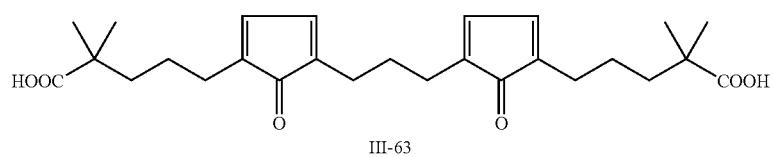

III-63

5-(5-{3-[5-(4-Carboxy-4-methyl-pentyl)-1-oxo-cyclopentadien-2-yl]-propyl}-1-oxo-
cyclopentadien-2-yl)-2,2-dimethyl-pentanoic acid TABLE 1-continued Compounds of the Invention

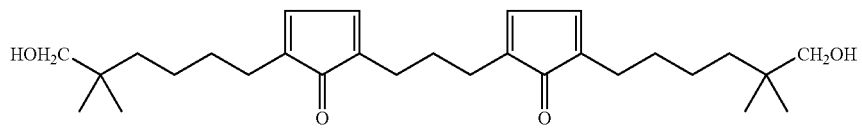

III-64

6-(5-{3-[5-(6-Hydroxy-5,5-dimethyl-hexyl)-1-oxo-cyclopentadien-2-yl]-propyl}-1-oxo-
cyclopentadien-2-yl)-2,2-dimethyl-hexan-1-ol

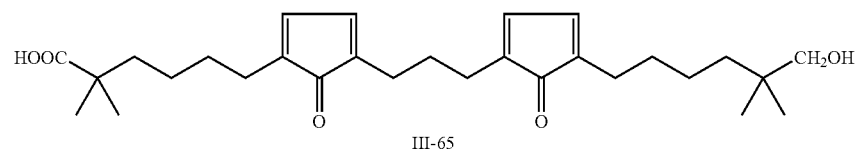

III-65

6-(5-{3-[5-(6-Hydroxy-5,5-dimethyl-hexyl)-1-oxo-cyclopentadien-2-yl]-propyl}-1-oxo-
cyclopentadien-2-yl)-2,2-dimethyl-hexanoic acid

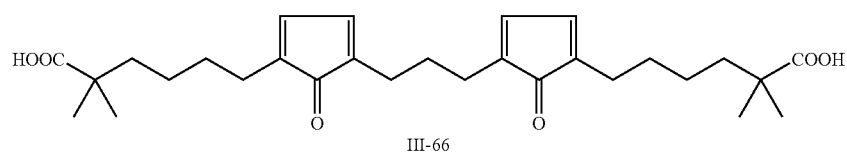

III-66

6-(5-{3-[5-(5-Carboxy-5-methyl-hexyl)-1-oxo-cyclopentadien-2-yl]-propyl}-1-oxo-
cyclopentadien-2-yl)-2,2-dimethyl-hexanoic acid

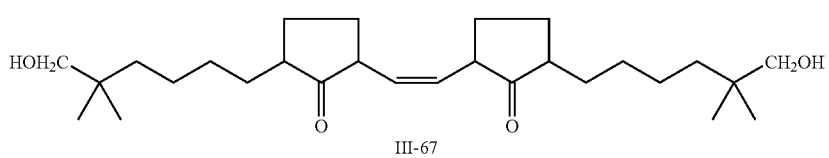

III-67

6-(5-{2-[5-(6-Hydroxy-5,5-dimethyl-hexyl)-1-oxo-cyclopentan-2-yl]-vinyl}-1-oxo-
cyclopentan-2-yl)-2,2-dimethyl-hexan-1-ol

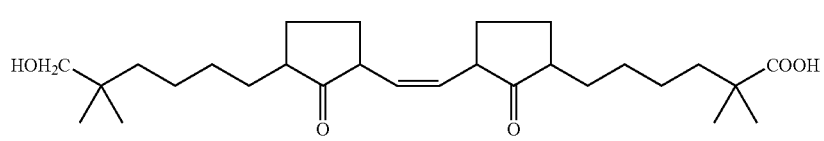

III-68

6-(5-{2-[5-(6-Hydroxy-5,5-dimethyl-hexyl)-1-oxo-cyclopentan-2-yl]-vinyl}-1-oxo-
cyclopentan-2-yl)-2,2-dimethyl-hexanoic acid

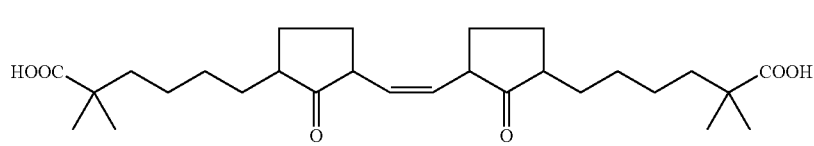

III-69

6-(5-{2-[5-(5-Carboxy-5-methyl-hexyl)-1-oxo-cyclopentan-2-yl]-vinyl}-1-oxo-cyclopentan-
2-yl)-2,2-dimethyl-hexanoic acid

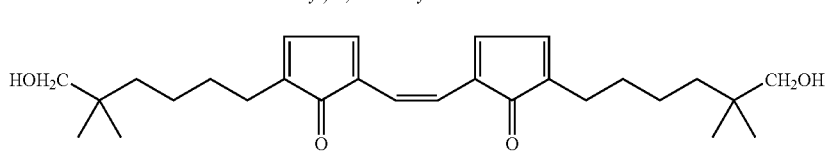

III-70

6-(5-{2-[5-(6-Hydroxy-5,5-dimethyl-hexyl)-1-oxo-cyclopentadien-2-yl]-vinyl}-1-oxo-
cyclopentadien-2-yl)-2,2-dimethyl-hexan-1-ol TABLE 1-continued Compounds of the Invention

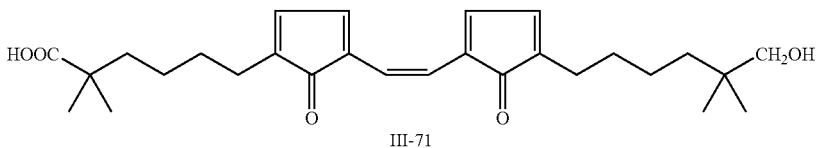
III-71

6-(5-{2-[5-(6-Hydroxy-5,5-dimethyl-hexyl)-1-oxo-cyclopentadien-2-yl]-vinyl}-1-oxo-
cyclopentadien-2-yl)-2,2-dimethyl-hexanoic acid

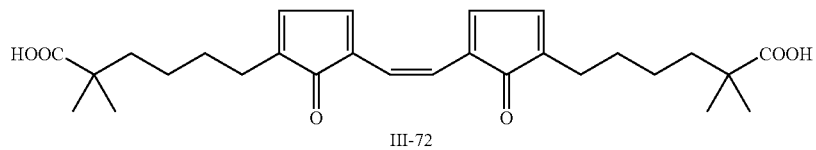
III-72

6-(5-{2-[5-(5-Carboxy-5-methyl-hexyl)-1-oxo-cyclopentadien-2-yl]-vinyl}-1-oxo-
cyclopentadien-2-yl)-2,2-dimethyl-hexanoic acid

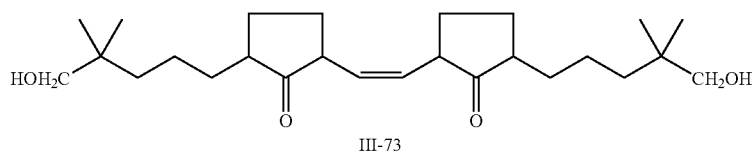
III-73

5-(5-{2-[5-(5-Hydroxy-4,4-dimethyl-pentyl)-1-oxo-cyclopentan-2-yl]-vinyl}-1-oxo-
cyclopentan-2-yl)-2,2-dimethyl-pentan-1-ol

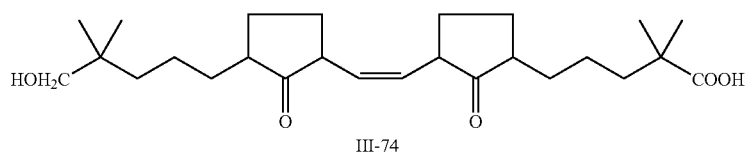
III-74

5-(5-{2-[5-(5-Hydroxy-4,4-dimethyl-pentyl)-1-oxo-cyclopentan-2-yl]-vinyl}-1-oxo-
cyclopentan-2-yl)-2,2-dimethyl-pentanoic acid

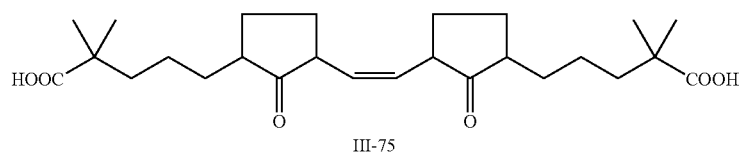
III-75

5-(5-{2-[5-(4-Carboxy-4-methyl-pentyl)-1-oxo-cyclopentan-2-yl]-vinyl}-1-oxo-
cyclopentan-2-yl)-2,2-dimethyl-pentarioic acid

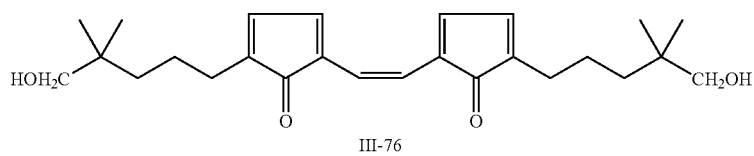
III-76

5-(5-{2-[5-(5-Hydroxy-4,4-dimethyl-pentyl)-1-oxo-cyclopentadien-2-yl]-vinyl}-1-oxo-
cyclopentadien-2-yl)-2,2-dimethyl-pentan-1-ol

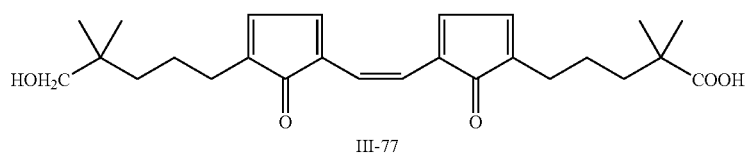
III-77

5-(5-{2-[5-(5-Hydroxy-4,4-dimethyl-pentyl)-1-oxo-cyclopentadien-2-yl]-vinyl}-1-oxo-
cyclopentadien-2-yl)-2,2-dimethyl-pentanoic acid TABLE 1-continued Compounds of the Invention

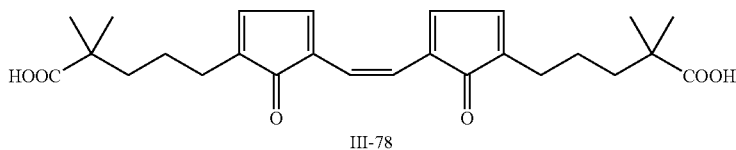
III-78

5-(5-{2-[5-(4-Carboxy-4-methyl-pentyl)-1-oxo-cyclopentadien-2-yl]-vinyl}-1-oxo-cyclopentadien-2-yl)-2,2-dimethyl-pentanoic acid

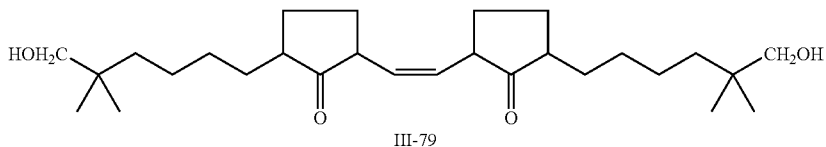
III-79

6-(5-{2-[5-(6-Hydroxy-5,5-dimethyl-hexyl)-1-oxo-cyclopentan-2-yl]-vinyl}-1-oxo-cyclopentan-2-yl)-2,2-dimethyl-hexan-1-ol

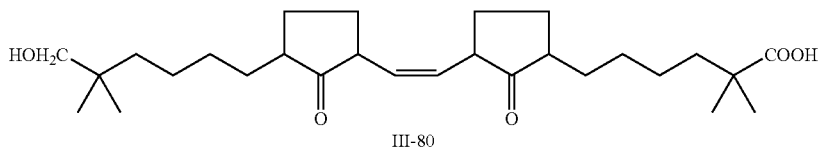
III-80

6-(5-{2-[5-(6-Hydroxy-5,5-dimethyl-hexyl)-1-oxo-cyclopentan-2-yl]-vinyl}-1-oxo-cyclopentan-2-yl)-2,2-dimethyl-hexanoic acid

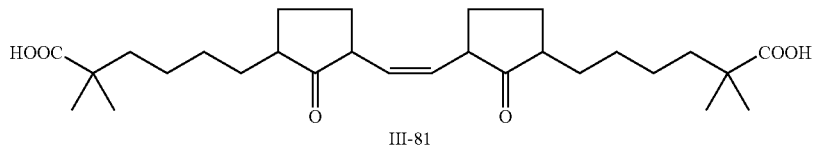
III-81

6-(5-{2-[5-(5-Carboxy-5-methyl-hexyl)-1-oxo-cyclopentan-2-yl]-vinyl}-1-oxo-cyclopentan-2-yl)-2,2-dimethyl-hexanoic acid

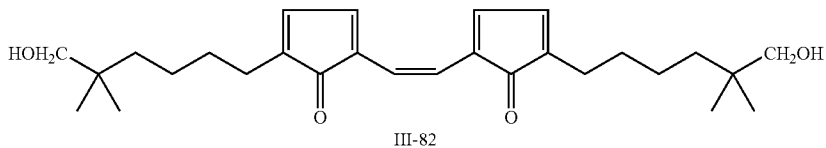
III-82

6-(5-{2-[5-(6-Hydroxy-5,5-dimethyl-hexyl)-1-oxo-cyclopentadien-2-yl]-vinyl}-1-oxo-cyclopentadien-2-yl)-2,2-dimethyl-hexan-1-ol

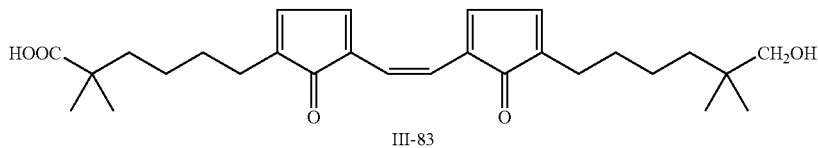
III-83

6-(5-{2-[5-(6-Hydroxy-5,5-dimethyl-hexyl)-1-oxo-cyclopentadien-2-yl]-vinyl}-1-oxo-cyclopentadien-2-yl)-2,2-dimethyl-hexanoic acid

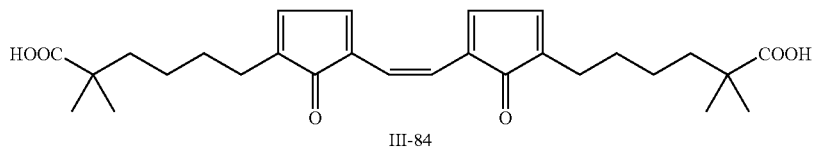
III-84

6-(5-{2-[5-(5-Carboxy-5-methyl-hexyl)-1-oxo-cyclopentadien-2-yl]-vinyl}-1-oxo-cyclopentadien-2-yl)-2,2-dimethyl-hexanoic acid TABLE 1-continued Compounds of the Invention

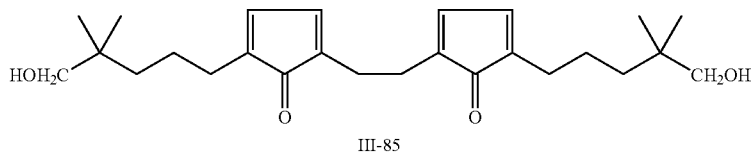

III-85

5-(5-{2-[5-(5-Hydroxy-4,4-dimethyl-pentyl)-1-oxo-cyclopentadien-2-yl]-ethyl}-1-oxo-
cyclopentadien-2-yl)-2,2-dimethyl-pentan-1-ol

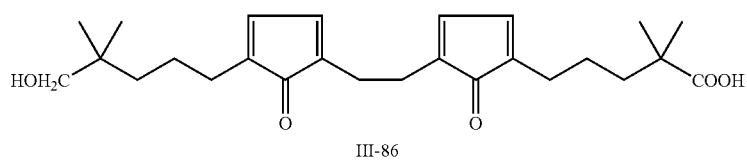

III-86

5-(5-{2-[5-(5-Hydroxy-4,4-dimethyl-pentyl)-1-oxo-cyclopentadien-2-yl]-ethyl}-1-oxo-
cyclopentadien-2-yl)-2,2-dimethyl-pentanoic acid

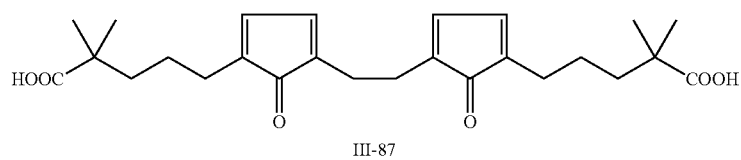

III-87

5-(5-{2-[5-(4-Carboxy-4-methyl-pentyl)-1-oxo-cyclopentadien-2-yl]-ethyl}-1-oxo-
cyclopentadien-2-yl)-2,2-dimethyl-pentanoic acid

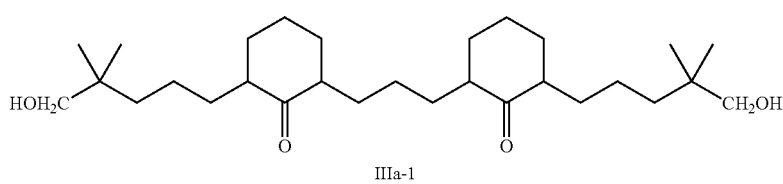

IIIa-1

5-(6-{3-[6-(5-Hydroxy-4,4-dimethyl-pentyl)-1-oxo-cyclohexan-2-yl]-propyl}-1-oxo-
cyclohexan-2-yl)-2,2-dimethyl-pentan-1-ol

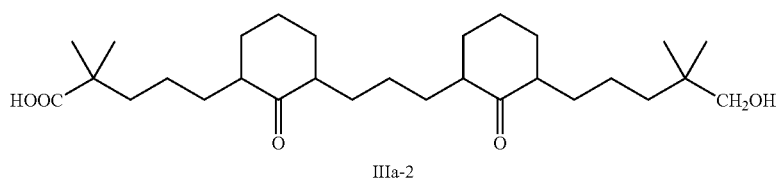

IIIa-2

5-(6-{3-[6-(4-Carboxy-4-methyl-pentyl)-1-oxo-cyclohexan-2-yl]-propyl}-1-oxo-
cyclohexan-2-yl)-2,2-dimethyl-pentanoic acid

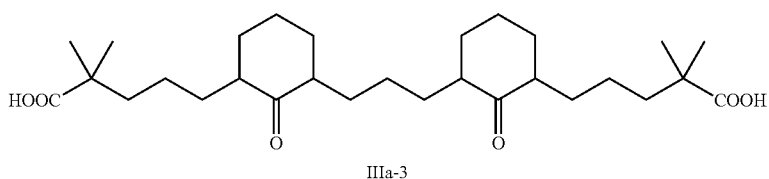

IIIa-3

5-(6-{3-[6-(4-Carboxy-4-methyl-pentyl)-1-oxo-cyclohexan-2-yl]-propyl}-1-oxo-
cyclohexan-2-yl)-2,2-dimethyl-pentanoic acid TABLE 1-continued Compounds of the Invention

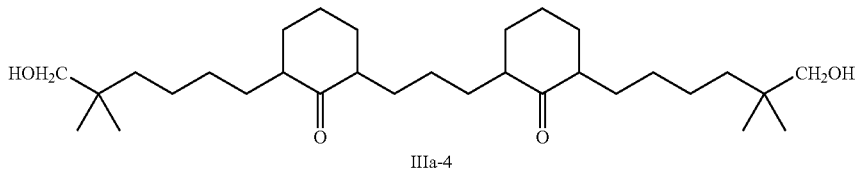

IIIa-4

6-(6-{3-[6-(6-Hydroxy-5,5-dimethyl-hexyl)-1-oxo-cyclohexan-2-yl]-propyl}-1-oxo-
cyclohexan-2-yl)-2,2-dimethyl-hexan-1-ol

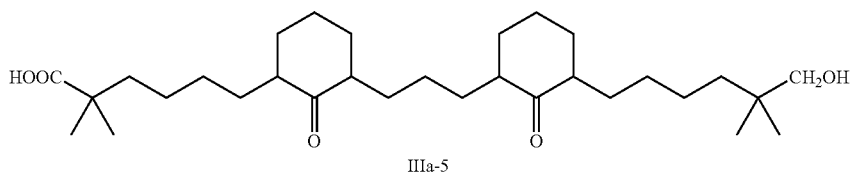

IIIa-5

6-(6-{3-[6-(6-Hydroxy-5,5-dimethyl-hexyl)-1-oxo-cyclohexan-2-yl]-propyl}-1-oxo-
cyclohexen-2-yl)-2,2-dimethyl-hexanoic acid

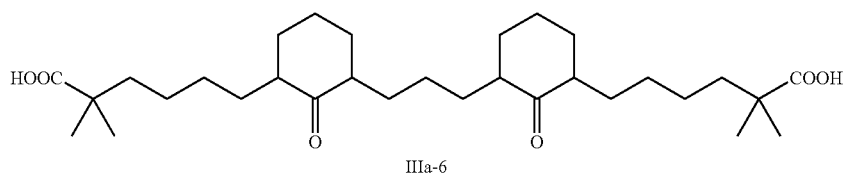

IIIa-6

6-(6-{3-[6-(5-Carboxy-5-methyl-hexyl)-1-oxo-cyclohoxan-2-yl]-propyl)-1-oxo-cyclohexan-
2-yl)-2,2-dimethyl-hexanoic acid

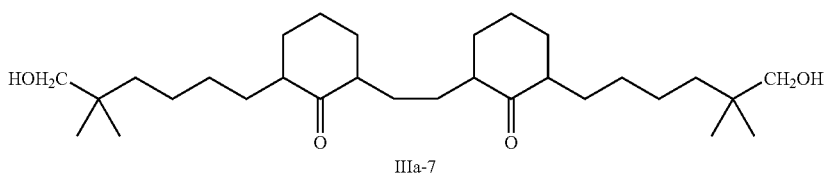

IIIa-7

6-(6-{2-[6-(6-Hydroxy-5,5-dimethyl-hexyl)-1-oxo-cyclohexan-2-yl]-ethyl}-1-oxo-
cyclohexan-2-yl)-2,2-dimethyl-hexan-1-ol

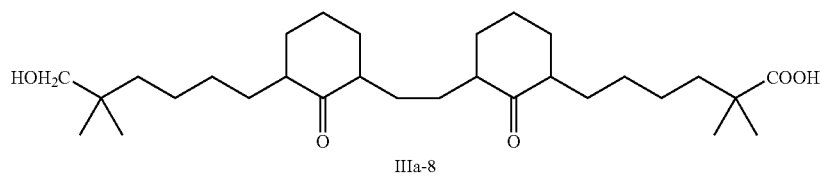

IIIa-8

6-(6-{2-[6-(6-Hydroxy-5,5-dimethyl-hexyl)-1-oxo-cyclohexan-2-yl]-ethyl}-1-oxo-
cyclohexan-2-yl)-2,2-dimethyl-hexanoic acid

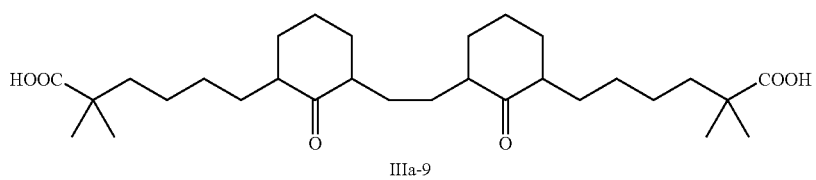

IIIa-9

6-(6-{2-[6-(5-Carboxy-5-methyl-hexyl)-1-oxo-cyclohexan-2-yl]-ethyl}-1-oxo-cyclohexan-
2-yl)-2,2-dimethyl-hexanoic acid TABLE 1-continued Compounds of the Invention

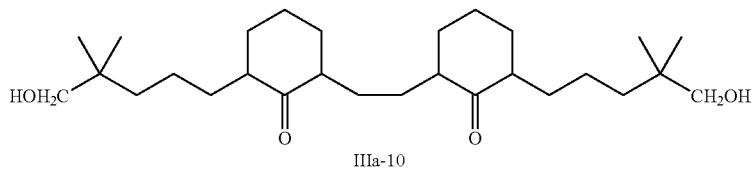

IIIa-10

5-(6-{2-[6-(6-Hydroxy-4,4-dimethyl-pentyl)-1-oxo-cyclohexan-2-yl]-ethyl}-1-oxo-cyclohexan-2-yl)-2,2-dimethyl-pentan-1-ol

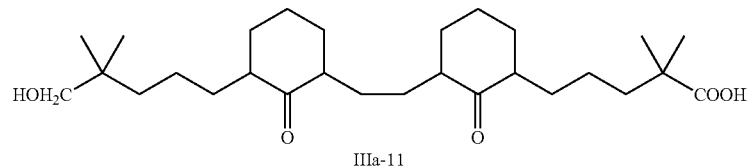

IIIa-11

S-(6-{2-[6-(5-Hydroxy-4,4-dimethyl-pentyl)-1-oxo-cyclohexan-2-yl]ethyl}-1-oxo-cyclohexan-2-yl)-2,2-dimethyl-pentanoic acid

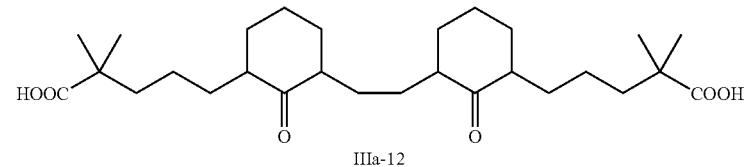

IIIa-12

5-(6-{2-[6-(4-Carboxy-4-methyl-pentyl)-1-oxo-cyclohexan-2-yl]-ethyl}-1-oxo-cyclohexan-2-yl)-2,2-dimethyl-pentanoic acid

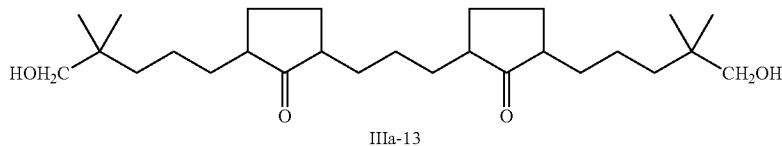

IIIa-13

5-(5-{3-[5-(5-Hydroxy-4,4-dimethyl-pentyl)-1-oxo-cyclopentan-2-yl]-propyl}-1-oxo-cyclopentan-2-yl)-2,2-dimethyl-pentan-1-ol

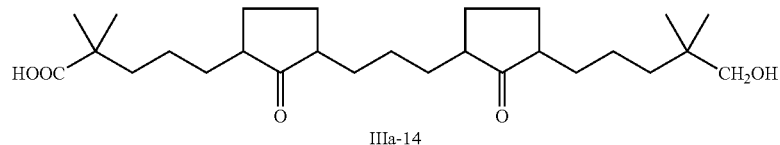

IIIa-14

5-(5-{3-[5-(5-Hydroxy-4,4-dimethyl-pentyl)-1-oxo-cyclopentan-2-yl]-propyl}-1-oxo-cyclopentan-2-yl)-2,2-dimethyl-pentanoic acid

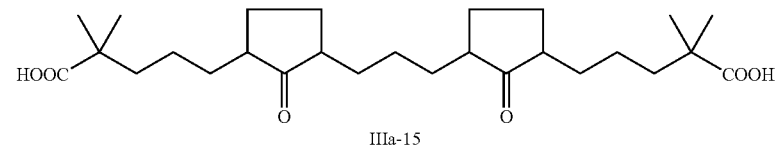

IIIa-15

5-(5-{3-[5-(4-Carboxy-4-methyl-pentyl)-1-oxo-cyclopentan-2-yl]propyl}-1-oxo-cyclopentan-2-yl)-2,2-dimethyl-pentanoic acid The compounds of the invention are useful in medical applications for treating or preventing cardiovascular diseases, dyslipidemias, dyslipoproteinemias, disorders of glucose metabolism, Alzheimer's Disease, Syndrome X, PPAR-associated disorders, septicemia, thrombotic disorders, obesity, pancreatitis, hypertension, renal diseases, cancer, inflammation, and impotence. As used herein, the phrase "compounds of the invention" means, collectively, the compounds of formulas I, II, and III and pharmaceutically acceptable salts, hydrates, solvates, clathrates, enantiomers, diasteriomers, racemates, or mixtures of stereoisomers thereof. Compounds of formula I encompass subgroup formulas Ia, Ib, and Ic. Compounds of formula II encompass subgroup formula IIa and compounds of formula III encompass subgroup of formula IIa. Thus, "compound of the invention" collectively means compound of formulas I, Ia, Ib, Ic, II, IIa, III, and IIIa and pharmaceutically acceptable salts, hydrates, solvates, clathrates, enantiomers, diasteriomers, racemates, or mixtures of stereoisomers thereof. The compounds of the invention are identified herein by their chemical structure and/or chemical name. Where a compound is referred to by both a chemical structure and a chemical name, and the chemical structure and chemical name conflict, the chemical structure is determinative of the compound's identity.

The present invention further provides pharmaceutical compositions comprising one or more compounds of the invention and a pharmaceutically acceptable vehicle, excipient, or diluent. A pharmaceutically acceptable vehicle can comprise a carrier, excipient, diluent, or a mixture thereof. These pharmaceutical compositions are useful for treating or preventing a disease or disorder including, but not limited to, aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, or enhancing bile production, or enhancing reverse lipid transport, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. These pharmaceutical composition are also useful for reducing the fat content of meat in livestock and reducing the cholesterol content of eggs.

The present invention provides a method for treating or preventing a aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, or enhancing bile production, or enhancing reverse lipid transport, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism, comprising administering to a patient in need of such treatment or prevention a therapeutically effective amount of a compound of the invention or a pharmaceutical composition comprising a compound of the invention and a pharmaceutically acceptable vehicle, excipient, or diluent.

The present invention further encompasses a method for reducing the fat content of meat in livestock comprising administering to livestock in need of such fat-content reduction a therapeutically effective amount of a compound of the invention or a pharmaceutical composition comprising a compound of the invention and a pharmaceutically acceptable vehicle, excipient, or diluent.

The invention also encompasses a method for inhibited hepatic fatty acid and sterol synthesis comprising administering to a patient in need thereof a therapeutically effective amount of a compound of the invention or a pharmaceutical composition comprising a compound of the invention and a pharmaceutically acceptable vehicle, excipient, or diluent.

The invention also encompasses a method of treating or preventing a disease or disorder that is capable of being treated or prevented by increasing HDL levels, which comprises administering to a patient in need of such treatment or prevention a therapeutically effective amount of a compound of the invention and a pharmaceutically acceptable vehicle, excipient, or diluent.

The invention also encompasses a method of treating or preventing a disease or disorder that is capable of being treated or prevented by lowering LDL levels, which comprises administering to such patient in need of such treatment or prevention a therapeutically effective amount of a compound of the invention and a pharmaceutically acceptable vehicle, excipient, or diluent.

The compounds of the invention favorably alter lipid metabolism in animal models of dyslipidemia at least in part by enhancing oxidation of fatty acids through the ACC/malonyl-CoA/CPT-I regulatory axis and therefore the invention also encompasses methods of treatment or prevention of metabolic syndrome disorders.

The present invention provides a method for reducing the cholesterol content of a fowl egg comprising administering to a fowl species a therapeutically effective amount of a compound of the invention or a pharmaceutical composition comprising a compound of the invention and a pharmaceutically acceptable vehicle, excipient, or diluent.

Thus, the compounds of the present invention are useful for the treatment of vascular disease, such as cardiovascular disease, stroke, and peripheral vascular disease; dyslipidemia; dyslipoproteinemia; a disorder of glucose metabolism; Alzheimer's Disease; Syndrome X; a peroxisome proliferator activated receptor-associated disorder; septicemia; a thrombotic disorder; obesity; pancreatitis; hypertension; renal disease; cancer; inflammation; inflammatory muscle diseases, such as polymyalgia rheumatica, polymyositis, and fibrositis; impotence; gastrointestinal disease; irritable bowel syndrome; inflammatory bowel disease; inflammatory disorders, such as asthma, vasculitis, ulcerative colitis, Crohn's disease, Kawasaki disease, Wegener's granulomatosis, (RA), systemic lupus erythematosus (SLE), multiple sclerosis (MS), and autoimmune chronic hepatitis; arthritis, such as rheumatoid arthritis, juvenile rheumatoid arthritis, and osteoarthritis; osteoporosis, soft tissue rheumatism, such as tendonitis; bursitis; autoimmune disease, such as systemic lupus and erythematosus; scleroderma; ankylosing spondylitis; gout; pseudogout; non-insulin dependent diabetes mellitus; polycystic ovarian disease; hyperlipidemias, such as familial hypercholesterolemia (FH), familial combined hyperlipidemia (FCH); lipoprotein lipase deficiencies, such as hypertriglyceridemia, hypoalphalipoproteinemia, and hypercholesterolemia; lipoprotein abnormalities associated with diabetes; lipoprotein abnormalities associated with obesity; and lipoprotein abnormalities associated with Alzheimer's Disease. The compounds and compositions of the invention are useful for treatment or prevention of high levels of blood triglycerides, high levels of low density lipoprotein cholesterol, high levels of apolipoprotein B, high levels of lipoprotein Lp(a) cholesterol, high levels of very low density lipoprotein cholesterol, high levels of fibrinogen, high levels of insulin, high levels of glucose, and low levels of high density lipoprotein cholesterol. The compounds and compositions of the invention also have utility for treatment of NIDDM without increasing weight gain. The sulfoxide and bis-sulfoxide compounds and compositions of the invention may also be used to reduce the fat content of meat in livestock and reduce the cholesterol content of eggs.

The present invention may be understood more fully by reference to the detailed description and examples, which are intended to exemplify non-limiting embodiments of the invention.

3.1. BRIEF DESCRIPTION OF THE DRAWINGS

Various aspects of the invention can be understood with reference to the figures described below:

Figure 1:
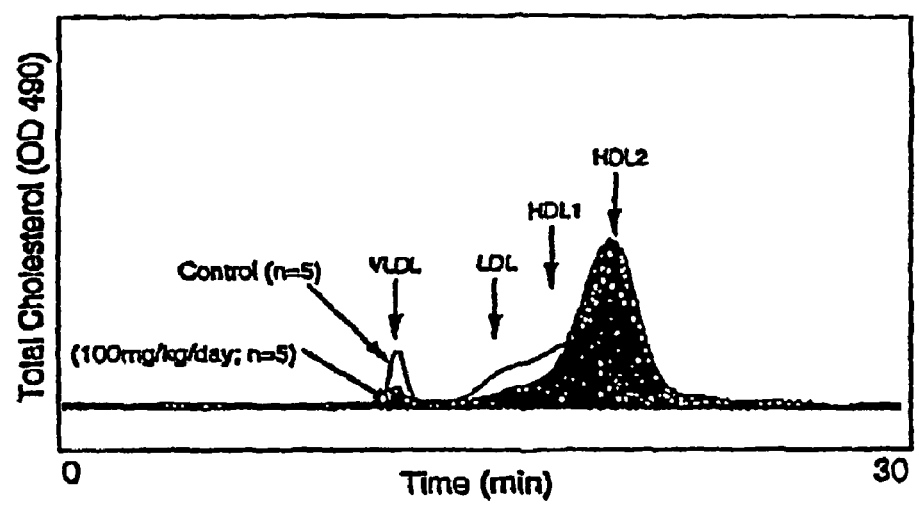
FIG. 1 illustrates the effect of one week of daily oral gavage treatment on lipoprotein total cholesterol in chow-fed male Sprague-Dawly rats.
Figure 2:
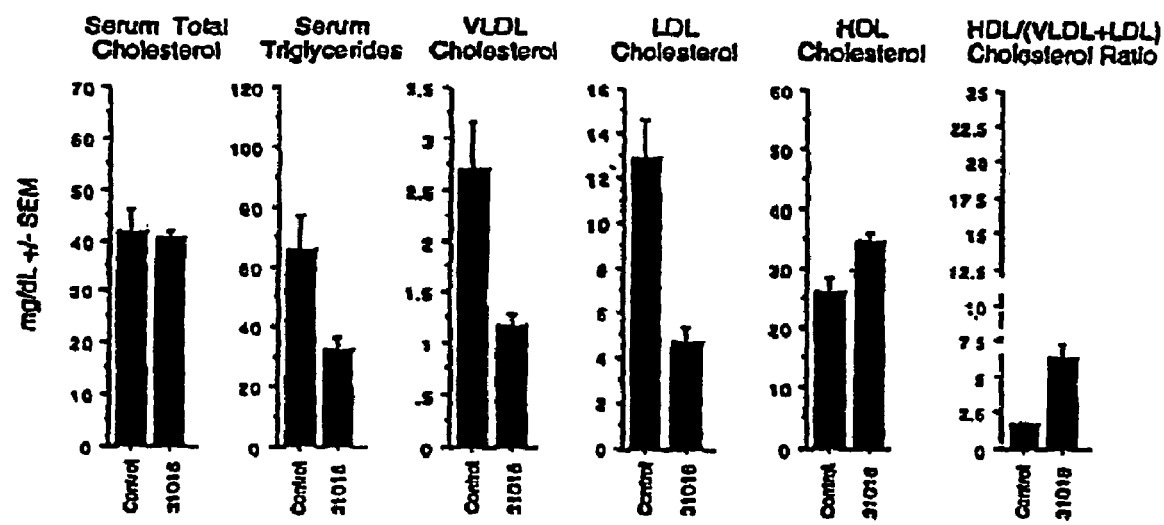
FIG. 2 illustrates the effect of one week of daily oral gavage treatment on serum lipids in chow-fed male Sprague-Dawly rats.
Figure 3:
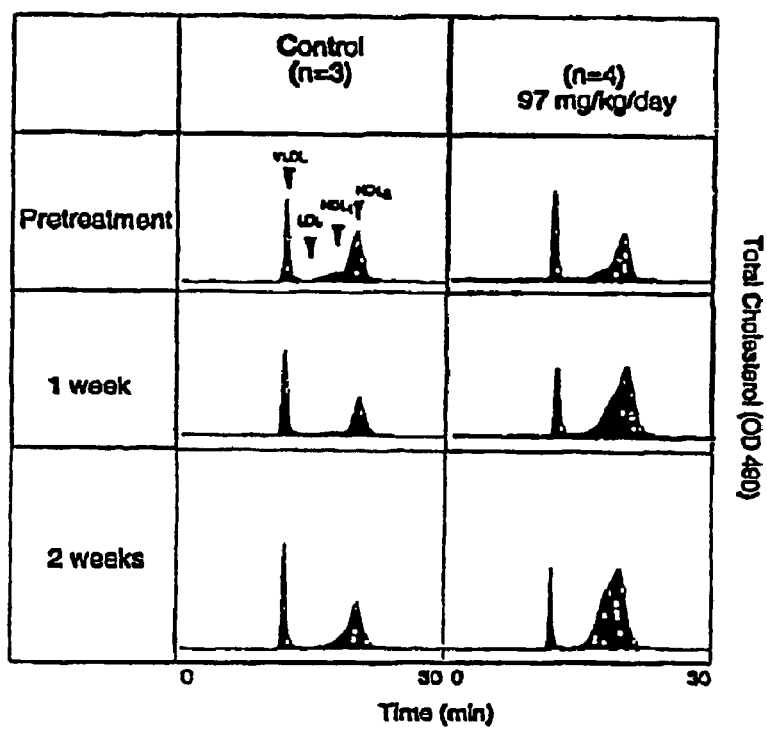
FIG. 3 illustrates the effect of two weeks of daily oral gavage treatment on lipoprotein total cholesterol in chow-fed obese female Zucker rats.
Figure 5:
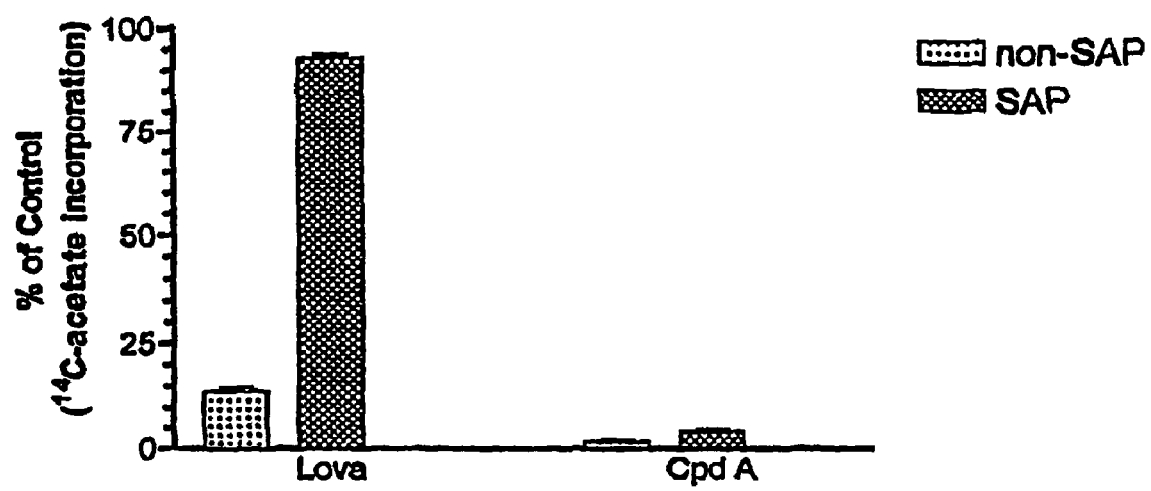

FIG. 4 is a table illustrating the effect of two weeks of daily oral gavage treatment using a specific compound of the invention in chow-fed obese female Zucker rats; and FIG. 5 is a table illustrating the effect of two weeks of daily oral gavage treatment using a specific compound of the invention on the synthesis of saponified and non-saponified lipids in hepatocyte cells isolated from male Sprague-Dawly rats.

4. DETAILED DESCRIPTION OF THE INVENTION

The present invention provides novel compounds useful for treating or preventing a aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, or enhancing bile production, or enhancing reverse lipid transport, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism.

In this regard, the compounds of the invention are particularly useful when incorporated in a pharmaceutical composition having a carrier, excipient, diluent, or a mixture thereof. A composition of the invention need not contain additional ingredients, such as an excipient, other than a compound of the invention. Accordingly, in one embodiment, the compositions of the invention can omit pharmaceutically acceptable excipients and diluents and can be delivered in a gel cap or drug delivery device. Accordingly, the present invention provides methods for treating or preventing aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, or enhancing bile production, or enhancing reverse lipid transport, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism, comprising administering to a patient in need thereof a therapeutically effective amount of a compound or composition of the invention.

In certain embodiments of the invention, a compound of the invention is administered in combination with another therapeutic agent. The other therapeutic agent provides additive or synergistic value relative to the administration of a compound of the invention alone. The therapeutic agent can be a lovastatin; a thiazolidinedione or fibrate; a bile-acid-binding-resin; a niacin; an anti-obesity drug; a hormone; a tyrophostine; a sulfonylurea-based drug; a biguanide; an α-glucosidase inhibitor, an apolipoprotein A-I agonist; apolipoprotein E; a cardiovascular drug; an HDL-raising drug; an HDL enhancer; or a regulator of the apolipoprotein A-I, apolipoprotein A-IV and/or apolipoprotein genes.

4.1. Definitions and Abbreviations

Apo(a): apolipoprotein(a)

Apo A-I: apolipoprotein A-I

Apo B: apolipoprotein B

Apo E: apolipoprotein E

FH: Familial hypercholesterolemia

FCH: Familial combined hyperlipidemia

GDM: Gestational diabetes mellitus

HDL: High density lipoprotein

IDL: Intermediate density lipoprotein

IDDM: Insulin dependent diabetes mellitus

LDH: Lactate dehydrogenase

LDL: Low density lipoprotein

Lp(a): Lipoprotein (a)

MODY: Maturity onset diabetes of the young

NIDDM: Non-insulin dependent diabetes mellitus

PPAR: Peroxisome proliferator activated receptor

RXR: Retinoid X receptor

VLDL: Very low density lipoprotein

The term "compound A" means the compound 1,13-dihydroxy-2,2,12,12-tetramethyl-tridecan-7-one having the structure:

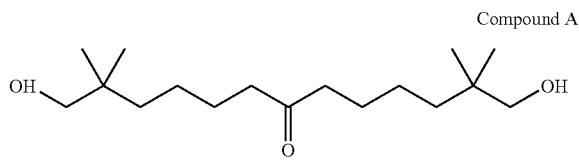

Compound A 1,13-Dihydroxy-2,2,12,12-tetramethyl-tridecan-7-one

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures.

A compound of the invention is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A compound of the invention is considered to be in enantiomerically-enriched form when the compound has an enantiomeric excess of greater than about 1% ee, preferably greater than about 5% ee, more preferably, greater than about 10% ee with respect to a particular chiral center. A compound of the invention is considered diastereomerically pure with respect to multiple chiral centers when the compound is about 90% de (diastereomeric excess) or greater, preferably, equal to or greater than 95% de with respect to a particular chiral center. A compound of the invention is considered to be in diastereomerically-enriched form when the compound has an diastereomeric excess of greater than about 1% de, preferably greater than about 5% de, more preferably, greater than about 10% de with respect to a particular chiral center. As used herein, a racemic mixture means about 50% of one enantiomer and about 50% of is corresponding enantiomer relative to all chiral centers in the molecule. Thus, the invention encompasses all enantiomerically-pure, enantiomerically-enriched, diastereomerically pure, diastereomerically enriched, and racemic mixtures of compounds of Formulas I through III.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The compounds of the invention are defined herein by their chemical structures and/or chemical names. Where a compound is referred to by both a chemical structure and a chemical name, and the chemical structure and chemical name conflict, the chemical structure is determinative of the compound's identity.

When administered to a patient, e.g., to an animal for veterinary use or for improvement of livestock, or to a human for clinical use, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single ether compound of the invention by weight of the isolate.

The phrase "pharmaceutically acceptable salt(s)," as used herein includes, but are not limited to, salts of acidic or basic groups that may be present in the compounds of the invention. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds of the invention that include an amino moiety also can form pharmaceutically acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, the term "solvate" means a compound of the invention or a salt thereof, that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a compound of the invention or a salt thereof, that further includes a stoichiometric or non-stoichiometric amount of water bound by non-covalent intermolecular forces.

As used herein, the term "clathrate" means a compound of the invention or a salt thereof in the form of a crystal lattice that contains spaces (e.g., channels) that have a guest molecule (e.g., a solvent or water) trapped within.

"Altering lipid metabolism" indicates an observable (measurable) change in at least one aspect of lipid metabolism, including but not limited to total blood lipid content, blood HDL cholesterol, blood LDL cholesterol, blood VLDL cholesterol, blood triglyceride, blood Lp(a), blood apo A-I, blood apo E and blood non-esterified fatty acids.

"Altering glucose metabolism" indicates an observable (measurable) change in at least one aspect of glucose metabolism, including but not limited to total blood glucose content, blood insulin, the blood insulin to blood glucose ratio, insulin sensitivity, and oxygen consumption.

As used herein, the term "alkyl group" means a saturated, monovalent unbranched or branched hydrocarbon chain. Examples of alkyl groups include, but are not limited to, ($C_1$-$C_6$)alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

An "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to ($C_2$-$C_6$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

An "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$)alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

An "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "($C_6$)aryl".

A "heteroaryl group" means a monocyclic- or polycyclic aromatic ring comprising carbon atoms, hydrogen atoms, and one or more heteroatoms, preferably 1 to 3 heteroatoms, independently selected from nitrogen, oxygen, and sulfur. Illustrative examples of heteroaryl groups include, but are not limited to, pyridinyl, pyridazinyl, pyrimidinyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thiophenyl, isoxazolyl, thiazolyl, furyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "($C_2$-$C_5$)heteroaryl".

A "cycloalkyl group" means a monocyclic or polycyclic saturated ring comprising carbon and hydrogen atoms and having no carbon-carbon multiple bonds. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. Preferably, the cycloalkyl group is a monocyclic ring or bicyclic ring.

A "heterocycloalkyl group" means a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as ($C_1$-$C_6$)heterocycloalkyl.

As used herein a "heterocyclic radical" or "heterocyclic ring" means a heterocycloalkyl group or a heteroaryl group.

The term "alkoxy group" means an —O-alkyl group, wherein alkyl is as defined above. An alkoxy group can be unsubstituted or substituted with one or two suitable substituents. Preferably, the alkyl chain of an alkyloxy group is from 1 to 6 carbon atoms in length, referred to herein as "($C_1$-$C_6$) alkoxy".

The term "aryloxy group" means an —O-aryl group, wherein aryl is as defined above. An aryloxy group can be unsubstituted or substituted with one or two suitable substituents. Preferably, the aryl ring of an aryloxy group is a monocyclic ring, wherein the ring comprises 6 carbon atoms, referred to herein as "($C_6$)aryloxy".

The term "benzyl" means —$CH_2$-phenyl.

The term "phenyl" means —$C_6H_5$. A phenyl group can be unsubstituted or substituted with one or two suitable substituents.

A "hydrocarbyl" group means a monovalent group selected from ($C_1$-$C_8$)alkyl, ($C_2$-$C_8$)alkenyl, and ($C_2$-$C_8$) alkynyl, optionally substituted with one or two suitable substituents. Preferably, the hydrocarbon chain of a hydrocarbyl group is from 1 to 6 carbon atoms in length, referred to herein as "($C_1$-$C_6$)hydrocarbyl".

A "carbonyl" group is a divalent group of the formula —C(O)—.

An "alkoxycarbonyl" group means a monovalent group of the formula —C(O)-alkoxy. Preferably, the hydrocarbon chain of an alkoxycarbonyl group is from 1 to 8 carbon atoms in length, referred to herein as a "lower alkoxycarbonyl" group.

A "carbamoyl" group means the radical —C(O)N(R')$_2$, wherein R' is chosen from the group consisting of hydrogen, alkyl, and aryl.

As used herein, "halogen" means fluorine, chlorine, bromine, or iodine. Correspondingly, the meaning of the terms "halo" and "Hal" encompass fluoro, chloro, bromo, and iodo.

As used herein, a "suitable substituent" means a group that does not nullify the synthetic or pharmaceutical utility of the compounds of the invention or the intermediates useful for preparing them. Examples of suitable substituents include, but are not limited to: ($C_1$-$C_8$)alkyl; ($C_1$-$C_8$)alkenyl; ($C_1$-$C_8$) alkynyl; ($C_6$)aryl; ($C_2$-$C_5$)heteroaryl; ($C_3$-$C_7$)cycloalkyl; ($C_1$-$C_8$)alkoxy; ($C_6$)aryloxy; —CN; —OH; oxo; halo, —$CO_2$H; —$NH_2$; —NH(($C_1$-$C_8$)alkyl); —N(($C_1$-$C_8$)alkyl)$_2$; —NH(($C_6$)aryl); —N(($C_6$)aryl)$_2$; —CHO; —CO(($C_1$-$C_8$) alkyl); —CO(($C_6$)aryl); —$CO_2$(($C_1$-$C_8$)alkyl); and —$CO_2$ (($C_6$)aryl). One of skill in the art can readily choose a suitable substituent based on the stability and pharmacological and synthetic activity of the compound of the invention.

4.2. Synthesis of the Compounds of the Invention

The compounds of the invention can be obtained via the synthetic methodology illustrated in Schemes 1-8. Starting materials useful for preparing the compounds of the invention and intermediates thereof, are commercially available or can be prepared from commercially available materials using known synthetic methods and reagents.

Scheme 1: Synthesis of Compounds of Formula X

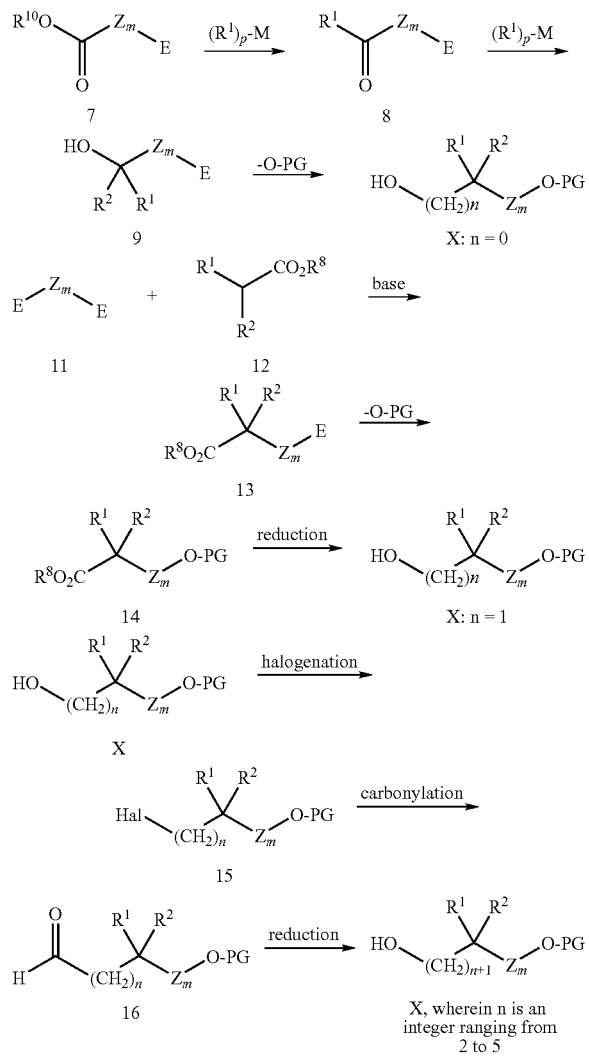

Scheme 1 illustrates the synthesis of mono-protected diols of the formula X, wherein n is an integer ranging from 0 to 4 and $R^1$ and $R^2$ are as defined above, and E is a leaving group as defined below. Scheme 1 first outlines the synthesis of mono-protected diols X, wherein n is 0, where esters 4 are successively reacted with a first $((R^1)_p$-M) then a second $((R^2)_p$-M) organometallic reagent providing ketones 5 and alcohols 6, respectively. M is a metal group and p is the metal's valency value (e.g., the valency of Li is 1 and that of Zn is 2). Suitable metals include, but are not limited to, Zn, Na, Li, and —Mg-Hal, wherein Hal is a halide selected from iodo, bromo, or chloro. Preferably, M is —Mg-Hal, in which case the organometallic reagents, $(R^1)_p$—Mg-Hal and $(R^2)_p$—Mg-Hal, are known in the art as a Grignard reagents. Esters 4 are available commercially (e.g., Aldrich Chemical Co., Milwaukee, Wis.) or can be prepared by well-known synthetic methods, for example, via esterification of the appropriate 5-halovaleric acid (commercially available, e.g., Aldrich Chemical Co., Milwaukee, Wis.). Both $(R^1)_p$-M and $(R^2)_p$-M are available commercially (e.g., Aldrich Chemical Co., Milwaukee, Wis.) or can be prepared by well-known methods (see e.g., Kharasch et al., *Grignard Reactions of Non-Metallic Substances*; Prentice-Hall, Englewood Cliffs, N.J., pp. 138-528 (1954) and Hartley; Patai, *The Chemistry of the Metal-Carbon Bond*, Vol. 4, Wiley: New York, pp. 159-306 and pp. 162-175 (1989), both citations are hereby expressly incorporated herein by reference). The reaction of a first $((R^1)_p$-M) then a second $((R^2)_p$-M) organometallic reagent with esters 4 can be performed using the general procedures referenced in March, J. *Advanced Organic Chemistry; Reactions Mechanisms, and Structure*, 4th ed., 1992, pp. 920-929 and Eicher, Patai, *The Chemistry of the Carbonyl Group*, pt. 1, pp. 621-693; Wiley: New York, (1966), hereby expressly incorporated herein by reference. For example, the synthetic procedure described in Comins et al., 1981, *Tetrahedron Lett*. 22:1085, hereby expressly incorporated herein by reference, can be used. As one example, the reaction can be performed by adding an organic solution of $(R^1)_p$-M (about 0.5 to about 1 equivalents) to a stirred, cooled (about 0° C. to about −80° C.) solution comprising esters 4, under an inert atmosphere (e.g., nitrogen) to give a reaction mixture comprising ketones 5. Preferably, $(R^1)_p$-M is added at a rate such that the reaction-mixture temperature remains within about one to two degrees of the initial reaction-mixture temperature. The progress of the reaction can be followed by using an appropriate analytical method, such as thin-layer chromatography or high-performance-liquid chromatography. Next, an organic solution of $(R^2)_p$-M (about 0.5 to about 1 equivalent) is added to the reaction mixture comprising ketones 5 in the same manner used to add $(R^1)_p$-M. After the reaction providing alcohols 6 is substantially complete, the reaction mixture can be quenched and the product can be isolated by workup. Suitable solvents for obtaining alcohols 6 include, but are not limited to, dichloromethane, diethyl ether, tetrahydrofuran, benzene, toluene, xylene, hydrocarbon solvents (e.g., pentane, hexane, and heptane), and mixtures thereof. Preferably, the organic solvent is diethyl ether or tetrahydrofuran. Next, alcohols 6 are converted to mono-protected diols X, wherein n is 0, using the well-known Williamson ether synthesis. This involves reacting alcohols 6 with —O-PG, wherein —PG is a hydroxy-protecting group. For a general discussion of the Williamson ether synthesis, See March, J. *Advanced Organic Chemistry; Reactions Mechanisms, and Structure*, 4th ed., 1992, pp. 386-387, and for a list of procedures and reagents useful in the Williamson ether synthesis, See, for example, Larock *Comprehensive Organic Transformations*; VCH: New York, 1989, pp. 446-448, both of which references are incorporated herein by reference. As used herein, a "hydroxy-protecting group" means a group that is reversibly attached to a hydroxy moiety that renders the hydroxy moiety unreactive during a subsequent reaction(s) and that can be selectively cleaved to regenerate the hydroxy moiety once its protecting purpose has been served. Examples of hydroxy-protecting groups are found in Greene, T. W., *Protective Groups in Organic Synthesis*, 3rd edition 17-237 (1999), hereby expressly incorporated herein by reference. Preferably, the hydroxy-protecting group is stable in a basic reaction medium, but can be cleaved by acid. Examples of suitable base-stable acid-labile hydroxy-protecting groups suitable for use with the invention include, but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahydrofuranyl, tetrahydrothiofuranyl, 1-ethoxyethyl, 1-methyl-1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, and triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably —PG is methoxymethyl($CH_3OCH_2$—). Reaction of alcohols 6 with —O-PG under the conditions of the Williamson ether synthesis involves adding a base to a stirred organic solution comprising HO-PG (e.g., methoxymethanol), maintained at a constant temperature within the range of about 0° C. to about 80° C., preferably at about room temperature. Preferably, the base is added at a rate such that the reaction-mixture temperature remains within about one to two degrees of the initial reaction-mixture temperature. The base can be added as an organic solution or in undiluted form. Preferably, the base will have a base strength sufficient to deprotonate a proton, wherein the proton has a $pK_a$ of greater than about 15, preferably greater than about 20. As is well known in the art, the $pK_a$ is a measure of the acidity of an acid H-A, according to the equation $pK_a = -\log K_a$, wherein $K_a$ is the equilibrium constant for the proton transfer. The acidity of an acid H-A is proportional to the stability of its conjugate base-A. For tables listing $pK_a$ values for various organic acids and a discussion on $pK_a$ measurement, see March, J. *Advanced Organic Chemistry; Reactions Mechanisms, and Structure,* 4th ed., 1992, pp. 248-272, incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. The preferred base is lithium diisopropylamide. Solvents suitable for reacting alcohols 6 with —OPG include, but are not limited, to dimethyl sulfoxide, dichloromethane, ethers, and mixtures thereof, preferably tetrahydrofuran. After addition of the base, the reaction mixture can be adjusted to within a temperature range of about 0° C. to about room temperature and alcohols 6 can be added, preferably at a rate such that the reaction-mixture temperature remains within about one to two degrees of the initial reaction-mixture temperature. Alcohols 6 can be diluted in an organic solvent or added in their undiluted form. The resulting reaction mixture is stirred until the reaction is substantially complete as determined by using an appropriate analytical method, preferably by gas chromatography, then the mono-protected diols X can be isolated by workup and purification.

Next, Scheme I outlines a method useful for synthesizing mono-protected diols X, wherein n is 1. First, compounds 7, wherein E is a suitable leaving group, are reacted with compounds 8, wherein $R^1$ and $R^2$ are as defined above and $R^8$ is H, ($C_1$-$C_6$)alkyl or ($C_6$)aryl, providing compounds 9. Suitable leaving groups are well known in the art, for example, but not limited to halides, such as chloride, bromide, and iodide; aryl- or alkylsulfonyloxy, substituted arylsulfonyloxy (e.g., tosyloxy or mesyloxy); substituted alkylsulfonyloxy (e.g., haloalkylsulfonyloxy); ($C_6$)aryloxy or substituted ($C_6$)aryloxy; and acyloxy groups. Compounds 7 are available commercially (e.g., Aldrich Chemical Co., Milwaukee, Wis.) or can be prepared by well-known methods such as halogenation or sulfonation of butanediol. Compounds 8 are also available commercially (e.g., Aldrich Chemical Co., Milwaukee, Wis.) or by well-known methods, such as those listed in Larock *Comprehensive Organic Transformations*; Wiley-VCH: New York, 1999, pp. 1754-1755 and 1765. A review on alkylation of esters of type 8 is given by J. Mulzer in *Comprehensive Organic Functional Transformations*, Pergamon, Oxford 1995, pp. 148-151 and exemplary synthetic procedures for reacting compounds 7 with compounds 8 are described in U.S. Pat. No. 5,648,387, column 6 and Ackerly, et al., *J. Med. Chem.* 1995, pp. 1608, all of which citations are hereby expressly incorporated herein by reference. The reaction requires the presence of a suitable base. Preferably, a suitable base will have a $pK_a$ of greater than about 25, more preferably greater than about 30. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; hydride bases such as sodium hydride and potassium hydride. Metal amide bases, such as lithium diisopropylamide are preferred. Preferably, to react compounds 7 with compounds 8, a solution of about 1 to about 2 equivalents of a suitable base is added to a stirred solution comprising esters 8 and a suitable organic solvent, under an inert atmosphere, the solution maintained at a constant temperature within the range of about −95° C. to about room temperature, preferably at about −78° C. to about −20° C. Preferably, the base is diluted in a suitable organic solvent before addition. Preferably, the base is added at a rate of about 1.5 moles per hour. Organic solvents suitable for the reaction of compounds 7 with the compounds 8 include, but are not limited to, dichloromethane, diethyl ether, tetrahydrofuran, dimethylformamide, dimethyl sulfoxide, benzene, toluene, xylene, hydrocarbon solvents (e.g., pentane, hexane, and heptane), and mixtures thereof. After addition of the base, the reaction mixture is allowed to stir for about 1 to about 2 hours, and a compound 7, preferably dissolved in a suitable organic solvent, is added, preferably at a rate such that the reaction-mixture temperature remains within about one to two degrees of the initial reaction-mixture temperature. After addition of compounds 7, the reaction-mixture temperature can be adjusted to within a temperature range of about −20° C. to about room temperature, preferably to about room temperature, and the reaction mixture is allowed to stir until the reaction is substantially complete as determined by using an appropriated analytical method, preferably thin-layer chromatography or high-performance liquid chromatography. Then the reaction mixture is quenched and compounds 9, wherein n is 1 can be isolated by workup. Compounds 10 are then synthesized by reacting compounds 9 with —O-PG according to the protocol described above for reacting alcohols 6 with —O-PG. Next, compounds 10 can be converted to mono-protected diols X, wherein n is 1, by reduction of the ester group of compounds 10 to an alcohol group with a suitable reducing agent. A wide variety of reagents are available for reduction of such esters to alcohols, e.g., see M. Hudlicky, *Reductions in Organic Chemistry,* 2nd ed., 1996 pp. 212-217, hereby expressly incorporated herein by reference. Preferably, the reduction is effected with a hydride type reducing agent, for example, lithium aluminum hydride, lithium borohydride, lithium triethyl borohydride, diisobutylaluminum hydride, lithium trimethoxyaluminum hydride, or sodium bis(2-methoxy)aluminum hydride. For exemplary procedures for reducing esters to alcohols, see Nystrom et al., 1947, *J. Am. Chem. Soc.* 69:1197; and Moffet et al., 1963, *Org. Synth., Collect.* 834(4), lithium aluminum hydride; Brown et al., 1965, *J. Am. Chem. Soc.* 87:5614, lithium trimethoxyaluminum hydride; Cerny et al., 1969, *Collect. Czech. Chem. Commun.* 34:1025, sodium bis(2-methoxy)aluminum hydride; Nystrom et al., 1949, *J. Am. Chem.* 71:245, lithium borohydride; and Brown et al., 1980, *J. Org. Chem.* 45:1, lithium triethyl borohydride, all of which citations are hereby expressly incorporated herein by reference. Preferably, the reduction is conducted by adding an organic solution of compounds 10 to a stirred mixture comprising a reducing agent, preferably lithium aluminum hydride, and an organic solvent. During the addition, the reaction mixture is maintained at a constant temperature within the range of about −20° C. to about 80° C., preferably at about room temperature. Organic solvents suitable for reacting 9 with —OPG include, but are not limited to, dichloromethane, diethyl ether, tetrahydrofuran or mixtures thereof, preferably tetrahydrofuran. After the addition, the reaction mixture is stirred at a constant temperature within the range of about room temperature to about 60° C., until the reaction is substantially complete as determined by using an appropriate analytical method, preferably thin-layer chromatography or high-performance-liquid chromatography. Then the reaction mixture can be quenched and mono-protected diols X, wherein n is 1, can be isolated by workup and purification.

Scheme 1 next illustrates a three step synthetic sequence for homologating mono-protected diols X comprising: (a) halogenation (converting —CH$_2$OH to —CH$_2$-Hal); (b) carbonylation (replacing -Hal with —CHO); and (c) reduction (converting —CHO to —CH$_2$OH), wherein a reaction sequence of (a), (b), and (c) increases the value of n by 1. In step (a) protected halo-alcohols 11, wherein Hal is a halide selected from the group of chloro, bromo, or iodo, preferably iodo, can be prepared by halogenating mono-protected diols X, by using well-known methods (for a discussion of various methods for conversion of alcohols to halides see March, J. *Advanced Organic Chemistry; Reactions Mechanisms, and Structure,* 4th ed., 1992, pp. 431-433, hereby expressly incorporated herein by reference). For example, protected iodo-alcohols 11 can be synthesized starting from mono-protected diols X by treatment with Ph$_3$/I$_2$/imidazole (Garegg et al., 1980, *J. C. S Perkin I* 2866); 1,2-dipheneylene phosphoro-chloridite/I$_2$ (Corey et al., 1967, *J. Org. Chem.* 82:4160); or preferably with Me$_3$SiCl/NaI (Olah et al., 1979, *J. Org. Chem.* 44:8, 1247), all of which citations are hereby expressly incorporated herein by reference. Step (b); carbonylation of alkyl halides, such as protected halo-alcohols 11, is reviewed in Olah et al., 1987, *Chem Rev.* 87:4, 671; and March, J., *Advanced Organic Chemistry; Reactions Mechanisms, and Structure,* 4th ed., 1992, pp. 483-484, both of which are hereby expressly incorporated herein by reference). Protected halo-alcohols 11 can be carbonylated with Li(BF$_3$·Et$_2$O)/HCONMe$_2$ using the procedure described in Maddaford et al., 1993, *J. Org. Chem.* 58:4132; Becker et al., 1982, *J. Org. Chem.* 3297 or Myers et al., 1992, *J. Am. Chem. Soc.* 114:9369 or, alternatively, with an organometallic/N-formylmorpholine using the procedure described in Olah et al., 1984, *J. Org. Chem.* 49:3856 or Vogtle et al., 1987, *J. Org. Chem.* 52:5560, all of which citations are hereby expressly incorporated herein by reference. The method described in Olah et al., 1984, *J. Org. Chem.* 49:3856 is preferred. Reduction step (c) useful for synthesizing mono-protected diols X from aldehydes 12, can be accomplished by well-known methods in the art for reduction of aldehydes to the corresponding alcohols (for a discussion see M. Hudlicky, *Reductions in Organic Chemistry,* 2nd ed., 1996 pp 137-139), for example, by catalytic hydrogenation (see e.g., Carothers, 1949, *J. Am. Chem. Soc.* 46:1675) or, preferably by reacting aldehydes 12 with a hydride reducing agent, such as lithium aluminum hydride, lithium borohydride, sodium borohydride (see e.g., the procedures described in Chaikin et al., 1949, *J. Am. Chem. Soc.* 71:3245; Nystrom et al., 1947, *J. Am. Chem. Soc.* 69:1197; and Nystrom et al., 1949, *J. Am. Chem.* 71:3245, all of which are hereby expressly incorporated herein by reference). Reduction with lithium aluminum hydride is preferred.

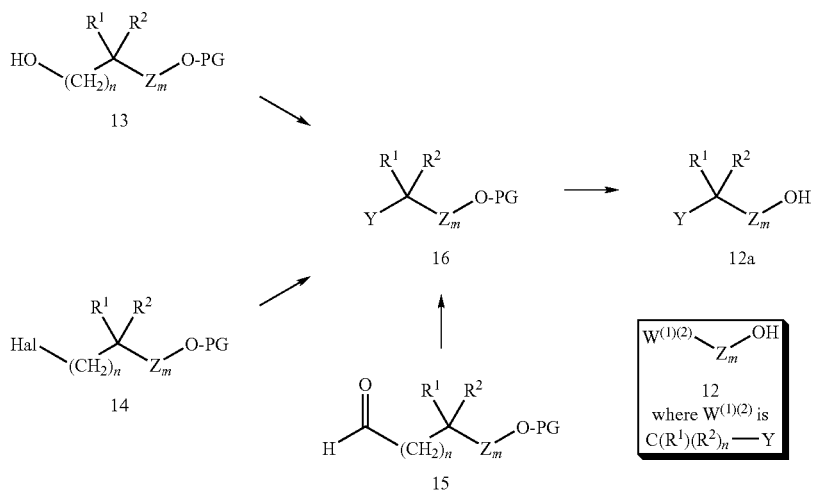

Scheme 2: Synthesis of Compounds of Formula 12a, which correspond to Compounds $W^{(1)(2)}$-$Z_m$-OH, Wherein $W^{(1)(2)}$ is $C(R^1)(R^2)_n$—Y Scheme 2 outlines the method for the synthesis of protected alcohols 12a wherein Y, $R^1$, $R^2$, Z, and m are defined as above. Protected alcohols 12a correspond to compounds of the formula $W^{(1)(2)}$-Zm-OPG, wherein $W^{(1)(2)}$ is $C(R^1)(R^2)$—Y.

Protected alcohols 16, wherein Y comprises a —C(O)OH group, can be synthesized by oxidizing mono-protected diols X with an agent suitable for oxidizing a primary alcohol to a carboxylic acid (for a discussion see M. Hudlicky, *Oxidations in Organic Chemistry,* ACS Monograph 186, 1990, pp. 127-

130, hereby expressly incorporated herein by reference). Suitable oxidizing agents include, but are not limited to, pyridinium dichromate (Corey et al., 1979, *Tetrahedron Lett.* 399); manganese dioxide (Ahrens et al., 1967, *J. Heterocycl. Chem.* 4:625); sodium permanganate monohydrate (Menger et al., 1981, *Tetrahedron Lett.* 22:1655); and potassium permanganate (Sam et al., 1972, *J. Am. Chem. Soc.* 94:4024), all of which citations are hereby expressly incorporated herein by reference. The preferred oxidizing reagent is pyridinium dichromate. In an alternative synthetic procedure, protected alcohols 16, wherein Y comprises a —C(O)OH group, can be synthesized by treatment of protected halo-alcohols 15, wherein X is iodo, with CO or $CO_2$, as described in Bailey et al., 1990, *J. Org. Chem.* 55:5404 and Yanagisawa et al., 1994, *J. Am. Chem. Soc.* 116:6130, the two of which citations are hereby expressly incorporated herein by reference. Protected alcohols 16, wherein Y comprises —C(O)OR$^5$, wherein R$^5$ is as defined above, can be synthesized by oxidation of mono-protected diols X in the presence of R$^5$OH (see generally, March, J. *Advanced Organic Chemistry; Reactions Mechanisms, and Structure*, 4th ed., 1992, p. 1196). An exemplary procedure for such an oxidation is described in Stevens et al., 1982, *Tetrahedron Lett.* 23:4647 (HOCl); Sundararaman et al., 1978, *Tetrahedron Lett.* 1627 ($O_3$/KOH); Wilson et al., 1982, *J. Org. Chem.* 47:1360 (t-BuOOH/Et$_3$N); and Williams et al., 1988, *Tetrahedron Lett.* 29:5087 (Br$_2$), the four of which citations are hereby expressly incorporated herein by reference. Preferably, protected alcohols 16, wherein Y comprises a —C(O)OR$^5$ group are synthesized from the corresponding carboxylic acid (i.e., 16, wherein Y comprises —C(O)OH) by esterification with R$^5$OH (e.g., see March, J., *Advanced Organic Chemistry; Reactions Mechanisms, and Structure*, 4th ed., 1992, p. 393-394, hereby expressly incorporated herein by reference). In another alternative synthesis, protected alcohols 16, wherein Y comprises —C(O)OR$^5$, can be prepared from protected halo-alcohols 14 by carbonylation with transition metal complexes (see e.g., March, J. *Advanced Organic Chemistry; Reactions Mechanisms, and Structure*, 4th ed., 1992, p. 484-486; Urata et al., 1991, *Tetrahedron Lett.* 32:36, 4733); and Ogata et al., 1969, *J. Org. Chem.* 3985, the three of which citations are hereby expressly incorporated herein by reference).

Protected alcohols 16, wherein Y comprises —OC(O)R$^5$, wherein R$^5$ is as defined above, can be prepared by acylation of mono-protected diols X with a carboxylate equivalent such as an acyl halide (i.e., R$^5$C(O)-Hal, wherein Hal is iodo, bromo, or chloro, see e.g., March, J. *Advanced Organic Chemistry; Reactions Mechanisms, and Structure*, 4th ed., 1992, p. 392 and *Org. Synth. Coll.* Vol. III, Wiley, N.Y., pp. 142, 144, 167, and 187 (1955)) or an anhydride (i.e., R$^5$C(O)—O—(O)CR$^5$, see e.g., March, J. *Advanced Organic Chemistry; Reactions Mechanisms, and Structure*, 4th ed., 1992, p. 392-393 and *Org. Synth. Coll.* Vol. III, Wiley, N.Y., pp. 11, 127, 141, 169, 237, 281, 428, 432, 690, and 833 (1955), all of which citations are hereby expressly incorporated herein by reference). Preferably, the reaction is conducted by adding a base to a solution comprising mono-protected diols X, a carboxylate equivalent, and an organic solvent, which solution is preferably maintained at a constant temperature within the range of 0° C. to about room temperature. Solvents suitable for reacting mono-protected diols X with a carboxylate equivalent include, but are not limited to, dichloromethane, toluene, and ether, preferably dichloromethane. Suitable bases include, but are not limited to, hydroxide sources, such as sodium hydroxide, potassium hydroxide, sodium carbonate, or potassium carbonate; or an amine such as triethylamine, pyridine, or dimethylaminopyridine, amines are preferred. The progress of the reaction can be followed by using an appropriate analytical technique, such as thin layer chromatography or high performance liquid chromatography and when substantially complete, the product can be isolated by workup and purified if desired.

Protected alcohols 16, wherein Y comprises one of the following phosphate ester groups

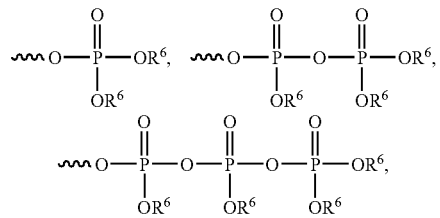

wherein R$^6$ is defined as above, can be prepared by phosphorylation of mono-protected diols X according to well-known methods (for a general reviews, see Corbridge *Phosphorus: An Outline of its Chemistry, Biochemistry, and Uses*, Studies in Inorganic Chemistry, 3rd ed., pp. 357-395 (1985); Ramirez et al., 1978, *Acc. Chem. Res.* 11:239; and Kalckare *Biological Phosphorylations*, Prentice-Hall, New York (1969); J. B. Sweeny in *Comprehensive Organic Functional Group Transformations*, A. R. Katritzky, O. Meth-Cohn and C. W. Rees, Eds. Pergamon: Oxford, 1995, vol 2, pp. 104-109, the four of which are hereby expressly incorporated herein by reference). Protected alcohols 16 wherein Y comprises a monophosphate group of the formula:

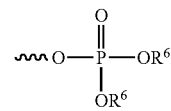

wherein R$^6$ is defined as above, can be prepared by treatment of mono-protected diol X with phosphorous oxychloride in a suitable solvent, such as xylene or toluene, at a constant temperature within the range of about 100° C. to about 150° C. for about 2 hours to about 24 hours. After the reaction is deemed substantially complete, by using an appropriate analytical method, the reaction mixture is hydrolyzed with R$^{10}$H. Suitable procedures are referenced in Houben-Weyl, Methoden der Organische Chemie, Georg Thieme Verlag Stuttgart 1964, vol. XII/2, pp. 143-210 and 872-879, hereby expressly incorporated herein by reference. Alternatively, when both R$^6$ are hydrogen, can be synthesized by reacting mono-protected diols X with silyl polyphosphate (Okamoto et al., 1985, *Bull Chem. Soc. Jpn.* 58:3393, hereby expressly incorporated herein by reference) or by hydrogenolysis of their benzyl or phenyl esters (Chen et al., 1998, *J. Org. Chem.* 63:6511, hereby expressly incorporated herein by reference). In another alternative procedure, when R$^6$ is ($C_1$-$C_6$)alkyl, ($C_2$-$C_6$)alkenyl, or ($C_2$-$C_6$)alkynyl, the monophosphate esters can be prepared by reacting mono-protected diols X with appropriately substituted phosphoramidites followed by oxidation of the intermediate with m-chloroperbenzoic acid (Yu et al., 1988, *Tetrahedron Lett.* 29:979, hereby expressly incorporated herein by reference) or by reacting mono-protected diols X with dialkyl or diaryl substituted phosphorochloridates (Pop, et al, 1997, *Org. Prep. and Proc. Int.* 29:341, hereby expressly incorporated herein by reference). The phosphoramidites are commercially available (e.g., Aldrich Chemical Co., Milwaukee, Wis.) or readily prepared according to literature procedures (see e.g., Uhlmann et al. 1986, *Tetrahedron Lett.* 27:1023 and Tanaka et al., 1988, *Tetrahe-* dron Lett. 29:199, both of which are hereby expressly incorporated herein by reference). The phosphorochloridates are also commercially available (e.g., Aldrich Chemical Co., Milwaukee, Wis.) or prepared according to literature methods (e.g., Gajda et al, 1995, *Synthesis* 25:4099. In still another alternative synthesis, protected alcohols 16, wherein Y comprises a monophosphate group and $R^6$ is alkyl or aryl, can be prepared by reacting $IP^+(OR^6)_3$ with mono-protected diols X according to the procedure described in Stowell et al., 1995, *Tetrahedron Lett.* 36:11, 1825 or by alkylation of protected halo alcohols 14 with the appropriate dialkyl or diaryl phosphates (see e.g., Okamoto, 1985, *Bull Chem. Soc. Jpn.* 58:3393, hereby expressly incorporated herein by reference).

Protected alcohols 16 wherein Y comprises a diphosphate group of the formula

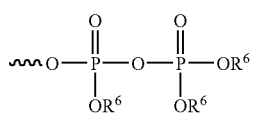

wherein $R^6$ is defined as above, can be synthesized by reacting the above-discussed monophosphates of the formula:

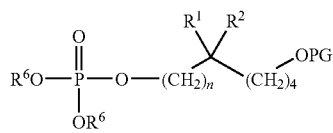

with a phosphate of the formula

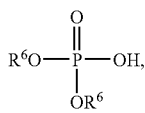

(commercially available, e.g., Aldrich Chemical Co., Milwaukee, Wis.), in the presence of carbodiimide such as dicyclohexylcarbodiimide, as described in Houben-Weyl, *Methoden der Organische Chemie*, Georg Thieme Verlag Stuttgart 1964, vol. XII/2, pp. 881-885. In the same fashion, protected alcohols 16, wherein Y comprises a triphosphate group of the formula:

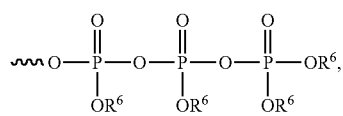

can be synthesized by reacting the above-discussed diphosphate protected alcohols, of the formula:

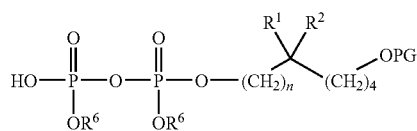

with a phosphate of the formula:

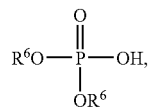

as described above. Alternatively, when $R^6$ is H, protected alcohols 16 wherein Y comprises the triphosphate group, can be prepared by reacting mono-protected diols X with salicyl phosphorochloridite and then pyrophosphate and subsequent cleavage of the adduct thus obtained with iodine in pyridine as described in Ludwig et al., 1989, *J. Org. Chem.* 54:631, hereby expressly incorporated herein by reference.

Protected alcohols 16, wherein Y is —$SO_3H$ or a heterocyclic group selected from the group consisting of:

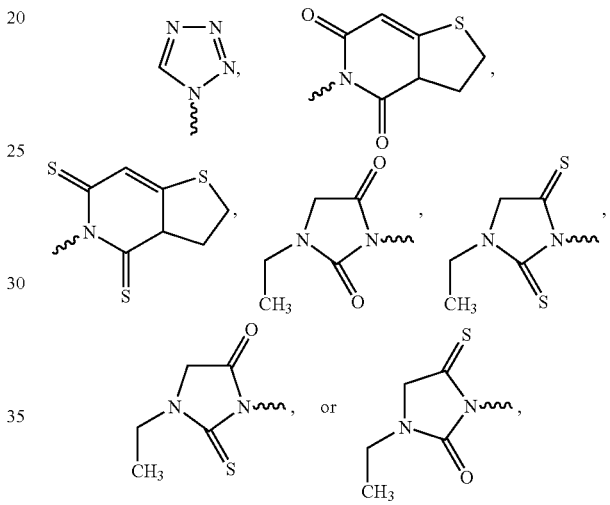

can be prepared by halide displacement from protected haloalcohols 14. Thus, when Y is —$SO_3H$, protected alcohols 16 can by synthesized by reacting protected halo-alcohols 14 with sodium sulfite as described in Gilbert *Sulfonation and Related Reactions*; Wiley: New York, 1965, pp. 136-148 and pp. 161-163; *Org. Synth. Coll.* Vol. II, Wiley, N.Y., 558, 564 (1943); and *Org. Synth. Coll.* Vol. IV, Wiley, N.Y., 529 (1963), all three of which are hereby expressly incorporated herein by reference. When Y is one of the above-mentioned heterocycles, protected alcohols 16 can be prepared by reacting protected halo-alcohols 14 with the corresponding heterocycle in the presence of a base. The heterocycles are available commercially (e.g., Aldrich Chemical Co., Milwaukee, Wis.) or prepared by well-known synthetic methods (see the procedures described in Ware, 1950, *Chem. Rev.* 46:403-470, hereby expressly incorporated herein by reference). Preferably, the reaction is conducted by stirring a mixture comprising 14, the heterocycle, and a solvent at a constant temperature within the range of about room temperature to about 100° C., preferably within the range of about 50° C. to about 70° C. for about 10 to about 48 hours. Suitable bases include hydroxide bases such as sodium hydroxide, potassium hydroxide, sodium carbonate, or potassium carbonate. Preferably, the solvent used in forming protected alcohols 16 is selected from dimethylformamide; formamide; dimethyl sulfoxide; alcohols, such as methanol or ethanol; and mixtures thereof. The progress of the reaction can be followed by using an appropriate analytical technique, such as thin layer chromatography or high performance liquid chromatography and when substantially complete, the product can be isolated by workup and purified if desired.

Protected alcohols 16, wherein Y is a heteroaryl ring selected from

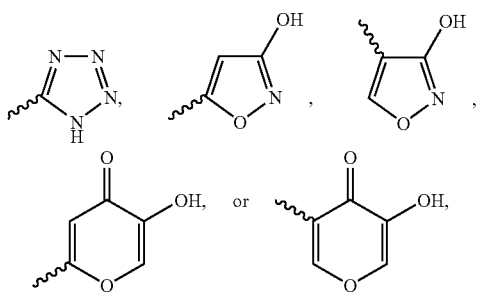

can be prepared by metallating the suitable heteroaryl ring then reacting the resulting metallated heteroaryl ring with protected halo-alcohols 14 (for a review, see Katritzky *Handbook of Heterocyclic Chemistry*, Pergamon Press: Oxford 1985). The heteroaryl rings are available commercially or prepared by well-known synthetic methods (see e.g., Joule et al., *Heterocyclic Chemistry*, 3rd ed., 1995; De Sarlo et al., 1971, *J. Chem. Soc.* (C) 86; Oster et al., 1983, *J. Org. Chem.* 48:4307; Iwai et al., 1966, *Chem. Pharm. Bull.* 14:1277; and U.S. Pat. No. 3,152,148, all of which citations are hereby expressly incorporated herein by reference). As used herein, the term "metallating" means the forming of a carbon-metal bond, which bond may be substantially ionic in character. Metallation can be accomplished by adding about 2 equivalents of strong organometallic base, preferably with a $pK_a$ of about 25 or more, more preferably with a $pK_a$ of greater than about 35, to a mixture comprising a suitable organic solvent and the heterocycle. Two equivalents of base are required: one equivalent of the base deprotonates the —OH group or the —NH group, and the second equivalent metallates the heteroaryl ring. Alternatively, the hydroxy group of the heteroaryl ring can be protected with a base-stable, acid-labile protecting group as described in Greene, T. W., *Protective Groups in Organic Synthesis*, 3rd edition 17-237 (1999), hereby expressly incorporated herein by reference. Where the hydroxy group is protected, only one equivalent of base is required. Examples of suitable base-stable, acid-labile hydroxyl-protecting groups, include but are not limited to, ethers, such as methyl, methoxy methyl, methylthiomethyl, methoxyethoxymethyl, bis(2-chloroethoxy)methyl, tetrahydropyranyl, tetrahydrothiopyranyl; tetrahydrofuranyl, tetrahydrothiofuranyl, 1-ethoxyethyl, 1-methyl-1-methoxyethyl, t-butyl, allyl, benzyl, o-nitrobenzyl, triphenylmethyl, x-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably, the $pK_a$ of the base is higher than the $pK_a$ of the proton of the heterocycle to be deprotonated. For a listing of $pK_a$s for various heteroaryl rings, see Fraser et al., 1985, *Can. J. Chem.* 63:3505, hereby expressly incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. If desired, the organometallic base can be activated with a complexing agent, such as N,N,N',N'-tetramethylethylenediamine or hexamethylphosphoramide (1970, *J. Am. Chem. Soc.* 92:4664, hereby expressly incorporated herein by reference). Solvents suitable for synthesizing protected alcohols 16, wherein Y is a heteroaryl ring include, but are not limited to, diethyl ether; tetrahydrofuran; and hydrocarbons, such as pentane. Generally, metallation occurs alpha to the heteroatom due to the inductive effect of the heteroatom, however, modification of conditions, such as the identity of the base and solvents, order of reagent addition, reagent addition times, and reaction and addition temperatures can be modified by one of skill in the art to achieve the desired metallation position (see e.g., Joule et al., *Heterocyclic Chemistry*, 3rd ed., 1995, pp. 30-42, hereby expressly incorporated herein by reference) Alternatively, the position of metallation can be controlled by use of a halogenated heteroaryl group, wherein the halogen is located on the position of the heteroaryl ring where metallation is desired (see e.g., Joule et al., *Heterocyclic Chemistry*, 3rd ed., 1995, p. 33 and Saulnier et al., 1982, *J. Org. Chem.* 47:757, the two of which citations are hereby expressly incorporated herein by reference). Halogenated heteroaryl groups are available commercially (e.g., Aldrich Chemical Co., Milwaukee, Wis.) or can be prepared by well-known synthetic methods (see e.g., Joule et al., *Heterocyclic Chemistry*, 3rd ed., 1995, pp. 78, 85, 122, 193, 234, 261, 280, 308, hereby expressly incorporated herein by reference). After metallation, the reaction mixture comprising the metallated heteroaryl ring is adjusted to within a temperature range of about 0° C. to about room temperature and protected halo-alcohols 14 (diluted with a solvent or in undiluted form) are added, preferably at a rate such that the reaction-mixture temperature remains within about one to two degrees of the initial reaction-mixture temperature. After addition of protected halo-alcohols 14, the reaction mixture is stirred at a constant temperature within the range of about room temperature and about the solvent's boiling temperature and the reaction's progress can be monitored by the appropriate analytical technique, preferably thin-layer chromatography or high-performance liquid chromatography. After the reaction is substantially complete, protected alcohols 16 can be isolated by workup and purification. It is to be understood that conditions, such as the identity of protected halo-alcohol 14, the base, solvents, orders of reagent addition, times, and temperatures, can be modified by one of skill in the art to optimize the yield and selectivity. Exemplary procedures that can be used in such a transformation are described in Shirley et al., 1995, *J. Org. Chem.* 20:225; Chadwick et al., 1979, *J. Chem. Soc., Perkin Trans.* 1 2845 Rewcastle, 1993, *Adv. Het. Chem.* 56:208; Katritzky et al., 1993, *Adv. Het. Chem.* 56:155; and Kessar et al., 1997, *Chem. Rev.* 97:721.

When Y is

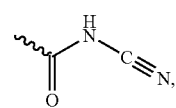

protected alcohols 16 can be prepared from their corresponding carboxylic acid derivatives (16, wherein Y is —CO$_2$H) as described in Belletire et al, 1988, *Synthetic Commun.* 18:2063 or from the corresponding acylchlorides (16, wherein Y is —CO-halo) as described in Skinner et al., 1995, *J. Am. Chem. Soc.* 77:5440, both citations are hereby expressly incorporated herein by reference. The acylhalides can be prepared from the carboxylic acids by well known procedures such as those described in March, J., *Advanced Organic Chemistry;*

Reactions Mechanisms, and Structure, 4th ed., 1992, pp. 437-438, hereby expressly incorporated herein by reference. When Y is

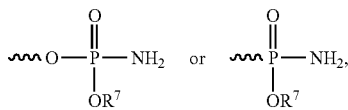

wherein $R^7$ is as defined above, protected alcohols 16 can be prepared by first reacting protected halo-alcohols 15 with a trialkyl phosphite according to the procedure described in Kosolapoff, 1951, *Org. React.* 6:273 followed by reacting the derived phosphonic diester with ammonia according to the procedure described in Smith et al., 1957, *J. Org. Chem.* 22:265, hereby expressly incorporated herein by reference. When Y is

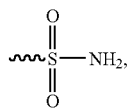

protected alcohols 16 can be prepared by reacting their sulphonic acid derivatives (i.e., 16, wherein Y is —SO₃H) with ammonia as described in Sianesi et al., 1971, *Chem. Ber.* 104:1880 and Campagna et al., 1994, *Farmaco, Ed. Sci.* 49:653, both of which citations are hereby expressly incorporated herein by reference).

As further illustrated in Scheme 2, protected alcohols 16 can be deprotected providing alcohols 20a. The deprotection method depends on the identity of the alcohol-protecting group, see e.g., the procedures listed in Greene, T. W., *Protective Groups in Organic Synthesis*, 3rd edition 17-237 (1999), particularly see pages 48-49, hereby expressly incorporated herein by reference. One of skill in the art will readily be able to choose the appropriate deprotection procedure. When the alcohol is protected as an ether function (e.g., methoxymethyl ether), the alcohol is preferably deprotected with aqueous or alcoholic acid. Suitable deprotection reagents include, but are not limited to, aqueous hydrochloric acid, p-toluenesulfonic acid in methanol, pyridinium-p-toluenesulfonate in ethanol, Amberlyst H-15 in methanol, boric acid in ethylene-glycol-monoethylether, acetic acid in a water-tetrahydrofuran mixture, aqueous hydrochloric acid is preferred. Examples of such procedures are described, respectively, in Bernady et al., 1979, *J. Org. Chem.* 44:1438; Miyashita et al., 1977, *J. Org. Chem.* 42:3772; Johnston et al., 1988, *Synthesis* 393; Bongini et al., 1979, *Synthesis* 618; and Hoyer et al., 1986, *Synthesis* 655; Gigg et al., 1967, *J. Chem. Soc. C*, 431; and Corey et al., 1978, *J. Am. Chem. Soc.* 100: 1942, all of which are hereby expressly incorporated herein by reference.

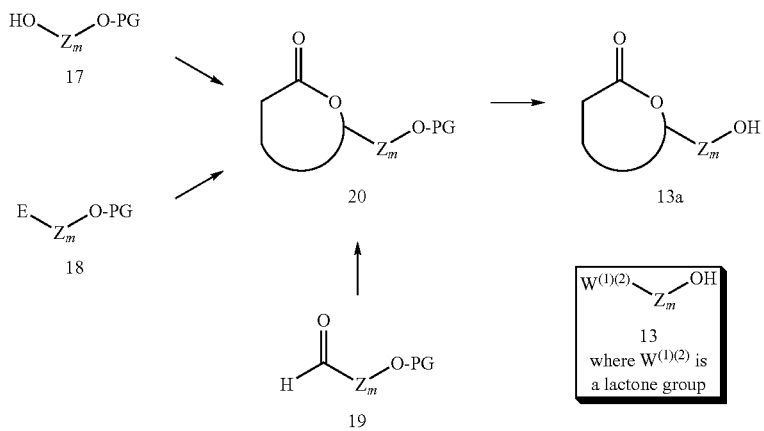

Scheme 3: Synthesis of Compounds of Formula 13a, which correspond to $W^{(1)(2)}$-$Z_m$-OH, Wherein $W^{(1)(2)}$ is a Lactone Group Scheme 3 depicts the synthesis of protected lactone alcohols 20 and lactone alcohols 13a. Compounds 20 and 13a correspond to compounds of the formula $W^{(1)(2)}$-Zm-OPG and $W^{(1)(2)}$-$Z_m$-OH respectively, wherein $W^{(1)(2)}$ is a lactone group selected from:

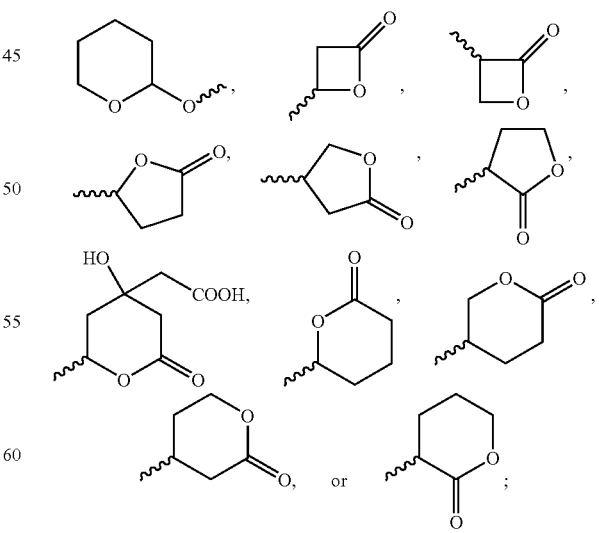

Protected lactone alcohols 20 can be prepared from compounds of the formula 17, 18, or 19 by using well-known condensation reactions and variations of the Michael reaction. Methods for the synthesis of lactones are disclosed in Multzer in *Comprehensive Organic Functional Group Transformations*, A. R. Katritzky, O. Meth-Cohn and C. W. Rees, Eds. Pergamon: Oxford, 1995, vol 5, pp. 161-173, hereby expressly incorporated herein by reference. Mono-protected diols 19, electrophilic protected alcohols 18, and aldehydes 19 are readily available ether commercially (e.g., Aldrich Chemical Co., Milwaukee, Wis.) or by well known synthetic procedures.

When $W^{(1)(2)}$ is a beta-lactone group of the formula:

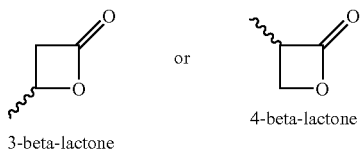

3-beta-lactone  4-beta-lactone protected lactone alcohols 20 can be prepared from aldehydes 19 and electrophilic protected alcohols 18, respectively, by a one-pot-addition-lactonization according to the procedure of Masamune et al., 1976, *J. Am. Chem. Soc.* 98:7874 and Danheiser et al., 1991, *J. Org. Chem.* 56:1176, both of which are hereby expressly incorporated herein by reference. This one-pot-addition-lactonization methodology has been reviewed by Multzer in *Comprehensive Organic Functional Group Transformations*, A. R. Katritzky, O. Meth-Cohn and C. W. Rees, Eds. Pergamon: Oxford, 1995, vol 5, pp. 161, hereby expressly incorporated herein by reference When $W^{(1)(2)}$ is a gamma- or delta-lactone group of the formula:

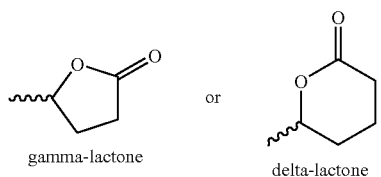

gamma-lactone  delta-lactone protected lactone alcohols 20 can be prepared from aldehydes 19 according to well known synthetic methodology. For example, the methodology described in Masuyama et al., 2000, *J. Org. Chem.* 65:494; Eisch et al., 1978, *J. Organo. Met. Chem.* C8 160; Eaton et al., 1947, *J. Org. Chem.* 37:1947; Yunker et al., 1978, *Tetrahedron Lett.* 4651; Bhanot et al., 1977, *J. Org. Chem.* 42:1623; Ehlinger et al., 1980, *J. Am. Chem. Soc.* 102:5004; and Raunio et al., 1957, *J. Org. Chem.* 22:570, all of which citations are hereby expressly incorporated herein by reference. For instance, as described in Masuyama et al., 2000, *J. Org. Chem.* 65:494, aldehydes 19 can be treated with about 1 equivalent of a strong organometallic base, preferably with a $pK_a$ of about 25 or more, more preferably with a $pK_a$ of greater than about 35, in a suitable organic solvent to give a reaction mixture. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. The reaction-mixture temperature is adjusted to within the range of about 0° C. to about 100° C., preferably about room temperature to about 50° C., and a halide of the formula:

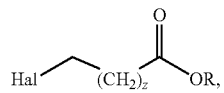

wherein z is 1 or 2 (diluted with a solvent or in undiluted form) is added. The reaction mixture is stirred for a period of about 2 hours to about 48 hours, preferably about 5 to about 10 hours, during which time the reaction's progress can be followed by using an appropriate analytical technique, such as thin layer chromatography or high performance liquid chromatography. When the reaction is deemed substantially complete, protected lactone alcohols 20 can be isolated by workup and purified if desired. When $W^{(1)(2)}$ is a gamma- or delta-lactone group of the formula:

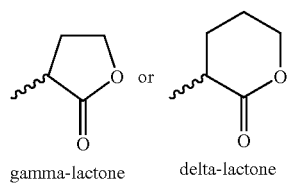

gamma-lactone  delta-lactone protected lactone alcohols 20 can be synthesized by deprotonating the corresponding lactone with a strong base providing the lactone enolate and reacting the enolate with electrophilic protected alcohols 20 (for a detailed discussion of enolate formation of active methylene compounds such as lactones, see House *Modern Synthetic Reactions*; W. A. Benjamin, Inc. Philippines 1972 pp. 492-570, and for a discussion of reaction of lactone enolates with electrophiles such as carbonyl compounds, see March, J. *Advanced Organic Chemistry; Reactions Mechanisms, and Structure,* 4th ed., 1992, pp. 944-945, both of which are hereby expressly incorporated herein by reference). Lactone-enolate formation can be accomplished by adding about 1 equivalent of a strong organometallic base, preferably with a $pK_a$ of about 25 or more, more preferably with a $pK_a$ of greater than about 35, to a mixture comprising a suitable organic solvent and the lactone. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Solvents suitable for lactone-enolate formation include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 18 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, protected lactone alcohols 20 can be isolated by workup and purified if desired. When $W^{(1)(2)}$ is a lactone group of the formula:

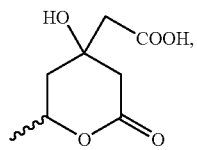

protected lactone alcohols 20 can be prepared from aldehydes 19 according to the procedure described in U.S. Pat. No. 4,622,338, hereby expressly incorporated herein by reference.

When $W^{(1)(2)}$ is a gamma- or delta-lactone group of the formula:

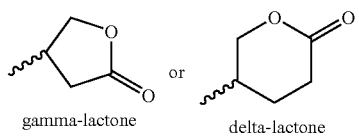

gamma-lactone                 delta-lactone protected lactone alcohols 20 can be prepared according to a three step sequence. The first step comprises base-mediated reaction of electrophilic protected alcohols 18 with succinic acid esters (i.e., $R^9O_2CCH_2CH_2CO_2R^9$, wherein $R^9$ is alkyl) or glutaric acid esters (i.e., $R^9O_2CCH_2CH_2CH_2CO_2R^9$, wherein $R^9$ is alkyl) providing a diester intermediate of the formula 21:

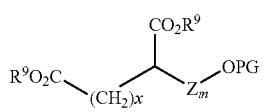

21 wherein x is 1 or 2 depending on whether the gamma or delta lactone group is desired. The reaction can be performed by adding about 1 equivalent of a strong organometallic base, preferably with a $pK_a$ of about 25 or more, more preferably with a $pK_a$ of greater than about 35, to a mixture comprising a suitable organic solvent and the succinic or glutaric acid ester. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 18 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, the diester intermediate be isolated by workup and purified if desired. In the second step, the intermediate diester can be reduced, with a hydride reducing agent, to yield a diol of the formula 22:

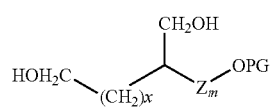

22

The reduction can be performed according to the procedures referenced in March, J. *Advanced Organic Chemistry; Reactions Mechanisms, and Structure*, 4th ed., 1992, p. 1214, hereby expressly incorporated herein by reference). Suitable reducing agents include, but are not limited to, lithium aluminum hydride, diisobutylaluminum hydride, sodium borohydride, and lithium borohydride). In the third step, the diol can be oxidatively cyclized with $RuH_2(PPh_3)_4$ to the product protected lactone alcohols 20 according to the procedure of Yoshikawa et al., 1986, *J. Org. Chem.* 51:2034 and Yoshikawa et al., 1983, *Tetrahedron Lett.* 26:2677, both of which citations are hereby expressly incorporated herein by reference. When $W^{(1)(2)}$ is a lactone group of the formula:

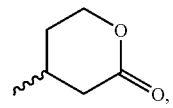

protected lactone alcohols 20 can be synthesized by reacting the Grignard salts of electrophilic protected alcohols 18, where E is a halide, with 5,6-dihydro-2H-pyran-2-one, commercially available (e.g., Aldrich Chemical Co., Milwaukee, Wis.), in the presence of catalytic amounts of a 1-dimethylaminoacetyl)pyrrolidine-2yl)methyl-diarylphosphine-copper (I) iodide complex as described in Tomioka et al., 1995, *Tetrahedron Lett.* 36:4275, hereby expressly incorporated herein by reference.

Scheme 4: Synthesis of Compounds of Formula 14

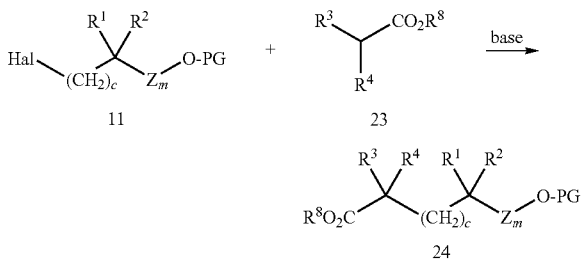

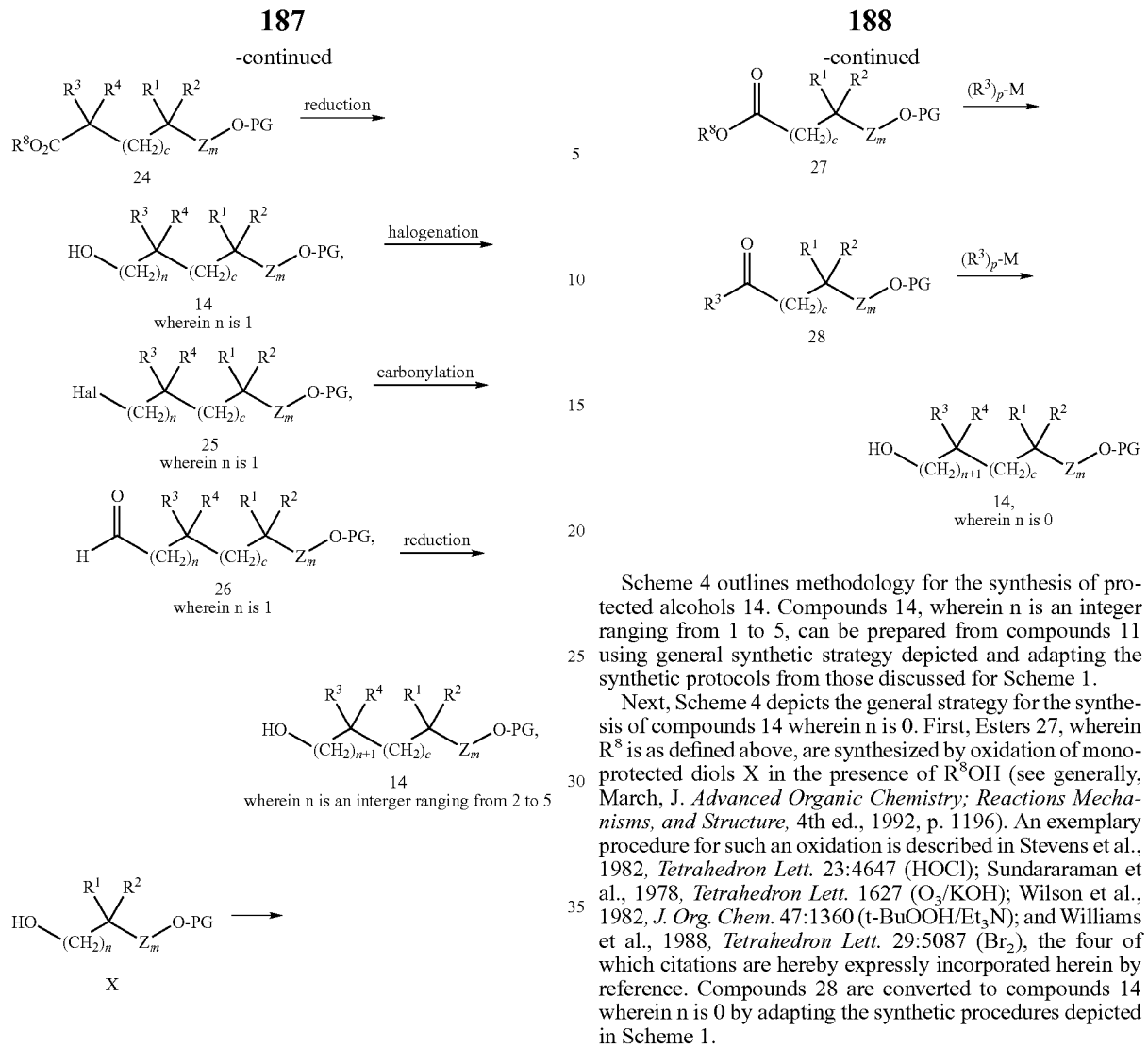

Scheme 4 outlines methodology for the synthesis of protected alcohols 14. Compounds 14, wherein n is an integer ranging from 1 to 5, can be prepared from compounds 11 using general synthetic strategy depicted and adapting the synthetic protocols from those discussed for Scheme 1.

Next, Scheme 4 depicts the general strategy for the synthesis of compounds 14 wherein n is 0. First, Esters 27, wherein $R^8$ is as defined above, are synthesized by oxidation of mono-protected diols X in the presence of $R^8OH$ (see generally, March, J. *Advanced Organic Chemistry; Reactions Mechanisms, and Structure,* 4th ed., 1992, p. 1196). An exemplary procedure for such an oxidation is described in Stevens et al., 1982, *Tetrahedron Lett.* 23:4647 (HOCl); Sundararaman et al., 1978, *Tetrahedron Lett.* 1627 ($O_3$/KOH); Wilson et al., 1982, *J. Org. Chem.* 47:1360 (t-BuOOH/$Et_3N$); and Williams et al., 1988, *Tetrahedron Lett.* 29:5087 ($Br_2$), the four of which citations are hereby expressly incorporated herein by reference. Compounds 28 are converted to compounds 14 wherein n is 0 by adapting the synthetic procedures depicted in Scheme 1.

Scheme 5: Synthesis of Compounds of Formula 15a, which correspond to compounds $W^{(1)(2)}$-$Z_m$-OH, Where $W^{(1)(2)}$ is $C(R^1)(R^2)$—$(CH_2)_c C(R^3)(R^4)$—Y

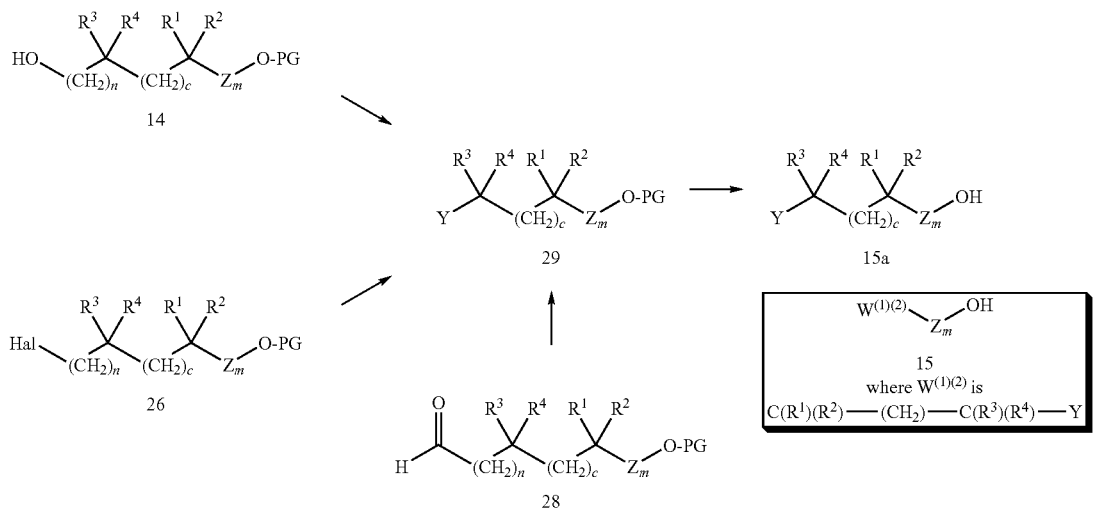

Scheme 5 outlines methodology for the synthesis of protected alcohols 29 and alcohols 15a, which correspond to $W^{(1)(2)}$-$Z_m$-OPG and $W^{(1)(2)}$-$Z_m$-OH, respectively, herein $W^{(1)(2)}$ is $C(R^1)(R^2)$—$(CH_2)_c C(R^3)(R^4)$—Y. The synthesis of starting materials 14, 26, and 28 are depicted in Scheme 4 and the synthetic methods and procedures can be adapted from those described for Scheme 2.

Scheme 6: Synthesis of Compounds of Formula 16, which correspond to compounds $W^{(1)(2)}$-$Z_m$-OH, Wherein $W^{(1)(2)}$ is $C(R^1)(R^2)(CH_2)_c$—V where V is a Lactone Group

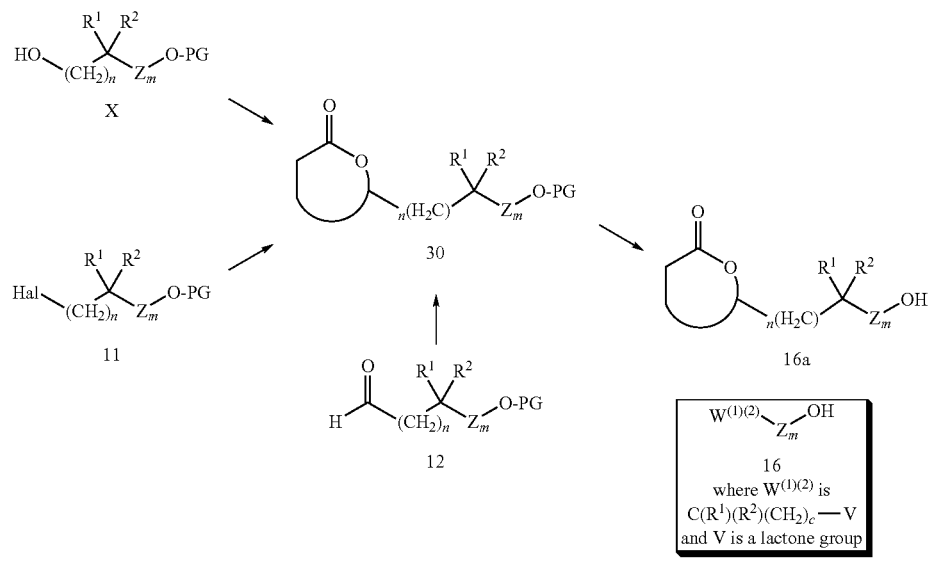

Scheme 6 depicts the synthesis of protected lactone alcohols 30 and lactone alcohols 16a. Compounds 30 and 16a correspond to compounds of the formula, which correspond to compounds $W^{(1)(2)}$-$Z_m$-OH, Wherein $W^{(1)(2)}$ is $C(R^1)(R^2)(CH_2)_c$—V and V is a Group selected from:

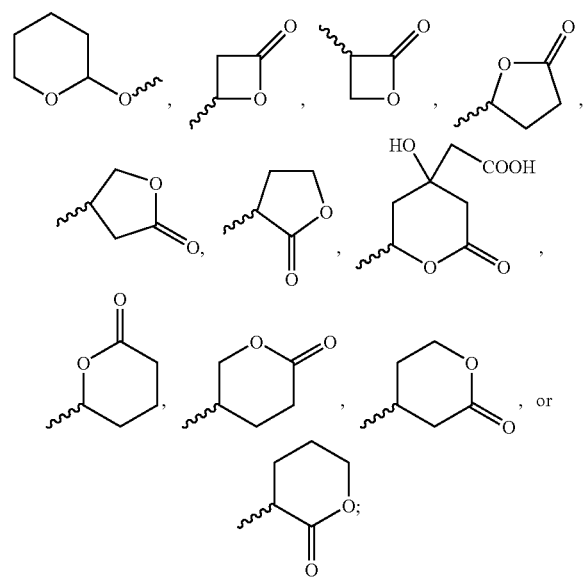

As shown in Scheme 6, protected lactone alcohols 30 and lactone alcohols 16a can be synthesized from compounds of the formula X, 11, or 12 by adaptation of the methods and procedures discussed above for Scheme 3.

Scheme 7: Conversion of Alcohols 18 to Halides 18e

Scheme 7 depicts the synthesis of halides 17. Halides 17 can be synthesized by a variety of methods. One method involves conversion of the alcohol to a leaving group such as a sulfonic ester, such as, for example, tosylate, brosylate, mesylate, or nosylate. This intermediate is then treated with a source of $X^-$, wherein $X^-$ is $I^-$, $Br^-$, or $Cl^-$ in a solvent such as THF or ether. A general method for converting vinyl and phenyl alcohols to thiols involves initially converting the alcohol to a leaving group (e.g., a tosylate) then treating with a halide nucleophile.

Scheme 8: Synthesis of Compounds of Formula I

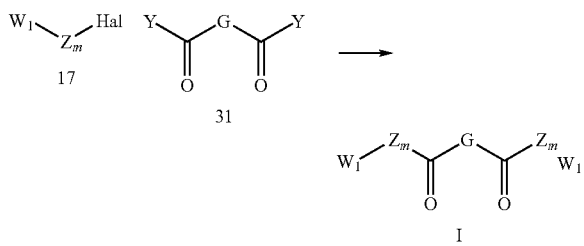

Scheme 8 outlines the synthesis of compounds I. In the first step, compounds I are synthesized by reacting compounds 17 (compounds X 11, 12, 13, 14, 15, and 16 are encompassed by 17) with compounds 31 under the conditions suitable for the formation of compounds I. The conditions and methods discussed in Scheme 1 above for the synthesis of mono-protected diols X from alcohols 6 can be adapted for the synthesis of compounds 17. Compounds 31, wherein Y is a suitable leaving group as defined above, preferably an anhydride, an ester, or an amide group, are readily obtained commercially (e.g., Aldrich Chemical Co. Milwaukee Wis.) or by well known synthetic methods. Compounds I are obtained by reacting compounds 31 with compounds 17 under the conditions suitable for alkyl-de-acyloxy substitution. (For a review, See Kharasch; Reinmuth, *Grignard Reactions of Nonmetallic Substances*; Prentice Hall: Englewood Cliffs, N.J., 1954, pp. 561-562 and 846-908. In a preferred procedure, the conversion of anhydrides, carboxylic esters, or amides to ketones with organometallic compounds. In a particular procedure, anhydrides and carboxylic esters give ketones when treated using inverse addition of Grignard reagents at low temperature with the solvent HMPA. See Newman, *J. Org. Chem.* 1948, 13, 592; Huet; Empotz; Jubier *Tetrahedron* 1973, 29, 479; and *Comprehensive Organic Transformations*; VCH: New York, 1989, pp. 685-686, 693-700. Ketones can also be prepare by the treatment of thioamides with organolithium compounds (alkyl or aryl). See Tominaga; Kohra; Hosomi *Tetrahedron Lett.* 1987, 28, 1529. Moreover, alkyllithium compounds have been used to give ketones from carboxylic esters. See Petrov; Kaplan; Tsir *J. Gen. Chem. USSR* 1962, 32, 691. The reaction must be carried out in a high-boiling solvent such as toluene. Di-substituted amides also can be used to synthesize ketones. See Evans J. Chem. Soc. 1956, 4691; and Wakefield *Organolithium Methods*; Academic Press: New York, 1988, pp. 82-88.

Scheme 9: Synthesis of Compounds 37

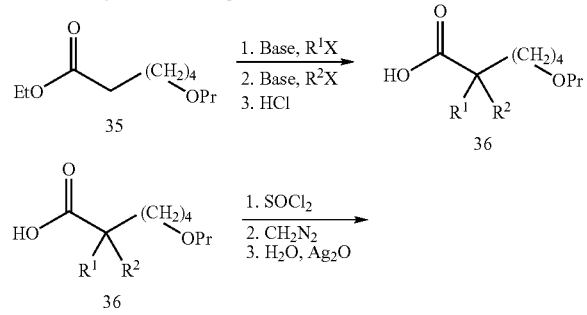

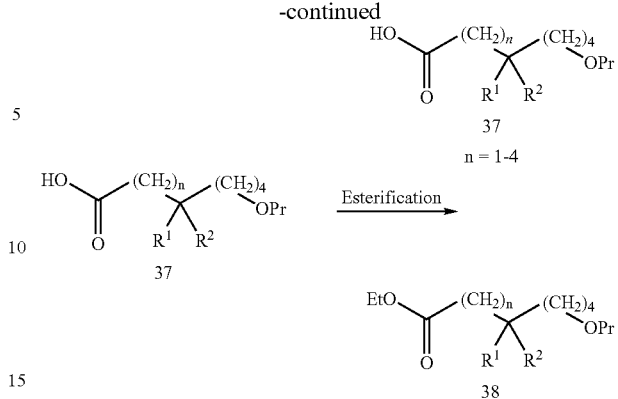

Scheme 9 illustrates the alpha disubstitution of an ester containing a terminal protected hydroxyl moiety. Compounds that contain strong electron withdrawing groups are easily converted to the corresponding enolates. These enolate ions can readilt attack an electrophile resulting in alpha substitution. See *Some Modern Methods of Organic Synthesis*, 3rd Ed.; Cambridge University Press: Cambridge, 1986, pp. 1-26, hereby expressly incorporated herein by reference. The reaction is successful for primary and secondary alkyl, allylic, and benzylic. The use of polar aprotic solvents, e.g., dimethylformamide or dimethylsulfoxide, are preferred. Phase transfer catalysts can also be used. See Tundo et al. *J. Chem. Soc., Perkin Trans.* 1, 1987, 2159, which is hereby expressly incorporated herein by reference.

The conversion to a carboxylic acid with an additional carbon is achieved by treating an acyl halide with diazomethane to generate an intermediate diazo ketone, which in the presence of water and silver oxide rearranges through a ketene intermediate to a carboxylic acid with an additional carbon atom 37. If the reaction is done in an alcohol instead of water an ester is recovered. See Meier et al. *Angew. Chem. Int. Ed. Eng.* 1975, 14, 32-43, which is hereby expressly incorporated herein by reference. Alternatively, the carboxylic acid can be esterified by known techniques. The reaction can be repeated to generate methylene groups adjacent to the carboxylic acid.

Scheme 10: Synthesis of Compounds of Formula 42a which correspond to Compounds
$W^{(1)(2)}$—$(CH_2)_4$—OH, wherein $W^{(1)(2)}$ is $C(R^1)(R^2)(CH_2)_nY$

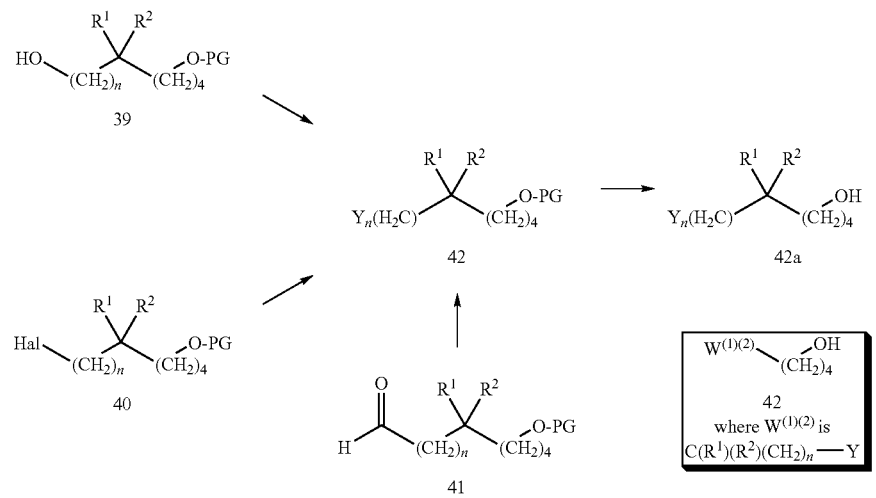

Scheme 10 outlines methodology for the synthesis of protected alcohols 42a wherein Y, $R^1$, $R^2$, Z, and m are defined as above. Protected alcohols 42a correspond to compounds of the formula $W^{(1)(2)}$-Zm-OPG, wherein $W^{(1)(2)}$ is $C(R^1)(R^2)$—Y.

Protected alcohols 42, wherein Y comprises a —C(O)OH group, can be synthesized by oxidizing mono-protected diols 39 with an agent suitable for oxidizing a primary alcohol to a carboxylic acid (for a discussion see M. Hudlicky, *Oxidations in Organic Chemistry*, ACS Monograph 186, 1990, pp. 127-130, hereby expressly incorporated herein by reference). Suitable oxidizing agents include, but are not limited to, pyridinium dichromate (Corey et al., 1979, *Tetrahedron Lett.* 399); manganese dioxide (Ahrens et al., 1967, *J. Heterocycl. Chem.* 4:625); sodium permanganate monohydrate (Menger et al., 1981, *Tetrahedron Lett.* 22:1655); and potassium permanganate (Sam et al., 1972, *J. Am. Chem. Soc.* 94:4024), all of which citations are hereby expressly incorporated herein by reference. The preferred oxidizing reagent is pyridinium dichromate. In an alternative synthetic procedure, protected alcohols 42, wherein Y comprises a —C(O)OH group, can be synthesized by treatment of protected halo-alcohols 40, wherein X is iodo, with CO or $CO_2$, as described in Bailey et al., 1990, *J. Org. Chem.* 55:5404 and Yanagisawa et al., 1994, *J. Am. Chem. Soc.* 116:6130, the two of which citations are hereby expressly incorporated herein by reference. Protected alcohols 42, wherein Y comprises —C(O)$OR^5$, wherein $R^5$ is as defined above, can be synthesized by oxidation of mono-protected diols 39 in the presence of $R^5OH$ (see generally, March, J. *Advanced Organic Chemistry; Reactions Mechanisms, and Structure*, 4th ed., 1992, p. 1196). An exemplary procedure for such an oxidation is described in Stevens et al., 1982, *Tetrahedron Lett.* 23:4647 (HOCl); Sundararaman et al., 1978, *Tetrahedron Lett.* 1627 ($O_3$/KOH); Wilson et al., 1982, *J. Org. Chem.* 47:1360 (t-BuOOH/$Et_3N$); and Williams et al., 1988, *Tetrahedron Lett.* 29:5087 ($Br_2$), the four of which citations are hereby expressly incorporated herein by reference. Preferably, protected alcohols 42, wherein Y comprises a —C(O)$OR^5$ group are synthesized from the corresponding carboxylic acid (i.e., 42, wherein Y comprises —C(O)OH) by esterification with $R^5OH$ (e.g., see March, J., *Advanced Organic Chemistry; Reactions Mechanisms, and Structure*, 4th ed., 1992, p. 393-394, hereby expressly incorporated herein by reference). In another alternative synthesis, protected alcohols 42, wherein Y comprises —C(O)$OR^5$, can be prepared from protected halo-alcohols 40 by carbonylation with transition metal complexes (see e.g., March, J. *Advanced Organic Chemistry; Reactions Mechanisms, and Structure*, 4th ed., 1992, p. 484-486; Urata et al., 1991, *Tetrahedron Lett.* 32:36, 4733); and Ogata et al., 1969, *J. Org. Chem.* 3985, the three of which citations are hereby expressly incorporated herein by reference).

Protected alcohols 42, wherein Y comprises —OC(O)$R^5$, wherein $R^5$ is as defined above, can be prepared by acylation of mono-protected diols 39 with a carboxylate equivalent such as an acyl halide (i.e., $R^5$C(O)—Hal, wherein Hal is iodo, bromo, or chloro, see e.g., March, J. *Advanced Organic Chemistry; Reactions Mechanisms, and Structure*, 4th ed., 1992, p. 392 and *Org. Synth. Coll.* Vol. III, Wiley, N.Y., pp. 142, 144, 167, and 187 (1955)) or an anhydride (i.e., $R^5$C(O)—O—(O)$CR^5$, see e.g., March, J. *Advanced Organic Chemistry; Reactions Mechanisms, and Structure*, 4th ed., 1992, p. 392-393 and *Org. Synth. Coll.* Vol. III, Wiley, N.Y., pp. 11, 127, 141, 169, 237, 281, 428, 432, 690, and 833 (1955)), all of which citations are incorporated herein by reference). Preferably, the reaction is conducted by adding a base to a solution comprising mono-protected diols 39, a carboxylate equivalent, and an organic solvent, which solution is preferably maintained at a constant temperature within the range of 0° C. to about room temperature. Solvents suitable for reacting mono-protected diols 39 with a carboxylate equivalent include, but are not limited to, dichloromethane, toluene, and ether, preferably dichloromethane. Suitable bases include, but are not limited to, hydroxide sources, such as sodium hydroxide, potassium hydroxide, sodium carbonate, or potassium carbonate; or an amine such as triethylamine, pyridine, or dimethylaminopyridine, amines are preferred. The progress of the reaction can be followed by using an appropriate analytical technique, such as thin layer chromatography or high performance liquid chromatography and when substantially complete, the product can be isolated by workup and purified if desired.

Protected alcohols 42, wherein Y comprises one of the following phosphate ester groups

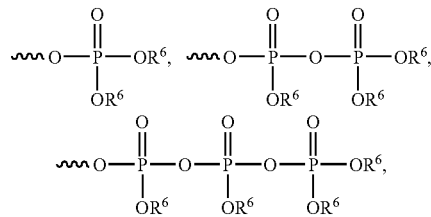

wherein $R^6$ is defined as above, can be prepared by phosphorylation of mono-protected diols X according to well-known methods (for a general reviews, see Corbridge *Phosphorus: An Outline of its Chemistry, Biochemistry, and Uses*, Studies in Inorganic Chemistry, 3rd ed., pp. 357-395 (1985); Ramirez et al., 1978, *Acc. Chem. Res.* 11:239; and Kalckare *Biological Phosphorylations*, Prentice-Hall, New York (1969); J. B. Sweeny in *Comprehensive Organic Functional Group Transformations*, A. R. Katritzky, O. Meth-Cohn and C. W. Rees, Eds. Pergamon: Oxford, 1995, vol 2, pp. 104-109, the four of which are hereby expressly incorporated herein by reference). Protected alcohols 42 wherein Y comprises a monophosphate group of the formula:

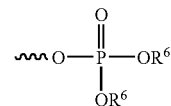

wherein $R^6$ is defined as above, can be prepared by treatment of mono-protected diol 39 with phosphorous oxychloride in a suitable solvent, such as xylene or toluene, at a constant temperature within the range of about 100° C. to about 150° C. for about 2 hours to about 24 hours. After the reaction is deemed substantially complete, by using an appropriate analytical method, the reaction mixture is hydrolyzed with $R^6$—OH. Suitable procedures are referenced in Houben-Weyl, Methoden der Organische Chemie, Georg Thieme Verlag Stuttgart 1964, vol. XII/2, pp. 143-210 and 872-879, hereby expressly incorporated herein by reference. Alternatively, when both $R^6$ are hydrogen, can be synthesized by reacting mono-protected diols X with silyl polyphosphate (Okamoto et al., 1985, *Bull Chem. Soc. Jpn.* 58:3393, hereby expressly incorporated herein by reference) or by hydrogenolysis of their benzyl or phenyl esters (Chen et al., 1998, *J. Org. Chem.* 63:6511, incorporated herein by reference). In another alternative procedure, when $R^6$ is ($C_1$-$C_6$)alkyl, ($C_2$-$C_6$)alkenyl, or ($C_2$-$C_6$)alkynyl, the monophosphate esters can be prepared by reacting mono-protected diols 39 with appropriately substituted phosphoramidites followed by oxidation of the intermediate with m-chloroperbenzoic acid (Yu et al., 1988, *Tetrahedron Lett.* 29:979, incorporated herein by reference) or by reacting mono-protected diols 39 with dialkyl or diaryl substituted phosphorochloridates (Pop, et al, 1997, *Org. Prep. and Proc. Int.* 29:341, incorporated herein by reference). The phosphoramidites are commercially available (e.g., Aldrich Chemical Co., Milwaukee, Wis.) or readily prepared according to literature procedures (see e.g., Uhlmann et al. 1986, *Tetrahedron Lett.* 27:1023 and Tanaka et al., 1988, *Tetrahedron Lett.* 29:199, both of which are incorporated herein by reference). The phosphorochloridates are also commercially available (e.g., Aldrich Chemical Co., Milwaukee, Wis.) or prepared according to literature methods (e.g., Gajda et al, 1995, *Synthesis* 25:4099. In still another alternative synthesis, protected alcohols 42, wherein Y comprises a monophosphate group and $R^6$ is alkyl or aryl, can be prepared by reacting $IP^+(OR^6)_3$ with mono-protected diols 39 according to the procedure described in Stowell et al., 1995, *Tetrahedron Lett.* 36:11, 1825 or by alkylation of protected halo alcohols 40 with the appropriate dialkyl or diaryl phosphates (see e.g., Okamoto, 1985, *Bull Chem. Soc. Jpn.* 58:3393, incorporated herein by reference).

Protected alcohols 42 wherein Y comprises a diphosphate group of the formula

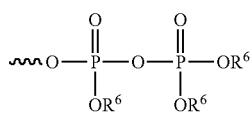

wherein $R^6$ is defined as above, can be synthesized by reacting the above-discussed monophosphates of the formula:

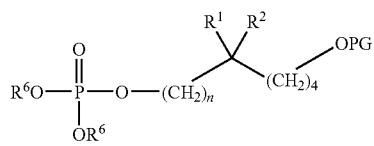

with a phosphate of the formula

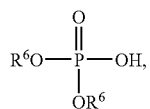

(commercially available, e.g., Aldrich Chemical Co., Milwaukee, Wis.), in the presence of carbodiimide such as dicyclohexylcarbodiimide, as described in Houben-Weyl, *Methoden der Organische Chemie*, Georg Thieme Verlag Stuttgart 1964, vol. XII/2, pp. 881-885. In the same fashion, protected alcohols 42, wherein Y comprises a triphosphate group of the formula:

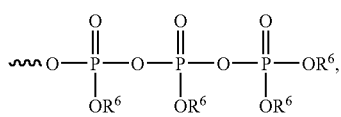

can be synthesized by reacting the above-discussed diphosphate protected alcohols, of the formula:

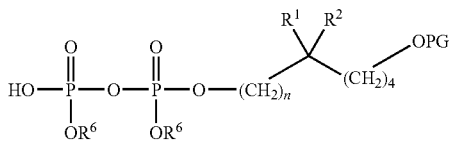

with a phosphate of the formula:

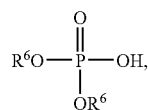

as described above. Alternatively, when $R^6$ is H, protected alcohols 42 wherein Y comprises the triphosphate group, can be prepared by reacting mono-protected diols 39 with salicyl phosphorochloridite and then pyrophosphate and subsequent cleavage of the adduct thus obtained with iodine in pyridine as described in Ludwig et al., 1989, *J. Org. Chem.* 54:631, incorporated herein by reference.

Protected alcohols 42, wherein Y is —$SO_3H$ or a heterocyclic group selected from the group consisting of:

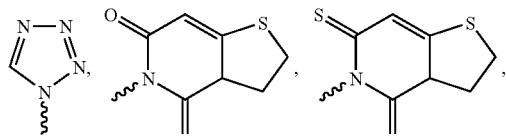

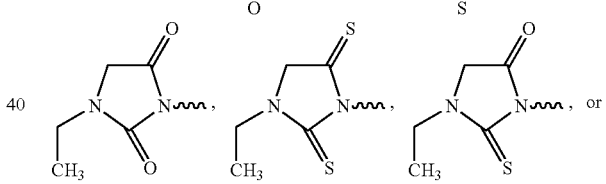

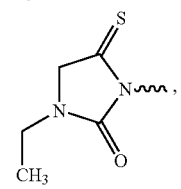

can be prepared by halide displacement from protected halo-alcohols 40. Thus, when Y is —$SO_3H$, protected alcohols 42 can by synthesized by reacting protected halo-alcohols with sodium sulfite as described in Gilbert *Sulfonation and Related Reactions*; Wiley: New York, 1965, pp. 136-148 and pp. 161-163; *Org. Synth. Coll.* Vol. II, Wiley, N.Y., 558, 564 (1943); and *Org. Synth. Coll.* Vol. IV, Wiley, N.Y., 529 (1963), all three of which are incorporated herein by reference. When Y is one of the above-mentioned heterocycles, protected alcohols 42 can be prepared by reacting protected halo-alcohols with the corresponding heterocycle in the presence of a base. The heterocycles are available commercially (e.g., Aldrich Chemical Co., Milwaukee, Wis.) or prepared by well-known synthetic methods (see the procedures described in Ware, 1950, *Chem. Rev.* 46:403-470, incorporated herein by reference). Preferably, the reaction is conducted by stirring a mixture comprising 40, the heterocycle, and a solvent at a constant temperature within the range of about room temperature to about 100° C., preferably within the range of about 50° C. to about 70° C. for about 10 to about 48 hours. Suitable bases include hydroxide bases such as sodium hydroxide, potassium hydroxide, sodium carbonate, or potassium carbonate. Preferably, the solvent used in forming protected alcohols 42 is selected from dimethylformamide; formamide; dimethyl sulfoxide; alcohols, such as methanol or ethanol; and mixtures thereof. The progress of the reaction can be followed by using an appropriate analytical technique, such as thin layer chromatography or high performance liquid chromatography and when substantially complete, the product can be isolated by workup and purified if desired.

Protected alcohols 42, wherein Y is a heteroaryl ring selected from

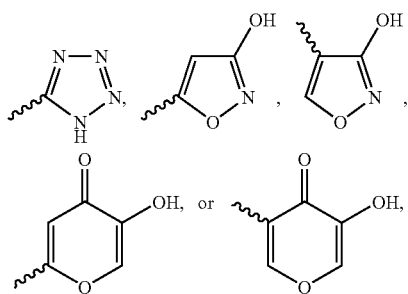

can be prepared by metallating the suitable heteroaryl ring then reacting the resulting metallated heteroaryl ring with protected halo-alcohols 40 (for a review, see Katritzky *Handbook of Heterocyclic Chemistry*, Pergamon Press: Oxford 1985). The heteroaryl rings are available commercially or prepared by well-known synthetic methods (see e.g., Joule et al., *Heterocyclic Chemistry*, 3rd ed., 1995; De Sarlo et al., 1971, *J. Chem. Soc. (C)* 86; Oster et al., 1983, *J. Org. Chem.* 48:4307; Iwai et al., 1966, *Chem. Pharm. Bull.* 14:1277; and U.S. Pat. No. 3,152,148, all of which citations are incorporated herein by reference). As used herein, the term "metallating" means the forming of a carbon-metal bond, which bond may be substantially ionic in character. Metallation can be accomplished by adding about 2 equivalents of strong organometallic base, preferably with a $pK_a$ of about 25 or more, more preferably with a $pK_a$ of greater than about 35, to a mixture comprising a suitable organic solvent and the heterocycle. Two equivalents of base are required: one equivalent of the base deprotonates the —OH group or the —NH group, and the second equivalent metallates the heteroaryl ring. Alternatively, the hydroxy group of the heteroaryl ring can be protected with a base-stable, acid-labile protecting group as described in Greene, T. W., *Protective Groups in Organic Synthesis,* 3rd edition 17-237 (1999), hereby expressly incorporated herein by reference. Where the hydroxy group is protected, only one equivalent of base is required. Examples of suitable base-stable, acid-labile hydroxyl-protecting groups, include but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahydrofuranyl, tetrahydrothiofuranyl, 1-ethoxyethyl, 1-methyl-1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably, the $pK_a$ of the base is higher than the $pK_a$ of the proton of the heterocycle to be deprotonated. For a listing of $pK_a$s for various heteroaryl rings, see Fraser et al., 1985, *Can. J. Chem.* 63:3505, incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. If desired, the organometallic base can be activated with a complexing agent, such as N,N,N',N'-tetramethylethylenediamine or hexamethylphosphoramide (1970, *J. Am. Chem. Soc.* 92:4664, hereby expressly incorporated herein by reference). Solvents suitable for synthesizing protected alcohols 42, wherein Y is a heteroaryl ring include, but are not limited to, diethyl ether, tetrahydrofuran; and hydrocarbons, such as pentane. Generally, metallation occurs alpha to the heteroatom due to the inductive effect of the heteroatom, however, modification of conditions, such as the identity of the base and solvents, order of reagent addition, reagent addition times, and reaction and addition temperatures can be modified by one of skill in the art to achieve the desired metallation position (see e.g., Joule et al., *Heterocyclic Chemistry,* 3rd ed., 1995, pp. 30-42, hereby expressly incorporated herein by reference) Alternatively, the position of metallation can be controlled by use of a halogenated heteroaryl group, wherein the halogen is located on the position of the heteroaryl ring where metallation is desired (see e.g., Joule et al., *Heterocyclic Chemistry,* 3rd ed., 1995, p. 33 and Saulnier et al., 1982, *J. Org. Chem.* 47:757, the two of which citations are hereby expressly incorporated herein by reference). Halogenated heteroaryl groups are available commercially (e.g., Aldrich Chemical Co., Milwaukee, Wis.) or can be prepared by well-known synthetic methods (see e.g., Joule et al., *Heterocyclic Chemistry,* 3rd ed., 1995, pp. 78, 85, 122, 193, 234, 261, 280, 308, hereby expressly incorporated herein by reference). After metallation, the reaction mixture comprising the metallated heteroaryl ring is adjusted to within a temperature range of about 0° C. to about room temperature and protected halo-alcohols 40 (diluted with a solvent or in undiluted form) are added, preferably at a rate such that the reaction-mixture temperature remains within about one to two degrees of the initial reaction-mixture temperature. After addition of protected halo-alcohols 40, the reaction mixture is stirred at a constant temperature within the range of about room temperature and about the solvent's boiling temperature and the reaction's progress can be monitored by the appropriate analytical technique, preferably thin-layer chromatography or high-performance liquid chromatography. After the reaction is substantially complete, protected alcohols 42 can be isolated by workup and purification. It is to be understood that conditions, such as the identity of protected halo-alcohol 40, the base, solvents, orders of reagent addition, times, and temperatures, can be modified by one of skill in the art to optimize the yield and selectivity. Exemplary procedures that can be used in such a transformation are described in Shirley et al., 1995, *J. Org. Chem.* 20:225; Chadwick et at., 1979, *J. Chem. Soc., Perkin Trans.* 1 2845; Rewcastle, 1993, *Adv. Het. Chem.* 56:208; Katritzky et al., 1993, *Adv. Het. Chem.* 56:155; and Kessar et al., 1997, *Chem. Rev.* 97:721.
When Y is

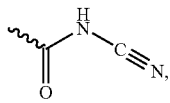

protected alcohols 42 can be prepared from their corresponding carboxylic acid derivatives (42, wherein Y is —$CO_2H$) as

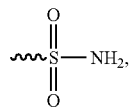

protected alcohols 42 can be prepared by reacting their sulphonic acid derivatives (i.e., 42, wherein Y is —$SO_3H$) with ammonia as described in Sianesi et al., 1971, *Chem. Ber.* 104:1880 and Campagna et al., 1994, *Farmaco, Ed. Sci.* 49:653, both of which citations are incorporated herein by reference).

Scheme 11: Synthesis of Compounds of Formula 46 which correspond to Compounds $W^{(1)(2)}$—$(CH_2)_4$—OH, wherein $W^{(1)(2)}$ is $C(R^1)(R^2)(CH_2)_4$-Lactone

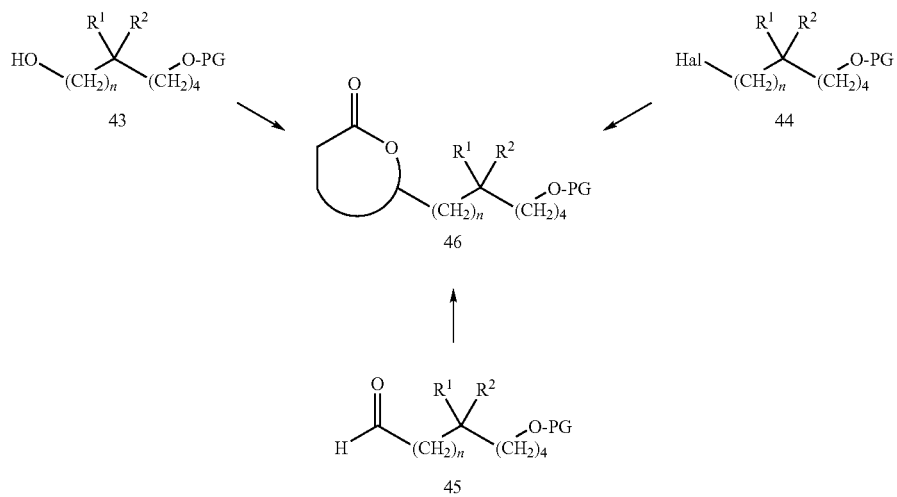

described in Belletire et al. 1988, *Synthetic Commun.* 18:2063 or from the corresponding acylchlorides (42, wherein Y is —CO-halo) as described in Skinner et al., 1995, *J. Am. Chem. Soc.* 277:5440, both citations are incorporated herein by reference. The acylhalides can be prepared from the carboxylic acids by well known procedures such as those described in March, J., *Advanced Organic Chemistry; Reactions Mechanisms, and Structure*, 4th ed., 1992, pp. 437-438, hereby expressly incorporated herein by reference. When Y is

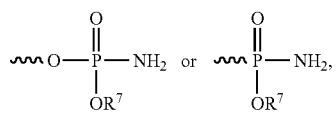

wherein $R^7$ is as defined above, protected alcohols 42 can be prepared by first reacting protected halo-alcohols 40 with a trialkyl phosphite according to the procedure described in Kosolapoff, 1951, *Org. React.* 6:273 followed by reacting the derived phosphonic diester with ammonia according to the procedure described in Smith et al., 1957, *J. Org. Chem.* 22:265, incorporated herein by reference. When Y is As further illustrated in Scheme 11, protected alcohols 42 can be deprotected providing alcohols 42a. The deprotection method depends on the identity of the alcohol-protecting group, see e.g., the procedures listed in Greene, T. W., *Protective Groups in Organic Synthesis*, 3rd edition 17-237 (1999), particularly see pages 48-49, incorporated herein by reference. One of skill in the art will readily be able to choose the appropriate deprotection procedure. When the alcohol is protected as an ether function (e.g., methoxymethyl ether), the alcohol is preferably deprotected with aqueous or alcoholic acid. Suitable deprotection reagents include, but are not limited to, aqueous hydrochloric acid, p-toluenesulfonic acid in methanol, pyridinium-p-toluenesulfonate in ethanol, Amberlyst H-15 in methanol, boric acid in ethylene-glycol-monoethylether, acetic acid in a water-tetrahydrofuran mixture, aqueous hydrochloric acid is preferred. Examples of such procedures are described, respectively, in Bernady et al., 1979, *J. Org. Chem.* 44:1438; Miyashita et al., 1977, *J. Org. Chem.* 42:3772; Johnston et al., 1988, *Synthesis* 393; Bongini et al., 1979, *Synthesis* 618; and Hoyer et al., 1986, *Synthesis* 655; Gigg et al., 1967, *J. Chem. Soc. C*, 431; and Corey et al., 1978, *J. Am. Chem. Soc.* 100:1942, all of which are incorporated herein by reference.

Scheme 11 depicts the synthesis of protected lactone alcohols 46 and lactone. Compound 46 corresponds to compounds of the formula $W^{(1)(2)}$-Zm-OPG and, wherein $W^{(1)(2)}$ is a lactone group selected from:

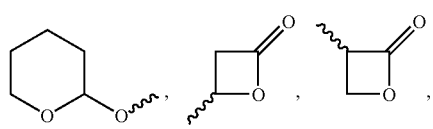

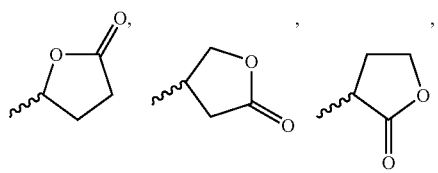

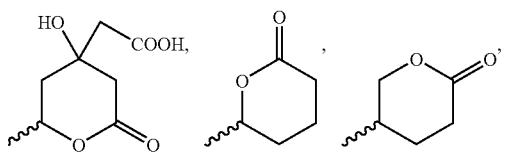

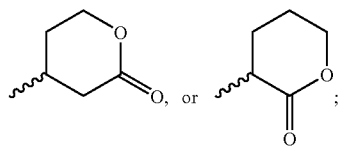

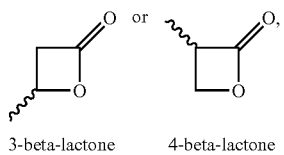

Protected lactone alcohols 46 can be prepared from compounds of the formula 46, 45, or 44 by using well-known condensation reactions and variations of the Michael reaction. Methods for the synthesis of lactones are disclosed in Multzer in *Comprehensive Organic Functional Group Transformations*, A. R. Katritzky, O. Meth-Cohn and C. W. Rees, Eds. Pergamon: Oxford, 1995, vol 5, pp. 161-173, incorporated herein by reference. Mono-protected diols 43, electrophilic protected alcohols 44, and aldehydes 45 are readily available ether commercially (e.g., Aldrich Chemical Co., Milwaukee, Wis.) or by well known synthetic procedures.

When $W^{(1)(2)}$ is a beta-lactone group of the formula:

3-beta-lactone     4-beta-lactone protected lactone alcohols 46 can be prepared from aldehydes 45 and electrophilic protected alcohols 44, respectively, by a one-pot-addition-lactonization according to the procedure of Masamune et al., 1976, *J. Am. Chem. Soc.* 98:7874 and Danheiser et al., 1991, *J. Org. Chem.* 56:1176, both of which are incorporated herein by reference. This one-pot-addition-lactonization methodology has been reviewed by Multzer in *Comprehensive Organic Functional Group Transformations*, A. R. Katritzky, O. Meth-Cohn and C. W. Rees, Eds. Pergamon: Oxford, 1995, vol 5, pp. 161, incorporated herein by reference When $W^{(1)(2)}$ is a gamma- or delta-lactone group of the formula:

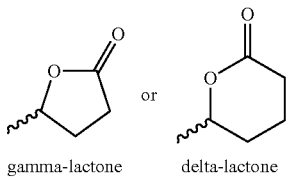

gamma-lactone     delta-lactone protected lactone alcohols 46 can be prepared from aldehydes 45 according to well known synthetic methodology. For example, the methodology described in Masuyama et al., 2000, *J. Org. Chem.* 65:494; Eisch et al., 1978, *J. Organo. Met. Chem. C*8 160; Eaton et al., 1947, *J. Org. Chem.* 37:1947; Yunker et al., 1978, *Tetrahedron Lett.* 4651; Bhanot et al., 1977, *J. Org. Chem.* 42:1623; Ehlinger et al., 1980, *J. Am. Chem. Soc.* 102:5004; and Raunio et al., 1957, *J. Org. Chem.* 22:570, all of which citations are incorporated herein by reference. For instance, as described in Masuyama et al., 2000, *J. Org. Chem.* 65:494, aldehydes 45 can be treated with about 1 equivalent of a strong organometallic base, preferably with a $pK_a$ of about 25 or more, more preferably with a $pK_a$ of greater than about 35, in a suitable organic solvent to give a reaction mixture. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. The reaction-mixture temperature is adjusted to within the range of about 0° C. to about 100° C., preferably about room temperature to about 50° C., and a halide of the formula:

$$Hal\diagdown(CH_2)_z\diagup C(O)OR,$$

wherein z is 1 or 2 (diluted with a solvent or in undiluted form) is added. The reaction mixture is stirred for a period of about 2 hours to about 48 hours, preferably about 5 to about 10 hours, during which time the reaction's progress can be followed by using an appropriate analytical technique, such as thin layer chromatography or high performance liquid chromatography. When the reaction is deemed substantially complete, protected lactone alcohols 46 can be isolated by workup and purified if desired. When $W^{(1)(2)}$ is a gamma- or delta-lactone group of the formula:

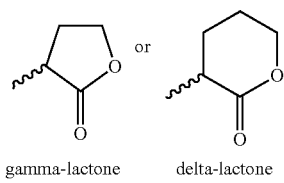

gamma-lactone     delta-lactone protected lactone alcohols 46 can be synthesized by deprotonating the corresponding lactone with a strong base providing the lactone enolate and reacting the enolate with electrophilic protected alcohols 44 (for a detailed discussion of enolate formation of active methylene compounds such as lactones, see House *Modern Synthetic Reactions*; W. A. Benjamin, Inc. Philippines 1972 pp. 492-570, and for a discussion of reaction of lactone enolates with electrophiles such as carbonyl compounds, see March, J. *Advanced Organic Chemistry; Reactions Mechanisms, and Structure*, 4th ed., 1992, pp. 944-945, both of which are incorporated herein by reference). Lactone-enolate formation can be accomplished by adding about 1 equivalent of a strong organometallic base, preferably with a $pK_a$ of about 25 or more, more preferably with a $pK_a$ of greater than about 35, to a mixture comprising a suitable organic solvent and the lactone. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Solvents suitable for lactone-enolate formation include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 44 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, protected lactone alcohols 46 can be isolated by workup and purified if desired. When $W^{(1)(2)}$ is a lactone group of the formula:

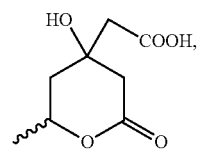

protected lactone alcohols 46 can be prepared from aldehydes 45 according to the procedure described in U.S. Pat. No. 4,622,338, hereby expressly incorporated herein by reference.

When $W^{(1)(2)}$ is a gamma- or delta-lactone group of the formula:

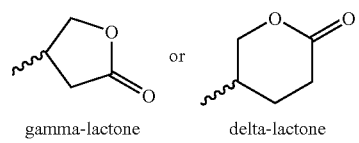

gamma-lactone      delta-lactone protected lactone alcohols 46 can be prepared according to a three step sequence. The first step comprises base-mediated reaction of electrophilic protected alcohols 44 with succinic acid esters (i.e., $R^9O_2CCH_2CH_2CO_2R^9$, wherein $R^9$ is alkyl) or glutaric acid esters (i.e., $R^9O_2CCH_2CH_2CH_2CO_2R^9$, wherein $R^9$ is alkyl) providing a diester intermediate of the formula 44i:

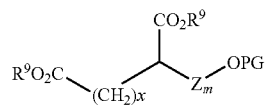

wherein x is 1 or 2 depending on whether the gamma or delta lactone group is desired. The reaction can be performed by adding about 1 equivalent of a strong organometallic base, preferably with a $pK_a$ of about 25 or more, more preferably with a $pK_a$ of greater than about 35, to a mixture comprising a suitable organic solvent and the succinic or glutaric acid ester. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 44 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, the diester intermediate be isolated by workup and purified if desired. In the second step, the intermediate diester can be reduced, with a hydride reducing agent, to yield a diol:

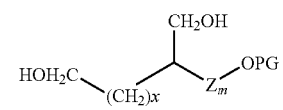

The reduction can be performed according to the procedures referenced in March, J. *Advanced Organic Chemistry; Reactions Mechanisms, and Structure*, 4th ed., 1992, p. 1214, incorporated herein by reference). Suitable reducing agents include, but are not limited to, lithium aluminum hydride, diisobutylaluminum hydride, sodium borohydride, and lithium borohydride). In the third step, the diol can be oxidatively cyclized with $RuH_2(PPh_3)_4$ to the product protected lactone alcohols 46 according to the procedure of Yoshikawa et al., 1986, *J. Org. Chem.* 51:2034 and Yoshikawa et al., 1983, *Tetrahedron Lett.* 26:2677, both of which citations are incorporated herein by reference. When $W^{(1)(2)}$ is a lactone group of the formula:

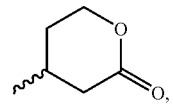

protected lactone alcohols 46 can be synthesized by reacting the Grignard salts of electrophilic protected alcohols 44, where E is a halide, with 5,6-dihydro-2H-pyran-2-one, commercially available (e.g., Aldrich Chemical Co., Milwaukee, Wis.), in the presence of catalytic amounts of a 1-dimethylaminoacetyl)pyrrolidine-2yl)methyl-diarylphosphine-copper (I) iodide complex as described in Tomioka et al., 1995, *Tetrahedron Lett.* 36:4275, incorporated herein by reference.

Scheme 12: Synthesis of Compounds of Formula II

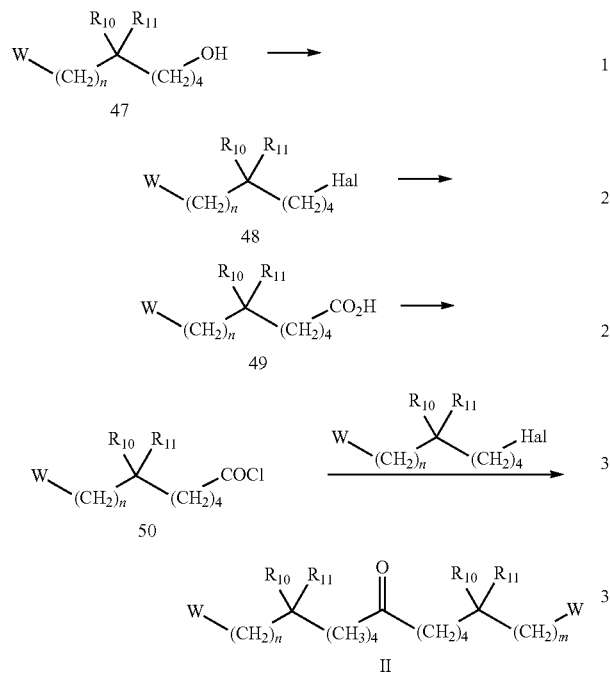

3Scheme 12 illustrates the synthesis of ketone II. The alcohol 47 is initially converted to a halogen 48. See Larock, *Comprehensive Organic Transformations*, VCH: New York, 1989, pp. 360-362; all references disclosed therein are incorporated herein by reference. The halide 48 is then converted to a carboxylic acid 49 with subsequent conversion to a acyl halide 50. See Larock, *Comprehensive Organic Transformations*, VCH: New York, 1989, pp. 850-851, 855-856, 859-860, 977, 980, and 985; all references discloses therein are incorporated herein by reference. The acyl halide 50 is then coupled with the halide to afford compound II. See Rappoport, *The Chemistry of the Functional Groups, Supp. D*, pt. 2; Wiley: New York, 1983; House, *Modern Synthetic Reactions*, 2nd Ed. Benjamin: New York, 1972, pp. 691-694, 734-765, which are incorporated herein by reference.

Scheme 13: Synthesis of Compounds III

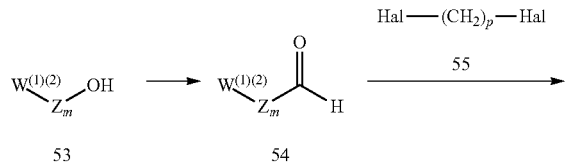

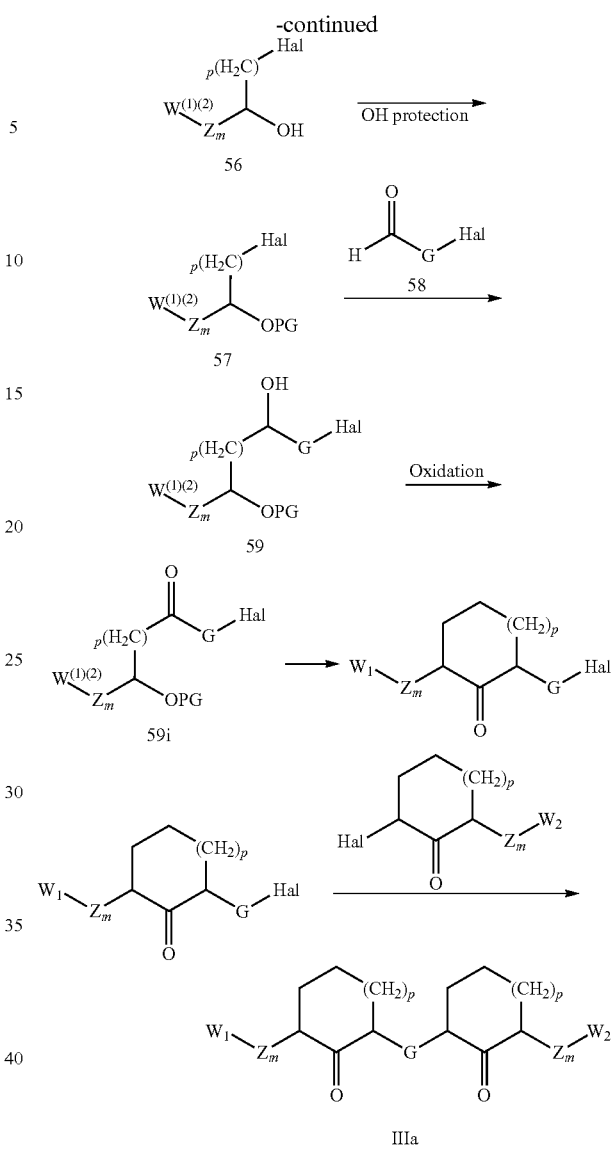

Scheme 13 depicts the synthesis of compounds ma, that is, compounds III where a double bond is not present in the ring. In the first step, compounds 53, prepared as discussed in Schemes 1 to 6 above, can be converted to compounds 54 by standard oxidation of the primary alcohol to an aldehyde group. Such oxidations are described in M. Hudlicky, *Oxidations in Organic Chemistry*, ACS Monograph 186, 1990, pp. 114-127, hereby expressly incorporated herein by reference. In the next step Grignard reaction of 54 with 55 followed by standard OH protection gives 57. Compounds 55 are commercially available (e.g., from Aldrich Chemical Co. Milwaukee, Wis.) or readily prepared by standard synthetic methodology. For exemplary procedures for Grignard reaction see March, J. *Advanced Organic Chemistry; Reactions Mechanisms, and Structure*, 4th ed., 1992, pp. 920-929, incorporated herein by reference. Similarly, in the next step, the Grignard salt of 57 is condensed with 58 to provide 59. Next 59 is oxidized and then cyclized to 60. When p is one, exemplary cyclization procedures are found in Friedrichsen, W. in *Comprehensive Heterocyclic Chemistry II*; Katritzky, A. R.; Rees, W. C.; Scriven, E. F. V. Eds.; Pergamon Press: Oxford, 1996; Vol. 2, p 351, and *Comprehensive Heterocyclic*

Chemistry; Katritzky, A. R.; Rees, W. C. Eds.; Pergamon Press: Oxford, 1986; Vol. 3. When p is 0, cyclization procedures are found in Hepworth, J. D. in *Comprehensive Heterocyclic Chemistry II*; Katritzky, A. R; Rees, W. C.; Scriven, E. F. V. Eds.; Pergamon Press: Oxford, 1996; Vol. 5, p 351 and *Comprehensive Heterocyclic Chemistry*; Katritzky, A. R.; Rees, W. C. Eds.; Pergamon Press: Oxford, 1986; Vol. 3, all of which citations are hereby expressly incorporated herein by reference.

The hydroxy ketone is subjected to cyclization, as described in the above Hepworth, J. D. in *Comprehensive Heterocyclic Chemistry II*; Katritzky, A. R.; Rees, W. C.; Scriven, E. F. V. Eds.; Pergamon Press: Oxford, 1996; Vol. 5, p 386. For compounds III where $W^{(1)(2)}$ is $HO(CH)_n$—$R^1R^2$: The hydroxy group is first deprotected as described in Greene, T. W., *Protective Groups in Organic Synthesis*, 3rd edition (1999). For other structures, where Y is a group such as an acid, aldehydes, etc., protection is needed (acids as esters, preferably pivaloyl, aldehydes as silyl derivatives such as TIPS, stable in both basic and acidic conditions). When $W^{(1)(2)}$ is a Lactone it can be introduced as discussed in Scheme 3 above. The compounds are then coupled to afford compound of the formula IIIa.

The reactions are performed under similar conditions for substituted cyclic compounds. After the formation of the mono-cyclic compounds, they are in situ reacted with electrophiles (e.g., MeI) at temperatures between −40° C. to +60° C., for a reaction time of 1 hr to 5 days. In addition, ing double bonds can be selectively added or reduced or otherwise manipulated by well known synthetic methods to give compounds III having one or two selectively-placed double bonds (i.e., the double bond(s) can be positioned in the desired location within the ring), for example, the methods disclosed in March, J. *Advanced Organic Chemistry; Reactions Mechanisms, and Structure*, 4th ed., 1992, pp. 771-780, incorporated herein by reference.

4.3. Therapeutic Uses of Compounds or Compositions of the Invention

In accordance with the invention, a compound of the invention or a composition of the invention, comprising a compound of the invention and a pharmaceutically acceptable vehicle, is administered to a patient, preferably a human, with or at risk of aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. In one embodiment, "treatment" or "treating" refers to an amelioration of a disease or disorder, or at least one discernible symptom thereof. In another embodiment, "treatment" or "treating" refers to inhibiting the progression of a disease or disorder, either physically, e.g., stabilization of a discernible symptom, physiologically, e.g., stabilization of a physical parameter, or both.

In certain embodiments, the compounds of the invention or the compositions of the invention are administered to a patient, preferably a human, as a preventative measure against such diseases. As used herein, "prevention" or "preventing" refers to a reduction of the risk of acquiring a given disease or disorder. In a preferred mode of the embodiment, the compositions of the present invention are administered as a preventative measure to a patient, preferably a human having a genetic predisposition to a aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. Examples of such genetic predispositions include but are not limited to the ∈4 allele of apolipoprotein E, which increases the likelihood of Alzheimer's Disease; a loss of function or null mutation in the lipoprotein lipase gene coding region or promoter (e.g., mutations in the coding regions resulting in the substitutions D9N and N291S; for a review of genetic mutations in the lipoprotein lipase gene that increase the risk of cardiovascular diseases, dyslipidemias and dyslipoproteinemias, see Hayden and Ma, 1992, Mol. Cell Biochem. 113:171-176); and familial combined hyperlipidemia and familial hypercholesterolemia.

In another preferred mode of the embodiment, the compounds of the invention or compositions of the invention are administered as a preventative measure to a patient having a non-genetic predisposition to a aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. Examples of such non-genetic predispositions include but are not limited to cardiac bypass surgery and percutaneous transluminal coronary angioplasty, which often lead to restenosis, an accelerated form of atherosclerosis; diabetes in women, which often leads to polycystic ovarian disease; and cardiovascular disease, which often leads to impotence. Accordingly, the compositions of the invention may be used for the prevention of one disease or disorder and concurrently treating another (e.g., prevention of polycystic ovarian disease while treating diabetes; prevention of impotence while treating a cardiovascular disease).

4.4. Treatment of Cardiovascular Diseases

The present invention provides methods for the treatment or prevention of a cardiovascular disease, comprising administering to a patient a therapeutically effective amount of a compound or a composition comprising a compound of the invention and a pharmaceutically acceptable vehicle. As used herein, the term "cardiovascular diseases" refers to diseases of the heart and circulatory system. These diseases are often associated with dyslipoproteinemias and/or dyslipidemias. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarction; cerebral infarction and restenosis.

4.5. Treatment of Dyslipidemias

The present invention provides methods for the treatment or prevention of a dyslipidemia comprising administering to a patient a therapeutically effective amount of a compound or a composition comprising a compound of the invention and a pharmaceutically acceptable vehicle.

As used herein, the term "dyslipidemias" refers to disorders that lead to or are manifested by aberrant levels of circulating lipids. To the extent that levels of lipids in the blood are too high, the compositions of the invention are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (http://www.americanheart.org/cholesterol/about_level.html and http://www.nhlbi.nih.gov/health/public/heart/chol/hbc_what.html, respectively). At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL. Dyslipidemias which the compositions of the present invention are useful for preventing or treating include but are not limited to hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of urea bodies (e.g. β-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, e.g., reducing LDL in the blood of a patient, reducing free triglycerides in the blood of a patient, increasing the ratio of HDL to LDL in the blood of a patient, and inhibiting saponified and/or non-saponified fatty acid synthesis, said methods comprising administering to the patient a compound or a composition comprising a compound of the invention in an amount effective alter lipid metabolism.

4.6. Treatment of Dyslipoproteinemias

The present invention provides methods for the treatment or prevention of a dyslipoproteinemia comprising administering to a patient a therapeutically effective amount of a compound or a composition comprising a compound of the invention and a pharmaceutically acceptable vehicle.

As used herein, the term "dyslipoproteinemias" refers to disorders that lead to or are manifested by aberrant levels of circulating lipoproteins. To the extent that levels of lipoproteins in the blood are too high, the compositions of the invention are administered to a patient to restore normal levels. Conversely, to the extent that levels of lipoproteins in the blood are too low, the compositions of the invention are administered to a patient to restore normal levels. Normal levels of lipoproteins are reported in medical treatises known to those of skill in the art.

Dyslipoproteinemias which the compositions of the present invention are useful for preventing or treating include but are not limited to high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with obesity; lipoprotein abnormalities associated with Alzheimer's Disease; and familial combined hyperlipidemia.

The present invention further provides methods for reducing apo C-II levels in the blood of a patient; reducing apo C-III levels in the blood of a patient; elevating the levels of HDL associated proteins, including but not limited to apo A-I, apo A-II, apo A-IV and apo E in the blood of a patient; elevating the levels of apo E in the blood of a patient, and promoting clearance of triglycerides from the blood of a patient, said methods comprising administering to the patient a compound or a composition comprising a compound of the invention in an amount effective to bring about said reduction, elevation or promotion, respectively.

4.7. Treatment of Glucose Metabolism Disorders

The present invention provides methods for the treatment or prevention of a glucose metabolism disorder, comprising administering to a patient a therapeutically effective amount of a compound or a composition comprising a compound of the invention and a pharmaceutically acceptable vehicle. As used herein, the term "glucose metabolism disorders" refers to disorders that lead to or are manifested by aberrant glucose storage and/or utilization. To the extent that indicia of glucose metabolism (i.e., blood insulin, blood glucose) are too high, the compositions of the invention are administered to a patient to restore normal levels. Conversely, to the extent that indicia of glucose metabolism are too low, the compositions of the invention are administered to a patient to restore normal levels. Normal indicia of glucose metabolism are reported in medical treatises known to those of skill in the art.

Glucose metabolism disorders which the compositions of the present invention are useful for preventing or treating include but are not limited to impaired glucose tolerance; insulin resistance; insulin resistance related breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; polycystic ovarian disease; and high levels of blood insulin and/or glucose.

The present invention further provides methods for altering glucose metabolism in a patient, for example to increase insulin sensitivity and/or oxygen consumption of a patient, said methods comprising administering to the patient a compound or a composition comprising a compound of the invention in an amount effective to alter glucose metabolism.

4.8. Treatment of PPAR-Associated Disorders

The present invention provides methods for the treatment or prevention of a PPAR-associated disorder, comprising administering to a patient a therapeutically effective amount of a compound or a composition comprising a compound of the invention and a pharmaceutically acceptable vehicle. As used herein, "treatment or prevention of PPAR associated disorders" encompasses treatment or prevention of rheumatoid arthritis; multiple sclerosis; psoriasis; inflammatory bowel diseases; breast; colon or prostate cancer; low levels of blood HDL; low levels of blood, lymph and/or cerebrospinal fluid apo E; low blood, lymph and/or cerebrospinal fluid levels of apo A-I; high levels of blood VLDL; high levels of blood LDL; high levels of blood triglyceride; high levels of blood apo B; high levels of blood apo C-III and reduced ratio of post-heparin hepatic lipase to lipoprotein lipase activity. HDL may be elevated in lymph and/or cerebral fluid.

4.9. Treatment of Renal Diseases

The present invention provides methods for the treatment or prevention of a renal disease, comprising administering to a patient a therapeutically effective amount of a compound or a composition comprising a compound of the invention and a pharmaceutically acceptable vehicle. Renal diseases that can be treated by the compounds of the present invention include glomerular diseases (including but not limited to acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (including but not limited to acute tubular necrosis and acute renal failure, polycystic renal disease medullary sponge kidney, medullary cystic disease, nephrogenic diabetes, and renal tubular acidosis), tubulointerstitial diseases (including but not limited to pyelonephritis, drug and toxin induced tubulointerstitial nephritis, hypercalcemic nephropathy, and hypokalemic nephropathy) acute and rapidly progressive renal failure, chronic renal failure, nephrolithiasis, or tumors (including but not limited to renal cell carcinoma and nephroblastoma). In a most preferred embodiment, renal diseases that are treated by the compounds of the present invention are vascular diseases, including but not limited to hypertension, nephrosclerosis, microangiopathic hemolytic anemia, atheroembolic renal disease, diffuse cortical necrosis, and renal infarcts.

4.10. Treatment of Cancer

The present invention provides methods for the treatment or prevention of cancer, comprising administering to a patient a therapeutically effective amount of a compound or a composition comprising a compound of the invention and a pharmaceutically acceptable vehicle. Types of cancer that can be treated using a Compound of the Invention include, but are not limited to, those listed in Table 2.

TABLE 2

| Solid tumors, including but not limited to |
| --- |
| fibrosarcoma |
| myxosarcoma |
| liposarcoma |
| chondrosarcoma |
| osteogenic sarcoma |
| chordoma |
| angiosarcoma |
| endotheliosarcoma |
| lymphangiosarcoma |
| lymphangioendotheliosarcoma |
| synovioma |
| mesothelioma |
| Ewing's tumor |
| leiomyosarcoma |
| rhabdomyosarcoma |
| colon cancer |
| colorectal cancer |
| kidney cancer |
| pancreatic cancer |
| bone cancer |
| breast cancer |
| ovarian cancer |
| prostate cancer |
| esophogeal cancer |
| stomach cancer |
| oral cancer |
| nasal cancer |
| throat cancer |
| squamous cell carcinoma |
| basal cell carcinoma |
| adenocarcinoma |
| sweat gland carcinoma |
| sebaceous gland carcinoma |
| papillary carcinoma |
| papillary adenocarcinomas |
| cystadenocarcinoma |
| medullary carcinoma |
| bronchogenic carcinoma |
| renal cell carcinoma |
| hepatoma |
| bile duct carcinoma |
| choriocarcinoma |
| seminoma |
| embryonal carcinoma |
| Wilms' tumor |
| cervical cancer |
| uterine cancer |
| testicular cancer |
| small cell lung carcinoma |
| bladder carcinoma |
| lung cancer |
| epithelial carcinoma |
| glioma |
| glioblastoma multiforme |
| astrocytoma |
| medulloblastoma |
| craniopharyngioma |
| ependymoma |
| pinealoma |
| hemangioblastoma |

TABLE 2-continued acoustic neuroma
oligodendroglioma
meningioma
skin cancer
melanoma
neuroblastoma
retinoblastoma
Blood-borne cancers, including but not limited to:

acute lymphoblastic B-cell leukemia
acute lymphoblastic T-cell leukemia
acute myeloblastic leukemia "AML"
acute promyelocytic leukemia "APL"
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia "CML"
chronic lymphocytic leukemia "CLL"
hairy cell leukemia
multiple myeloma
Acute and chronic leukemias Lymphoblastic
myelogenous
lymphocytic
myelocytic leukemias
Lymphomas:

Hodgkin's disease
non-Hodgkin's Lymphoma
Multiple myeloma
Waldenström's macroglobulinemia
Heavy chain disease
Polycythemia vera Cancer, including, but not limited to, a tumor, metastasis, or any disease or disorder characterized by uncontrolled cell growth, can be treated or prevented by administration of a Compound of the Invention.

4.11. Treatment of Other Diseases

The present invention provides methods for the treatment or prevention of aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism, comprising administering to a patient a therapeutically effective amount of a compound or a composition comprising a compound of the invention and a pharmaceutically acceptable vehicle.

As used herein, "treatment or prevention of Alzheimer's Disease" encompasses treatment or prevention of lipoprotein abnormalities associated with Alzheimer's Disease. As used herein, "treatment or prevention of Syndrome X or Metabolic Syndrome" encompasses treatment or prevention of a symptom thereof, including but not limited to impaired glucose tolerance, hypertension and dyslipidemia/dyslipoproteinemia.

As used herein, "treatment or prevention of septicemia" encompasses treatment or prevention of septic shock.

As used herein, "treatment or prevention of thrombotic disorders" encompasses treatment or prevention of high blood levels of fibrinogen and promotion of fibrinolysis. In addition to treating or preventing obesity, the compositions of the invention can be administered to an individual to promote weight reduction of the individual.

As used herein, "treatment or prevention of diabetic nephropathy" encompasses treating or preventing kidney disease that develops as a result of diabetes mellitus (DM). Diabetes mellitus is a disorder in which the body is unable to metabolize carbohydrates (e.g., food starches, sugars, cellulose) properly. The disease is characterized by excessive amounts of sugar in the blood (hyperglycemia) and urine; inadequate production and/or utilization of insulin; and by thirst, hunger, and loss of weight. Thus, the compounds of the invention can also be used to treat or prevent diabetes mellitus.

As used herein, "treatment or prevention of diabetic retinopathy" encompasses treating or preventing complications of diabetes that lead to or cause blindness. Diabetic retinopathy occurs when diabetes damages the tiny blood vessels inside the retina, the light-sensitive tissue at the back of the eye.

As used herein, "treatment or prevention of impotence" includes treating or preventing erectile dysfunction, which encompasses the repeated inability to get or keep an erection firm enough for sexual intercourse. The word "impotence" may also be used to describe other problems that interfere with sexual intercourse and reproduction, such as lack of sexual desire and problems with ejaculation or orgasm. The term "treatment or prevention of impotence includes, but is not limited to impotence that results as a result of damage to nerves, arteries, smooth muscles, and fibrous tissues, or as a result of disease, such as, but not limited to, diabetes, kidney disease, chronic alcoholism, multiple sclerosis, atherosclerosis, vascular disease, and neurologic disease.

As used herein, "treatment or prevention of hypertension" encompasses treating or preventing blood flow through the vessels at a greater than normal force, which strains the heart; harms the arteries; and increases the risk of heart attack, stroke, and kidney problems. The term hypertension includes, but is not limited to, cardiovascular disease, essential hypertension, hyperpiesia, hyperpiesis, malignant hypertension, secondary hypertension, or white-coat hypertension.

As used herein, "treatment or prevention of inflammation" encompasses treating or preventing inflammation diseases including, but not limited to, chronic inflammatory disorders of the joints including arthritis, e.g., rheumatoid arthritis and osteoarthritis; respiratory distress syndrome, inflammatory bowel diseases such as ileitis, ulcerative colitis and Crohn's disease; and inflammatory lung disorders such as asthma and chronic obstructive airway disease, inflammatory disorders of the eye such as corneal dystrophy, trachoma, onchocerciasis, uveitis, sympathetic ophthalmitis, and endophthalmitis; inflammatory disorders of the gum, e.g., periodontitis and gingivitis; tuberculosis; leprosy; inflammatory diseases of the kidney including glomerulonephritis and nephrosis; inflammatory disorders of the skin including acne, sclerodermatitis, psoriasis, eczema, photoaging and wrinkles; inflammatory diseases of the central nervous system, including AIDS-related neurodegeneration, stroke, neurotrauma, Alzheimer's disease, encephalomyelitis and viral or autoimmune encephalitis; autoimmune diseases including immune-complex vasculitis, systemic lupus and erythematodes; systemic lupus erythematosus (SLE); and inflammatory diseases of the heart such as cardiomyopathy.

4.12. Combination Therapy

In certain embodiments of the present invention, the compounds and compositions of the invention can be used in combination therapy with at least one other therapeutic agent. The compound of the invention and the therapeutic agent can act additively or, more preferably, synergistically. In a preferred embodiment, a compound or a composition comprising a compound of the invention is administered concurrently with the administration of another therapeutic agent, which can be part of the same composition as the compound of the invention or a different composition. In another embodiment, a compound or a composition comprising a compound of the invention is administered prior or subsequent to administration of another therapeutic agent. As many of the disorders for which the compounds and compositions of the invention are useful in treating are chronic disorders, in one embodiment combination therapy involves alternating between administering a compound or a composition comprising a compound of the invention and a composition comprising another therapeutic agent, e.g., to minimize the toxicity associated with a particular drug. The duration of administration of each drug or therapeutic agent can be, e.g., one month, three months, six months, or a year. In certain embodiments, when a composition of the invention is administered concurrently with another therapeutic agent that potentially produces adverse side effects including but not limited to toxicity, the therapeutic agent can advantageously be administered at a dose that falls below the threshold at which the adverse side is elicited.

The present compositions can be administered together with a statin. Statins for use in combination with the compounds and compositions of the invention include but are not limited to atorvastatiti, pravastatin, fluvastatin, lovastatin, simvastatin, and cerivastatin.

The present compositions can also be administered together with a PPAR agonist, for example a thiazolidinedione or a fibrate. Thiazolidinediones for use in combination with the compounds and compositions of the invention include but are not limited to 5 ((4 (2 (methyl 2 pyridinylamino)ethoxy) phenyl)methyl) 2,4 thiazolidinedione, troglitazone, pioglitazone, ciglitazone, WAY 120,744, englitazone, AD 5075, darglitazone, and rosiglitazone. Fibrates for use in combination with the compounds and compositions of the invention include but are not limited to gemfibrozil, fenofibrate, clofibrate, or ciprofibrate. As mentioned previously, a therapeutically effective amount of a fibrate or thiazolidinedione often has toxic side effects. Accordingly, in a preferred embodiment of the present invention, when a composition of the invention is administered in combination with a PPAR agonist, the dosage of the PPAR agonist is below that which is accompanied by toxic side effects.

The present compositions can also be administered together with a bile acid binding resin. Bile acid binding resins for use in combination with the compounds and compositions of the invention include but are not limited to cholestyramine and colestipol hydrochloride. The present compositions can also be administered together with niacin or nicotinic acid. The present compositions can also be administered together with a RXR agonist. RXR agonists for use in combination with the compounds of the invention include but are not limited to LG 100268, LGD 1069, 9-cis retinoic acid, 2 (1 (3,5,5,8,8 pentamethyl 5,6,7,8 tetrahydro 2 naphthyl) cyclopropyl)pyridine 5 carboxylic acid, or 4 ((3,5,5,8,8 pentamethyl 5,6,7,8 tetrahydro 2 naphthyl)2 carbonyl)benzoic acid. The present compositions can also be administered together with an anti-obesity drug. Anti-obesity drugs for use in combination with the compounds of the invention include but are not limited to β-adrenergic receptor agonists, preferably β-3 receptor agonists, fenfluramine, dexfenfluramine, sibutramine, bupropion, fluoxetine, and phentermine. The present compositions can also be administered together with a hormone. Hormones for use in combination with the compounds of the invention include but are not limited to thyroid hormone, estrogen and insulin. Preferred insulins include but are not limited to injectable insulin, transdermal insulin, inhaled insulin, or any combination thereof. As an alternative to insulin, an insulin derivative, secretagogue, sensitizer or mimetic may be used. Insulin secretagogues for use in combination with the compounds of the invention include but are not limited to forskolin, dibutryl cAMP or isobutylmethylxanthine (IBMX).

The present compositions can also be administered together with a phosphodiesterase type 5 ("PDE5") inhibitor to treat or prevent disorders, such as but not limited to, impotence. In a particular, embodiment the combination is a synergistic combination of a composition of the invention and a PDE5 inhibitor.

The present compositions can also be administered together with a tyrophostine or an analog thereof. Tyrophostines for use in combination with the compounds of the invention include but are not limited to tryophostine 51.

The present compositions can also be administered together with sulfonylurea-based drugs. Sulfonylurea-based drugs for use in combination with the compounds of the invention include, but are not limited to, glisoxepid, glyburide, acetohexaride, chorpropamide, glibornuride, tolbutamide, tolazamide, glipizide, gliclazide, gliquidone, glyhexamide, phenbutamide, and tolcyclamide. The present compositions can also be administered together with a biguanide. Biguanides for use in combination with the compounds of the invention include but are not limited to metformin, phenformin and buformin.

The present compositions can also be administered together with an α-glucosidase inhibitor. α-glucosidase inhibitors for use in combination with the compounds of the invention include but are not limited to acarbose and miglitol.

The present compositions can also be administered together with an apo A-I agonist. In one embodiment, the apo A-I agonist is the Milano form of apo A-I (apo A-IM). In a preferred mode of the embodiment, the apo A-IM for administration in conjunction with the compounds of the invention is produced by the method of U.S. Pat. No. 5,721,114 to Abrahamsen. In a more preferred embodiment, the apo A-I agonist is a peptide agonist. In a preferred mode of the embodiment, the apo A-I peptide agonist for administration in conjunction with the compounds of the invention is a peptide of U.S. Pat. No. 6,004,925 or 6,037,323 to Dasseux.

The present compositions can also be administered together with apolipoprotein E (apo E). In a preferred mode of the embodiment, the apoE for administration in conjunction with the compounds of the invention is produced by the method of U.S. Pat. No. 5,834,596 to Ageland.

In yet other embodiments, the present compositions can be administered together with an HDL-raising drug; an HDL enhancer; or a regulator of the apolipoprotein A-I, apolipoprotein A-IV and/or apolipoprotein genes.

In one embodiment, the other therapeutic agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

In another embodiment, the other therapeutic agent can be an hematopoietic colony stimulating factor. Suitable hematopoietic colony stimulating factors include, but are not limited to, filgrastim, sargramostim, molgramostim and erythropoietin alfa. In still another embodiment, the other therapeutic agent can be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

4.13. Combination Therapy of Cardiovascular Diseases

The present compositions can be administered together with a known cardiovascular drug. Cardiovascular drugs for use in combination with the compounds of the invention to prevent or treat cardiovascular diseases include but are not limited to peripheral antiadrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., aminone, milrinone, enoximone, fenoximone, imazodan, sulmazole), antidysrhythmic drugs, calcium entry blockers, ranitine, bosentan, and rezulin.

4.14. Combination Therapy of Cancer

The present invention includes methods for treating cancer, comprising administering to an animal in need thereof an effective amount of a Compound of the Invention and another therapeutic agent that is an anti-cancer agent. Suitable anti-cancer agents include, but are not limited to, those listed in Table 3.

TABLE 3

| Alkylating agents | |
| --- | --- |
| Nitrogen mustards: | Cyclophosphamide |
| | Ifosfamide |
| | trofosfamide |
| | Chlorambucil |
| | Treos |
| Nitrosoureas: | carbustine (BCNU) |
| | Lomustine (CCNU) |
| Alkylsulphonates | Busulfan |
| | Treosulfan |
| Triazenes: | Dacarbazine |
| Platinum containing compounds: | Cisplatin |
| | carboplatin |

TABLE 3-continued

| Plant Alkaloids | |
| --- | --- |
| Vinca alkaloids: | Vicristine |
| | Vinblastine |
| | Vindesine |
| | Vinorelbine |
| Taxoids: | paclitaxel |
| | Docetaxol |
| DNA Topoisomerase Inhibitors | |
| Epipodophyllins: | Etoposide |
| | Teniposide |
| | Topotecan |
| | 9-aminocamptothecin |
| | camptothecin |
| | crisnatol |
| mitomycins: | Mitomycin C |
| Anti-metabolites | |
| Anti-folates: | |
| DHFR inhibitors: | METHOTREXATE |
| | Trimetrexate |
| IMP dehydrogenase Inhibitors: | Mycophenolic acid |
| | Tiazofurin |
| | Ribavirin |
| | EICAR |
| Ribonucleotide reductase Inhibitors: | Hydroxyurea |
| | deferoxamine |
| Pyrimidine analogs: | |
| Uracil analogs | 5-Fluorouracil |
| | Floxuridine |
| | Doxifluridine |
| | Ratitrexed |
| Cytosine analogs | cytarabine (ara C) |
| | Cytosine arabinoside |
| | fludarabine |
| Purine analogs: | mercaptopurine |
| | Thioguanine |
| Hormonal therapies: | |
| Receptor antagonists: | |
| Anti-estrogen | Tamoxifen |
| | Raloxifene |
| | megestrol |
| | goscrelin |
| | Leuprolide acetate |
| LHRH agonists: | flutamide |
| | bicalutamide |
| Retinoids/Deltoids | |
| Vitamin D3 analogs: | EB 1089 |
| | CB 1093 |
| | KH 1060 |
| Photodynamic therapies: | vertoporfin (BPD-MA) |
| | Phthalocyanine |
| | photosensitizer Pc4 |
| | Demethoxy-hypocrellin A |
| | (2BA-2-DMHA) |
| Cytokines: | Interferon-α |
| | Interferon-γ |
| | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Actinomycines: | Actinomycin D |
| | Dactinomycin |
| Bleomycins: | bleomycin A2 |
| | Bleomycin B2 |
| | Peplomycin |

| | |
|---|---|
| TABLE 3-continued | |
| Anthracyclines: | daunorubicin |
| | Doxorubicin (adriamycin) |
| | Idarubicin |
| | Epirubicin |
| | Pirarubicin |
| | Zorubicin |
| | Mitoxantrone |
| MDR inhibitors | verapamil |
| $Ca^{2+}$ ATPase inhibitors: | thapsigargin |

In a specific embodiment, a composition of the invention further comprises one or more chemotherapeutic agents and/or is administered concurrently with radiation therapy. In another specific embodiment, chemotherapy or radiation therapy is administered prior or subsequent to administration of a present composition, preferably at least an hour, five hours, 12 hours, a day, a week, a month, more preferably several months (e.g., up to three months), subsequent to administration of a composition of the invention. In other embodiments, the invention provides methods for treating or preventing cancer, comprising administering to an animal in need thereof an effective amount of a Compound of the Invention and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Compounds of the Invention can be administered to an animal that has also undergone surgery as treatment for the cancer.

In one embodiment, the additional method of treatment is radiation therapy. In a specific embodiment, the Compound of the Invention is administered concurrently with the chemotherapeutic agent or with radiation therapy. In another specific embodiment, the chemotherapeutic agent or radiation therapy is administered prior or subsequent to administration of a Compound of the Invention, preferably at least an hour, five hours, 12 hours, a day, a week, a month, more preferably several months (e.g., up to three months), prior or subsequent to administration of a Compound of the Invention.

A chemotherapeutic agent can be administered over a series of sessions, any one or a combination of the chemotherapeutic agents listed in Table 3 can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered. Additionally, the invention provides methods of treatment of cancer with a Compound of the Invention as an alternative to chemotherapy or radiation therapy where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The Compounds of the Invention can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the patient's remaining bone-marrow cell population is then eradicated via the administration of a high dose of a Compound of the Invention with or without accompanying high dose radiation therapy, and the stem cell graft is infused back into the animal. Supportive care is then provided while bone marrow function is restored and the animal recovers.

4.15. Surgical Uses

Cardiovascular diseases such as atherosclerosis often require surgical procedures such as angioplasty. Angioplasty is often accompanied by the placement of a reinforcing a metallic tube shaped structure known as a "stent" into a damaged coronary artery. For more serious conditions, open heart surgery such as coronary bypass surgery may be required. These surgical procedures entail using invasive surgical devices and/or implants, and are associated with a high risk of restenosis and thrombosis. Accordingly, the compounds and compositions of the invention may be used as coatings on surgical devices (e.g., catheters) and implants (e.g., stents) to reduce the risk of restenosis and thrombosis associated with invasive procedures used in the treatment of cardiovascular diseases.

4.16. Veterinary and Livestock Uses

A composition of the invention can be administered to a non-human animal for a veterinary use for treating or preventing a disease or disorder disclosed herein.

In a specific embodiment, the non-human animal is a household pet. In another specific embodiment, the non-human animal is a livestock animal. In a preferred embodiment, the non-human animal is a mammal, most preferably a cow, horse, sheep, pig, cat, dog, mouse, rat, rabbit, or guinea pig. In another preferred embodiment, the non-human animal is a fowl species, most preferably a chicken, turkey, duck, goose, or quail.

In addition to veterinary uses, the compounds and compositions of the invention can be used to reduce the fat content of livestock to produce leaner meats. Alternatively, the compounds and compositions of the invention can be used to reduce the cholesterol content of eggs by administering the compounds to a chicken, quail, or duck hen. For non-human animal uses, the compounds and compositions of the invention can be administered via the animals' feed or orally as a drench composition.

4.17. Therapeutic/Prophylactic Administration and Compositions

Due to the activity of the compounds and compositions of the invention, they are useful in veterinary and human medicine. As described above, the compounds and compositions of the invention are useful for the treatment or prevention of aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, enhancing bile production, enhancing reverse lipid transport, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. The invention provides methods of treatment and prophylaxis by administration to a patient of a therapeutically effective amount of a compound or a composition comprising a compound of the invention. The patient is an animal, including, but not limited, to an animal such a cow, horse, sheep, pig, chicken, turkey, quail, cat, dog, mouse, rat, rabbit, guinea pig, etc., and is more preferably a mammal, and most preferably a human.

The compounds and compositions of the invention, are preferably administered orally. The compounds and compositions of the invention may also be administered by any other convenient route, for example, by intravenous infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

In certain embodiments, for example, for the treatment of Alzheimer's Disease, it may be desirable to introduce one or more compounds of the invention into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds and compositions of the invention can be delivered in a vesicle, in particular a liposome (see Langer, 1990, Science 249:1527 1533; Treat et al., in Liposomes in the Therapy of Infectious Disease and Cancer, Lopez-Berestein and Fidler (eds.), Liss, New York, pp. 353 365 (1989); Lopez Berestein, ibid., pp. 317 327; see generally ibid.).

In yet another embodiment, the compounds and compositions of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of the target area to be treated, e.g., the liver, thus requiring only a fraction of the systemic dose (see, e.g., Goodson, in Medical Applications of Controlled Release, supra, vol. 2, pp. 115 138 (1984)). Other controlled-release systems discussed in the review by Langer, 1990, Science 249:1527 1533) may be used.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds and compositions of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the compounds and compositions of the invention are formulated in accordance with routine procedures as a pharmaceutical composition adapted for intravenous administration to human beings. Typically, compounds and compositions of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by intravenous infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compounds and compositions of the invention for oral delivery may be in the form of tablets, lozenges, aqueous or oily suspensions, granules, powders, emulsions, capsules, syrups, or elixirs. Compounds and compositions of the invention for oral delivery can also be formulated in foods and food mixes. Orally administered compositions may contain one or more optionally agents, for example, sweetening agents such as fructose, aspartame or saccharin; flavoring agents such as peppermint, oil of wintergreen, or cherry, coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds and compositions of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 2000 milligrams of a compound of the invention per kilogram body weight. In specific preferred embodiments of the invention, the oral dose is 0.01 milligram to 1000 milligrams per kilogram body weight, more preferably 0.1 milligram to 100 milligrams per kilogram body weight, more preferably 0.5 milligram to 25 milligrams per kilogram body weight, and yet more preferably 1 milligram to 10 milligrams per kilogram body weight. In a most preferred embodiment, the oral dose is 5 milligrams of a compound of the invention per kilogram body weight. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

Suitable dosage ranges for intravenous (i.v.) administration are 0.01 milligram to 1000 milligrams per kilogram body weight, 0.1 milligram to 350 milligrams per kilogram body weight, and 1 milligram to 100 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a compound of the invention and another lipid-mediating compound, including but not limited to a statin, a thiazolidinedione, or a fibrate.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for lowering fatty acid synthesis. The compounds and compositions of the invention may also be demonstrated to be effective and safe using animal model systems.

Other methods will be known to the skilled artisan and are within the scope of the invention.

The following examples are provided by way of illustration and not limitation.

5. EXAMPLES

5.1. Keto-Substituted α-Cycloalkyldicarboxylic Acids

The cycloalkyl substituted keto-derivatives H are prepared as shown in Scheme 14 by methods already described in Dasseux, J.-L. H. et al. Ketone compounds and compositions for cholesterol management and related uses. U.S. patent application publication 20030078239, Oct. 11, 2001. The key step in the syntheses of most of the compounds of the invention is the alkylation of the formaldehyde synthon: Tosylmethyl Isocyanide (TosMIC) (Possel, O. et al. *Tetrahedron Lett.*, 1977, 17, 4229-4232; Kurosawa, K. et al. *Tetrahedron Lett.*, 1982, 23, 5335-5338; Yadav, J. S. et al. *Tetrahedron Lett.*, 1990, 31, 6217-6218; van Leusen, D. et al. Synthetic Uses of Tosylmethyl Isocyanide (TosMIC). In Organic Reactions, Vol. 57; Overman, L. E., Editor-in-Chief; John Wiley and Sons, Inc.: New York, 2001; pp 417-666) with a properly functionalized halo-ester, which is available commercially (e.g., Aldrich Chemical Co., Milwaukee, Wis.) or can be prepared by well-known methods such as halogenation or sulfonation of butanediol.

Scheme 14

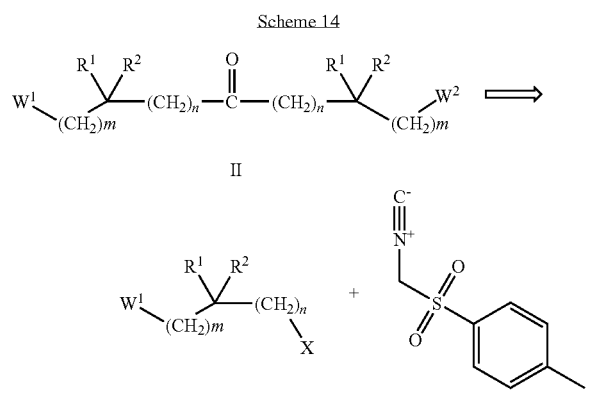

In a typical procedure, a halo-ester is prepared via alkylation of commercially available or known esters of type 101 with a dihaloalkane of type 102 of proper length as described in Scheme 15. Cycloakyl carboxylic esters of type 101 prepared for this invention are used for the preparation of haloesters described in Table 1. Ethyl, butyl and t-butyl ester analogues of 101 could be used as starting material. As an example, ethyl cyclopropylcarboxylate, which is known to self-condensate on treatment with various bases, as described in Pinnick, H. W. et al. *J. Org. Chem.*, 1980, 45, 4505-4507, cannot be used for this reaction, and the corresponding t-butyl analogue is used instead, which is prepared as described in the literature (Haener, R. et al. *Helv. Chim. Acta,* 1986, 69, 1655-1665). In a typical procedure, bromo-esters 103a-g are prepared via treatment of 101 with LDA and a large excess of a dibromoalkane (102, X=Br) or bromo-chloroalkane (102, X=Cl) in THF at low temperatures. The crude product 104 is separated from excess of 102 via fractional distillation. If iododerivatives are needed due to the lack of reactivity of the chloro-ester derivatives (104a-c), the latter are converted to the corresponding iodides (105a-c) by methods known in the literature prior to their reaction with TosMIC. In the case of the bromo-esters (103a-g) treatment with a catalytic amount of Bu$_4$NI suffices to form the corresponding iodo compounds in situ.

Scheme 15.

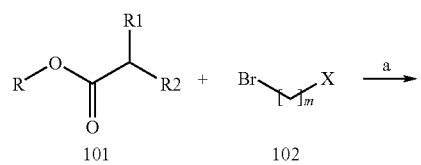

-continued

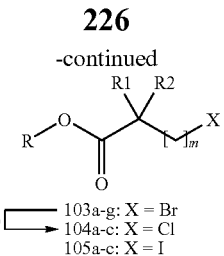

103a-g: X = Br
104a-c: X = Cl
105a-c: X = I (a) LDA, THF, -60° C.-rt; (b) NaI, 2-butanone, Δ.

TABLE 1

Synthesis of halo-esters 103a-g, 104a-c and 105a-c.

| Compound | m | R | R1 | R2 | X | Yield (%) |
|---|---|---|---|---|---|---|
| 103a | 4 | Et | Me | Me | Br | a |
| 103b | 4 | tBu | cyclo-Propyl | | Br | 34 [b] |
| 103c | 4 | Bu | cyclo-Pentyl | | Br | 49 |
| 103d | 4 | Et | CO$_2$Et | Me | Br | c |
| 103e | 5 | Et | Me | Me | Br | a |
| 103f | 5 | Bu | cyclo-Pentyl | | Br | 61 [b] |
| 103g | 7 | Et | Me | Me | Br | 45 |
| 104a | 4 | tBu | cyclo-Propyl | | Cl | 52 |
| 104b | 4 | Et | cyclo-Butyl | | Cl | 86 |
| 104c | 5 | tBu | cyclo-Propyl | | Cl | 73 |
| 105a | 4 | tBu | cyclo-Propyl | | I | 94 [b] |
| 105b | 4 | Et | cyclo-Butyl | | I | 99 |
| 105c | 5 | tBu | cyclo-Propyl | | I | 99 |

[a] See: Ackerley, N. et al. J. Med. Chem., 1995, 38, 1608-1628.
[b] Purity >90%.
[c] See: Astles, P. C. et al. J. Med. Chem., 1996, 39, 1423-1432.

Symmetrical ketones are prepared by Method A (e.g. TosMIC, NaH, 3, Bu$_4$NI in DMSO) as described in Scheme 16. The intermediate dialkylated TosMIC derivatives is treated with cone HCl in CH$_2$Cl$_2$ to provide keto-diesters 106d, g-h, j, m-n in moderate to good yield as shown in Scheme 15 and Table 2. For the preparation of keto-diacids 106c, e-f, k-l Method B is applied (e.g., KOtBu, 105 in N,N-dimethylacetamide at temperatures between −10° C. to 35° C., preferably room temperature), which is similar to the one described by Haener, R. et al. *Helv. Chim. Acta,* 1986, 69, 1655-1665 and products are obtained as described in Table 2.

Scheme 16.

R1 R2
R—O—C(=O)—C(R1)(R2)—(CH$_2$)$_m$—X  —a or b→

103b-d, f-g: X = Br
105c: X = I

R—O—C(=O)—C(R1)(R2)—(CH$_2$)$_m$—C(=O)—(CH$_2$)$_n$—C(R4)(R5)—C(=O)—O—R3

106d, f-h, l-n: m = n, R = R3, R1 = R4, R2 = R5
107d, f-h, l-n: R = R3 = H

Symmetrical ketones: (a) Method A: (1) NaH, TosMIC, Bu$_4$NI, DMSO, rt, (2) HCl (conc), CH$_2$Cl$_2$, rt; (b) Method B: (1) KOtBu, TosMIC, DMAc, 0° C.-rt, (2) HCl (conc), CH$_2$Cl$_2$, rt; (c) 106d,l: Method E: HCO$_2$H, rt, 106f-g, m-n: Method D: LiOH, EtOH/H$_2$O, Δ, 106h: KOH, EtOH/H$_2$O, rt.

For the preparation of asymmetrical ketones 106c, e, k a set of mono-alkylated TosMIC derivatives (108a,b) are used as starting materials that are prepared as described in Scheme 17. As such intermediates could only be produced in low yield via Method A the more selective conditions ($K_2CO_3$, DMAc) are applied, providing 108a,b in good yield (Table 3). Subsequent treatment of 108a,b as reported for Method A or B afforded the asymmetrical ketones 106c, e, k (Table 2). The target keto-diacids (107) were prepared from the corresponding ester analogues (106) by saponification of the linear alkane esters (Et, Bu), treatment of the t-butyl esters with $HCO_2H$ or a combination of the two (Schemes 3 and 4). Preparations are similar for compounds with other terminal groups than acids, as described in Dasseux, J.-L. H. et al. Ketone compounds and compositions for cholesterol management and related uses. U.S. patent application 20030078239, Oct. 11, 2001

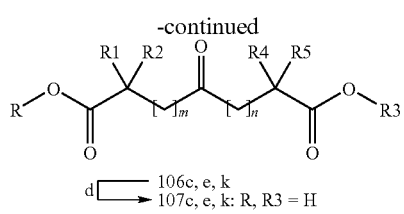

d ⎡— 106c, e, k
  ⎣→ 107c, e, k: R, R3 = H

Asymmetrical ketones: (a) $K_2CO_3$, $Bu_4NI$, DMF, rt; (b) Method A: (1) NaH, TosMIC, $Bu_4NI$, DMSO, rt, (2) HCl (conc), $CH_2Cl_2$, rt; (c) Method B: (1) KOtBu, TosMIC, DMAc, 0° C.,-rt, (2) HCl (conc), $CH_2Cl_2$, rt; (d) 106c,k: Method F: (1) $HCO_2H$, rt, (2) NaOH, $EtOH/H_2O$, Δ, 106e: Method D: LiOH, $EtOH/H_2O$, Δ.

TABLE 2

Syntheses of keto-esters (106) and corresponding keto-acids (107) using TosMIC chemistry.

| | | | | | | | | | | Compound 6 | Compound 107 | | | |
|---|---|---|---|---|---|---|---|---|---|---|---|---|---|---|
| | | | | | | | | | | | 106→107 | Elemental Analysis | | |
| | | | | | | | | | | Yield | Yield | Found (Calculated) | | mp |
| 106 | m | n | R | R1 | R2 | R3 | R4 | R5 | Method[6] | (%) | Method[6] | (%) | C | H | (° C.) |
| c | 4 | 4 | $CO_2Et$ | $CO_2tBu$ | Me | Me | cyclo-Propyl | C | 43[b] | F | 80[b] | 65.06 (65.36) | 9.02 (9.03) | 49-52 |
| d | 4 | 4 | $CO_2tBu$ | $CO_2tBu$ | cyclo-Propyl | cyclo-Propyl | A | 49 | E | 99 | 65.40 (65.78) | 8.37 (8.44) | 132-134 |
| e | 4 | 4 | $CO_2Et$ | $CO_2Et$ | Me | Me | cyclo-Butyl | C | 75[b] | D | 76 | — | — | 53-55 |
| f | 4 | 4 | $CO_2Et$ | $CO_2Et$ | cyclo-Butyl | cyclo-Butyl | B | 82 | D | 56 | 67.19 (67.43) | 8.97 (8.93) | 69-70 |
| g | 4 | 4 | $CO_2Bu$ | $CO_2Bu$ | cyclo-Pentyl | cyclo-Pentyl | A | 56 | D | 94[b] | 68.78 (68.82) | 9.47 (9.35) | 104-106 |
| h | 4 | 4 | $CO_2Et$ | $CO_2Et$ | Me | $CO_2Et$ | Me | $CO_2Et$ | A | 71 | c | 81 | — | — | — |
| k | 5 | 5 | $CO_2Et$ | $CO_2tBu$ | Me | Me | cyclo-Propyl | C | 57[b] | F | 84 | 66.86 (67.03) | 9.50 (9.47) | 65-66 |
| l | 5 | 5 | $CO_2tBu$ | $CO_2tBu$ | cyclo-Propyl | cyclo-Propyl | B | 46[b] | E | 99 | 67.20 (67.43) | 9.05 (8.93) | 122-123 |
| m | 5 | 5 | $CO_2Bu$ | $CO_2Bu$ | cyclo-Pentyl | cyclo-Pentyl | A | 68[b] | D | 83 | 70.37 (70.02) | 9.72 (9.71) | 78-85 |
| n | 7 | 7 | $CO_2Et$ | $CO_2Et$ | Me | Me | Me | Me | A | 57 | D | 74 | 69.41 (69.31) | 10.73 (10.62) | 74-77 |

[a] See ref 6.
[b] Purity >90%.
[c] KOH, EtOH, rt.

Scheme 17.

R1 R2
R—O—C(—)—[ ]m—Br  →a
   ‖
   O
103a,e

R1 R2   C⁻
         ‖
         N⁺
R—O—C(—)—[ ]m—C—S(=O)(=O)—C6H4—CH3   +
   ‖           H
   O
108a-b

R4 R5
R3—O—C(—)—[ ]n—I   ←b or c
     ‖
     O
105a-c

TABLE 3

Synthesis of 108a-b.

| Compound | m | R | R1 | R2 | Yield (%) |
|---|---|---|---|---|---|
| 8a | 4 | Et | Me | Me | 67 |
| 8b | 5 | Et | Me | Me | 61 | t-Butyl 1-(4-bromo-butyl)-cyclopropanecarboxylate (103b). Under a $N_2$ atmosphere at −60° C., a solution of t-butyl cyclopropanecarboxylate (80.05 g, 0.507 mol) and 1,4-dibromobutane (219.3 g, 1.01 mol) in dry THF (800 mL) was added dropwise to a solution of LDA (2 M in THF/heptane/ethylbenzene, 380 mL, 0.76 mol) in 1.5 h. Stirring was continued for 5 h, during which the reaction mixture was allowed to slowly reach rt. After that, the reaction mixture was poured into saturated aqueous $NH_4Cl$ (1 L). The organic layer was separated and concentrated in vacuo to a smaller volume. The aqueous layer was extracted with $Et_2O$ (3×200 mL). The combined organic layers were washed with saturated aqueous $NH_4Cl$ (2×400 mL) and brine (400 mL) and dried. The remaining residue was purified by fractional distillation under reduced pressure to give 103b (51.4 g, 94% pure by GC, 34%) as a slightly yellow oil. bp: T=93-96° C. (p=0.075-0.087 Torr). $^1H$ NMR: δ 3.40 (t, J=6.8 Hz, 2H), 1.85 (quintet, J=7.1 Hz, 2H), 1.65-1.46 (m, 4H), 1.43 (s, 9H), 1.12 (q, J=3.5 Hz, 2H), 0.60 (q, J=3.5 Hz, 2H). $^{13}C$ NMR: δ 174.0, 79.8, 33.6, 33.2, 32.8, 27.9 (3×), 26.3, 23.9, 15.1 (2×). HRMS calcd for $C_{12}H_{21}BrO_2$ ($MH^+$): 277.0803. found: 277.0807.

Butyl 1-(4-bromo-butyl)-cyclopentanecarboxylate (103c). Compound 103c was prepared, likewise the procedure described for 103b, starting from butyl cyclopentanecarboxylate (Payne, G. B. et al. *J. Org. Chem.,* 1957, 22, 1680-1682) (80.0 g, 0.42 mol), 1,4-dibromobutane (183.3 g, 0.84 mol) and LDA (2 M in THF/heptane/ethylbenzene, 250 mL, 0.50 mol) to give, after purification by fractional distillation under reduced pressure, 103c (62.8 g, 49%) as a light yellow liquid. bp: T=116-117° C. (p=0.040-0.051 Torr). $^1$H NMR: δ 4.07 (t, J=6.6 Hz, 2H), 3.38 (t, J=6.8 Hz, 2H), 2.16-2.10 (m, 2H), 1.83 (quintet, J=7.1 Hz, 2H), 1.65-1.59 (m, 8H), 1.50-1.31 (m, 6H), 0.94 (t, J=7.2 Hz, 3H). $^{13}$C NMR: δ 177.6, 64.1, 53.9, 38.2, 36.0 (2×), 33.3, 33.0, 30.6, 24.8 (2×), 24.6, 19.1, 13.6. HRMS calcd for $C_{14}H_{25}BrO_2$ ($M^+$): 304.1038. found: 304.1042.

Butyl 1-(5-bromo-pentyl)-cyclopentanecarboxylate (103f). Compound 103f was prepared, likewise the procedure described for 103b, starting from butyl cyclopentanecarboxylate (40.2 g, 0.236 mol), 1,5-dibromopentane (64 mL, 0.45 mol) and LDA (2 M in THF/heptane/ethylbenzene, 200 mL, 0.40 mol) to give, after purification by fractional distillation under reduced pressure, 3f (49.1 g, 93% pure by GC, 61%) as a bright yellow liquid. bp: T=123° C. (p=0.001 Torr). $^1$H NMR: δ 4.06 (t, J=6.6 Hz, 2H), 3.38 (t, J=6.9 Hz, 2H), 2.15-2.07 (m, 2H), 1.89-1.79 (quintet, J=7.1 Hz, 2H), 1.69-1.56 (m, 8H), 1.49-1.32 (m, 6H), 1.28-1.17 (m, 2H), 0.94 (t, J=7.4 Hz, 3H). $^{13}$C NMR: δ 177.7, 64.0, 54.0, 39.0, 36.0 (2×), 33.6, 32.5, 30.7, 28.5, 25.1, 24.8 (2×), 19.1, 13.6. HRMS calcd for $C_{15}H_{27}BrO_2$ ($MH^+$): 318.1195. found: 318.1192.

Ethyl 2,2-dimethyl-9-bromononanoate (103g). Under a $N_2$ atmosphere at 0° C., LDA (2 M in THF/heptane/ethylbenzene, 13.0 mL, 26.0 mmol) was added dropwise to a mixture of ethyl isobutyrate (3.5 mL, 25.9 mmol) and 1,7-dibromoheptane (9.84 g, 38.2 mmol) in dry THF (50 mL) in 1.5 h, while keeping the temperature below 5° C. After 3 h, the mixture was poured into ice-cold saturated aqueous NHC (150 mL). The layers were separated and the aqueous phase was extracted with $Et_2O$ (3×100 mL). The combined organic layers were washed with aqueous HCl (1 M, 100 mL), saturated aqueous $NaHCO_3$ (100 mL) and brine (100 mL) and dried. The remaining residue was purified by column chromatography (heptane:EtOAc=40:1) twice to give 103g (3.42 g, 45%) as a colorless liquid. $^1$H NMR: δ 4.11 (q, J=7.2 Hz, 2H), 3.40 (t, J=6.9 Hz, 2H), 1.85 (quintet, J=6.9 Hz, 2H), 1.52-1.47 (m, 2H), 1.45-1.36 (m, 2H), 1.35-1.20 (m, 6H), 1.24 (t, J=7.2 Hz, 3H), 1.15 (s, 6H). $^{13}$C NMR: δ 177.8, 60.0, 42.0, 40.5, 33.7, 32.7, 29.7, 28.5, 28.0, 25.0 (2×), 24.7, 14.1. HRMS calcd for $C_{13}H_{25}BrO_2$ ($M^+$): 292.1038. found: 292.1034.

t-Butyl 1-(4-chlorobutyl)-1-cyclopropanecarboxylate (104a). Compound 104a was prepared, likewise the procedure described for 103b, starting from t-butyl cyclopropanecarboxylate (Kohlrausch, K. W. F. et al. *Z. Elektrochem. Angew. Phys. Chem,* 1937, 43, 282-285) (12.5 g, 88 mmol), 1-bromo-4-chlorobutane (13.7 mL, 117 mmol) and LDA (prepared from BuLi (2.5M in hexanes, 37 mL, 92.5 mmol) and $iPr_2NH$ (12.3 mL, 88 mmol, distilled from NaOH)) to give, after purification by fractional distillation under reduced pressure, 104a (10.73 g 52%) as a colorless oil. bp: T=57-61° C. (p=0.001 mbar). $^1$H NMR: δ 3.52 (t, J=6.6 Hz, 2H), 1.76 (quintet, J=6.8 Hz, 2H), 1.64-1.54 (m, 2H), 1.51-1.46 (m, 2H), 1.42 (s, 9H), 1.12 (dd, J=6.6, 3.9 Hz, 2H), 0.60 (dd, J=6.6, 3.9 Hz, 2H). $^{13}$C NMR: δ 173.9, 80.0, 45.1, 33.6, 32.9, 28.2 (3×), 25.3, 24.2, 15.4 (2×). HRMS calcd for $C_{12}H_{22}ClO_2$ ($MH^+$): 233.1308. found: 233.1308.

Ethyl 1-(4-chlorobutyl)-1-cyclobutanecarboxylate (104b). Compound 104b was prepared, likewise the procedure described for 104c, starting from LDA (prepared from BuLi (2.5M in hexanes, 52.8 mL, 132 mmol) and $iPr_2NH$ (18.52 mL, 132 mmol, distilled from NaOH)), ethyl 1-cyclobutanecarboxylate (Török, B. et al. *J. Chem. Soc. Perkin Trans. 1,* 1993, 7, 801-804) (14.05 g, 110 mmol) (the resulting mixture was allowed to warm to 0° C. and cooled again to −60° C.) and 1-bromo-4-chlorobutane (19.1 mL, 165 mmol) to give, after purification by fractional distillation under reduced pressure, 104b (20.53 g, 86%) as a thin, colorless oil. bp: T=64-71° C. (p=0.001 Torr). $^1$H NMR: δ 4.13 (q, J=7.1 Hz, 2H), 3.51 (t, J=6.8 Hz, 2H), 2.50-2.32 (m, 2H), 1.96-1.70 (m, 8H), 1.40-1.20 (m, 2H), 1.26 (t, J=7.2 Hz, 3H). $^{13}$C NMR: δ 176.6, 60.3, 47.6, 44.8, 37.3, 32.8, 30.1 (2×), 22.4, 15.8, 14.4.

t-Butyl 1-(5-chloropentyl)-1-cyclopropanecarboxylate (104c). Under an Ar atmosphere at 0° C., BuLi (2.5M in hexanes, 80 mL, 0.20 mol) was added dropwise to a solution of $iPr_2NH$ (27.2 mL, 194 mmol, distilled from NaOH) in dry THF (200 mL) in min. The reaction mixture was stirred for 30 min, cooled to −70° C. and then, t-butyl cyclopropanecarboxylate (25.0 g, 176 mmol) was added dropwise in 30 min. The resultant mixture was allowed to warm up to −35° C., cooled again to −70° C. and then 1-bromo-5-chloropentane (36 mL, 50.7 g, 273 mmol) was added dropwise in 15 min. The reaction mixture was allowed to reach −5° C., stirred for 3 h, poured into a mixture of ice (100 mL), $H_2O$ (100 mL), brine (200 mL) and aqueous HCl (2 M, 200 mL) and extracted with $Et_2O$ (2×300 mL). The combined organic layers were washed with a mixture of brine and saturated aqueous $NaHCO_3$ (10:1, 300 mL) and dried. The remaining oil was purified by fractional distillation under reduced pressure to give 104c (31.5 g, 73%) as a colorless liquid. bp: T=67-74° C. (p=0.001 mbar). $^1$H NMR: 3.52 (t, J=6.6 Hz, 2H), 1.77 (quintet, J=6.8 Hz, 2H), 1.48-1.38 (m, 6H), 1.42 (s, 9H), 1.10 (dd, J=6.5 Hz, 3.8 Hz, 2H), 0.59 (dd, J=6.6, 3.9 Hz, 2H). $^{13}$C NMR: δ 174.1, 79.9, 45.2, 34.2, 32.7, 28.2 (3×), 27.20, 27.17, 24.3, 15.4 (2×). HRMS calcd for $C_{13}H_{24}ClO_2$ ($MH^+$): 247.1465. found: 247.1465.

t-Butyl 1-(4-iodobutyl)-1-cyclopropanecarboxylate (105a). To a solution of t-butyl 1-(4-chlorobutyl)-1-cyclopropanecarboxylate (104a, 10.6 g, 45.7 mmol) in 2-butanone (50 mL) was added Na (8.23 g, 54.5 mmol). The reaction mixture was stirred under reflux overnight, diluted with $Et_2O$ (100 mL), washed with a mixture of $H_2O$ (100 mL) and aqueous $Na_2S_2O_4$ (0.5 M, 10 mL) and brine (50 mL) and dried to give 105a (14.8 g, 94% pure by GC, 94%) as a slightly yellow liquid. $^1$H NMR: δ 3.18 (t, J=6.9 Hz, 2H), 1.76 (quintet, J=7.1 Hz, 2H), 1.62-1.45 (m, 4H), 1.43 (s, 9H), 1.12 (dd, J=6.7 Hz, 3.8 Hz, 2H), 0.60 (dd, J=6.6 Hz, 3.9 Hz, 2H). $^{13}$C NMR: δ 173.9, 80.0, 33.8, 33.3, 28.9, 28.2 (3×), 24.2, 15.5 (2×), 7.2. HRMS calcd for $C_{12}H_{21}IO_2$ ($M^+$): 324.0587. found: 324.0587.

Ethyl 1-(4-iodobutyl)-1-cyclobutanecarboxylate (105b). Compound 105b was prepared, likewise the procedure described for 5a, starting from ethyl 1-(4-chlorobutyl)-1-cyclobutanecarboxylate (104b, 21.21 g, 97.0 mmol) and NaI (19.07 g, 127 mmol) to give 105b (29.91 g, 99%) as a slightly yellow oil. $^1$H NMR: δ 4.14 (q, J=7.1 Hz, 2H), 3.17 (t, J=6.9 Hz, 2H), 2.49-2.32 (m, 2H), 1.98-1.69 (m, 8H), 1.37-1.19 (m, 2H), 1.27 (t, J=7.1 Hz, 3H). $^{13}$C NMR: δ 176.5, 60.3, 47.5, 36.9, 33.7, 30.1 (2×), 26.0, 15.7, 14.5, 6.8.

t-Butyl 1-(5-iodopentyl)-1-cyclopropanecarboxylate (105c). To a solution of t-butyl 1-(5-chloropentyl)-1-cyclopropanecarboxylate (104c, 31.5 g, 128 mmol) in 2-butanone (150 mL) was added NaI (24.9 g, 166 mmol). The reaction mixture was stirred under reflux for 24 h, diluted with heptane (220 mL) and filtered through a layer of silicagel (~2 cm) in a glassfilter. The residue was eluted with a mixture of heptane and EtOAc (3:1, 5×100 mL). The combined filtrate and elutes were evaporated in vacuo to give 5c (42.3 g, 99%) as a slightly yellow liquid. $^1$H NMR: δ 3.18 (t, J=7.1 Hz, 2H), 1.82 (quintet, J=7.1 Hz, 2H), 1.48-1.33 (m, 6H), 1.42 (s, 9H), 1.10 (dd, J=6.8 Hz, Hz, 2H), 0.58 (dd, J=6.6, 3.9 Hz, 2H). $^{13}$C NMR: δ 174.0, 79.9, 34.1, 33.6, 30.8, 28.2 (3×), 26.8, 24.3, 15.4 (2×), 7.4. HRMS calcd for $C_{13}H_{23}IO_2$ (M$^+$): 338.0743. found: 338.0743.

{7-Ethoxy-6,6-dimethyl-1-[(4-methylphenyl)sulfonyl]-7-oxoheptyl}(methylidyne) ammonium (108a). To a mixture of $K_2CO_3$ (13.18 g, 95.6 mmol) and $Bu_4NI$ (2.35 g, 6.36 mmol) in dry DMF (50 mL) was added a solution of 103a (24.00 g, 95.6 mmol) and TosMIC (12.41 g, 63.7 mmol) in dry DMF (50 mL) in 20 min under a $N_2$ atmosphere while stirring vigorously. After 4 d, $H_2O$ (100 mL) was added dropwise while keeping the temperature below 25° C. by cooling with an ice-bath. The resulting mixture was extracted with $Et_2O$ (3×200 mL). The combined organic layers were washed with saturated aqueous $NaHCO_3$ (2×200 mL) and dried. The remaining residue was purified by column chromatography (silica; heptane:EtOAc=6:1; a layer of $NaHCO_3$ was put on the base of the column) to give 108a (15.68 g, 42.8 mmol, 67%) as a slightly yellow oil which slowly solidified on standing. An analytical sample was obtained after recrystallization (0.43 g) from $iPr_2O$/heptane at ~4° C. to give 108a (0.30 g) as a white solid. mp=38-39° C. $^1$H NMR: δ 7.84 (d, J=8.4 Hz, 2H), 7.40 (d, J=7.8 Hz, 2H), 4.43 (dd, J=3.3, 10.8 Hz, 1H), 4.10 (q, J=7.1 Hz, 2H), 2.48 (s, 3H), 2.23-2.12 (m, 1H), 1.90-1.77 (m, 1H), 1.66-40 (m, 4H), 1.38-1.22 (m, 2H), 1.24 (t, J=7.1 Hz, 3H), 1.15 (s, 6H). $^{13}$C NMR: δ 177.3, 164.6, 146.3, 131.0, 129.93 (2×), 129.87 (2×), 72.8, 60.4, 42.2, 40.2, 28.4, 26.0, 25.35, 25.30, 24.2, 22.0, 14.5.

{8-Ethoxy-7,7-dimethyl-1-[(4-methylphenyl)sulfonyl]-8-oxooctyl}(methylidyne) ammonium (108b). Under a $N_2$ atmosphere, TosMIC (10.01 g, 51.3 mmol) and 103e (20.41 g, 77.0 mmol) were dissolved in dry DMF (100 mL) and $Bu_4NI$ (1.89 g, 5.12 mmol) and $K_2CO_3$ (10.62 g, 76.8 mmol) were added while stirring vigorously. After 5 d, the reaction mixture was poured in an ice/$H_2O$ mixture (500 mL) and extracted with $Et_2O$ (1×200 mL, 2×100 mL). The combined organic layers were washed with brine (2×50 mL) and dried. The remaining residue was purified by column chromatography (silica, heptane:EtOAc=3:1) to give in order of elution 103e (5.67 g, 90% pure by GC), an impure batch of 108b (0.94 g), and pure 108b (11.83 g, 61%) as a colorless oil. $^1$H NMR: δ 7.86 (d, J=8.1 Hz, 2H), 7.43 (d, J=8.1 Hz, 2H), 4.45 (dd, J=10.9, 3.5 Hz, 1H), 4.11 (q, J=7.2 Hz, 2H), 2.49 (s, 3H), 2.22-2.11 (m, 1H), 1.90-1.77 (m, 1H), 1.67-1.57 (m, 1H), 1.53-1.42 (m, 3H), 1.24 (t, J=7.2 Hz, 3H), 1.39-1.20 (m, 4H), 1.15 (s, 6H). $^{13}$C NMR: δ 177.8, 164.8, 146.5, 131.1, 130.1 (2×), 130.0 (2×), 72.8, 60.2, 42.0, 40.3, 29.0, 28.3, 25.12, 25.06 (2×), 24.5, 21.7, 14.2. HRMS calcd for $C_{20}H_{29}NNaO_4S$ (MNa$^+$): 402.1715. found: 402.1736.

General Procedures for Alkylation of TosMIC

Method A. t-Butyl 1-[9-[1-(tert-butoxycarbonyl)cyclopropyl]-5-oxononyl]-1-cyclopropanecarboxylate (106d). Under a $N_2$ atmosphere, NaH (60% (w/w) in mineral oil, 2.91 g, 72.8 mmol) was added portionwise to a solution of TosMIC (5.85 g, 30.0 mmol) and $Bu_4NI$ (1.10 g, 2.98 mmol) in dry DMSO (100 mL) while stirring vigorously and cooling with a water bath. After 10 min, 103b (16.56 g, 94% pure by GC, 56.2 mmol) was added dropwise in 20 min and stirring was continued for 1 h and 50 min. Then, $H_2O$ (100 mL) was added dropwise and the resulting mixture was extracted with $Et_2O$ (3×100 mL). The combined organic layers were washed with brine (2×100 mL) and dried. The remaining oil was purified by column chromatography (silica, heptane:EtOAc=6:1) to give t-butyl 1-{9-[1-(t-butoxycarbonyl)cyclopropyl]-5-isocyano-5-[(4-methylphenyl)sulfonyl]nonyl}-1-cyclopropanecarboxylate (10.00 g) as a slightly yellow oil.

Acidic hydrolysis of alkylated TosMIC intermediate. The above mentioned oil (10.00 g) was dissolved in $CH_2Cl_2$ (200 mL) and conc aqueous HCl (4 mL) was added. After stirring vigorously for 1 h, $H_2O$ (100 mL) was added and the layers were separated. The aqueous phase was extracted with $CH_2Cl_2$ (100 mL) and the combined organic layers were washed with saturated aqueous $NaHCO_3$ (3×100 mL) and dried. The remaining residue was purified by column chromatography (silica, heptane:EtOAc=10:1) to give 106d (5.80 g, 49%) as a colorless oil. $^1$H NMR: δ 2.39 (t, J=7.3 Hz, 4H), 1.63-1.38 (m, 30H), 1.10 (dd, J=6.6, 3.9 Hz, 4H), 0.59 (dd, J=6.7, 3.9 Hz, 4H). $^{13}$C NMR: δ 211.1, 174.4 (2×), 79.9 (2×), 42.7 (2×), 33.9 (2×), 28.0 (6×), 27.4 (2×), 24.1 (2×), 24.0 (2×), 15.2 (4×). HRMS calcd for $C_{25}H_{43}O_5$ (MH$^+$): 423.3111. found: 423.3111.

Method B. Ethyl 1-9-[1-(ethoxycarbonyl)cyclobutyl]-5-oxononyl-1-cyclobutanecarboxylate (106f). Under a $N_2$ atmosphere at 0° C., KOtBu (8.61 g, 76.7 mmol) was added portionwise to a solution of 105b (24.83 g, 80.1 mmol) and TosMIC (7.26 g, 36.4 mmol) in N,N-dimethylacetamide (DMAc, 150 mL). After 30 min, the reaction mixture was allowed to warm to rt, stirred for 1.5 h and diluted with DMAc (10 mL). Then, 105b (2.01 g, 6.5 mmol) and KOtBu (0.81 g, 7.2 mmol) were added followed by another portion of 105b (1.00 g, 3.2 mmol) and KOtBu (0.86 g, 7.7 mmol) after 1 h. After 1 h, the reaction mixture was poured into a mixture of $Et_2O$ (700 mL) and aqueous NaCl (10%, 500 mL) and the layers were separated. The organic layer was washed with brine (1×500 mL, 1×300 mL) and dried. The remaining residue was purified by column chromatography (silica, heptane:EtOAc=6:1) to give ethyl 1-9-[1-(ethoxycarbonyl)cyclobutyl]-5-isocyano-5-[(4-methylphenyl)sulfonyl]nonyl-1-cyclobutanecarboxylate (18.35 g) as a slightly yellow oil. Part of this oil (15.62 g, 27.9 mmol) was hydrolyzed with conc aqueous HCl (75 mL) according to the procedure described for 106d to give, after purification by column chromatography (silica, heptane:EtOAc=6:1), 106f (9.99 g, 82%) as a slightly yellow liquid, after evaporation from $CH_2Cl_2$ (100 mL). $^1$H NMR: δ 4.12 (q, J=7.1 Hz, 4H), 2.44-2.32 (m, 8H), 1.93-1.79 (m, 8H), 1.77-1.72 (m, 4H), 1.55 (quintet, J=7.5 Hz, 4H), 1.25 (t, J=7.1 Hz, 6H), 1.21-1.10 (m, 4H). $^{13}$C NMR: δ 210.2, 176.7 (2×), 60.2 (2×), 47.6 (2×), 42.6 (2×), 37.9 (2×), 30.1 (4×), 24.7 (2×), 24.1 (2×), 15.7 (2×), 14.4 (2×). HRMS calcd for $C_{23}H_{38}O_5$ (M$^+$): 394.2719. found: 394.2703.

Method C. Ethyl 13-[1-(t-butoxycarbonyl)cyclopropyl]-2,2-dimethyl-8-oxotridecanoate (106k). Under a $N_2$ atmosphere at 0° C., a solution of 108b (28.4 g, 75.0 mmol) in N,N-dimethylacetamide (DMAc, 125 mL) followed by a solution of 105c (25.4 g, 75.0 mmol) in DMAc (125 mL) were added dropwise in 60 and 30 min, respectively to a solution of KOtBu (8.83 g, 79.0 mmol) in DMAc (250 mL). The mixture was allowed to reach rt and stirring was continued for 2 h. Then, the reaction mixture was quenched by the dropwise addition of $H_2O$ (250 mL) while cooling with an ice-bath. The resulting mixture was extracted with $Et_2O$ (3×250 mL) and the combined organic layers were washed with brine (2×250 mL) and dried to give a yellow oil (43.02 g). Part of this oil (42.50 g) was hydrolyzed with conc aqueous HCl (34 mL) according to the procedure described for 106d to give, after purification by column chromatography (silica, heptane:EtOAc=8:1), 106k (19.0 g, 95% pure by $^1$H NMR, 57%) as a slightly yellow oil. $^1$H NMR: δ 4.09 (q, J=7.2 Hz, 2H), 2.37 (t, J=7.2 Hz, 2H), 2.36 (t, J=7.2 Hz, 2H), 1.62-1.35 (m, 10H), 1.41 (s, 9H), 1.30-1.21 (m, 6H), 1.24 (t, J=7.2 Hz, 3H), 1.14

(s, 6H), 1.09 (dd, J=6.6, 3.9 Hz, 2H), 0.58 (dd, J=6.3, 3.6 Hz, 2H). $^{13}$C NMR: δ 210.8, 177.6, 174.1, 79.8, 60.2, 42.9, 42.8, 42.2, 40.6, 34.1, 29.8, 29.6, 28.2 (3×), 27.6, 25.3 (2×), 24.9, 24.3, 23.9, 23.8, 15.3 (2×), 14.4.

Ethyl 11-[1-(t-butoxycarbonyl)cyclopropyl]-2,2-dimethyl-7-oxoundecanoate (106c). Compound 6c was prepared likewise Method C starting from 108a (20.5 g, 55.9 mmol), 105a (18.11 g, 55.9 mmol) and KOtBu (6.57 g, 58.7 mmol) to give a yellow oil (31.79 g). Part of this oil (30.63 g) was treated with conc aqueous HCl (23 mL), as described for 106d, to give, after purification by column chromatography (silica, heptane:EtOAc=40:1), 106c (9.83 g, >90% pure by NMR, 43%) as a colorless oil. $^1$H NMR: δ 4.09 (q, J=7.2 Hz, 2H), 2.38 (t, J=7.2 Hz, 4H), 1.62-1.35 (m, 10H), 1.41 (s, 9H), 1.26-1.17 (m, 2H), 1.24 (t, J=7.2 Hz, 3H), 1.14 (s, 6H), 1.09 (dd, J=6.9, 4.2 Hz, 2H), 0.59 (dd, J=6.3, 3.6 Hz, 2H). $^{13}$C NMR: δ 210.5, 177.4, 174.0, 79.8, 60.2, 42.8, 42.6, 42.1, 40.5, 34.0, 28.2 (3×), 27.5, 25.2 (2×), 24.7, 24.3, 24.2, 24.1, 15.3 (2×), 14.4.

Ethyl 11-[1-(ethoxycarbonyl)cyclobutyl]-2,2-dimethyl-7-oxoundecanoate (106e). Compound 106e was prepared likewise Method C starting from 108a (11.01 g, 30.1 mmol), 105b (10.28 g, 33.1 mmol) and KOtBu (4.06 g, 36.2 mmol) to give, after purification by column chromatography (silica, heptane:EtOAc=6:1; a layer of NaHCO$_3$ was put on the base of the column), ethyl 1-[11-ethoxy-5-isocyano-10,10-dimethyl-5-[(4-methylphenyl)sulfonyl]-11-oxoundecyl]-1-cyclobutanecarboxylate (14.11 g) as a colorless oil. Part of this oil (13.86 g, 25.3 mmol) was treated with conc aqueous HCl (50 mL), as described for 106d, to give crude 106e, which was stirred up in heptane (50 mL) and the resulting precipitate was filtered off and washed with heptane (3×50 mL). The combined filtrates were washed with aqueous NaOH (1M, 2×50 mL) and brine (50 mL) and dried to give 106e (9.44 g, >90% pure by $^1$H NMR, 75%) as a slightly yellow oil. $^1$H NMR: δ 4.12 (q, J=7.1 Hz, 2H), 4.09 (q, J=7.1 Hz, 2H), 2.50-2.29 (m, 2H), 2.37 (t, J=7.4 Hz, 4H), 1.95-1.70 (m, 6H), 1.61-1.44 (m, 6H), 1.30-1.09 (m, 4H), 1.25 (t, J=7.1 Hz, 3H), 1.24 (t, J=7.1 Hz, 3H), 1.14 (s, 6H). $^{13}$C NMR: δ 210.1, 177.3, 176.6, 60.1 (2×), 47.5, 42.57 (2×), 42.1, 40.4, 37.8, 30.0 (2×), 25.2 (2×), 24.7, 24.6, 24.2, 24.1, 15.7, 14.4, 14.3.

Butyl 1-9-[1-(butoxycarbonyl)cyclopentyl]-5-oxononyl-1-cyclopentanecarboxylate (106 g). Compound 106g was prepared likewise Method A starting from TosMIC (6.58 g, 33.0 mmol), Bu$_4$NI (1.31 g, 3.55 mmol), NaH (60% (w/w) in mineral oil, 3.20 g and 0.56 g after 2 h, 80.0 and 14.0 mmol) and 103c (21.59 g, 67.2 mmol) to give, after purification by column chromatography (silica, heptane:EtOAc=8:1), butyl 1-{9-[1-(butoxycarbonyl)cyclopentyl]-5-isocyano-5-[(4-methylphenyl)sulfonyl]nonyl}-1-cyclopentanecarboxylate as a yellow oil (13.38 g). This oil (13.38 g) was treated with conc aqueous HCl (75 mL), as described for 106d, to give, after purification by column chromatography (silica, heptane:EtOAc=10:1), 106g (9.05 g, 56%) as a slightly yellow liquid. $^1$H NMR: δ 4.05 (t, J=6.5 Hz, 4H), 2.36 (t, J=7.5 Hz, 4H), 2.14-2.05 (m, 4H), 1.65-1.32 (m, 28H), 1.24-1.16 (m, 4H), 0.96 (t, J=7.2 Hz, 6H). $^{13}$C NMR: δ 210.8, 177.8 (2×), 64.1 (2×), 54.0 (2×), 42.6 (2×), 39.0 (2×), 36.0 (4×), 30.7 (2×), 25.6 (2×), 24.9 (4×), 24.1 (2×), 19.1 (2×), 13.6 (2×). HRMS calcd for C$_{29}$H$_{50}$O$_5$ (M$^+$): 478.3658. found 478.3663.

Tetraethyl 7-oxo-2,2,12,12-tridecanetetracarboxylate (106h). Compound 106h was prepared likewise Method A starting from TosMIC (10.63 g, 53.4 mmol), Bu$_4$NI (3.99 g, 10.7 mmol), NaH (60% (w/w) in mineral oil, 4.27 g, 107 mmol) and 103d (30.0 g, 97.0 mmol) to give, after filtration through silica (elute: heptane:EtOAc=2:1), 7-ethoxy-6-(ethoxycarbonyl)-1-[6-ethoxy-5-(ethoxycarbonyl)-5-methyl-6-oxohexyl]-6-methyl-1-[(4-methylphenyl)sulfonyl]-7-oxoheptyl(methylidyne)ammonium (27.9 g) as a yellow oil. Part of this oil (26.9 g) was treated with conc aqueous HCl (50 mL), as described for 106d, to give, after purification by column chromatography (silica, heptane:EtOAc=4:1), 106h (16.21 g, 71%) as a yellow oil. $^1$H NMR: δ 4.17 (q, J=7.1 Hz, 8H), 2.40 (t, J=7.4 Hz, 4H), 1.87-1.82 (m, 4H), 1.58 (quintet, J=7.4 Hz, 4H), 1.38 (s, 6H), 1.28-1.18 (m, 4H), 1.25 (t, J=7.2 Hz, 12H). $^{13}$C NMR: δ 210.0, 172.0 (4×), 60.8 (4×), 53.3 (2×), 42.1 (2×), 35.0 (2×), 23.6 (4×), 19.5 (2×), 13.8 (4×). HRMS calcd for C$_{25}$H$_{43}$O$_9$ (MH$^+$): 487.2907. found: 487.2944.

t-Butyl 1-11-[1-(t-butoxycarbonyl)cyclopropyl]-6-oxoundecyl-1-cyclopropanecarboxylate (106l). Compound 106l was prepared likewise Method B starting from TosMIC (13.84 g, 70.9 mmol), 105c (24.0 and 24.0 g after 1.5 h in 15 min, 71.0 and 71.0 mmol) and KOtBu (8.35 and 8.35 g after 1.5 h, 74.6 and 74.6 mmol) to give, after dissolving the crude product in EtOAc (100 mL) and filtration through silica (elute: heptane:EtOAc=1:1, 5×80 mL) an oil (42.38 g). This oil (42.38 g) was treated with conc aqueous HCl (11.4 mL), as described for 106d, to give, after purification by column chromatography (silica, heptane:EtOAc=12:1), 106i (16.3 g, >90% pure by $^1$H NMR, 46%) as a colorless oil. $^1$H NMR: δ 2.37 (t, J=7.4 Hz, 4H), 1.62-1.49 (quintet, J=7.4 Hz, 4H), 1.48-1.36 (m, 8H), 1.41 (s, 18H), 1.33-1.20 (m, 4H) 1.09 (dd, J=6.5, 3.8 Hz, 4H), 0.58 (dd, J=6.6, 3.9 Hz, 4H). $^{13}$C NMR: δ 210.9, 174.1 (2×), 79.8 (2×), 42.9 (2×), 34.1 (2×), 29.6 (2×), 28.2 (6×), 27.7 (2×), 24.4 (2×), 24.0 (2×), 15.4 (4×).

Butyl 1-{11-[1-(butoxycarbonyl)cyclopentyl]-6-oxoundecyl}-1-cyclopentanecarboxylate (106m). Compound 106m was prepared likewise Method A starting from TosMIC (12.48 g, 62.6 mmol), Bu$_4$NI (2.56 g, 6.93 mmol), NaH (60% (w/w) in mineral oil, 7.55 g and 1.20 g after 2 h, 189 mmol and 30.0 mmol) and 103f (44.46 g, 93% pure by GC, 129 mmol) to give, after purification by column chromatography (silica, heptane/EtOAc=8:1), butyl 1-{11-[1-(butoxycarbonyl)cyclopentyl]-6-isocyano-6-[(4-methylphenyl)sulfonyl]undecyl}-1-cyclopentanecarboxylate as a yellow oil (32.79 g). This oil (32.79 g) was treated with conc aqueous HCl (150 mL), as described for 106d, to give, after purification by column chromatography (silica, heptane:EtOAc=6:1), 106m (24.11 g, 90% pure by $^1$H NMR, 68%) as a slightly yellow liquid. $^1$H NMR: δ 4.06 (t, J=6.6 Hz, 4H), 2.36 (t, J=7.4 Hz, 4H), 2.15-2.06 (m, 4H), 1.65-1.52 (m, 20H), 1.49-1.32 (m, 8H), 1.27-1.19 (m, 8H), 0.94 (t, J=7.4 Hz, 6H). $^{13}$C NMR: δ 210.9, 177.6 (2×), 63.8 (2×), 54.0 (2×), 42.5 (2×), 38.9 (2×), 35.8 (4×), 30.6 (2×), 29.5 (2×), 25.6 (2×), 24.7 (4×), 23.4 (2×), 19.0 (2×), 13.5 (2×). HRMS calcd for C$_{31}$H$_{54}$O$_5$ (M$^+$): 506.3971. found: 506.3981.

Diethyl 10-oxo-2,2,18,18-tetramethyl-nonadecanedioate (106n). Compound 106n was prepared likewise Method A starting from TosMIC (2.43 g, 12.5 mmol), Bu$_4$NI (0.462 g, 1.25 mmol), NaH (60% (W/w) in mineral oil, 1.21 g, 30.3 mmol) and 103g (7.65 g, 88% pure by GC, 23.0 mmol) to give, after purification by column chromatography (silica, heptane:EtOAc=6:1), {10-ethoxy-1-(9-ethoxy-8,8-dimethyl-9-oxononyl)-9,9-dimethyl-1-[(4-methylphenyl)sulfonyl]-10-oxodecyl}(methylidyne)ammonium (5.41 g) as a yellow oil. Part of this oil (5.03 g) was treated with conc aqueous HCl (30 mL), as described for 106d, to give, after purification by column chromatography (silica, heptane:EtOAc=7:1), 106n (3.21 g, 57%) as a colorless oil. $^1$H NMR: δ 4.11 (q, J=7.2 Hz, 4H), 2.37 (t, J=7.4 Hz, 4H), 1.57-1.46 (m, 8H), 1.28-1.23 (m, 16H), 1.24 (t, J=7.1 Hz, 6H), 1.15 (s, 12H). $^{13}$C NMR: δ 211.5, 178.0 (2×), 60.08 (2×), 60.07 (2×), 42.7 (2×), 42.1 (2×), 40.7 (2×), 29.9 (2×), 29.21 (2×), 29.15

(2×), 25.1 (2×), 24.8 (2×), 23.8 (2×), 14.2 (2×). HRMS calcd for $C_{27}H_{50}O_5$ (M+): 454.3658. found: 454.3663.

General Procedures for Ester Hydrolysis

Method D. 1-[9-(1-Carboxycyclobutyl)-5-oxononyl]-1-cyclo-butanecarboxylic acid (107O). LiOH.H$_2$O (3.94 g, 93.9 mmol) and H$_2$O (30 mL) were added to a solution of 106f (9.20 g, 23.3 mmol) in EtOH (90 mL) and the resulting mixture was stirred at reflux temperature for 17 h, allowed to cool to rt and concentrated in vacuo to a smaller volume. H$_2$O (150 mL) was added and the resulting mixture was extracted with Et$_2$O (50 mL), acidified with aqueous HCl (6 M, 25 mL) and extracted with Et$_2$O (1×100 mL, 2×50 mL). The latter organic layers were combined, washed with brine (50 mL) and dried. The remaining residue was recrystallized from iPr$_2$O/heptane to give 7f (4.41 g, 56%) as small, white granules. mp 69-70° C. $^1$H NMR: δ 11.2 (br s, 2H), 2.50-2.37 (m, 4H), 2.39 (t, J=7.2 Hz, 4H), 1.96-1.84 (m, 8H), 1.81-1.75 (m, 4H), 1.57 (quintet, J=7.4 Hz, 4H), 1.26-1.12 (m, 4H). $^{13}$C NMR: δ 210.6, 183.4 (2×), 47.6 (2×), 42.7 (2×), 37.8 (2×), 30.1 (4×), 24.7 (2×), 24.1 (2×), 15.7 (2×). Anal. calcd for $C_{19}H_{30}O_5$: C, 67.43; H, 8.93. found: C, 67.19; H, 8.97.

Method E. 1-[9-(1-Carboxycyclopropyl)-5-oxononyl]-1-cyclopropanecarboxylic acid (107d). A solution of 106d (5.31 g, 12.6 mmol) in HCO$_2$H (50 mL) was stirred for 3 h, evaporated in vacuo and coevaporated from toluene (3×25 mL) to give 107d (3.89 g, 99%) as a white solid. An analytical sample was obtained after recrystallization from iPr$_2$O/heptane. mp 132-134° C. $^1$H NMR: (CD$_3$OD) δ 2.45 (t, J=6.9 Hz, 4H), 1.58-1.39 (m, 12H), 1.14 (dd, J=6.6, 3.7 Hz, 4H), 0.70 (dd, J=6.8, 3.9 Hz, 4H). $^{13}$C NMR: (CD$_3$OD) δ 214.4, 179.4 (2×), 43.5 (2×), 34.9 (2×), 28.5 (2×), 25.1 (2×), 24.2 (2×), 16.2 (4×). Anal. calcd for $C_{17}H_{26}O_5$: C, 65.78; H, 8.44. found: C, 65.40; H, 8.37.

Method F. 11-(1-Carboxycyclopropyl)-2,2-dimethyl-7-oxoundecanoic acid (107c). A solution of 106c (9.27 g, >90% pure by NMR, 21.0 mmol) in HCO$_2$H (50 mL) was stirred for 1.5 h, evaporated in vacuo and coevaporated from toluene (10 mL). The remaining residue was dissolved in EtOH:H$_2$O (2:1, 100 mL) and NaOH (5.33 g, 132 mmol) was added. The resulting clear solution was warmed to 80° C. and after 5 h, EtOH was evaporated in vacuo. The remaining solution was diluted with H$_2$O to ~100 mL, extracted with Et$_2$O (3×100 mL), acidified to pH ~1 with conc aqueous HCl (~9 mL) and extracted with Et$_2$O (3×100 mL). The latter organic layers were combined and dried. The remaining residue was purified by column chromatography (heptane:EtOAc=2:1 (containing 1% (v/v) HOAc)) to give 7c (5.83 g, >90% pure by $^1$H-NMR, 80%) as a slightly yellow oil which turns solid when stored at −18° C. for several days. mp=49-52° C. $^1$H NMR: (CD$_3$OD) δ 2.44 (t, J=7.2 Hz, 4H), 1.57-1.42 (m, 10H), 1.30-1.19 (m, 2H), 1.17-1.07 (m, 2H), 1.14 (s, 6H), 0.59 (dd, J=6.6, 3.9 Hz, 2H). $^{13}$C NMR: (CD$_3$OD) δ 213.5, 181.4, 178.9, 43.5, 43.4, 43.0, 41.7, 34.9, 28.5, 25.9 (3×), 25.5, 25.2, 24.3, 16.4 (2×).

11-(1-Carboxycyclobutyl)-2,2-dimethyl-7-oxoundecanoic acid (107e). Compound 107e was prepared likewise Method D starting from 106e (8.83 g, >90% pure by $^1$H NMR, 20.8 mmol) and LiOH.H$_2$O (2.91 and 1.94 g after 18 h, 69.4 and 46.2 mmol) to give, after recrystallized from iPr$_2$O/heptane, 7e (5.19 g, 76%) as a white solid. mp=53-55° C. $^1$H NMR: δ 10.80 (br s, 2H), 2.50-2.35 (m, 2H), 2.39 (t, J=7.2 Hz, 4H), 1.98-1.74 (m, 6H), 1.65-1.49 (m, 6H), 1.31-1.11 (m, 4H), 1.18 (s, 6H). $^{13}$C NMR: δ 210.6, 184.3, 183.4, 47.6, 42.7, 42.6, 42.2, 40.5, 37.8, 30.1 (2×), 25.1 (2×), 24.8, 24.7, 24.2, 24.1, 15.7.

1-[9-(1-Carboxycyclopentyl)-5-oxononyl]-1-cyclopentanecarboxylic acid (107g). Compound 107g was prepared likewise Method D starting from 106g (7.25 g, 15.0 mmol) and LiOH.H$_2$O (3.21 g, 76.4 mmol) to give 107g (5.46 g, 95% pure by $^1$H NMR, 94%, mp=99-103° C.) as a white solid. An analytical sample was obtained after recrystallization from iPr$_2$O/heptane. mp=104-106° C. $^1$H NMR: δ 2.39 (t, J=6.9 Hz, 4H), 2.18-2.10 (m, 4H), 1.69-141 (m, 20H), 1.27-1.14 (m, 4H). $^{13}$C NMR: δ 211.1, 184.6 (2×), 53.9 (2×), 42.5 (2×), 39.0 (2×), 35.9 (4×), 25.7 (2×), 24.9 (4×), 24.0 (2×). Anal. calcd for $C_{21}H_{34}O_5$: C, 68.82; H, 9.35. found: C, 68.78; H, 9.47.

2,12-Di(ethoxycarbonyl)-2,12-dimethyl-7-oxotridecanedioic acid (107h). A solution of KOH (2.44 g, >85%, >37.0 mmol) in EtOH (80 mL) was added to 106h (9.00 g, 18.5 mmol). After stirring for 54 h, another portion of KOH (1.21 g, >85%, >18.5 mmol) was added and stirring was continued for 16 h. The reaction mixture was evaporated in vacuo and Et$_2$O (250 mL) and H$_2$O (250 mL) were added. The aqueous layer was separated, acidified with aqueous HCl (2 M, 50 mL) and extracted with Et$_2$O (250 mL) and CH$_2$Cl$_2$ (250 mL). The combined organic layers were dried and the remaining residue was purified by column chromatography (silica, heptane:EtOAc:HOAc=3:2:0.01) and vacuum dried at 50° C. to give 107h (6.43 g, 81%) as a yellow oil. $^1$H NMR: δ 10.40 (br s, 2H), 4.21 (q, J=7.1 Hz, 4H), 2.42 (t, J=7.4 Hz, 4H), 1.90-1.84 (m, 4H), 1.59 (quintet, J=7.4 Hz, 4H), 1.43 (s, 6H), 1.32-1.19 (m, 4H), 1.27 (t, J=7.2 Hz, 6H). $^{13}$C NMR: δ 210.9, 177.7 (2×), 172.1 (2×), 61.5 (2×), 53.5 (2×), 42.2 (2×), 35.3 (2×), 23.8 (2×), 23.7 (2×), 19.8 (2×), 13.9 (2×). HRMS calcd for $C_{21}H_{35}O_9$ (MH+): 431.2281. found: 431.2298.

13-(1-Carboxycyclopropyl)-2,2-dimethyl-8-oxotridecanoic acid (107k). Compound 107k was prepared likewise Method F starting from 6k (18.34 g, 95% pure by $^1$H NMR, 41.0 mmol) to give 1-(11-ethoxy-10,10-dimethyl-5,11-dioxoundecyl)-1-cyclopropanecarboxylic acid, which was treated with NaOH (9.68 g, 241 mmol) to give, after recrystallized from iPr$_2$O/heptane, 107k (9.47 g, 68%) as a white solid. The mother liquor was evaporated in vacuo and the remaining residue was purified by column chromatography (heptane:EtOAc=2:1 (containing 1% (v/v) HOAc)) and recrystallization from iPr$_2$O/heptane to give a second batch 107k (2.23 g, 16%) as a white solid. mp=65-66° C. $^1$H NMR: (CD$_3$OD) δ 2.43 (t, J=7.2 Hz, 4H), 1.58-1.42 (m, 10H), 1.35-1.20 (m, 6H), 1.14 (s, 6H), 1.15-1.06 (m, 2H), 0.70 (dd, J=6.6, 3.9 Hz, 2H). $^{13}$C NMR: (CD$_3$OD) δ 213.8, 181.6, 179.0, 43.6, 43.5, 43.1, 41.9, 35.1, 31.0, 30.6, 28.7, 26.2, 25.9 (2×), 25.02, 24.96, 24.4, 16.4 (2×).

1-[11-(1-Carboxycyclopropyl)-6-oxoundecyl]-1-cyclopropanecarboxylic acid (107l). Compound 107l was prepared likewise Method E starting from 106l (7.50 g, >90% pure by $^1$H NMR, 15.0 mmol) to give, after recrystallized from toluene, 107l (5.06 g, 99%) as colorless crystals. mp=122-123° C. $^1$H NMR: (DMSO-d6) δ 11.96 (br s, 2H), 2.39 (t, J=7.4 Hz, 4H), 1.50-1.33 (m, 12H), 1.25-1.15 (m, 4H), 1.03 (dd, J=6.5, 3.5 Hz, 4H), 0.68 (dd, J=6.6, 3.6 Hz, 4H). $^{13}$C NMR: (DMSO-d6) δ 209.9, 175.7 (2×), 41.8 (2×), 33.2 (2×), 28.8 (2×), 27.2 (2×), 23.3 (2×), 22.9 (2×), 14.8 (4×). Anal. calcd for $C_{19}H_{30}O_5$: C, 67.43; H, 8.93. found: C, 67.20; H, 9.05.

1-[11-(1-Carboxycyclopentyl)-6-oxoundecyl]-1-cyclopentanecarboxylic acid (107m). Compound 107m was prepared likewise Method D starting from 106m (21.03 g, 90% pure by $^1$H NMR, 37.3 mmol) and LiOH.H$_2$O (7.83 g, 187 mmol) to give, after recrystallization from iPr$_2$O/heptane, 107m (12.15 g, 83%) as white granules. mp=78-85° C. $^1$H NMR: δ 2.37 (t, J=7.4 Hz, 4H), 2.18-2.10 (m, 4H), 1.65-1.45 (m, 20H), 1.29-1.25 (m, 8H). $^{13}$C NMR: δ 211.5, 184.8 (2×), 54.0 (2×), 42.4 (2×), 38.9 (2×), 35.9 (4×), 29.2 (2×), 25.5 (2×), 24.9 (4×), 23.5 (2×). Anal. calcd for $C_{22}H_{38}O_5$: C, 70.02; H, 9.71. found: C, 70.37; H, 9.72.

10-Oxo-2,2,18,18-tetramethyl-nonadecanedioic acid (107n). Compound 107n was prepared likewise Method D starting from 106n (11.63 g, 25.6 mmol) and KOH (4.31 g, 77.0 mmol) to give, after recrystallization from iPr$_2$O/heptane, 107n (7.56 g, 74%) as white crystals. mp=74-77° C. $^1$H NMR: (CD$_3$OD) δ 2.43 (t, J=7.3 Hz, 4H), 1.57-1.50 (m, 8H), 1.33-1.21 (m, 16H), 1.14 (s, 12H). $^{13}$C NMR: δ 214.5, 182.1 (2×), 43.6 (2×), 43.2 (2×), 42.0 (2×), 31.2 (2×), 30.4 (2×), 30.38 (2×), 26.2 (2×), 25.9 (4×), 25.0 (2×). Anal. calcd for $C_{23}H_{42}O_5$: C, 69.31; H, 10.62. found: C, 69.41; H, 10.73.

5.2. Synthesis of 9-hydroxy-3-(6-hydroxy-5,5-dimethyl-hexyl-8,8-dimethyl-nonan-2-one

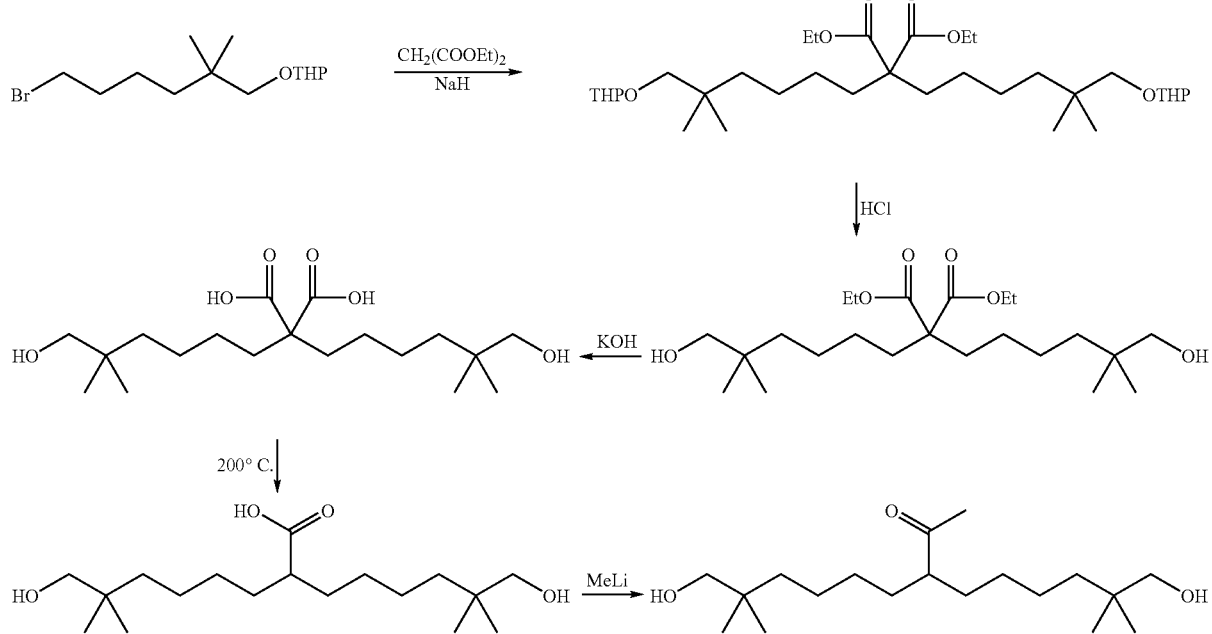

2,2-Bis-[5,5-dimethyl-6-(tetrahydropyran-2-yloxy)-hexyl]-malonic acid diethyl ester. Under nitrogen atmosphere, to a solution of 2-(6-bromo-2,2-dimethyl-hexyloxy)-tetrahydropyran (17.6 g, 60 mmol) and diethyl malonate (4.8 g, 30 mmol) in anhydrous DMSO (145 mL) was added sodium hydride (60% dispersion in mineral oil, 2.88 g, 72 mmol) under cooling with a water-bath. Tetra-n-butylammonium iodide (2.1 g, 3.6 mmol) was then added. The mixture was stirred for 16 h at room temperature. Water (140 mL) was added carefully to the reaction mixture under cooling with water-bath. The product was extracted with diethyl ether (3 60 mL) and the combined organic layers were washed with water (4 50 mL) and brine (50 mL). The solution was dried over sodium sulfate and concentrated in vacuo to give 2,2-bis-[5,5-dimethyl-6-(tetrahydropyran-2-yloxy)-hexyl]-malonic acid diethyl ester (17.3 g, 82.3%) as an oil $^1$H NMR (300 MHz, CDCl$_3$/TMS): (ppm) 4.41 (t, J=3.1 Hz, 2H), 4.01 (q, J=7.0 Hz, 4H), 3.82-3.70 (m, 2H), 3.50-3.30 (m, 4H), 2.87 (d, J=9.1 Hz, 2H), 1.80-1.35 (m, 16H), 1.30-0.95 (m, 18H), 0.88-0.74 (m, 12H). $^{13}$C NMR (75 MHz, CDCl$_3$/TMS): (ppm) 172.0, 99.1, 76.6, 61.9, 60.9, 57.6, 39.2, 34.3, 32.3, 30.7, 25.7, 25.0, 24.6, 24.6, 24.3, 19.5, 14.2.

2,2-Bis(6-hydroxy-5,5-dimethyl-hexyl)-malonic acid diethyl ester. A solution of 2,2-bis-[5,5-dimethyl-6-(tetrahydropyran-2-yloxy)-hexyl]-malonic acid diethyl ester (2.92 g, 5 mmol) in concentrated HCl (2.4 mL) and water (1.6 mL) was refluxed for 1 h. Ethanol (8.2 mL) was added and the reaction mixture was heated to reflux for 3 h. The reaction mixture was diluted with water (20 mL) and extracted with diethyl ether (3×20 mL). The combined organic layers were washed with water (20 mL), brine (20 mL), and dried over Na$_2$SO$_4$. The solution was concentrated to furnish 2,2-bis(6-hydroxy-5,5-dimethyl-hexyl)-malonic acid diethyl ester (1.74 g, 84%). $^1$H NMR (300 MHz, CDCl$_3$/TMS): (ppm) 4.13 (q, J=7.2 Hz, 4H), 3.25 (s, 4H), 2.42 (s, 2H), 1.90-1.75 (m, 4H), 1.30-1.12 (m, 18H), 0.84 (s, 12H). $^{13}$C NMR (75 MHz, CDCl$_3$/TMS): (ppm) 172.0, 71.7, 60.9, 57.4, 38.2, 34.9, 32.1, 24.8, 24.0, 23.7, 14.0.

2,2-Bis-(6-hydroxy-5,5-dimethyl-hexyl)-malonic acid. To a stirred solution of KOH (4.83 g, 75 mmol) in water (4.2 mL) and ethanol (15 mL) was added 2,2-bis(6-hydroxy-5,5-dimethyl-hexyl)-malonic acid diethyl ester (15 g). The reaction mixture was heated to reflux for 14 h, then concentrated in vacuo, and extracted with chloroform. The aqueous layer was acidified with HCl until pH 1 and extracted with diethyl ether (3×50 mL). The ethereal solution was dried over anhydrous MgSO$_4$ and concentrated in vacuo to afford get 2,2-bis-(6-hydroxy-5,5-dimethyl-hexyl)-malonic acid (7.8 g, 82.3%) as a yellow solid. $^1$H NMR (300 MHz, CD$_3$OD/TMS): (ppm) 4.86 (s, 4H), 3.22 (s, 4H), 1.9-1.8 (m, 4H), 1.36-1.10 (m, 12H), 0.84 (s, 12H). $^{13}$C NMR (75 MHz, CD$_3$OD/TMS): (ppm) 176.0, 72.0, 58.7, 39.8, 36.0, 34.1, 26.5, 25.5, 24.5. Mp.: 178-180 C.

8-Hydroxy-2-(6-hydroxy-5,5-dimethyl-hexyl)-7,7-dimethyl-octanoic acid. 2,2-Bis-(6-hydroxy-5,5-dimethyl-hexyl)-malonic acid was heated to 200 C using an oil-bath. This temperature was kept for 30 minutes until the effervescence ceased. 8-Hydroxy-2-(6-hydroxy-5,5-dimethyl-hexyl)-7,7-dimethyl-octanoic acid was obtained as an oil (4.04 g, 98%). $^1$H NMR (300 MHz, CDCl$_3$/TMS): (ppm) 4.88 (s, 3H), 3.22 (s, 4H), 2.29 (m, 1H), 1.70-1.40 (m, 4H), 1.4-1.1 (m, 12H), 0.84 (s, 12H). $^{13}$C NMR (75 MHz, CDCl$_3$/TMS): (ppm) 180.5, 72.1, 47.1, 39.9, 36.0, 33.8, 29.7, 25.0, 24.6.

9-Hydroxy-3-(6-hydroxy-5,5-dimethyl-hexyl)-8,8-dimethyl-nonan-2-one. 8-Hydroxy-2-(6-hydroxy-5,5-dimethylhexyl)-7,7-dimethyl-octanoic acid (1.0 g, 3.16 mmol) was dissolved in THF (40 mL) and cooled in an ice-water bath. Methyl lithium (27 mL) was then added at once. The reaction was continued for 2 h at 0° C. The reaction mixture was poured into dilute hydrochloric acid (5 mL concentrated hydrochloric acid in 60 mL water). The organic layer was separated and the aqueous layer was extracted with diethyl ether (2×50 mL). The combined organic layers were dried over sodium sulfate and concentrated in vacuo to give the crude product (1.0 g). The crude product was purified by column chromatography (hexanes:ethyl acetate=4:1, then 1:1) to give 9-hydroxy-3-(6-hydroxy-5,5-dimethyl-hexyl)-8,8-dimethyl-nonan-2-one (0.41 g, yield 41%) and 7-(1-hydroxy-1-methylethyl)-2,2,12,12-tetramethyltridecan-1,13-diol (0.4 g, 38%, not shown) as a by-product $^1$H NMR (300 MHz, CDCl$_3$/TMS): (ppm) 3.46 (s, 4H), 2.65-2.50 (m, 1H), 2.28 (s, 3H), 2.60 (br., 2H), 1.82-1.50 (m, 4H), 1.50-1.25 (m, 12H), 1.02 (s, 12H). $^{13}$C NMR (75 MHz, CDCl$_3$/TMS): (ppm) 213.4, 71.7, 53.2, 38.3, 34.9, 31.6, 28.7, 28.3, 23.8. HRMS (LSIMS, nba): Calcd. for C$_{19}$H$_{39}$O$_3$ (MH$^+$): 315.2899. found: 315.2866.

5.3. Synthesis of Keto-dialkyldicarboxylic Acids bis-Amides

3.1. Synthesis of 2,2,12,12-tetramethyl-7-oxo-tridecanedioic acid bis-methylamide 6-[2-(5-Ethoxycarbonyl-5-methyl-hexyl)-[1,3]dithian-2-yl]-2,2-dimethyl-hexanoic acid ethyl ester. Under N$_2$ atmosphere, to a solution of 2,2,12,12-tetramethyl-7-oxo-tridecanedioic acid diethyl ester (1.0 g, 2.70 mmol) and 1,3-propanedithiol (361 mg, 361 L, 3.24 mmol) in dichloromethane (20 mL; dried with Aluminum oxide, activated, neutral, Brockmann I) was added boron trifluoride diethyl etherate (100 L) at rt. The reaction mixture was stirred for 3 h, diluted with dichloromethane (100 mL), and extracted with 5% NaOH solution (100 mL) and water (75 mL). The organic phase was dried over MgSO$_4$, concentrated in vacuo, and dried in high vacuo to furnish 6-[2-(5-ethoxycarbonyl-5-methyl-hexyl)-[1,3]dithian-2-yl]-2,2-dimethyl-hexanoic acid ethyl ester (1.0 g, 80%) as a yellowish oil. $^1$H NMR (300 MHz, CDCl$_3$/TMS): (ppm): 4.11 (q, 4H, J=7.1), 2.79 (t, 4H, J=5.6), 1.94 (m, 2H), 1.84 (m, 4H), 1.54 (m, 4H), 1.39 (m, 4H), 1.24 (t, 6H, J=7.1), 1.30-1.20 (m, 4H), 1.16 (s, 12H). $^{13}$C NMR (75 MHz, CDCl$_3$/TMS): (ppm): 178.08, 60.33, 53.32, 42.27, 40.69, 38.28, 26.14, 25.67, 25.28, 24.71, 14.41. HRMS (LSIMS, nba): Calcd. for C$_{24}$H$_{45}$S$_2$O$_4$ (MH$^+$): 461.2759. found 461.2774.

6-[2-(5-Carboxy-5-methyl-hexyl)-[1,3]dithian-2-yl]-2,2-dimethyl-hexanoic acid. A solution of 6-[2-(5-ethoxycarbonyl-5-methyl-hexyl)-[1,3]dithian-2-yl]-2,2-dimethyl-hexanoic acid ethyl ester (870 mg, 1.89 mmol) and potassium hydroxide (85%, 750 mg, 11.33 mmol) in ethanol (16 mL)

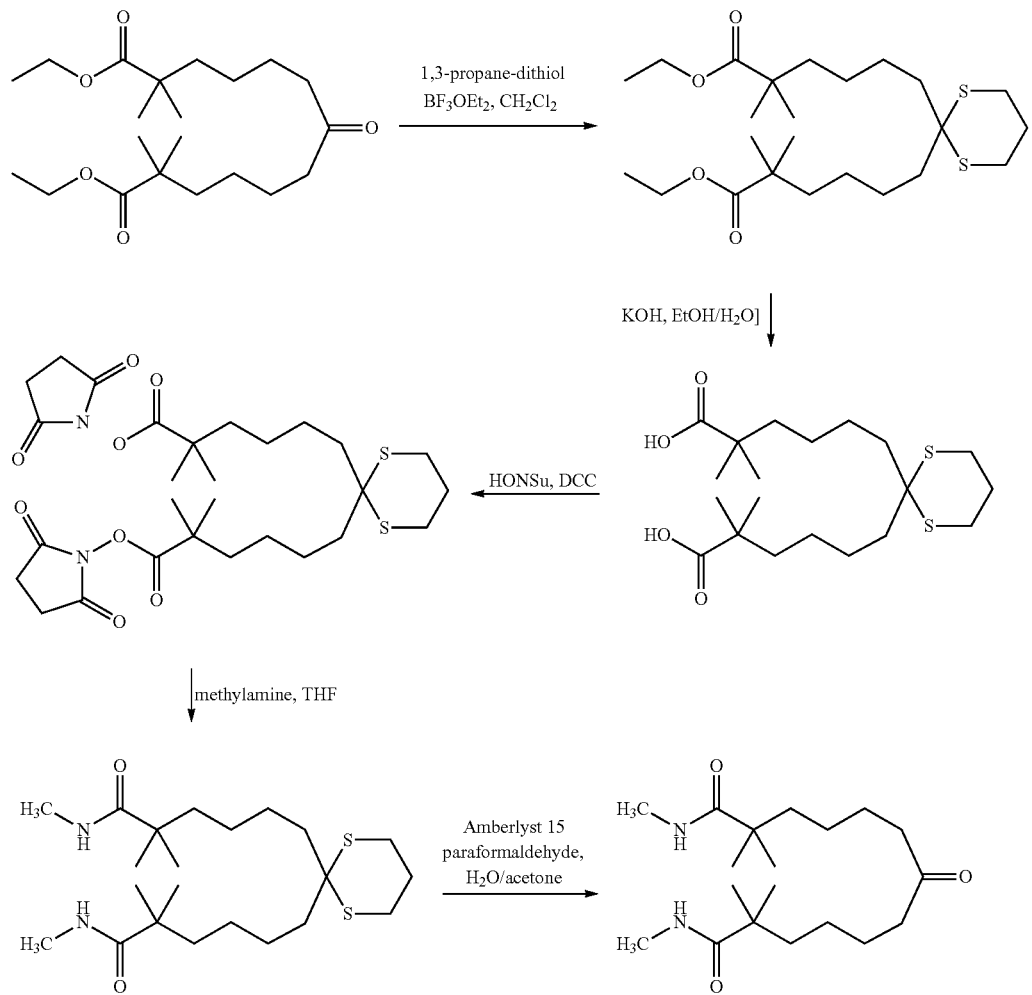

and water (4 mL) was heated under reflux for 3 h. The reaction mixture was diluted with water (100 mL) and acidified to pH 4 with 1 N HCl (8 mL). The emulsion was extracted with dichloromethane (3 75 mL). The combined organic phases were washed with water (50 mL), dried over MgSO$_4$, concentrated in vacuo, and dried in high vacuo to furnish 6-[2-(5-carboxy-5-methyl-hexyl)-[1,3]dithian-2-yl]-2,2-dimethyl-hexanoic acid (730 mg, 95%) as a viscous, yellowish oil. $^1$H NMR (300 MHz, CDCl$_3$/TMS): (ppm): 2.80 (m, 4H), 1.94 (m, 2H), 1.85 (m, 4H), 1.56 (m, 4H), 1.41 (m, 4H), 1.30 (m, 4H), 1.19 (s, 12H). $^{13}$C NMR (75 MHz, CDCl$_3$/TMS): (ppm): 185.08, 53.36, 42.28, 40.52, 38.27, 26.18, 25.69, 25.23, 25.11, 24.73. HRMS (LSIMS, nba): Calcd. for C$_{20}$H$_{37}$O$_4$S$_2$ (MH$^+$): 405.2133. found: 405.2115.

2,2-Dimethyl-6-[2-(5-methyl-5-methylcarbamoyl-hexyl)-[1,3]dithian-2-yl]-hexanoic acid methylamide. Under N$_2$ atmosphere, to a solution of 6-[2-(5-carboxy-5-methyl-hexyl)-[1,3]dithian-2-yl]-2,2-dimethyl-hexanoic acid (280 mg, 0.67 mmol) and N-hydroxysuccinimide (170 mg, 1.47 mmol) in dichloromethane (5 mL; dried with Aluminum oxide, neutral, Brockmann I) was added dicyclohexyl carbodiimide (305 mg, 1.47 mmol). The reaction mixture was stirred and rt for 2 h, the urea was removed by filtration and washed with dichloromethane (2 mL). The filtrate was concentrated in vacuo and dried in high vacuo to give crude 6-{2-[5-(2,5-dioxo-pyrrolidin-1-yloxycarbonyl)-5-methyl-hexyl]-[1,3]dithian-2-yl}-2,2-dimethyl-hexanoic acid 2,5-dioxo-pyrrolidin-1-yl ester (500 mg, 125%) as a foamy, yellow oil. Under N$_2$ atmosphere, to a solution of this crude intermediate (370 mg, 0.62 mmol) in anhydrous THF (10 mL) was added a solution of methylamine in anhydrous THF (5 mL, 10 mmol, 2.0 M in THF), resulting in the immediate formation of a white precipitate. The reaction mixture was stirred at rt for 1.5 h, then diluted with dichloromethane (100 mL), and extracted with saturated NaHCO$_3$ solution (2 50 mL), water (50 mL), 1 N HCl (50 mL), and saturated NaCl solution. The organic phase was concentrated in vacuo and the residue purified by flash chromatography (silica, hexanes/ethyl acetate=50/50, then 25/75, then 0/100) to furnish 2,2-dimethyl-6-[2-(5-methyl-5-methylcarbamoyl-hexyl)-[1,3]dithian-2-yl]-hexanoic acid methylamide (100 mg, 37%) as a colorless oil. Mp.: 104-106 C. $^1$H NMR (300 MHz, CDCl$_3$/TMS): (ppm): 5.92 (m br, 2H), 2.81 (d, 6H, J=4.6), 2.78 (m, 4H), 1.94 (m, 2H), 1.82 (m, 4H), 1.52 (m, 4H), 1.37 (m, 4H), 1.30-1.14 (m, 4H), 1.17 (s, 12H). $^{13}$C NMR (75 MHz, CDCl$_3$/TMS): (ppm): 178.46, 53.23, 42.10, 41.32, 38.18, 26.56, 26.08, 25.62, 25.56, 25.16, 24.64. HRMS (LSIMS, nba): Calcd. for C$_{22}$H$_{43}$N$_2$S$_2$O$_2$ (M$^+$): 431.2766. found: 431.2762.

2,2,12,12-Tetramethyl-7-oxo-tridecanedioic acid bis-methylamide. A suspension of 2,2-dimethyl-6-[2-(5-methyl-5-methylcarbamoyl-hexyl)-[1,3]dithian-2-yl]-hexanoic acid methylamide (3.30 g, 7.66 mmol), paraformaldehyde (6.9 g), and Amberlyst 15 (3.85 g) in acetone (100 mL) and water (10 mL) was heated to reflux for 16 h. The acetone was removed under reduced pressure, the reaction mixture was filtered, and the resin was washed with ethyl acetate (3 75 mL). The combined layers were extracted with saturated NaHCO$_3$ solution (30 mL) and saturated NaCl solution (30 mL), dried over MgSO$_4$, and concentrated in vacuo. The residue was purified by flash chromatography (silica; ethyl acetate, then ethyl acetate/ethanol=50/50) to furnish 2,2,12,12-tetramethyl-7-oxo-tridecanedioic acid bis-methylamide (2.45 g, 94%) as a colorless, viscous oil that solidified on standing. Mp.: 91.5-93.5 C. $^1$H NMR (300 MHz, CDCl$_3$/TMS): (ppm): 6.05 (d br., 2H, J=4.6), 2.78 (d, 6H, J=4.6), 2.36 (t, 4H, J=7.3), 1.58-1.45 (m, 8H), 1.27-1.12 (m, 4H), 1.15 (s, 12H). $^{13}$C NMR (75 MHz, CDCl$_3$/TMS): (ppm): 211.50, 178.43, 42.56, 41.99, 41.03, 26.52, 25.48, 24.48, 24.20. HRMS (LSIMS, nba): Calcd. for C$_{19}$H$_{37}$N$_2$O$_3$ (MH$^+$): 341.2804. found: 341.2804.

5.4. Synthesis of 2,2,12,12-tetramethyl-7-oxo-tridecanedioic acid bis-phenylamide

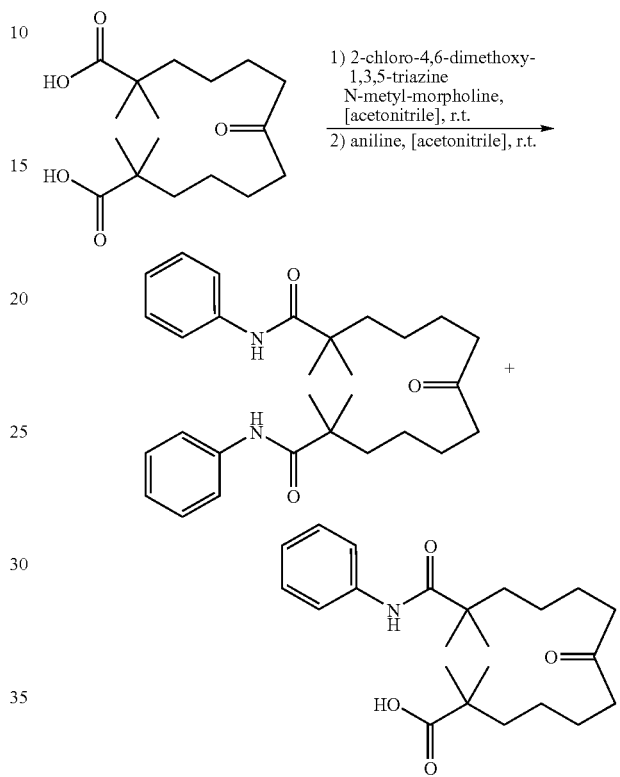

2,2,12,12-Tetramethyl-7-oxo-tridecanedioic acid bis-phenylamide. Under N$_2$ atmosphere, to a stirred solution of 22,12,12-tetramethyl-7-oxo-tridecanedioic acid (3.40 g, 10.9 mmol) in acetonitrile (50 ml) was added N-methyl-morpholine (2.42 g, 2.63 ml, 23.9 mmol) and 2-chloro-4,6-dimethoxy-1,3,5-triazine (4.20 g, 23.9 mmol) at rt. After h, aniline (5.08 g, 5.0 ml, 54.5 mmol) was added and the reaction mixture was stirred for 26 h. The reaction mixture was diluted with ethyl acetate (100 mL) and extracted with ice-cold 1 N HCl (2 100 mL), saturated NaCl solution (100 mL), saturated NaHCO$_3$ solution (2 100 mL), and saturated NaCl solution (100 mL). The organic layer was dried over MgSO$_4$, concentrated in vacuo, and dried in high vacuo to give a viscous, crude oil (4.50 g). 2,2,12,12-Tetramethyl-7-oxo-tridecanedioic acid bis-phenylamide and 2,2,12-trimethyl-7-oxo-12-phenylcarbamoyl-tridecanoic acid were isolated from this crude product mixture by flash chromatography (silica; chloroform, then chloroform/acetone=98/2, then chloroform/acetone=95/5). Additional purification of 2,2,12,12-tetramethyl-7-oxo-tridecanedioic acid bis-phenylamide by crystallization (1.0 g oil in ca. 7.5 ml hexanes/chloroform/ethanol=10/4/1) was necessary to give the clean bis-amide (290 mg, 6%) as a white solid. Mp.: 113-114 C. $^1$H NMR (300 MHz, CDCl$_3$): (ppm): 7.52 (d, 2H, J=7.5), 7.50 (s, 2H), 7.27 (t, 4H, J=7.5), 7.07 (t, 2H, J=7.5), 2.34 (t, 4H, J=7.3), 1.64-1.44 (m, 8H), 1.34-1.14 (m, 4H), 1.24 (s, 12H). $^{13}$C NMR (75 MHz, CDCl$_3$): (ppm): 211.31, 176.08, 138.09, 128.93, 124.28, 120.36, 42.96, 42.84, 41.13, 25.58, 24.53, 24.20. HRMS (LSIMS, nba): Calcd. for C$_{29}$H$_{40}$N$_2$O$_3$ (MH$^+$): 465.3118. found: 465.3129.

2,2,12-Trimethyl-7-oxo-12-phenylcarbamoyl-tridecanoic acid. Viscous oil (1.15 g, 25%). $^1$H NMR (300 MHz, CDCl$_3$): (ppm): 8.90 (m br., 1H), 7.57 (s br, 1H), 7.51 (d, 2H, J=7.9), 7.28 (m, 2H), 7.08 (t, 1H, J=7.3), 2.38 (t, 2H, J=7.2), 2.36 (t, 2H, J=7.2H), 1.53 (m, 8H), 1.34-1.20 (m, 4H), 1.26 (s, 6H), 1.16 (s, 6H). $^{13}$C NMR (75 MHz, CDCl$_3$): (ppm): 211.54, 183.74, 176.28, 138.02, 128.92, 124.35, 120.46, 42.97, 42.55, 42.53, 42.06, 41.12, 40.21, 25.56, 25.05, 24.55, 24.52, 24.21, 24.17. HRMS (LSIMS, nba): Calcd. for C$_{23}$H$_{36}$NO$_4$ (M$^+$): 390.2644. found: 390.2650.

5.5. Synthesis of 2,2,12,12-tetramethyl-7-oxo-tridecanedoic acid bis-3-carboxyphenylamide

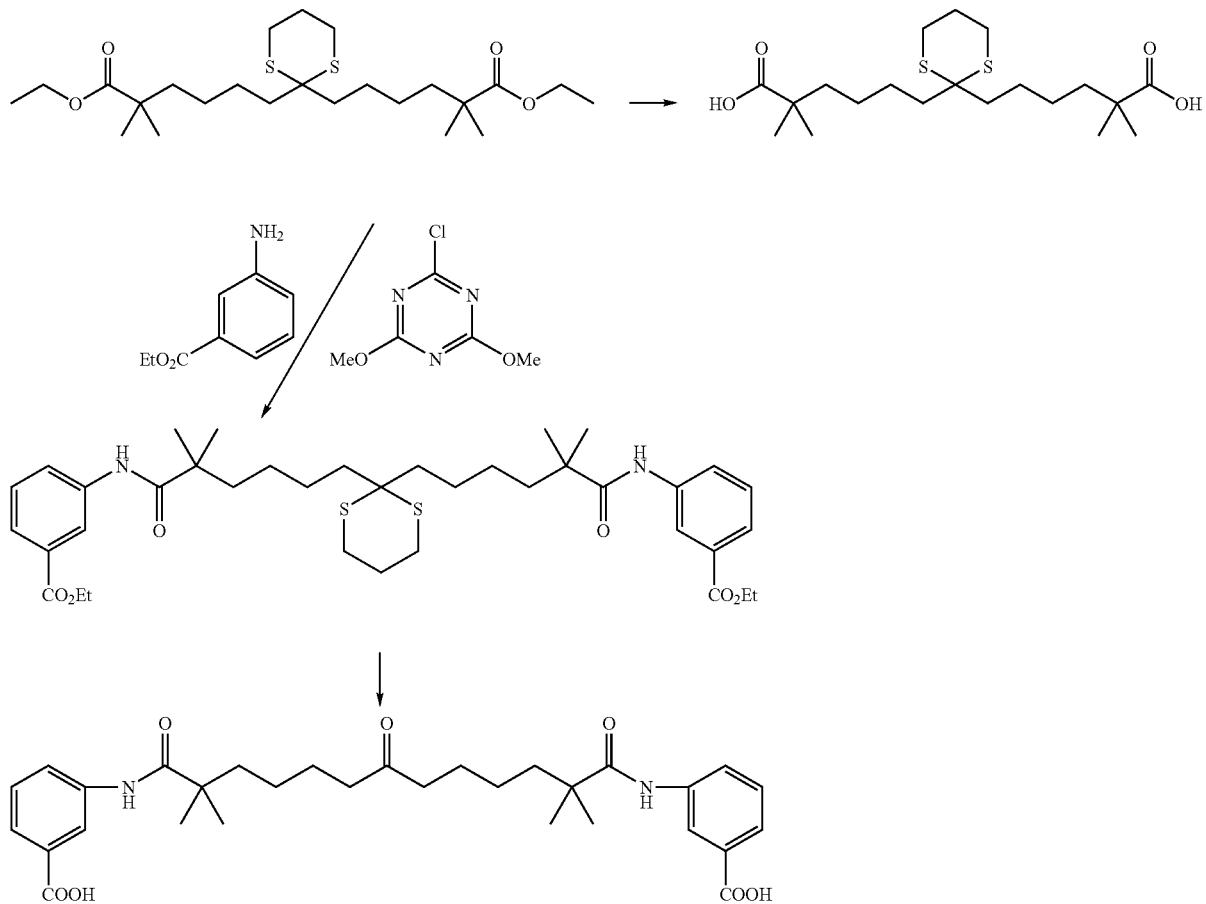

6-[2-(5-Carboxy-5-methyl-hexyl)-[1,3]dithian-2-yl]-2,2-dimethyl-hexanoic acid. A solution of the ester (AL056-97, 870 mg, 1.89 mmol) and potassium hydroxide (85%, 750 mg, 11.33 mmol) in ethanol (16 mL) and water (4 mL) was heated under reflux for 3 h. The reaction mixture was diluted with water (100 mL) and acidified to pH 4 with 1 N HCl (8 mL). The emulsion was extracted with dichloromethane (3' 75 mL). The combined organic phases were washed with water (50 mL), dried over MgSO4, concentrated in vacuo, and dried in high vacuo to furnish ET06802 (730 mg, 95%) as a viscous, yellowish oil. 2.80 (m, 4H), 1.94 (m, 2H), 1.85 (m, 4H), 1.56 (m, 4H), 1.41 (m, 4H), 1.30 (m, 4H), 1.19 (s, 12H). Carboxyl proton resonances were not visible. Estimated purity by $^1$H NMR: ca. 85%, contains ca. 10% starting material. 185.08, 42, 28, 40.52, 38.27, 26.18, 25.69, 25.31, 25.23, 25.11, 24.73. Calcd. for C20H37O4S2 (MH+): 405.2133. found: 405.2115.

3-(6-2-5-(3-Ethoxycarbonyl-phenylcarbamoyl)-5-methyl-hexyl-1,3 dithian-2-yl-2,2-dimethyl-hexanoylamino)-benzoic acid ethyl ester. To a solution of 2-chloro-4,6-dimethoxy-1,3,5-triazine (CDMT, 12.1 g, 68.6 mmol) and ET06802 (12.1 g, 29.7 mmol) in THF (50 mL), N-methylmorpholine (NMM, 6.72 g, 66.5 mmol) was added dropwise at −5° C. The reaction mixture was stirred for 4 h at this temperature. Ethyl-3-aminobenzoate (39.2 g, 237.8 mmol) was added at once and the mixture was stirred at rt for 7 days. The reaction mixture was filtered to remove the solids. The filtrate was diluted with ethyl acetate (250 mL) and washed with ice-cold 1N HCl (3 180 mL), brine (150 mL), saturated NaHCO3 solution (2 300 mL), and brine (200 mL). The organic phase was dried over anhydrous Na2SO4, and concentrated in vacuo to yield a crude solid that was washed with a solvent mixture of ethyl acetate/hexanes=1/20 (500 mL) to furnish the product (12.8 g, 61.8%) as a white solid, M.p. 60-70° C. 60-70° C. 8.02 (s, 2H), 7.96 (d, J=7.8 Hz, 2H), 7.78 (d, J=7.8 Hz, 2H), 7.59 (s, 2H), 7.41 (t, J=6.0 Hz, 2H), 4.38 (q, J=7.2 Hz, 4H), 2.76 (t, J=7.2 Hz, 4H), 1.95-1.51 (m, 10H), 1.38 (t, J=7.2 Hz, 6H), 1.40-1.21 (m, 8H), 1.29 (s, 12H). 176.35, 166.41, 138.31, 131.21, 129.18, 125.37, 124.84, 121.03, 61.31, 53.17, 43.17, 41.44, 38.20, 26.10, 25.64, 25.24, 24.74, 14.48. Calcd. for C$_{38}$H$_{55}$N$_2$O$_6$S$_2$ (MH$^+$): 699.3496. found: 699.3508.

2,2,12,12-Tetramethyl-7-oxo-tridecanedioic acid bis-3-carboethoxy-phenylamide. To a solution of 3-(6-2-5-(3-ethoxycarbonyl-phenylcarbamoyl)-5-methyl-hexyl-1,3 dithian-2-yl-2,2-dimethyl-hexanoylamino)-benzoic acid ethyl ester (430 mg, 0.62 mmol) in dimethoxy ethane (DME, 5 mL) and concentrated hydrochloric acid (0.74 mL), methyl sulfoxide (DMSO, 0.35 mL) was added dropwise over 5 minutes. The reaction mixture was stirred for 30 minutes at rt. The resulting mixture was slowly poured into saturated sodium bicarbonate solution (60 mL) and extracted with diethyl ether (2 80 mL). The combined organic layers were washed with water (3 50 mL), dried over sodium sulfate and concentrated in vacuo. The crude product was washed with hexanes (60 mL) to yield ET07002 (300 mg, 79.0%) as a colorless oil. 8.05 (s, 2H), 7.91 (d, J=7.8 Hz, 2H), 7.77 (m, 4H), 7.35 (t, J=7.8 Hz, 2H), 4.36 (t, J=6.9 Hz, 4H), 2.37 (t, J=7.2 Hz, 4H), 1.62-1.39 (m, 10H), 1.46 (t, J=6.9 Hz, 6H), 1.37-1.17 (m, 2H), 1.26 (s, 12H). 211.29, 176.33, 166.36, 138.36, 131.07, 129.01, 125.24, 124.86, 121.13, 61.22, 43.06, 42.53, 41.05, 25.55, 25.17, 24.53, 24.16, 14.43. Calcd. for $C_{35}H_{49}N_2O_7$ ($MH^+$): 609.3534. found: 609.3569.

2,2,12,12-Tetramethyl-7-oxo-tridecanedoic acid bis-3-carboxyphenylamide. To a homogenous solution of KOH (85%, 1.24 g, 18.66 mmol) and 2,2,12,12-tetramethyl-7-oxo-tridecanedioic acid bis-carboethoxy-phenylamide (1.9 g, 3.13 mmol) in water (7 ml) and ethanol (33 ml) was heated to reflux for 5 h. the ethanol was removed under reduced pressure. the residue was diluted with water (55 ml). the solution was acidified with concd. hcl (4 ml) to ph 1 and extracted with diethyl ether (2 80 ml). the combined organic layers were washed with brine (50 ml), dried over anhydrous na2so4 and concentrated in vacuo to yield a crude solid that was washed with hexanes (200 ml) and a solvent mixture of ethyl acetate/hexanes=1/40 (200 ml) to furnish a white solid (1.4 g, 81.4% yield, 94.9% pure by hplc), m.p 78-80° C. mp 78-80° C. 12.87 (br, 2h), 9.35 (s, 2h), 8.24 (s, 2h), 7.91 (d, j=8.1 hz, 2h), 7.62 (d, j=7.8 hz, 2h), 7.42 (t, j=7.8 hz, 2h), 2.35 (t, j=4.5 hz, 4h), 1.62-1.50 (m, 4 h), 1.45-1.30 (m, 4h), 1.30-1.11 (m, 4 h), 1.15 (s, 12 h). 210.33, 176.05, 167.29, 139.58, 131.02, 128.63, 124.38, 124.00, 121.14, 42.55, 40.36, 38.89, 25.11, 23.99, 23.71. calcd. for c31h41n2o7 (mh): 553.2914. found: 553.2911.

5.6. α,α-Dialkyl or -Arylalkyl-Substituted Keto-dialkyldicarboxylic Acids

Long hydrocarbon chain keto-diols and -acids was synthesized as described in Schemes 18 and 19, and Table 4 (Dasseux, J.-L. H. et al. Ketone compounds and compositions for cholesterol management and related uses. U.S. patent application 20030078239, Oct. 11, 2001). The side chains connected to the central ketone functionality varied both in length (m, m=3-7) and in the attached geminal modifying groups ($R^1$, $R^2$=Me, Ph, 4-Me-$C_6H_4$, 4-iBu-$C_6H_4$). The majority of target compounds fell in the category of either symmetrical ketodiacids (210b-210g, 210i, 210j, Scheme 18) or symmetrical ketodiols (214a-214i, Scheme 19).

Scheme 18.
Synthesis of Ethyl ω-Bromoalkanoates and
ω-Bromoalkyloxy THP-ethers[a]

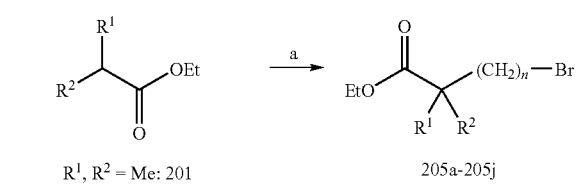

$R^1$, $R^2$ = Me: 201
$R^1$ = Me, $R^2$ = Ph: 202
$R^1$ = Me, $R^2$ = 4-Me$C_6H_4$: 203
$R^1$ = Me, $R^2$ = 4-iBu$C_6H_4$: 204

205a-205j

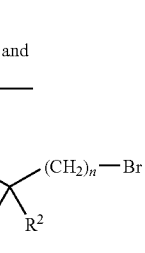

-continued

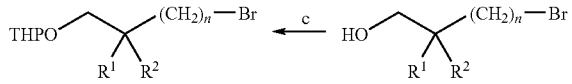

207a-e, 207g, 207h      206a-206e, 206g, 206h

[a]Reagents: (a) lithium diisopropylamide, Br—$(CH_2)_n$—Br, [THF/DMPU]; (b) lithium borohydride, MeOH, [$CH_2Cl_2$]; (c) 3,4-dihydro-2H-pyran, pTosOH, [$CH_2Cl_2$].

Scheme 19. Synthesis of Symmetrical Ketodiacids[a]

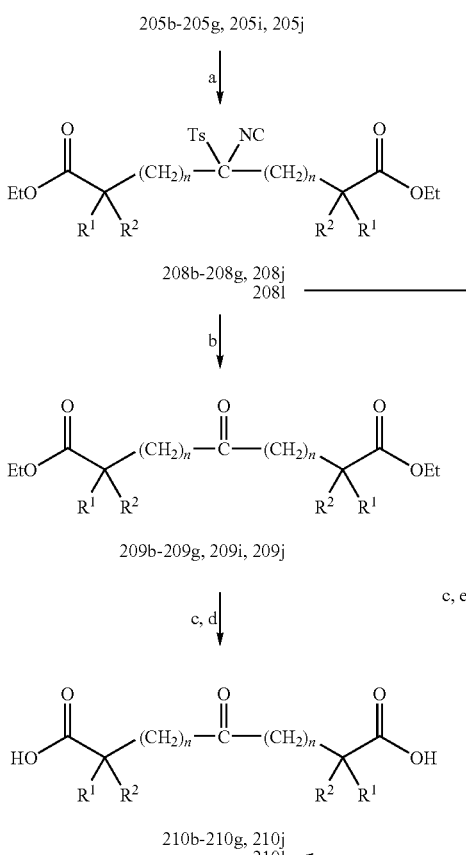

[a]Reagents: (a) TosMIC, NaH, NBu4I, [DMSO]; (b) aq. HCl, [$CH_2Cl_2$]; (c) KOH, [EtOH/$H_2O$]; (d) aq. HCl; (e) aq. $H_2SO_4$.

TABLE 4

Synthesis of Symmetrical Ketodiacids

| No. | n | $R^1$ | $R^2$ | Yield (%) |
|---|---|---|---|---|
| 209b | 3 | Me | Ph | 61 |
| 209c | 4 | Me | Me | 67 |
| 209d | 4 | Me | Ph | 66 |
| 209e | 4 | Me | 4-Me-$C_6H_4$ | 54 |
| 209f | 4 | Me | 4-iBu-$C_6H_4$ | 82 |
| 209g | 5 | Me | Me | 61 |
| 209i | 6 | Me | Me | 40 |
| 209j | 7 | Me | Me | 61[a] |
| 210b | 3 | Me | Ph | 31 |
| 210c | 4 | Me | Me | 86 |
| 210d | 4 | Me | Ph | 87 |
| 210e | 4 | Me | 4-Me-$C_6H_4$ | 39 |

TABLE 4-continued

Synthesis of Symmetrical Ketodiacids

| No. | n | $R^1$ | $R^2$ | Yield (%) |
|---|---|---|---|---|
| 210f | 4 | Me | 4-iBu-$C_6H_4$ | 86 |
| 210g | 5 | Me | Me | 57 |
| 210i | 6 | Me | Me | 57[b] |
| 210j | 7 | Me | Me | 74 |

[a]Intermediate 208j was purified by column chromatography;
[b]prepared by direct base hydrolysis of 208i.

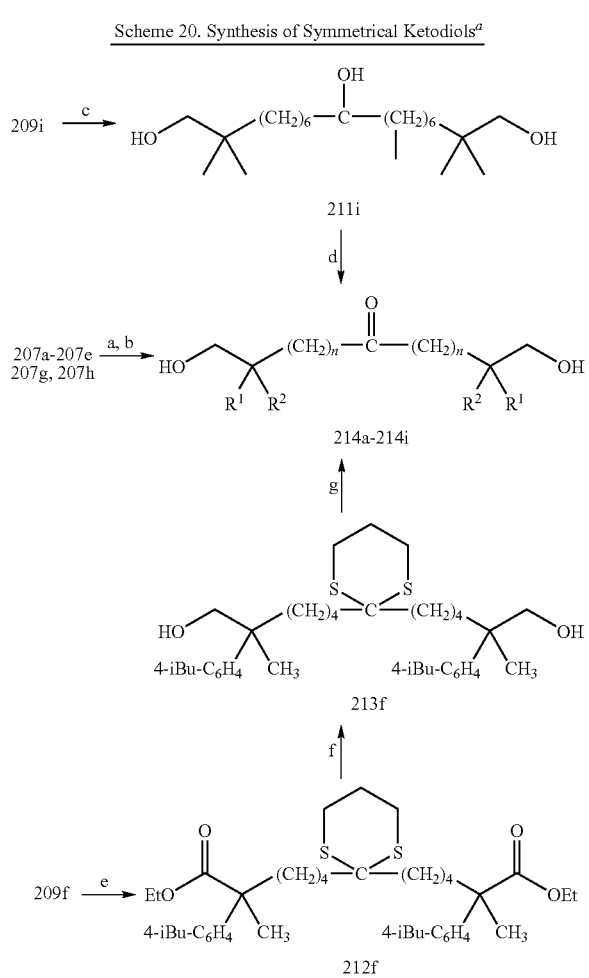

Scheme 20. Synthesis of Symmetrical Ketodiols[a]

[a]Reagents: (a) TosMIC, NaH, NBu$_4$I, [DMSO]; (b) aq. HCl, [MeOH/H$_2$O]; (c) LiAlH$_4$, [MTBE]; (d) aq. NaOCl, [HOAc]; (e) 1,3-propanedithiol, BF$_3$—Et$_2$O, [CH$_2$Cl$_2$]; (f) LiAlH$_4$, [THF]; (g) concd HCl, DMSO, dimethoxyethane.

TABLE 5

Synthesis of Symmetrical Ketodiols.

| No. | n | $R^1$ | $R^2$ | Yield (%) |
|---|---|---|---|---|
| 211i | 5 | Me | Me | 66 |
| 212f | 4 | Me | 4-iBu-$C_6H_4$ | 98 |
| 213f | 4 | Me | 4-iBU-$C_6H_4$ | 94 |
| 214a | 3 | Me | Me | 30 |
| 214b | 3 | Me | Ph | 38 |
| 214c | 4 | Me | Me | 68 |

TABLE 5-continued

Synthesis of Symmetrical Ketodiols.

| No. | n | $R^1$ | $R^2$ | Yield (%) |
|---|---|---|---|---|
| 214d | 4 | Me | Ph | 61 |
| 214e | 4 | Me | 4-Me-$C_6H_4$ | 21 |
| 214f | 4 | Me | 4-iBu-$C_6H_4$ | 83 |
| 214g | 5 | Me | Me | 79 |
| 214h | 5 | Me | Ph | 56 |
| 214i | 6 | Me | Me | 35 |

A series of unsymmetrical keto-diols and -acids with chains of different lengths or with a different substitution pattern (217-219, Scheme 20 and 225, 226, Scheme 21) was included in this study as well. In addition, the aryl-bridged compounds 231 and 232 with a benzophenone backbone (Scheme 22) were prepared and examined for comparison.

Scheme 21: Synthesis of Unsymmetrical Ketodiols[a]

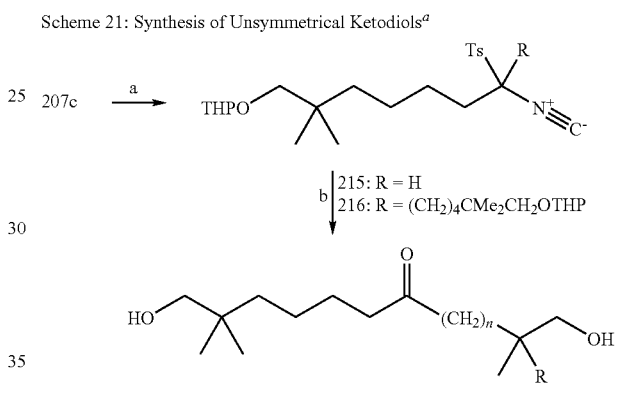

[a]Reagents: (a) TosMIC, NaH, NBu$_4$I, [DMSO], 27%, or K$_2$CO$_3$, NBu$_4$I, [DMF], 69%; (b) for 217: 207a, NaH, NBu$_4$I, [DMSO], then concd HCl, [MeOH], 58%; for 218: 207d, NaH, NBu$_4$I, [DMSO], then concd HCl, [MeOH], 71%; for 219: 207g, NaH, NBu$_4$I, [DMSO], then concd HCl, [MeOH], 48%.

Scheme 22: Synthesis of Usymmetrical Ketodiacids[a]

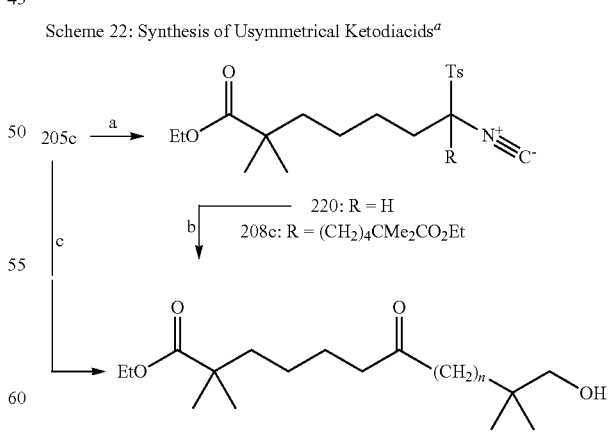

-continued

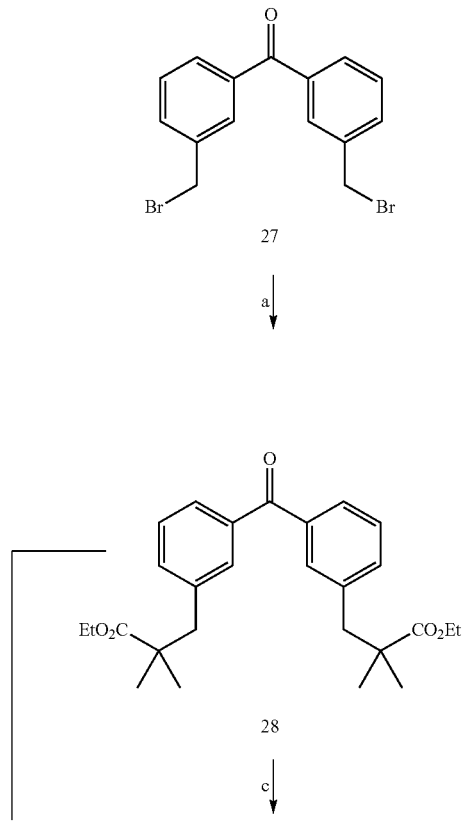

223: n = 3
224: n = 5 e ↓

225: n = 3; 226: n = 5

[a]Reagents: (a) TosMIC, NaH, NBu₄I, [DMSO], 12%; (b) for n = 3: 207a, NaH, NBu₄I, [DMSO], then aq. H₂SO₄, [MeOH], 60%; (c) for n = 5:1. TosMIC, NaH, NBu₄I, [DMSO]; 2. 207g, NaH; 3. aq. H₂SO₄, [MeOH], 36%; (d) PDC, [DMF]; n = 3, 79%; n = 5, 68%; (e) KOH, [EtOH/H₂O]; n = 3, 60%; n = 5, 43%.

Scheme 23: Synthesis of Aryl-Bridged Compounds[a]

-continued

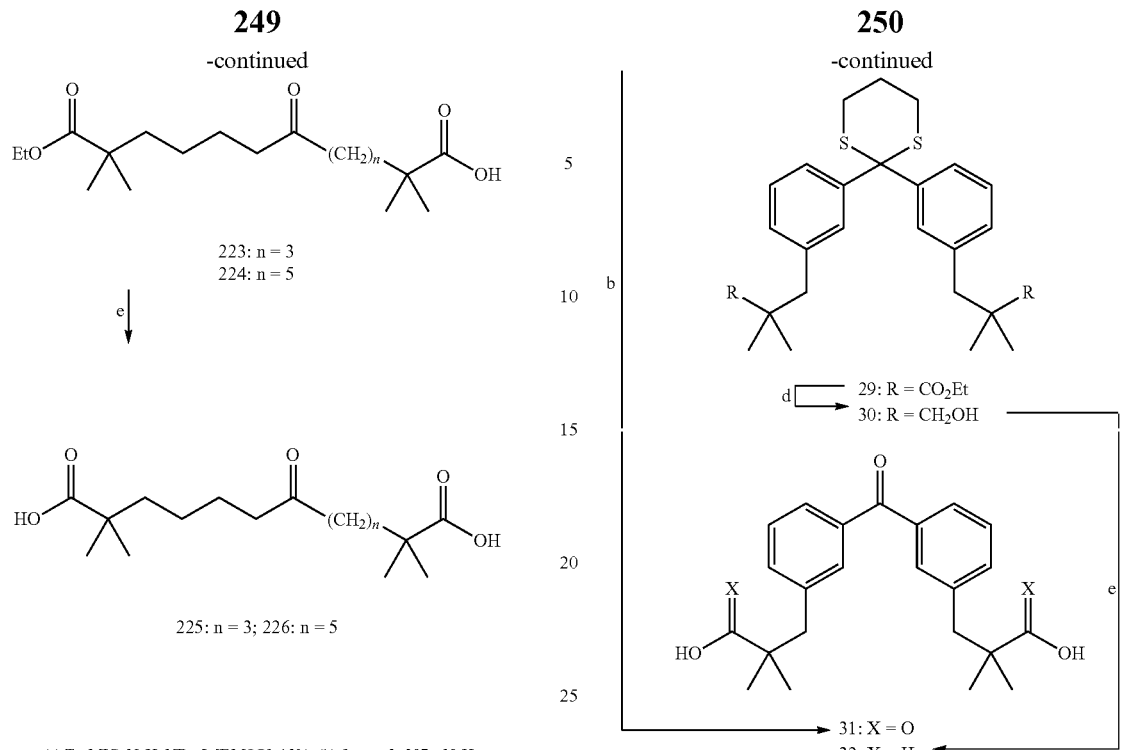

29: R = CO₂Et
30: R = CH₂OH

31: X = O
32: X = H₂

[a]Reagents: (a) Ethyl isobutyrate, LDA, [THF/DMPU], 89%; (b) KOH, [EtOH/H₂O], quantitative; (c) 1,3-propanedithiol, BF₃—Et₂O, [CH₂Cl₂], 87%; (d) LiBH₄, MeOH, [CH₂Cl₂], 85%; (e) CuO, CuCl₂, [acetone/DMF], 71%.

The key step in the syntheses of all ketones with aliphatic chains was the alkylation of tosylmethyl isocyanide (TosMIC) (Possel, O. et al. Tosylmethyl Isocyanide Employed in a Novel Synthesis of Ketones. A New Masked Formaldehyde Reagent. *Tetrahedron Lett.* 1977, 17, 4229-4232; Kurosawa, K. et al. Facile Synthesis of [3″]Cyclophanes, in which Aromatic Rings are Connected with —CH₂—CO—CH₂— Bridges. *Tetrahedron Lett.* 1982, 23, 5335-5338; Yadav, J. S. et al. TosMIC in the Preparation of Spiroacetals: Synthesis of Pheromone Components of Olive Fruit Fly. *Tetrahedron Lett.* 1990, 31, 6217-6218; van Leusen, D. et al. Synthetic Uses of Tosylmethyl Isocyanide (TosMIC). In *Organic Reactions*, Vol. 57; Overman, L. E., Editor-in-Chief; John Wiley and Sons, Inc.: New York, 2001; pp 417-666) with appropriately substituted alkyl bromides (Schemes 18-22). These alkyl bromide building blocks were generally synthesized via lithiation of commercially available or readily accessible ethyl esters 201, 202 (Shiner, V. J., Jr. et al. The Arrhenius Parameters of the Deuterium Isotope Rate Effect in a Base-promoted Elimination Reaction: Evidence for Proton Tunneling. *J. Am. Chem. Soc.* 1961, 83, 593-598), 203 (Ghosh, S. et al. Ester Enolates from α-Acetoxy Esters. Synthesis of Aryl Malonic and α-Aryl Alkanoic Esters from Aryl Nucleophiles and α-Keto Esters. *J. Org. Chem.* 1982, 47, 4692-4702; Chounan, Y. et al. 1,2-Asymmetric Induction in the Conjugate Addition of Organocopper Reagents to γ-Aryl α,β-Unsaturated Carbonyl Derivatives. *Tetrahedron* 2000, 56, 2821-2831), and 204 with lithium diisopropylamide in anhydrous THF in the presence of N,N'-dimethylpropyleneurea (DMPU) at −78° C. followed by subsequent reaction with an α,ω-dibromoalkane (a) Ackerley, N. et al. A Novel Approach to Dual-Acting Thromboxane Receptor Antagonist/Synthase Inhibitors Based on the Link of 1,3-

Dioxane-Thromboxane Receptor Antagonists and -Thromboxane Synthase Inhibitors. *J. Med. Chem.* 1995, 38, 1608-1628; Manley, P. W. et al. Thromboxane Synthase Inhibitors. Synthesis and Pharmocological Activity of (R)-, (S)-, and (±)-2,2-Dimethyl-6-[2-(1H-imidazol-1-yl)-1-[[(4-methoxyphenyl)-methoxy]ethoxy]hexanoic Acids. *J. Med. Chem.* 1987, 30, 1812-1818) of the required chain length (Scheme 18). Thus, bromo esters 205a-205j were obtained in moderate to good yields (Table 4). Reduction of bromo esters with lithium borohydride and methanol (Brown, H. C. et al. 30. Effect of Cation and Solvent on the Reactivity of Saline Borohydrides for Reduction of Carboxylic Esters. Improved Procedures for the Conversion of Esters to Alcohols by Metal Borohydrides. *J. Org. Chem.* 1982, 47, 4702-4708; Soai, K. et al. Mixed Solvents Containing Methanol as Useful Reaction Media for Unique Chemoselective Reductions with Lithium Borohydride. *J. Org. Chem.* 1986, 51, 4000-4005) in refluxing dichloromethane afforded the bromo alcohols 206a-206e, 206g, and 206h in excellent yields and purities without effecting the bromide moiety. The chemoselectivity of reduction of similar bromo esters with $LiAlH_4$ depended on the conditions. In ether at room temperature the bromo alcohol was the single product whereas in THF at reflux the reaction gave the alcohols exclusively. See: Beckwith, A. L. J. et al. Stereochemistry of the Reversible Cyclization of ω-Formyl Radicals. *J. Org. Chem.* 1992, 57, 4954-4962. Reduction with lithium aluminum hydride or sodium borohydride on the other hand was not chemoselective and the reactions were not reproducible. Another chemoselective reducing agent was diisobutylaluminum hydride (Brown, H. C. et al. Selective Reductions. 30. Effect of Cation and Solvent on the Reactivity of Saline Borohydrides for Reduction of Carboxylic Esters. Improved Procedures for the Conversion of Esters to Alcohols by Metal Borohydrides. *J. Org. Chem.* 1982, 47, 4702-4708). Bromo alcohols were treated with 3,4-dihydro-2H-pyran and catalytic amounts of p-toluenesulfonic acid (Brown, H. C. et al. Selective Reductions. 30. Effect of Cation and Solvent on the Reactivity of Saline Borohydrides for Reduction of Carboxylic Esters. Improved Procedures for the Conversion of Esters to Alcohols by Metal Borohydrides. *J. Org. Chem.* 1982, 47, 4702-4708) to give the THP ethers 207a-207e, 207g, and 207h (Scheme 18, Table 4) in moderate to good yields.

The synthesis of symmetrical ketodiacids 210b-210g, 210i, and 210j from bromo esters 205b-205g, 205i, and 205j was accomplished employing TosMIC methodology as described above (Scheme 2). Accordingly, TosMIC was deprotonated with sodium hydride in either DMSO or in a DMSO/diethyl ether mixture (Possel, O. et al. Tosylmethyl Isocyanide Employed in a Novel Synthesis of Ketones. A New Masked Formaldehyde Reagent. *Tetrahedron Lett.* 1977, 17, 4229-4232) at room temperature and then reacted with suitable bromo esters 205b-205g, 205i, and 205j in the presence of catalytic amounts of tetrabutylammonium iodide to give the corresponding dialkylated TosMIC intermediates 208a-208g, 208i, and 208j. These alkylations of TosMIC proceeded also without catalytic amounts of $NBu_4I$, but required a slightly longer reaction time. In most cases, these intermediates were not purified or characterized but directly treated with coned aqueous HCl in dichloromethane (Prato, M. et al. Cleavage of the 1,3-Dithiane Protective Group. *Synthesis* 1982, 679-680) to give ketodiesters 209b-209g, 209i, and 209j in good yields after chromatographic purification (Table 2). Finally, hydrolysis of the ester groups with potassium hydroxide in aqueous ethanol and subsequent acidification with coned HCl (steps c, d) provided the target diacids 210b-210g, and 210j in variable yields ranging from 31 to 87%. According to a different protocol, ketodiacid 210i was prepared by simultaneous hydrolysis of the tosyl isocyanide and the ester groups in 281 with potassium hydroxide in aqueous ethanol followed by acidification with dilute sulfuric acid (steps c, e) in 57% yield.

Scheme 3 illustrates three different strategies that were studied for the synthesis of symmetrical ketodiols. The standard procedure used in most cases employed the dialkylation protocol of TosMIC as described above. Bromo THP ethers 207a-7e, 7g, and 7h were used as electrophiles and the resulting TosMIC intermediates were directly hydrolyzed to give the ketodiols 214a-214e, 214g, and 214h in acceptable yields after purification by column chromatography (Table 3). An alternative pathway was elected for the synthesis of ketodiol 214i. In this case, ketodiester 209i was first reduced to triol 211i by treatment with lithium aluminum hydride (66%). Selective oxidation of the secondary alcohol moiety in 211i with aqueous sodium hypochlorite solution in acetic acid (Stevens, R. V. et al. Further Studies on the Utility of Sodium Hypochlorite in Organic Synthesis. Selective Oxidation of Diols and Direct Conversion of Aldehydes to Esters. *Tetrahedron Lett.* 1982, 23, 4647-4650; Stevens, R. V. et al. Convenient and Inexpensive Procedure for Oxidation of Secondary Alcohols to Ketones. *J. Org. Chem.* 1980, 45, 2030-2032) then produced 214i in low yield (35%). Better results were obtained when the ketone functionality in a ketodiester was protected prior to the reduction of the esters. Thus, protection of 209f with 1,3-propanedithiol and boron trifluoride diethyl etherate (Hatch, R. P. et al. Studies on Total Synthesis of the Olivomycins. *J. Org. Chem.* 1978, 43, 4172-4177) led to formation of 212f, which was subsequently reduced with lithium aluminum hydride to 213f. Removal of the 1,3-dithiane protective group with DMSO in dimethoxyethane and coned HCl (Prato, M. et al. Cleavage of the 1,3-Dithiane Protective Group. *Synthesis* 1982, 679-680) afforded ketodiol 214f (63% from 205f). Despite the superior yields attained, this method was not generally applied for the synthesis of 214a-214i because of the malodorous reagent involved.

The unsymmetrical ketodiols 217-219 were prepared via the mono-alkylated TosMIC derivative 215 as a common intermediate (Scheme 21). However, reaction of TosMIC with one equivalent of 207c under the previously utilized reaction conditions (NaH and $NBu_4I$ in DMSO) gave a mixture of mono- and dialkylated products 215 and 216 (For similar successive alkylations of TosMIC with alkyl halides of different chain lengths, see: Rao, A. V. R. et al. A New Route for the Synthesis of 1,4-Dicarbonyl Compounds: Synthesis of Jasmone, Dihydrojasmone and a Prostaglandin Intermediate. *Synth. Commun.* 1984, 14, 469-475). Contaminant 216 had to be removed by chromatography to prevent formation of mixtures of 217 or 219, respectively, with 214e in the next step, which were practically impossible to separate; the yield of this purification was very low (27%). Modification of the conditions ($K_2CO_3$ in DMF) circumvented this problem as 215 was produced in 69% yield without formation of 216, even when an excess of 7c was used. Further alkylation of 215 with the respective bromo THP-ethers 207a, 207d, and 207g, followed by deprotection with coned HCl in refluxing methanol furnished the unsymmetrical products 217-219 in respectable yields.

Similar problems with an unwanted dialkylated by-product (208c, Scheme 19) were also encountered in the synthetic route to diacids 225 and 226. Alkylation of TosMIC with 205e by treatment with NaH and $NBu_4I$ in DMSO led to a mixture of compounds 220 and 208c that was very difficult to separate by chromatographic means (For similar mono-alkylations of TosMIC with long chain bromo esters, see: Johnson, D. W. A Synthesis of Unsaturated Very Long Chain Fatty Acids. *Chem. Phys. Lipids* 1990, 56, 65-71). As a result, the yield of pure 220 was only 12%. To ensure the complete removal of the symmetrical ketodiester 209e that results from intermediate 208c, compound 220 was reacted with the bromo THP-ether 207a and subsequently hydrolyzed to give hydroxy ester 221. Purification of 221 from traces of 209c was now easily accomplished by chromatography (60% yield). Subsequent oxidation of this alcohol with pyridinium dichromate (PDC) in DMF (Vedejs, E. et al. *J. Am. Chem. Soc.* 1987, 109, 5437-5446) afforded diacid monoester 223 (79%), which was further saponified to provide 225 in 60% yield after crystallization from diethyl ether/hexanes.

The same strategy was applied for the synthesis of the unsymmetrical ketodiacid 226. In this case, intermediate 220 was not isolated, but further alkylated in situ with bromo THP-ether 207g. After deprotecting the ketone group by acid treatment and purification of the crude product by chromatography, hydroxy ester 222 was isolated in 36% yield. In analogy to its shorter chain homologue 221, oxidation of compound 222 with PDC in DMF led to ketodiacid monoester 224 (68%). Subsequent hydrolysis of 224 with potassium hydroxide in aqueous ethanol followed by chromatographic purification and crystallization furnished 226 in 43% yield.

Benzophenone derivative 227, prepared similarly to the method described in Shultz, D. A. et al. The Effect of Phenyl Rin Torsional Rigidity on the Photophysical Behavior of Tetraphenylethylenes. *J. Am. Chem. Soc.* 1989, 111, 6311-6320, was used as starting material for the synthesis of aryl-bridged ketones 231 and 232. Bromide displacement in 227 by reaction with lithio ethyl isobutyrate in THF/DMPU at −78° C. produced the diester 228 in 89% yield. Conversion of 228 to diacid 231 performed by saponification with KOH resulted in practically quantitative yield. For the synthesis of the related diol 232, the ketone moiety in intermediate 228 was first protected as S,S-acetal 229 (87%) as described in Rao, A. V. R. et al. A New Route for the Synthesis of 1,4-Dicarbonyl Compounds: Synthesis of Jasmone, Dihydrojasmone and a Prostaglandin Intermediate. *Synth. Commun.* 1984, 14, 469-475. Reduction with lithium borohydride and methanol gave diol 230 in 85% yield. Finally, deprotection with copper(II) oxide and copper(II) chloride in a refluxing acetone/DMF solvent mixture as described in Stütz, P. et al. 3-Alkylated and 3-Acylated Indoles from a Common Precursor: 3-Benzylindole and 3-Benzoylindole. In *Organic Syntheses Collective Volume VI*; Noland, W. E., Editor-in-Chief; John Wiley and Sons, Inc.: New York, 1988; pp 109-114 afforded ketodiol 232 in 71% yield.

Representative Procedure for the Synthesis of Ketodiesters: 2,2,12,12-Tetramethyl-7-oxotridecanedioic acid diethyl ester (209c). Under $N_2$-atmosphere, to a solution of 205c (22.4 g, 89.2 mmol) in anhydrous DMSO (300 mL) was added TosMIC (8.71 g, 44.6 mmol), NaH (60% w/w in mineral oil, 4.28 g, 107.0 mmol), and tetrabutylammonium iodide (3.30 g, 8.9 mmol) under cooling with an ice-bath. After the addition, the reaction mixture was stirred for 23 h at room temperature, then cooled with an ice-bath, and carefully hydrolyzed with water (300 mL). The solution was extracted with $CH_2Cl_2$ (3×150 mL). The combined organic layers were washed with water (100 mL) and half-saturated aqueous NaCl solution (100 mL), dried over anhydrous $MgSO_4$, concentrated in vacuo, and dried in high vacuo to give the crude intermediate 208c (26.2 g) as an oil [$^1$H NMR ($CDCl_3$): δ 7.85 (d, 2H, J=8.3), 7.42 (d, 2H, J=8.3), 4.12 (q, 4H, J=7.0), 2.49 (s, 3H), 1.94 (m, 4H), 1.60-1.34 (m, 8H), 1.30-1.15 (m, 4H), 1.25 (t, 6H, J=7.0), 1.15 (s, 12H). $^{13}$C NMR ($CDCl_3$): δ 177.77, 164.08, 146.43, 131.20, 130.34, 129.96, 81.78, 60.37, 42.12, 40.27, 33.21, 25.25, 25.19, 24.97, 24.26, 21.86, 14.34]. To a solution of 208c (26.0 g) in $CH_2Cl_2$ (400 mL) was added coned HCl (100 mL) and the reaction mixture was stirred for 45 min at room temperature. The solution was diluted with water (400 mL) and the layers were separated. The aqueous layer was extracted with $CH_2Cl_2$ (300 mL). The combined organic layers were washed with saturated aqueous $NaHCO_3$ solution (100 mL) and saturated aqueous NaCl solution (100 mL). The organic phases were dried over anhydrous $MgSO_4$, concentrated in vacuo, and dried in high vacuo. The residue was purified by flash chromatography (silica gel; hexanes/ethyl acetate=95/5, then 90/10) to give 209c (11.0 g, 67%) as an oil. $^1$H NMR ($CDCl_3$): δ 4.03 (q, 4H, J=7.1), 2.31 (t, 4H, J=7.5), 1.45 (m, 8H), 1.20-1.08 (m, 4H), 1.16 (t, 6H, J=7.1), 1.07 (s, 12H). $^{13}$C NMR ($CDCl_3$): δ 211.14, 178.05, 60.34, 42.69, 42.20, 40.52, 25.24, 24.71, 24.30, 14.35. HRMS (LSIMS, nba): Calcd for $C_{21}H_{39}O_5$ ($MH^+$): 371.2797. found: 371.2763.

2,10-Dimethyl-6-oxo-2,10-diphenylundecanedioic acid diethyl ester (209b). According to the procedure described for the synthesis of 209c, 205b (25.0 g, 76.4 mmol), tetrabutylammonium iodide (2.78 g, 7.5 mmol) and TosMIC (7.34 g, 37.6 mmol) in anhydrous DMSO (400 mL) and diethyl ether (150 mL) was reacted with sodium hydride (60% dispersion in mineral oil, 3.80 g, 95.0 mmol) first under cooling with an ice-bath, then at room temperature for 24 h. Hydrolysis and extraction afforded the intermediate 208b (28.0 g) as a brown oil. A portion of this crude intermediate (25.0 g) was then treated with coned aqueous HCl (140 mL) in $CH_2Cl_2$ (500 mL) for 2 h at room temperature. Aqueous workup, extraction, and purification by flash chromatography (silica gel; ethyl acetate/hexanes=1/20, 1/10) furnished 209b (9.5 g, 61%) as a light yellowish oil. $^1$H NMR ($CDCl_3$): δ 7.40-7.10 (m, 10H), 4.20-4.05 (m, 4H), 2.38 (m, 4H), 2.05-1.80 (m, 4H), 1.60 (s, 6H), 1.50-1.20 (m, 4H), 1.22 (m, 6H). $^{13}$C NMR ($CDCl_3$): δ 210.24, 176.06, 143.71, 128.42, 126.72, 125.97, 60.83, 50.13, 42.97, 38.91, 22.73, 22.47, 19.09, 14.13. HRMS (LSIMS, nba): Calcd for $C_{29}H_{39}O_5$ ($MH^+$): 467.2797. found: 467.2772.

7-Oxo-2,12-dimethyl-2,12-diphenyltridecanedioic acid diethyl ester (209d). In analogy to the procedure described for the synthesis of 209c, 205d (9.59 g, 30.6 mmol) in anhydrous DMSO (50 mL) was reacted with TosMIC (3.02 g, 15.5 mmol), sodium hydride (60% w/w in mineral oil, 1.44 g, 36.0 mmol), and tetrabutyl ammonium iodide (1.10 g, 3.0 mmol), first under cooling with a water-bath, then for 96 h at room temperature. Hydrolysis and extraction afforded the crude intermediate 208d (30.0 g) as an oil. A solution of this oil (30.0 g) in $CH_2Cl_2$ (300 mL) and coned aqueous HCl (40 mL) was stirred for 2 h at room temperature. After extractive workup and flash chromatography (silica gel; hexanes/ethyl acetate=10/1), 209d (5.0 g, 66%) was obtained as a clear oil together with a less pure fraction (1.17 g, 16%). $^1$H NMR ($CDCl_3$): δ 7.40-7.10 (m, 10H), 4.11 (q, 4H, J=7.0), 2.34 (t, 4H, J=7.1), 2.10-1.70 (m, 4H), 1.6-1.4 (m, 4H), 1.52 (s, 6H), 1.30-1.00 (m, 10H). $^{13}$C NMR ($CDCl_3$): δ 210.7, 176.0, 143.8, 128.2, 126.5, 125.8, 60.6, 50.0, 42.4, 38.9, 24.3, 24.1, 22.6, 14.0. HRMS (LSIMS, nba): Calcd for $C_{31}H_{43}O_5$ ($MH^+$): 495.3110. found: 495.3106. HPLC: 94.8% pure.

2,12-Dimethyl-7-oxo-2,12-di-p-tolyltridecanedioic acid diethyl ester (209e). In analogy to the procedure described for the synthesis of 209c, 205e (21.0 g, 64.2 mmol) was reacted with tetrabutylammonium iodide (2.37 g, 6.4 mmol), TosMIC (6.26 g, 32.1 mmol) and NaH (60% dispersion in mineral oil, 3.24 g, 81.0 mmol) in anhydrous DMSO (320 mL) and diethyl ether (110 mL) for 24 h at room temperature. After hydrolysis and extraction, the crude intermediate 208e was stirred in CH$_2$Cl$_2$ (500 mL) and concd HCl (140 mL) for 2 h at room temperature. Extraction and purification by flash chromatography (silica gel; ethyl acetate/hexanes=1/20, 1/9) afforded 209e (9.0 g, 54%) as a light yellowish oil. $^1$H NMR (CDCl$_3$): δ 7.10 (d, 4H, J=7.9), 7.02 (d, 4H, J=7.9), 4.05 (q, 4H, J=7.0), 2.25 (t, 4H, J=7.3), 2.20 (s, 6H), 1.95-1.70 (m, 4H), 1.42 (s, 6H), 1.50-1.05 (m, 8H), 1.08 (t, 6H, J=7.0). $^{13}$C NMR (CDCl$_3$): δ 211.10, 176.00, 141.00, 135.80, 128.50, 124.51, 60.50, 49.50, 42.01, 39.50, 24.28, 24.05, 22.10, 20.50, 13.00. HRMS (LSIMS, nba): Calcd for C$_{33}$H$_{47}$O$_5$ (MH$^+$): 523.3423. found: 523.3405.

2,12-Bis-(4-isobutylphenyl)-2,12-dimethyl-7-oxotridecanedioic acid diethyl ester (209f). Similar to the procedure given for 209c, 205f (14.13 g, 38.3 mmol) was reacted with TosMIC (3.73 g, 19.1 mmol), tetrabutylammonium iodide (1.30 g, 3.5 mmol), and NaH (2.0 g, 60%, 50.0 mmol) in freshly distilled DMSO (200 mL) for 18 h at room temperature. The crude intermediate 208f obtained after hydrolysis and extraction was stirred in CH$_2$Cl$_2$ (100 mL) and concentrated HCl (50 mL) for 1 h at room temperature. Extractive workup and purification by flash chromatography (silica gel; ethyl acetate/hexanes=10/90, then 20/80) yielded 209f (9.49 g, 82%) as a colorless oil. $^1$H NMR (CDCl$_3$): δ 7.18 (d, 4H, J=8.0), 7.07 (d, 4H, J=8.0), 4.10 (q, 4H, J=7.0), 2.43 (d, 4H, J=7.0), 2.34 (t, 4H, J=7.6), 2.10-1.92 (m, 2H), 1.92-1.78 (m, 4H), 1.60-1.50 (m, 4H), 1.50 (s, 6H), 1.19-1.11 (m, 5H), 1.17 (t, 3H, J=7.0), 0.88 (d, 12H, J=6.6). $^{13}$C NMR (CDCl$_3$): δ 211.06, 176.39, 141.36, 140.04, 129.16, 125.71, 60.77, 49.90, 45.06, 42.66, 39.18, 30.27, 24.59, 24.35, 22.86, 22.56, 14.23. HRMS (LSIMS, nba): Calcd for C$_{39}$H$_{59}$O$_5$ (MH$^+$): 607.4362. found: 607.4337.

2,2,14,14-Tetramethyl-8-oxopentadecanedioic acid diethyl ester (209g). According to the procedure described for the synthesis of 209c, a solution of 205g (32.3 g, 115.3 mmol), tetrabutylammonium iodide (3.69 g, 10.0 mmol) and TosMIC (9.80 g, 50.2 mmol) in anhydrous DMSO (300 mL) was treated with NaH (4.80 g, 120.0 mmol, 60% in mineral oil) at room temperature for 20 h. The intermediary dialkylated TosMIC derivative 208g obtained after aqueous workup (36.8 g) was then hydrolyzed with concd hydrochloric acid (110 mL) in CH$_2$Cl$_2$ (450 mL) at room temperature for 1 h. Extractive workup and purification by column chromatography (silica gel; hexanes/ethyl acetate=11/1) afforded 209g (12.20 g, 61%) as a colorless oil. $^1$H NMR (CDCl$_3$): δ 4.11 (q, 4H, J=6.9 Hz), 2.37 (t, 4H, J=7.5), 1.58-1.47 (m, 8H), 1.35-1.10 (m, 8H), 1.24 (t, 6H, J=7.2), 1.15 (s, 12H). $^{13}$C NMR (CDCl$_3$): δ 211.6, 178.3, 60.5, 43.1, 42.5, 40.9, 30.1, 25.5, 25.1, 24.1, 14.7. HRMS (LSIMS, gly): Calcd for C$_{23}$H$_{43}$O$_5$ (MH$^+$): 399.3110. found: 399.3129.

2,2,18,18-Tetramethyl-10-oxononadecanedioic acid diethyl ester (209j). Under N$_2$ atmosphere, NaH (60% w/w in mineral oil, 1.21 g, 30.2 mmol) was added in portions to a solution of TosMIC (2.43 g, 12.5 mmol) and tetrabutylammonium iodide (0.462 g, 1.25 mmol) in dry DMSO (100 mL) while stirring vigorously and cooling with a water bath. After 15 min, 205j (7.65 g, 26.1 mmol) was added dropwise in 20 min. After 1 h, H$_2$O (100 mL) was added dropwise and the resulting mixture was extracted with Et$_2$O (3×100 mL). The combined organic layers were washed with brine (2×100 mL), dried over anhydrous Na$_2$SO$_4$ and evaporated in vacuo. The residue was purified by column chromatography (silica, heptane:ethyl acetate=6:1) to give 208j (5.41 g) as a yellow oil. To a portion of this oil (5.03 g), dissolved in CH$_2$Cl$_2$ (100 mL), was added aqueous HCl (concd, 30 mL) and the resulting mixture was stirred vigorously for 17.5 h. Water (100 mL) was added and the layers were separated. The aqueous phase was extracted with CH$_2$Cl$_2$ (100 mL) and the combined organic layers were washed with NaHCO$_3$ solution (2×100 mL) and brine (100 mL), dried over anhydrous Na$_2$SO$_4$ and evaporated in vacuo. The residue was purified by column chromatography (silica, heptane:ethyl acetate=7:1) to give 209j (3.21 g, 61%) as a colorless oil. $^1$H NMR (CDCl$_3$): δ (ppm): 4.11 (q, J=7.2, 4H), 2.37 (t, J=7.4, 4H), 1.57-1.46 (m, 8H), 1.28-1.23 (m, 16H), 1.24 (t, J=7.1, 6H), 1.15 (s, 12H). $^{13}$C NMR (CDCl$_3$): δ (ppm): 211.5, 178.0, 60.08, 60.07, 42.7, 42.1, 40.7, 29.9, 29.21, 29.15, 25.1, 24.8, 23.8, 14.2. HRMS: Calcd for C$_{27}$H$_{50}$O$_5$ (MH$^+$): 454.3658. found: 454.3663.

9-Isocyano-2,2,16,16-tetramethyl-9-(toluene-4-sulfonyl)-heptadecanedioic acid diethyl ester (208i). To a solution of 205i (35.0 g, 125.4 mmol), tetrabutylammonium iodide (4.6 g, 12.5 mmol), and TosMIC (12.2 g, 62.5 mmol) in anhydrous DMSO (450 mL) was added NaH (60% dispersion in mineral oil, 6.3 g, 158 mmol) under cooling with an ice-water bath and under N$_2$ atmosphere. The reaction mixture was stirred for 23 h at ambient temperature, then carefully hydrolyzed with ice-water (500 mL) and extracted with MTBE (3×200 mL). The organic layers were washed with water (300 mL) and brine (150 mL), dried over anhydrous MgSO$_4$, and concentrated in vacuo to give crude 8i (37.0 g, 100%) as an oil. $^1$H NMR (CDCl$_3$): δ (ppm): 7.88 (d, J=7.9, 2H), 7.42 (d, J=7.9, 2H), 4.10 (q, J=7.5, 4H), 2.48 (s, 3H), 2.05-1.75 (m, 3H), 1.65-1.20 (m, 21H), 1.15 (t, J=7.5, 6H), 1.10 (s, 12H). $^{13}$C NMR (CDCl$_3$): δ (ppm): 177.89, 163.75, 146.23, 131.08, 130.28, 129.82, 81.79, 60.17, 42.09, 40.57, 33.09, 29.68, 29.31, 25.17, 24.78, 23.66, 21.08, 14.31. HRMS (LSIMS, gly): Calcd for C$_{37}$H$_{54}$NO$_6$S (MH$^+$): 592.3672. found: 592.3667.

2,2,16,16-Tetramethyl-9-oxoheptadecanedioic acid diethyl ester (209i). To a solution of 208i (12.0 g, 20.3 mmol) in CH$_2$Cl$_2$ (200 mL) was added concd HCl (47 mL). The reaction mixture was stirred for 80 min at room temperature and diluted with water (200 mL). The layers were separated and the aqueous layer was extracted with CH$_2$Cl$_2$ (3×70 mL). The combined organic layers were washed with saturated NaHCO$_3$ solution (3×40 mL) and brine (50 mL), dried over anhydrous MgSO$_4$, and concentrated in vacuo to yield the crude product (7.52 g). Purification by column chromatography (silica gel, ethyl acetate/hexanes=1/9) gave 209i (3.5 g, 40.0%) as a colorless oil. $^1$H NMR (CDCl$_3$): δ (ppm): 4.14 (q, J=7.1, 4H), 2.41 (t, J=7.0, 4H), 1.66-1.45 (m, 8H), 1.35-1.20 (m, 12H), 1.25 (t, J=7.1, 6H), 1.17 (s, 12H). $^{13}$C NMR (CDCl$_3$): δ (ppm): 211.24, 177.89, 60.01, 42.69, 42.07, 40.64, 29.86, 29.07, 25.13, 24.73, 23.74, 14.24. HRMS (LSIMS, gly): Calcd for C$_{25}$H$_{47}$O$_5$ (ME): 427.3423. found: 427.3430.

Representative Procedure for the Saponification of Ketodiesters: 2,12-Bis-(4-isobutylphenyl)-2,12-dimethyl-7-oxotridecanedioic acid (210f). A solution of 209f (3.0 g, 4.95 mmol) and KOH (85%, 4.4 g, 66.7 mmol) in ethanol (40 mL) and water (10 mL) was heated to reflux for 6 h. The ethanol was removed under reduced pressure and the mixture was diluted with water (200 mL). The solution was extracted with Et$_2$O (100 mL) and the aqueous layer was acidified with concentrated HCl (10 mL) to pH 1. The product was extracted with Et$_2$O (2×100 mL). The ether fractions were combined, dried over Na$_2$SO$_4$, concentrated and dried in high vacuo to yield 210f (2.35 g, 86%) as a light yellow foam. $^1$H NMR (CDCl$_3$): δ 10.02 (br., 2H), 7.24 (d, 4H, J=8.0), 7.09 (d, 4H, J=8.0), 2.43 (d, 4H, J=7.0), 2.33 (t, 4H, J=7.3), 2.05-1.88 (m, 2H), 1.96-1.77 (m, 4H), 1.55-1.42 (m, 10H), 1.22-1.08 (m, 4H), 0.88 (d, 12H, J=6.6). $^{13}$C NMR (CDCl$_3$): δ 211.48, 182.94, 140.43, 140.24, 129.27, 125.94, 49.71, 45.06, 42.58, 42.58, 38.91, 30.25, 24.45, 24.24, 22.58, 22.40. HRMS (LSIMS, nba): Calcd for $C_{35}H_{50}O_5Na$ (MNa$^+$): 573.355. found: 573.3459. HPLC: 86.9% pure. Anal. ($C_{35}H_{50}O_5$) C, H.

2,10-Dimethyl-6-oxo-2,10-diphenylundecanedioic acid (210b). According to the procedure given for 210f, 209b (14.5 g, 31.1 mmol) was saponified with KOH (85%, 7.2 g, 108.6 mmol) in water (15 mL) and ethanol (45 mL) at reflux for 6 h. After the usual extractive workup, the crude material was purified by flash chromatography (silica gel; ethyl acetate/hexanes=1/20, 1/10, 1/2) to give 210b (4.0 g, 31%) as a white solid. Mp 44-46° C. $^1$H NMR (CDCl$_3$): 10.25 (br., 2H), 7.35-7.22 (m, 10H), 2.32 (m, 4H), 1.94-1.86 (m, 4H), 1.57 (s, 6H), 1.51-1.22 (m, 4H). $^{13}$C NMR (CDCl$_3$): δ 210.64, 182.66, 142.69, 128.66, 127.18, 126.29, 50.07, 42.97, 38.62, 22.20, 19.11. HRMS (LSIMS, gly): Calcd for $C_{25}H_{31}O_5$ (MH$^+$): 411.2171. found: 411.2144. HPLC: 95.2% pure.

7-Oxo-2,2,12,12-tetramethyltridecanedioic acid (210c). According to the procedure given for 210f, 209c (30.0 g, 81.0 mmol) was saponified with KOH (85%, 18.9 g, 286 mmol) in ethanol (143 mL) and water (48 mL) at reflux for 5 h. The solid product obtained after extraction and drying was purified by flash chromatography (silica; hexanes/ethyl acetate=90/10) to afford 210c (22.0 g, 86%) as a white solid. Mp 60-61.5° C. $^1$H NMR (CDCl$_3$): δ 11.40 (br., 2H), 2.41 (t, 4H, J=7.3), 1.62-1.48 (m, 8H), 1.32-1.18 (m, 4H), 1.18 (s, 12H). $^{13}$C NMR (CDCl$_3$=77.0 ppm): δ 211.11, 184.74, 42.49, 42.14, 40.42, 24.92, 24.62, 23.99. HRMS (LSIMS, gly): Calcd for $C_{17}H_{31}O_5$ (MH$^+$): 315.2171. found: 315.2183. HPLC: 94.5% pure. Anal. ($C_{17}H_{30}O_5$) C, H.

2,12-Dimethyl-7-oxo-2,12-diphenyltridecanedioic acid (210d). According to the procedure given for 210f, 209d (3.93 g, 7.9 mmol) was hydrolyzed with KOH (85%, 4.0 g, 60.6 mmol) in ethanol (60 mL) and water (10 mL) at reflux for 3 h and at room temperature overnight. After the usual workup and drying, 210d (3.0 g, 87%) was obtained as an oil $^1$H NMR (CDCl$_3$): δ 7.40-7.10 (m, 10H), 2.32 (t, 4H, J=7.2), 2.10-1.80 (m, 4H), 1.60-1.45 (m, 4H), 1.54 (s, 6H), 1.25-1.10 (m, 4H). $^{13}$C NMR (CDCl$_3$): δ 211.1, 182.5, 142.8, 128.4, 126.9, 126.0, 49.9, 42.3, 38.7, 24.2, 24.0, 22.3. HRMS (LSIMS, nba): Calcd for $C_{27}H_{35}O_5$ (MH$^+$): 439.2484. found: 439.2497. HPLC: 93.7% pure.

2,12-Dimethyl-7-oxo-2,12-di-p-tolyltridecanedioic acid (210e). According to the procedure given for 210f, 209e (9.0 g, 17.2 mmol) was hydrolyzed with KOH (85%, 4.0 g, 60.6 mmol) in water (10 mL) and ethanol (30 mL) at reflux for 6 h. After the usual extractive workup, the crude material was purified by flash chromatography (silica gel; ethyl acetate/hexanes=1/10, 1/6, 1/2) to give 210e (3.1 g, 39%) as a white solid. Mp 48-50° C. $^1$H NMR (CDCl$_3$): δ 10.8-8.8 (br., 2H), 7.22 (d, 4H, J=8.1), 7.12 (d, 4H, J=8.1), 2.36 (t, 4H, J=7.5), 2.31 (s, 6H), 1.98-1.80 (m, 4H), 1.56-1.44 (m, 4H), 1.51 (s, 6H), 1.24-1.15 (m, 4H). $^{13}$C NMR (CDCl$_3$): δ 211.63, 183.07, 140.40, 137.00, 129.58, 126.43, 50.02, 42.82, 39.10, 24.74, 24.50, 22.82, 21.39. HRMS (LSIMS, gly): Calcd for $C_{29}H_{39}O_5$ (MH$^+$): 467.2797. found: 467.2785. HPLC: 92.4% pure. Anal. ($C_{29}H_{38}O_5$) C, H.

2,2,14,14-Tetramethyl-8-oxopentadecanedioic acid (210g). According to the procedure given for 210f, 209g (8.54 g, 21.4 mmol) was saponified with KOH (85%, 4.53 g, 68.6 mmol) in ethanol (13 mL) and water (5 mL) at reflux for 4 h. The solid product obtained after usual workup was recrystallized from Et$_2$O/hexanes (50 mL/50 mL), affording 210g (4.16 g, 57%) as colorless needles. Mp 82-83° C. $^1$H NMR (CDCl$_3$): δ 11.53 (br., 2H), 2.39 (t, 4H, J=7.3), 1.60-1.50 (m, 8H), 1.30-1.20 (m, 8H), 1.18 (s, 12H). $^{13}$C NMR (CDCl$_3$): δ 211.7, 185.0, 42.8, 42.3, 40.4, 29.7, 25.1, 24.8, 23.8. HRMS (LSIMS, gly): Calcd for $C_{19}H_{35}O_5$ (MH$^+$): 343.2484. found: 343.2444. HPLC: 92.6% pure. Anal. ($C_{19}H_{34}O_5$) C, H.

2,2,16,16-Tetramethyl-9-oxoheptadecanedioic acid (210i). To a solution of KOH (85%, 8.4 g, 127.3 mmol) in deionized water (3.6 mL) and ethanol (11.5 mL) was added 208i (15.0 g, 25.3 mmol) and the mixture was heated to reflux for 7 h. The reaction mixture was diluted with water (40 mL) and extracted with MTBE (2×30 mL). The aqueous layer was cooled with an ice-bath and the pH was adjusted to 1 by addition of 5 N sulfuric acid (45 mL). The aqueous layer was extracted with MTBE (3×30 mL) and the combined organic layers were washed with brine (50 mL), dried over anhydrous MgSO$_4$, and concentrated in vacuo to give a crude oil (12.5 g). Purification by chromatography (silica gel, ethyl acetate/hexanes=10% to 100%) and recrystallization from MTBE/hexanes (4 mL/50 mL) yielded 210i (5.37 g, 57%) as a white powder. Mp 74.5-76.0° C. $^1$H NMR (CDCl$_3$): δ (ppm): 12.40-11.20 (br, 2H), 2.39 (t, J=7.3, 4H), 1.62-1.48 (m, 8H), 1.38-1.22 (m, 12H), 1.11 (s, 12H). $^{13}$C NMR (CDCl$_3$=77.02 ppm): δ (ppm): 211.88, 184.93, 42.70, 42.19, 40.63, 29.63, 29.09, 24.96, 24.83, 23.83. HRMS (LSIMS, gly): Calcd for $C_{21}H_{39}O_5$ (MH$^+$): 371.2797. found: 371.2804.

2,2,18,18-Tetramethyl-10-oxononadecanedioic acid (210j). To a solution of 209j (11.63 g, 25.6 mmol) in EtOH and H$_2$O (3:1, 200 mL) was added powdered KOH (85%, 4.31 g, 65.3 mmol). The resulting mixture was refluxed for 19 h and concentrated in vacuo until all of the EtOH was removed. Water (200 mL) was added and the resulting mixture was extracted with Et$_2$O (2×200 mL). The aqueous phase was acidified with aqueous HCl (4 M) to pH ~1 and extracted with Et$_2$O (3×200 mL). The combined Et$_2$O layers of the latter extraction were dried over anhydrous Na$_2$SO$_4$ and evaporated in vacuo. The remaining white solid was recrystallized from heptane/iPr$_2$O to give 210j (7.56 g, 74%) as white crystals. Mp 74.3-77.3° C. $^1$H NMR (CD$_3$OD): δ (ppm): 2.43 (t, J=7.3, 4H), 1.57-1.50 (m, 8H), 1.33-1.21 (m, 16H), 1.14 (s, 12H). $^{13}$C NMR (CD$_3$OD): δ (ppm): 214.5, 182.1, 43.6, 43.2, 42.0, 31.2, 30.4, 30.38, 26.2, 25.9, 25.0. HRMS: Calcd for $C_{23}H_{42}O_5$ (M$^+$): 398.3028. found: 398.3032.

2,2,16,16-Tetramethylheptadecane-1,9,17-triol (211i). Under N$_2$-atmosphere, methyl tert-butyl ether (MTBE, 80 mL) was added to LiAlH$_4$ (0.67 g, 17.65 mmol) and the suspension was stirred under cooling with an ice-water bath. A solution of 209i (3.0 g, 7.03 mmol) in MTBE (20 mL) was added dropwise, followed by additional MTBE (40 mL). After 2 h at 0° C., the reaction mixture was carefully quenched by addition of ethyl acetate (8 mL) and allowed to warm to room temperature overnight. The mixture was cooled with an ice-water bath and carefully hydrolyzed by addition of crushed ice (15 g) and water (15 mL). The pH was adjusted to 1 by addition of 2 N aqueous sulfuric acid (28 mL) and the solution was stirred at room temperature for 15 min. The layers were separated and the aqueous layer was extracted with MTBE (40 mL). The combined organic layers were washed with deionized water (50 mL), saturated NaHCO$_3$ solution (40 mL), and brine (40 mL), dried over anhydrous MgSO$_4$, concentrated in vacuo and dried in high vacuo. The crude product (2.65 g) was purified by recrystallization from hot CH$_2$Cl$_2$ (20 mL). The crystals were filtered, washed with ice-cold CH$_2$Cl$_2$ (20 mL) and dried in high vacuo to furnish 211i (1.59 g, 66%) as a white solid. Mp 75-77° C. $^1$H NMR (CDCl$_3$): δ (ppm): 3.57 (m, 1H), 3.30 (s, 4H), 1.72 (br, 2H), 1.50-1.16 (m, 25H), 0.85 (s, 12H). $^{13}$C NMR (CDCl$_3$): δ (ppm): 72.09, 38.79, 37.61, 35.21, 30.70, 29.85, 25.78, 24.06, 23.92. HRMS (LSIMS, gly): Calcd for $C_{21}H_{45}O_3$ (MH$^+$): 345.3369. found: 345.3364. HPLC: 95.0% pure.

Representative Procedure for the Dialkylation of TosMIC and Deprotection to Ketodiols: 1,15-Dihydroxy-2,2,14,14-tetramethylpentadecan-8-one (214g). Under Argon atmosphere, to a solution of 207g (26.0 g, 84.6 mmol) and TosMIC (7.8 g, 40.0 mmol) in anhydrous DMSO (200 mL) and THF (10 mL) was added NaH (3.8 g, 95.0 mmol, 60% in mineral oil) in five portions at 20-30° C. under cooling with a water bath. After the addition of tetrabutylammonium iodide (3.0 g, 8.1 mmol), the reaction mixture was stirred at room temperature for 20 h and then hydrolyzed with water (400 mL). The mixture was extracted with Et$_2$O (3×100 mL). The combined organic layers were washed with saturated aqueous NaCl solution (100 mL), dried over MgSO$_4$, and concentrated in vacuo to yield the crude dialkylated intermediate (28.2 g) as an orange oil, which was used without purification. To a solution of this crude product (28.0 g) in methanol (115 mL) was added dilute H$_2$SO$_4$ (46 g, 12 mL of concd H$_2$SO$_4$ in 24 mL of water) over a period of 10 min, and the mixture was stirred for 80 min at room temperature. The solution was diluted with water (120 mL) and extracted with CH$_2$Cl$_2$ (150 mL, 100 mL, 50 mL). The combined organic layers were washed with saturated aqueous Na$_2$CO$_3$ solution (2×100 mL), saturated aqueous NaHCO$_3$ solution (100 mL), water (200 mL), and saturated aqueous NaCl solution (150 mL). The organic extract was dried over anhydrous MgSO$_4$ and concentrated in vacuo. The residue (18.4 g) was purified by column chromatography (silica gel; hexanes, then CH$_2$Cl$_2$, then hexanes/ethyl acetate=4/3) to give 214g (9.97 g, 79%) as a colorless oil. $^1$H NMR (CDCl$_3$): δ 3.30 (s, 4H), 2.39 (t, 4H, J=7.2), 2.07 (br. s, 2H), 1.60-1.55 (m, 4H), 1.28-1.17 (m, 12H), 0.85 (s, 12H). $^{13}$C NMR (CDCl$_3$): δ 212.0, 72.0, 43.0, 38.6, 35.2, 30.3, 24.0, 23.8. HRMS (LSIMS, gly): Calcd for $C_{19}H_{39}O_3$ (MH$^+$): 315.2899. found: 315.2886. HPLC: 94.7% pure.

1,11-Dihydroxy-2,2,10,10-tetramethylundecan-6-one (214a). In analogy to the procedure described for the synthesis of 214g, 207a (40.0 g, 143.3 mmol) was reacted with TosMIC (13.99 g, 71.7 mmol), tetrabutylammonium iodide (5.28 g, 14.3 mmol), and NaH (6.86 g, 171.5 mmol) in anhydrous DMSO (400 mL). After extractive workup and drying, the crude intermediate (47.9 g) was dissolved in methanol (200 mL) and water (40 mL) and treated with concd sulfuric acid (20 mL) at room temperature. Workup and purification by chromatography (silica gel; hexanes/ethyl acetate=90/10, 70/30, then 50/50) afforded 214a (5.6 g, 30%) as an oil. $^1$H NMR (CDCl$_3$): δ 3.30 (s, 4H), 2.68 (br. s, 2H), 2.40 (t, 4H, J=7.2), 1.53 (m, 4H), 1.20 (m, 4H), 0.86 (s, 12H). $^{13}$C NMR (CDCl$_3$=77.0 ppm): δ 212.25, 70.99, 43.15, 37.69, 34.94, 23.89, 17.91. HRMS (LSIMS, gly): Calcd for $C_{15}H_{29}O_2$ (MH$^+$—H$_2$O): 241.2168. found: 241.2169. HPLC: 96.7% pure.

1,11-Dihydroxy-2,10-dimethyl-2,10-diphenylundecan-6-one (14b). In analogy to the procedure given for 214g, to a solution of 207b (25.0 g, 73.3 mmol), tetrabutylammonium iodide (3.0 g, 8.2 mmol), and TosMIC (7.23 g, 37.0 mmol) in anhydrous DMSO (350 mL) was added NaH (60% dispersion in mineral oil, 3.73 g, 93.3 mmol) while controlling the temperature with an ice bath. After the addition of Et$_2$O (100 mL), the mixture was stirred at room temperature for 24 h, hydrolyzed, extracted, and dried to afford the dialkylated TosMIC intermediate (28.0 g) as a brown oil. This crude intermediate was heated to reflux for 3 h in methanol (500 mL), concd HCl (60 mL), and water (120 mL). Extractive workup and purification by flash chromatography (silica gel; hexanes, then ethyl acetate/hexanes=1/20, 1/10, 1/2, 1/1) gave 214b (5.3 g, 38%) as a light yellowish oil. $^1$H NMR (CDCl$_3$): δ (ppm) 7.38-7.30 (m, 8H), 7.26-7.18 (m, 2H), 3.62 (d, 2H, J=10.5 Hz), 3.48 (d, 2H, J=10.5 Hz), 2.25 (m, 6H) 1.76-1.64 (m, 2H), 1.58-1.16 (m, 6H), 1.32 (s, 6H). $^{13}$C NMR (CDCl$_3$): δ (ppm) 211.43, 144.84, 128.32, 126.58, 126.03, 71.79, 43.11, 42.89, 37.61, 21.68, 18.12. HRMS (LSIMS, nba): Calcd for $C_{25}H_{33}O_2$ (MH$^+$—H$_2$O): 365.2481. found: 365.2482. HPLC: 89.5% pure.

1,13-Dihydroxy-2,2,12,12-tetramethyltridecan-7-one (214c). Similar to the procedure given for the synthesis of 214g, 207c (13.0 g, 44.3 mmol) was treated with TosMIC (4.33 g, 22.17 mmol), NaH (60% dispersion in mineral oil, 2.13 g, 53.2 mmol), and tetrabutylammonium iodide (1.64 g, 4.4 mmol) in anhydrous DMSO (100 mL) and anhydrous diethyl ether (50 mL) at room temperature overnight. Hydrolysis and extraction afforded the dialkylated TosMIC intermediate (15.5 g) as an oil that was dissolved in methanol (180 mL), concd HCl (20 mL), and water (40 mL) and heated to reflux for 2 h. Extractive workup and purification by flash chromatography (silica gel; hexanes/ethyl acetate=50/50) furnished 214e (4.3 g, 68%) as a colorless oil. $^1$H NMR (CDCl$_3$): δ 3.28 (s, 4H), 2.80 (br. m, 2H), 2.42 (t, 4H, J=7.3), 1.54 (m, 4H), 1.25 (m, 8H), 0.84 (s, 12H). $^{13}$C NMR (CDCl$_3$): δ 212.06, 71.24, 42.47, 38.11, 34.76, 24.45, 23.72, 23.25. HRMS (LSIMS, gly): Calcd for $C_{17}H_{35}O_5$ (MH$^+$): 287.2556. found: 287.2585. HPLC: 97.5% pure.

1,13-Dihydroxy-2,12-dimethyl-2,12-diphenyltridecan-7-one (214d). According to the procedure described for the synthesis of 214g, 207d (10.0 g, 28.2 mmol) was reacted with tetrabutylammonium iodide (1.06 g, 2.9 mmol), TosMIC (2.34 g, 12.0 mmol) and NaH (60% dispersion in mineral oil, 1.42 g, 35.5 mmol) in anhydrous DMSO (100 mL) and anhydrous Et$_2$O (50 mL) at room temperature for 24 h. After aqueous workup and extraction, the dialkylated TosMIC intermediate (11.0 g) was heated to reflux in a mixture of methanol (180 mL), concd HCl (20 mL), and water (40 mL) for 3 h. After extraction, the crude oil was purified by flash chromatography (silica gel; hexanes/ethyl acetate=80/20, then 60/40), affording 214d (3.0 g, 61%) as a colorless oil. $^1$H NMR (CDCl$_3$): 7.37-7.28 (m, 8H), 7.24-7.17 (m, 2H), 3.69 (dd, 2H, J=10.9, 5.2), 3.52 (dd, 2H, J=10.9, 7.5), 2.26 (t, 4H, J=7.3), 1.75 (m, 2H), 1.61 (s, 2H), 1.57-1.40 (m, 6H), 1.33 (s, 6H), 1.29-1.06 (m, 2H), 1.04-0.80 (m, 2H). $^{13}$C NMR (CDCl$_3$), δ (ppm): 211.21, 144.72, 128.23, 126.50, 125.92, 72.17, 43.14, 42.38, 38.06, 24.27, 23.34, 21.42. HRMS (LSIMS): Calcd for $C_{27}H_{39}O_3$ (MH$^+$): 411.2899. found: 411.2899. HPLC: 92.7% pure.

1,13-Dihydroxy-2,12-dimethyl-2,12-di-p-tolyltridecan-7-one (214e). According to the procedure for the synthesis of 214g, 207e (21.5 g, 75.3 mmol) was reacted with tetrabutylammonium iodide (2.36 g, 6.4 mmol), TosMIC (5.68 g, 29.1 mmol) and NaH (60% dispersion in mineral oil, 2.94 g, 73.5 mmol) in anhydrous DMSO (300 mL) and anhydrous Et$_2$O (100 mL) at room temperature for 24 h. The crude intermediate (18.4 g) obtained after aqueous workup and extraction was then heated to reflux in methanol (300 mL), concd HCl (36 mL), and water (70 mL) for 3 h. Extractive workup and purification by flash chromatography (silica gel; hexanes/ethyl acetate=20/1, 15/1, 10/1, 5/1, and 1/1) gave 214e (2.72 g, 21%) as a colorless oil. $^1$H NMR (CDCl$_3$): δ 7.18 (d, 4H, J=8.1), 7.12 (d, 4H, J=8.1), 3.61 (d, 2H, J=11.0), 3.48 (d, 2H, J=11.0 Hz), 2.31 (s, 6H), 2.26 (t, 4H, J=7.8), 1.78-1.40 (m, 10H), 1.29 (s, 6H), 1.24-0.82 (m, 4H). $^{13}$C NMR (CDCl$_3$): δ 211.51, 141.75, 135.64, 129.23, 126.64, 72.54, 43.06, 42.65, 38.28, 24.53, 23.59, 21.66, 20.98. HRMS (LSIMS, gly): Calcd for $C_{29}H_{43}O_3$ (MH$^+$): 439.3212. found: 439.3222. HPLC: 95.4% pure.

1,15-Dihydroxy-2,14-dimethyl-2,14-diphenylpentadecan-8-one (214h). In analogy to the procedure of 214g, to a solution of 207h (18.0 g, 63.1 mmol), tetrabutylammonium iodide (2.0 g, 5.4 mmol) and TosMIC (4.8 g, 24.6 mmol) in anhydrous DMSO (250 mL) and Et$_2$O (80 mL) was added NaH (60% dispersion in mineral oil, 2.5 g, 62.5 mmol) while cooling with an ice bath under N$_2$ atmosphere. After 24 h at room temperature, the mixture was hydrolyzed and worked up by extraction to give the crude intermediate (18.0 g) as a brown oil. This crude material was heated to reflux in methanol (300 mL), concd HCl (36 mL) and water (70 mL) for 3 h. Extractive workup and purification by flash chromatography (silica gel; hexanes/ethyl acetate/hexanes=10/1, 5/1, 2/1) yielded 214h (6.1 g, 56%) as a yellowish oil. $^1$H NMR (CDCl$_3$): δ 7.32-7.19 (m, 10H), 3.68 (d, 2H, J=10.8), 3.50 (d, 2H, J=10.8), 2.26 (t, 4H, J=7.50H), 1.88-1.42 (m, 10H), 1.25 (s, 6H), 1.22-0.85 (m, 8H). $^{13}$C NMR (CDCl$_3$): δ 211.68, 144.94, 128.56, 126.82, 126.23, 72.68, 43.50, 42.79, 38.42, 30.01, 23.74, 23.68, 21.62. HRMS (LSIMS, nba): Calcd for $C_{29}H_{43}O_3$ (MH$^+$): 439.3212. found: 439.3207. HPLC: 95.3% pure.

2,12-Bis-(4-isobutylphenyl)-2,12-dimethyl-7-([1,3] dithianyl)-tridecanedioic acid diethyl ester (212f). Compound 209f (5.50 g, 9.06 mmol) was dissolved in CH$_2$Cl$_2$ (freshly distilled from CaH$_2$, 60 mL) with boron trifluoride diethyl etherate (0.45 mL, 0.50 g, 3.55 mmol) and 1,3-propanedithiol (1.0 mL, 1.08 g, 9.99 mmol). The solution was stirred for 3 h at room temperature under a nitrogen atmosphere. An additional volume of CH$_2$Cl$_2$ (100 mL) was added and the solution was extracted with 5% sodium hydroxide solution (2×50 mL) and water (100 mL). After drying with anhydrous Na$_2$SO$_4$, filtration, and concentration, the product was purified by flash chromatography (silica gel; ethyl acetate/hexanes=10/90), affording 212f (6.16 g, 98%) as a colorless oil. $^1$H NMR (CDCl$_3$): δ 7.20 (d, 4H, J=8.0), 7.07 (d, 4H, J=8.0), 4.10 (q, 4H, J=7.0), 2.76 (t, 4H, J=5.3), 2.43 (d, 4H, J=7.0), 2.09-1.95 (m, 2H), 1.94-1.78 (m, 10H), 1.51 (s, 6H), 1.46-1.36 (m, 4H), 1.25-1.12 (m, 4H), 1.18 (t, 6H, J=7.0), 0.88 (d, 12H, J=6.5). $^{13}$C NMR (CDCl$_3$): δ 176.42, 141.43, 140.00, 129.14, 125.74, 60.74, 53.30, 49.97, 45.05, 39.22, 38.29, 30.26, 26.10, 25.64, 25.17, 24.76, 22.99, 22.56, 14.26. HRMS (EI): Calcd for $C_{42}H_{64}O_4S_2$ (M$^+$): 696.4246. found: 696.4234. HPLC: 96.2% pure.

2,12-Bis-(4-isobutylphenyl)-2,12-dimethyl-7-([1,3] dithianyl)-tridecane-1,13-diol (213f). A solution of 212f (5.81 g, 8.33 mmol) in freshly distilled THF (50 mL) was added dropwise to a suspension of LiAlH$_4$ (1.0 g, 26.4 mmol) in THF (50 mL) at −78° C. under a nitrogen atmosphere. The solution was warmed to room temperature over 4 h, then cooled back to −78° C., and quenched with ethyl acetate (5.0 mL). After warming to room temperature, water (100 mL) was added and the product was extracted with Et$_2$O (2×100 mL). The ether extracts were combined, dried with sodium sulfate, filtered, and concentrated. After drying under high vacuum for 4 h, 213f (4.80 g, 94%) was obtained as a colorless oil. $^1$H NMR (CDCl$_3$): δ 7.20 (d, 4H, J=8.0), 7.09 (d, 4H, J=8.0), 3.64 (d, 2H, J=10.7), 3.48 (d, 2H, J=10.7), 2.71 (t, 4H, J=5.1), 2.50-2.35 (m br., 2H), 2.43 (d, 4H, J=7.0), 1.90-1.80 (m, 4H), 1.80-1.68 (m, 6H), 1.58-1.42 (m, 2H), 1.38-1.25 (m, 4H), 1.30 (s, 6H), 1.26-1.10 (m, 2H), 1.10-0.95 (m, 2H), 0.89 (d, 12H, J=6.6). $^{13}$C NMR (CDCl$_3$): δ 141.94, 139.39, 129.20, 126.44, 72.48, 53.30, 44.97, 43.09, 38.45, 38.18, 30.21, 26.01, 25.64, 24.84, 24.09, 22.55, 21.64. HRMS (LSIMS, nba): Calcd for $C_{38}H_{61}O_2S_2$ (MH$^+$): 613.4113. found: 613.4075. HPLC: 97.6% pure.

1,13-Dihydroxy-2,12-bis-(4-isobutylphenyl)-2,12-dimethyltridecan-7-one (214f). To a mixture of 213f (4.50 g, 7.34 mmol) in dimethoxyethane (50 mL) and concentrated HCl (10 mL) was added dropwise DMSO (5.0 mL) over 5 min. The solution was stirred for 30 min at room temperature, then slowly poured into saturated aqueous NaHCO$_3$ solution (100 mL) and extracted with Et$_2$O (2×100 mL). The ether fractions were combined, dried with anhydrous Na$_2$SO$_4$, filtered, and concentrated. The product was purified by flash chromatography (silica gel; ethyl acetate/hexanes=30/70), affording 214f (3.2 g, 83%) as a colorless oil. $^1$H NMR (CDCl$_3$): δ 7.19 (d, 4H, J=8.0), 7.09 (d, 4H, J=8.0), 3.63 (d, 2H, J=11.0), 3.49 (d, 2H, J=11.0), 2.43 (d, 4H, J=7.0), 2.26 (t, 4H, J=7.3), 1.88-1.66 (m, 4H), 1.52-1.41 (m, 8H), 1.29 (s, 6H), 1.15-1.10 (m, 2H), 0.98-0.88 (m, 2H), 0.89 (d, 12H, J=6.6). $^{13}$C NMR (CDCl$_3$): δ 211.47, 141.97, 139.51, 129.28, 126.45, 72.53, 45.02, 43.11, 42.69, 38.36, 30.26, 24.57, 23.63, 22.58, 21.72. HRMS (LSIMS, nba): Calcd for $C_{35}H_{55}O_3$ (MH$^+$): 523.4151. found: 523.4144. HPLC: 96.3% pure.

1,17-Dihydroxy-2,2,16,16-tetramethylheptadecan-9-one (214i). To a solution of 211i (2.42 g, 7.02 mmol) in acetic acid (10 mL) was added dropwise sodium hypochlorite solution (1.76 mL, ca. 3.5 mmol) at 18° C. Additional sodium hypochlorite solution (3×1.0 mL, ca. 6.0 mmol) was added after 20, 40, and 60 min under monitoring by TLC. The reaction was quenched with 2-propanol (4 mL) and diluted with deionized water (100 mL). The reaction mixture was extracted with ethyl acetate (3×60 mL). The combined organic layers were washed with saturated NaHCO$_3$ solution (3×60 mL), water (60 mL) and brine (60 mL), dried over anhydrous MgSO$_4$, and concentrated in vacuo. Purification of the crude product (2.38 g) by column chromatography (silica gel, ethyl acetate/hexanes=1/1) gave 214i (0.83 g, 35%) as a colorless wax. $^1$H NMR (CDCl$_3$): δ (ppm): 3.33 (s, 4H), 2.41 (t, J=7.4, 4H), 1.85 (br, 2H), 1.62-1.45 (m, 4H), 1.35-1.18 (m, 16H), 0.87 (s, 12H). $^{13}$C NMR (CDCl$_3$): δ(ppm): 212.09, 72.10, 42.99, 38.75, 35.20, 30.48, 29.42, 24.05, 23.99, 23.82. HRMS (LSIMS, gly): Calcd for $C_{21}H_{43}O_3$ (MH$^+$): 343.3212. found: 343.3208. HPLC: 96.4% pure.

2-[7-Isocyano-2,2-dimethyl-7-(toluene-4-sulfonyl)-heptyloxy]-tetrahydropyran (215). Method A. To a solution of TosMIC (9.75 g, 49.9 mmol) and tetrabutylammonium iodide (1.69 g, 4.6 mmol) in anhydrous DMSO (240 mL) was added NaH (2.2 g, 55.0 mmol, 60% in mineral oil), while cooling with an ice bath. 207c (14.65 g, 50 mmol) was added dropwise over 1 h and the reaction mixture was stirred at room temperature overnight. The mixture was quenched with water (100 mL) and extracted with CH$_2$Cl$_2$ (3×100 mL). The combined organic layers were washed with water (100 mL) and half-saturated aqueous NaCl solution (100 mL), dried over anhydrous Na$_2$SO$_4$, and concentrated in vacuo to afford the crude product (30 g), which was purified by column chromatography (silica gel; hexanes/ethyl acetate=90/10) to obtain 215 (5.4 g, 27%) as a colorless oil. $^1$H NMR (CDCl$_3$): δ 7.87 (d, 2H, J=8.2), 7.43 (d, 2H, J=8.2), 4.56-4.40 (m, 2H), 3.83 (t, 1H, J=8.1), 3.58-3.38 (m, 1H), 3.46 (d, 1H, J=9.2), 2.97 (d, 1H, J=9.2), 2.49 (s, 3H), 2.30-1.20 (m, 16H), 0.88 (s, 6H). $^{13}$C NMR (CDCl$_3$): δ 164.7, 146.5, 131.1, 130.1, 99.1, 76.2, 62.0, 38.7, 34.1, 30.6, 28.3, 26.2, 25.5, 24.5, 23.0, 21.8, 19.5. HRMS (LSIMS, nba): Calcd for $C_{22}H_{34}NSO_4$ (MH$^+$): 408.2209. found: 408.2205.

Method B. To a solution of TosMIC (3.9 g, 20.0 mmol) in anhydrous DMF (100 mL) was added K$_2$CO$_3$ (5.52 g, 39.9 mmol), 207c (11.72 g, 40.0 mmol), and tetrabutylammonium iodide (0.74 g, 1.95 mmol). The reaction mixture was stirred at room temperature for 20 h and then heated to 50° C. for 4 h. The reaction mixture was poured into ice water (300 mL) and extracted with $CH_2Cl_2$ (3×60 mL). The combined organic layers were washed with water (2×100 mL), dried over anhydrous $Na_2SO_4$ and concentrated in vacuo to afford the crude product, which was purified by column chromatography (silica gel; hexanes/ethyl acetate=90/10) to give 215 (5.6 g, 69%) as a colorless oil.

1,12-Dihydroxy-2,2,11,11-tetramethyldodecan-6-one (217). To a solution of 215 (6.5 g, 15.9 mmol) in anhydrous DMSO (70 mL) was added NaH (0.77 g, 19.3 mmol, 60% in mineral oil), 207a (4.91 g, 17.6 mmol), and tetrabutylammonium iodide (0.59 g, 1.6 mmol). The reaction mixture was stirred at room temperature for 24 h and hydrolyzed with water (100 mL). The product was extracted with $CH_2Cl_2$ (3×100 mL). The combined organic layers were washed with water (3×100 mL), dried over anhydrous $Na_2SO_4$ and concentrated in vacuo to give the crude intermediate (14.0 g). This crude material was heated to reflux in concentrated HCl (17 mL) and methanol (100 mL) overnight. The reaction mixture was poured into ice water (200 mL) and extracted with $Et_2O$ (3×100 mL). The combined organic layers were washed with 5% NaOH solution (60 mL) and water (2×100 mL), dried over $Na_2SO_4$, and concentrated in vacuo. The residue was purified by column chromatography (silica gel; hexanes/ethyl acetate=80/20), affording 217 (2.5 g, 58%) as a colorless oil. $^1$H NMR (CDCl$_3$): δ 3.31 (s, 2H), 3.28 (s, 2H), 2.42-2.37 (m, 4H), 2.4-1.8 (m br., 2H), 1.56-1.48 (m, 4H), 1.22-1.14 (m, 6H), 0.85 (s, 6H), 0.84 (s, 6H). $^{13}$C NMR (CDCl$_3$): δ 212.0, 71.5, 71.1, 43.0, 42.7, 38.2, 37.7, 35.0, 34.9, 30.8, 24.6, 23.9, 23.8, 23.4, 17.8. HRMS (LSIMS, gly): Calcd for $C_{16}H_{33}O_3$ (MH$^+$): 273.2430. found: 273.2422. HPLC: 91.4% pure.

1,13-Dihydroxy-2,2,12-trimethyl-12-phenyltridecan-7-one (218). To a solution of 215 (5.3 g, 13.0 mmol) in anhydrous DMSO (60 mL) was added NaH (0.62 g, 15.5 mmol, 60% in mineral oil), 207d (4.6 g, 12.9 mmol), and tetrabutylammonium iodide (0.48 g, 1.3 mmol). The reaction mixture was stirred at room temperature overnight and hydrolyzed with water (100 mL). The product was extracted with $CH_2Cl_2$ (3×100 mL) and the combined organic phases were washed with water (100 mL) and half-saturated aqueous NaCl solution (100 mL), dried over sodium sulfate and concentrated in vacuo to get the crude intermediate (9.0 g). This crude material was heated to reflux in concentrated HCl (13.4 mL) and methanol (60 mL) overnight. The reaction mixture was poured into water (200 mL) and the product was extracted with $Et_2O$ (3×60 mL). The combined organic layers were washed with water (3×20 ml), dried over anhydrous $Na_2SO_4$ and concentrated in vacuo. The residue was purified by column chromatography (silica gel; hexanes/ethyl acetate=2/1), affording 218 (3.2 g, 71%) as a colorless oil. $^1$H NMR (CDCl$_3$): δ 7.38-7.16 (m, 5H), 3.67 (d, 1H, J=10.9), 3.52 (d, 1H, J=10.9), 3.26 (s, 2H), 2.40-2.20 (m, 4H), 1.85-1.60 (m, 3H), 1.60-1.40 (m, 5H), 1.33 (s, 3H), 1.28-1.10 (m, 5H), 1.10-0.90 (m, 1H), 0.83 (s, 6H). $^{13}$C NMR (CDCl$_3$=77.0 ppm): δ 211.5, 144.6, 128.3, 126.6, 126.0, 72.3, 71.6, 43.3, 42.5, 38.2, 34.9, 24.6, 24.4, 23.8, 23.4, 21.5. HRMS (LSIMS, gly): Calcd for $C_{22}H_{37}O_3$ (MH$^+$): 349.2743. found: 349.2731. HPLC: Alltima C-8 column, 250×4.6 mm, 5; 50% acetonitrile/50% water, flow rate 1.0 mL/min; RI, retention time 12.87 min, 84.9% pure.

1,14-Dihydroxy-2,2,13,13-tetramethyltetradecan-7-one (219). According to the procedure described for the synthesis of 217, 215 (6.98 g, 17.1 mmol) was reacted with NaH (0.82 g, 20.5 mmol, 60% in mineral oil), 207g (5.8 g, 18.9 mmol), and tetrabutylammonium iodide (0.63 g, 1.7 mmol) in anhydrous DMSO (100 mL) for 24 h at room temperature. The crude intermediate (10.9 g) obtained after aqueous workup was heated to reflux in concentrated HCl (18 mL) and methanol (100 mL) overnight. After extraction and column chromatography (silica gel; hexanes/ethyl acetate=80/20), 219 (2.3 g, 48%) was obtained as a colorless oil. $^1$H NMR (CDCl$_3$): δ 3.30 (s, 4H), 2.48-2.34 (m, 4H), 1.85 (br., 2H), 1.66-1.46 (m, 4H), 1.24-1.14 (m, 10H), 0.85 (s, 12H). $^{13}$C NMR (CDCl$_3$): δ 211.8, 71.8, 71.6, 42.7, 42.6, 38.4, 38.2, 34.9, 30.1, 24.6, 23.8, 23.8, 23.7, 23.6, 23.4. HRMS (LSIMS, gly): Calcd for $C_{18}H_{37}O_3$ (MH$^+$): 301.2743. found: 301.2745. HPLC: 97.4% pure.

7-Isocyano-2,2-dimethyl-7-(toluene-4-sulfonyl)-heptanoic acid ethyl ester (220). Under nitrogen atmosphere, to a stirred solution of tetrabutylammonium iodide (4.23 g, 11.5 mmol) and TosMIC (27.56 g, 141.2 mmol) in anhydrous DMSO (500 mL) was added NaH (60% w/w in mineral oil, 5.80 g, 145.0 mmol), while keeping the internal temperature between 10 and 15° C. After the dropwise addition of 205e (36.60 g, 145.7 mmol), the mixture was stirred at room temperature for 20 h, then cooled with an ice-bath and carefully hydrolyzed with water (600 mL). The solution was extracted with $CH_2Cl_2$ (4×150 mL). The combined organic layers were washed with water (200 mL) and half-saturated aqueous NaCl solution (200 mL), dried over anhydrous MgSO$_4$, and concentrated in vacuo to obtain the crude product mixture (40.9 g) as an orange oil. A portion of this crude product (13.0 g) was purified by column chromatography (silica gel; hexanes/ethyl acetate=10/1, then 9/1), affording 220 (1.92 g, 12%) as a pale yellow oil, 208c (0.70 g, 3%) as a colorless oil, and a mixture of both (2.50 g, ratio 9/1). $^1$H NMR (CDCl$_3$): δ 7.86 (d, 2H, J=8.1), 7.43 (d, 2H, J=8.1), 4.48 (dd, 1H, J=7.2, 3.6), 4.11 (q, 2H, J=7.2), 2.49 (s, 3H), 2.21-2.16 (m, 1H), 1.90-1.78 (m, 1H), 1.56-1.50 (m, 4H), 1.35-1.20 (m, 2H), 1.25 (t, 3H, J=7.2), 1.16 (s, 6H). $^{13}$C NMR (CDCl$_3$): δ 177.8, 165.0, 146.7, 131.3, 130.3, 130.2, 72.9, 60.5, 42.2, 40.2, 28.3, 25.8, 25.3, 25.2, 24.2, 21.9, 14.4. HRMS (LSIMS, nba): Calcd for $C_{19}H_{28}NO_4S$ (MH$^+$): 366.1739. found: 366.1746.

Ethyl 12-hydroxy-2,2,11,11-tetramethyl-7-oxo-dodecanoate (221). Under nitrogen atmosphere, to a solution of 220 (1.72 g, 4.68 mmol), tetrabutylammonium iodide (0.17 g, 0.46 mmol) and 207a (1.45 g, 5.19 mmol) in anhydrous DMSO (20 mL) was added NaH (60% w/w in mineral oil, 0.19 g, 4.75 mmol), while keeping the internal temperature between 10 and 15° C. The reaction mixture was stirred for 20 h at room temperature and then carefully hydrolyzed with ice-water (100 mL). The mixture was extracted with $CH_2Cl_2$ (3×15 mL). The combined organic layers were washed with water (40 mL) and saturated aqueous NaCl solution (2×20 mL), dried over anhydrous MgSO$_4$, and concentrated in vacuo to obtain the crude intermediate (3.50 g) as brown oil. A solution of this intermediate in 48% $H_2SO_4$ (6 mL) and methanol (12 mL) was stirred for 100 min at room temperature. The mixture was diluted with water (50 mL) and extracted with $CH_2CO_2$ (3×15 mL). The combined organic layers were washed with water (100 mL) and saturated aqueous NaCl solution (100 mL), dried over anhydrous MgSO$_4$, and concentrated in vacuo to obtain the crude product (2.70 g) as yellow oil. A portion of the crude product (2.50 g) was subjected to column chromatography (silica gel; hexanes/ethyl acetate=80/20, then 75/25) to give 221 (0.82 g, 60%) as a pale yellow oil. $^1$H NMR (CDCl$_3$): δ 4.14-4.03 (m, 2H), 3.31 (br. s, 2H), 2.42 (br., 1H), 2.39 (m, 4H), 1.54-1.48 (m, 6H), 1.24-1.18 (m, 7H), 1.14 (s, 6H), 0.86 (s, 6H). $^{13}$C NMR (CDCl$_3$): δ 211.7, 178.0, 71.2, 60.3, 43.2, 42.7, 42.1, 40.4, 37.9, 35.1, 25.2, 24.6, 24.2, 24.1, 18.0, 14.3. HRMS (LSIMS, gly): Calcd for $C_{18}H_{35}O_4$ (MH$^+$): 315.2535. found: 315.2541.

Ethyl 14-Hydroxy-2,2,13,13-tetramethyl-7-oxotetradecanoate (222). According to the procedure for the synthesis of 220, 205c (45.6 g, 182 mmol) was reacted with TosMIC (35.2 g, 180 mmol), tetrabutylammonium iodide (4.3 g, 11.6 mmol) and NaH (60% w/w in mineral oil, 7.3 g, 183 mmol) in anhydrous DMSO (500 mL). To this solution was added tetrabutylammonium iodide (4.3 g, 11.6 mmol) and 207g (43.8 g, 143 mmol) in anhydrous DMSO (20 mL), and then NaH (7.4 g, 185 mmol, 60% w/w in mineral oil) at 10° C. The reaction mixture was stirred at room temperature for 20 h, cooled with an ice-bath, and carefully hydrolyzed with ice-water (1000 mL). The product was extracted with $CH_2Cl_2$ (5×100 mL). The combined organic layers were dried over anhydrous $MgSO_4$ and concentrated in vacuo to obtain the crude intermediate (115 g) as a red oil. This intermediate was dissolved in 48% $H_2SO_4$ (147 mL) and methanol (480 mL) and the mixture was stirred for 100 min at room temperature. After dilution with water (1500 mL), the product was extracted with $CH_2Cl_2$ (2×150 mL, 100 mL, 50 mL). The combined organic layers were washed with saturated aqueous sodium carbonate solution (150 mL) and saturated aqueous NaCl solution (150 mL), dried over $MgSO_4$, filtered through a short column (aluminum oxide; ethyl acetate), and concentrated in vacuo to obtain the crude product (89 g) as a yellow oil. The crude product was subjected to column chromatography (silica gel; hexanes/ethyl acetate=6:1, then 3:1) to give 222 (17.6 g, 36%) as a pale yellow oil. $^1$H NMR (CDCl$_3$): δ 4.10 (q, 2H, J=6.9), 3.30 (br. s, 2H), 2.39 (t, 4H, J=6.9), 1.98 (br., 1H), 1.56-1.48 (m, 6H), 1.27-1.18 (m, 11H), 1.14 (s, 6H), 0.85 (s, 6H). $^{13}$C NMR (CDCl$_3$): δ 211.5, 178.0, 71.9, 60.3, 42.9, 42.7, 42.2, 40.5, 38.6, 35.1, 30.3, 25.2, 24.7, 24.2, 24.0, 23.8, 14.4. HRMS (LSIMS, gly): Calcd for $C_{20}H_{39}O_4$ (MH$^+$): 343.2848. found: 343.2846.

2,2,11,11-Tetramethyl-7-oxododecanedioic acid 1-ethyl ester (223). A mixture of 221 (3.26 g, 10.4 mmol) and pyridinium dichromate (14.0 g, 37.2 mmol) in DMF (45 mL) was stirred at room temperature for 46 h. The solution was diluted with 48% $H_2SO_4$ (30 mL) and water (300 mL) and extracted with ethyl acetate (5×100 mL). The combined organic layers were washed with saturated aqueous NaCl solution (5×100 mL), dried over anhydrous $MgSO_4$, and concentrated in vacuo to give the crude product (3.19 g) as greenish oil. The crude product was subjected to column chromatography (silica gel; hexanes/ethyl acetate=3:1, 2:1), affording 223 (2.69 g, 79%) as a pale yellow oil. $^1$H NMR (CDCl$_3$): δ 11.30 (br., 1H), 4.10 (q, 2H, J=7.2), 2.39 (t, 4H, J=7.2), 1.56-1.48 (m, 8H), 1.25-1.15 (m, 2H), 1.24 (t, 3H, J=7.2), 1.20 (s, 6H), 1.15 (s, 6H). $^{13}$C NMR (CDCl$_3$): δ 210.9, 184.4, 178.1, 60.4, 43.1, 42.7, 42.2, 40.5, 39.8, 25.3, 25.0, 24.7, 24.3, 19.3, 14.4. HRMS (LSIMS, gly): Calcd for $C_{18}H_{33}O_5$ (MH$^+$): 329.2328. found: 329.2330.

2,2,13,13-Tetramethyl-7-oxotetradecanedioic acid 1-ethyl ester (224). A mixture of 222 (10.53 g, 30.7 mmol) and pyridinium dichromate (32.5 g, 86.4 mmol) in DMF (120 mL) was stirred at 30° C. for 40 h. The mixture was poured into 48% sulfuric acid (50 mL) and water (700 mL). The product was extracted with ethyl acetate (3×200 mL, 2×100 mL). The combined organic layers were washed with saturated aqueous NaCl solution (4×100 mL), dried over anhydrous $MgSO_4$, and concentrated in vacuo to give the crude product (10.3 g) as a pale yellow oil. This crude material was purified by column chromatography (silica gel; hexanes/ethyl acetate=75/25) to afford 224 (7.40 g, 68%) as a yellowish oil. $^1$H NMR (CDCl$_3$): δ 4.10 (q, 2H, J=7.5), 2.39 (m, 4H), 1.56-1.49 (m, 8H), 1.26-1.21 (m, 10H), 1.18 (s, 6H), 1.15 (s, 6H). $^{13}$C NMR (CDCl$_3$): δ 211.4, 184.2, 178.0, 60.3, 42.8, 42.7, 42.1, 40.5, 40.4, 29.7, 25.2, 24.8, 24.7, 24.3, 23.7, 14.3. HRMS (LSIMS, gly): Calcd for $C_{20}H_{37}O_5$ (MH$^+$): 357.2641. found: 357.2641.

2,2,11,11-Tetramethyl-6-oxododecanedioc acid (225). According to the procedure given for 209f, 223 (2.50 g, 7.6 mmol) was saponified with KOH (1.80 g, 27.3 mmol) in water (3 mL) and ethanol (8 mL) at reflux for 4 h. After the usual workup, the crude product (2.17 g) was recrystallized from Et$_2$O/hexanes (15 mL/25 mL) to give 225 (1.36 g, 60%) as white needles. Mp 72-73° C. $^1$H NMR (CDCl$_3$): δ 12.0-11.2 (br., 2H), 2.41 (m, 4H), 1.60-1.52 (m, 8H), 1.29-1.24 (m, 2H), 1.20 (s, 6H), 1.18 (s, 6H). 3° C. NMR (CDCl$_3$): δ 211.2, 185.1, 184.9, 43.9, 42.7, 42.2, 40.3, 39.8, 25.1, 25.0, 24.7, 24.2, 19.3. HRMS (LSIMS, gly): Calcd for $C_{16}H_{29}O_5$ (MH$^+$): 301.2015. found: 301.2023. HPLC: 95.8% pure.

2,2,13,13-Tetramethyl-7-oxotetradecanedioc acid (226). According to the procedure for the synthesis of 209f, a solution of 224 (7.4 g, 20.8 mmol) and KOH (85%, 4.6 g, 69.6 mmol) in water (5 mL) and ethanol (15 mL) was heated to reflux for 4 h. The crude product (6.8 g) obtained after the usual workup was purified by repeated column chromatography (silica gel; first: hexanes/ethyl acetate=2/1, then 1/1. Second: hexanes/ethyl acetate=1/) and crystallization (Et$_2$O/hexanes, 20 mL/10 mL), affording 226 (2.95 g, 43%) as colorless needles. Mp 61-62° C. $^1$H NMR (CDCl$_3$): δ 11.91 (br., 2H), 2.41 (t, 4H, J=6.9), 2.39 (t, 4H, J=6.9), 1.58-1.52 (m, 8H), 1.30-1.22 (m, 6H), 1.18 (s, 12H). $^{13}$C NMR (CDCl$_3$): δ 211.8, 184.5, 185.4, 43.0, 42.9, 42.5, 40.7, 40.6, 29.9, 25.4, 25.1, 25.0, 24.6, 23.9. HRMS (LSIMS, gly): Calcd for $C_1H_{33}O_5$ (MH$^+$): 329.2328. found: 329.2324. HPLC: 93.5% pure.

3-{3-[3-Ethoxycarbonyl-2-methylpropyl)-benzoyl]-phenyl}-2,2-dimethylpropionic acid ethyl ester (228). Under inert gas atmosphere and at −78° C., to a stirred solution of ethyl isobutyrate (9.78 g, 84.2 mmol) in anhydrous THF (30 mL) was added dropwise a solution of lithium diisopropylamide (2.0 M, 42.2 mL, 84.4 mmol). After 1 h, 227 (10.34 g, 28.1 mmol) was added, followed by addition of N,N'-dimethylpropyleneurea (DMPU, 2.7 g, 21.1 mmol). The mixture was stirred for 30 min and then allowed to warm to room temperature over 30 min. The THF was distilled off under reduced pressure. The residue was dissolved in saturated aqueous NH$_4$Cl solution (280 mL) and extracted with ethyl acetate (3×100 mL). The combined organic layers were washed with saturated aqueous NaCl solution (200 mL), 5% HCl (100 mL) and saturated aqueous NaHCO$_3$ solution (50 mL). Drying over anhydrous Na$_2$SO$_4$ and concentration in vacuo afforded 228 (11.0 g, 89%) as an oil. $^1$H NMR (CDCl$_3$): δ 7.8-7.2 (m, 8H), 3.98 (q, 4H, J=6.9), 2.83 (s, 4H), 1.2-0.8 (m, 18H). $^{13}$C NMR (CDCl$_3$=77.0 ppm): δ 196.5, 176.8, 138.1, 137.2, 134.0, 131.4, 128.1, 127.7, 60.3, 45.7, 43.3, 24.8, 13.9.

3-(3-{2-[3-(2-Ethoxycarbonyl-2-methylpropyl}-phenyl]-[1,3]dithian-2-yl}-phenyl)-2,2-dimethylpropionic acid ethyl ester (229). To a solution of 228 (6.2 g, 14.1 mmol) and 1,3-propanedithiol (1.9 g, 17.6 mmol) in CH$_2$Cl$_2$ (100 mL) was added boron trifluoride diethyl etherate (0.52 mL, 0.58 g, 4.1 mmol). The solution was stirred at room temperature overnight. After the addition of 5% NaOH solution (17:5 mL), the organic layer was separated, washed with water (50 mL), dried over anhydrous Na$_2$SO$_4$, and evaporated to afford 229 (6.5 g, 87%) as an oil. $^1$H NMR (CDCl$_3$): δ 7.58-6.96 (m, 8H), 4.10 (q, 4H, J=7.2), 2.85 (s, 4H), 2.76 (t, 4H, J=5.6), 1.98 (m, 2H), 1.22 (t, 6H, J=7.2) 1.13 (s, 12H). $^{13}$C NMR (CDCl₃=77.0 ppm): δ 177.17, 142.18, 138.07, 131.12, 129.30, 127.84, 127.33, 60.35, 46.16, 43.48, 29.38, 24.90, 14.13.

3-(3-{2-[3-(3-Hydroxy-2,2-dimethylpropyl)-phenyl]-[1,3]dithian-2-yl}-phenyl)-2,2-dimethylpropan-1-ol (230). To a suspension of LiBH₄ (0.78 g, 35.8 mmol) in CH₂Cl₂ (55 mL) was added methanol (1.04 g, 32.5 mmol) at room temperature. After the addition of 229 (6.5 g, 12.3 mmol), the reaction mixture was heated to reflux for 6 h. After cooling to room temperature, saturated aqueous NH₄Cl solution (20 mL) and CH₂Cl₂ (15 mL) were added and the layers were separated. The aqueous layer was extracted with CH₂Cl₂ (2×10 mL). The combined organic layers were dried over anhydrous Na₂SO₄ and concentrated in vacuo to afford 230 (4.66 g, 85%) as an oil. ¹H NMR (CDCl₃): δ 7.42 (s br., 2H), 7.17 (m, 4H), 6.97 (m, 2H), 3.63 (s, 4H), 3.16 (s, 4H), 2.69 (m, 2H), 2.47 (m, 4H), 1.88 (m, 2H), 0.75 (s, 12H). ¹³C NMR (CDCl₃): δ 142.39, 139.18, 131.69, 129.88, 128.05, 127.01, 71.12, 44.89, 43.74, 36.70, 29.63, 24.22.

3-{3-[3-(2-Carboxy-2-methylpropyl)-benzoyl]-phenyl}-2,2-dimethylpropionic acid (231). According to the procedure for the synthesis of 209f, a mixture of 228 (4.38 g, 10.0 mmol) and KOH (85%, 1.57 g, 23.8 mmol) was heated to reflux in water (1.5 mL) and ethanol (5 mL) for 3 h. After extraction and drying in high vacuo, 231 (3.88 g, quantitative) was obtained as a white solid. Mp 46-48° C. ¹H NMR (CDCl₃): δ 11.2-10.6 (br., 2H), 7.8-7.2 (m, 8H), 2.83 (s, 4H), 1.25 (s, 12H). ¹³C NMR (CDCl₃): δ 198.02, 183.86, 138.61, 137.73, 134.56, 130.54, 128.41, 128.10, 46.69, 43.77, 24.83. HRMS (LSIMS, nba): Calcd for C₂₃H₂₇O₅ (MH⁺): 383.1858. found: 383.1858. HPLC: 88.3% pure.

Bis[3-(3-hydroxy-2,2-dimethylpropyl)-phenyl]-methanone (232). A suspension of copper(II) oxide (0.96 g, 12.1 mmol) and anhydrous copper(II) chloride (3.2 g, 23.8 mmol) in acetone (80 mL) was heated to reflux. A solution of 230 (4.44 g, 10.0 mmol) in acetone (20 mL) and DMF (1.2 mL) was added dropwise over 5 min. After 90 min at reflux temperature, the reaction mixture was cooled to room temperature and filtered. The insoluble material was washed with CH₂Cl₂ (3×20 mL). The combined organic solutions were washed with aqueous 2 N Na₂CO₃ solution (50 mL), dried over anhydrous Na₂SO₄, and concentrated in vacuo. The residue was purified by column chromatography (silica gel; hexanes/acetone=80/20) to give 232 (2.5 g, 71%) as an oil. ¹H NMR (CDCl₃): δ 7.68-7.30 (m, 8H), 3.31 (s, 4H), 3.03 (s br., 2H), 2.65 (s, 4H), 0.88 (s; 12H). ¹³C NMR (CDCl₃=77.00 ppm): δ 197.42, 139.06, 136.96, 134.60, 131.88, 127.78, 127.55, 70.39, 44.07, 36.30, 23.80. HRMS (LSIMS, nba): Calcd for C₂₃H₃₁O₃ (MH⁺): 355.2273. found: 355.2263. HPLC: 94.5% pure.

Syntheses of Intermediates

2-Phenylpropionic acid ethyl ester (202). Under N₂ atmosphere, a solution of ethyl phenylacetate (800.0 g, 4.87 mol) in anhydrous THF (6.4 L) was cooled to −40° C. and a solution of LDA (2.0 M in heptane/THF, ethylbenzene, 2.43 L, 4.86 mol) was added dropwise over 30 min. The reaction mixture was stirred for 1 h, and methyl iodide (968 g, 6.82 mol) was added dropwise over 20 min, followed by the addition of DMPU (320 mL). After 1 h, the reaction mixture was allowed to warm to room temperature and stirred overnight. The reaction mixture was poured into water (6.4 L) and extracted with ethyl acetate (3×1.6 L). The combined organic layers were washed with saturated aqueous NH₄Cl solution (1.6 L), 1 N HCl (1.6 L), saturated aqueous NaHCO₃ solution (1.6 L), and saturated aqueous NaCl solution (1.6 L). The solution was dried over MgSO₄ and concentrated in vacuo. The residue was distilled in high vacuo to give 202 (620.0 g, 72%) as a colorless oil. Bp 55-60° C./0.2 Torr (lit. (Shiner, V. J. et al. *J. Am. Chem. Soc.* 1961, 83, 593-598) bp 59-60° C./0.3 Torr). ¹H NMR (CDCl₃): δ 7.36-7.18 (m, 5H), 4.11 (m, 2H), 3.69 (q, 1H, J=7.1), 1.49 (d, 3H, J=7.1), 1.19 (t, 3H, J=7.1). ¹³C NMR (CDCl₃): δ 174.44, 140.73, 128.57, 127.48, 127.04, 60.66, 45.59, 18.66, 14.16.

Ethyl 2-p-Tolylpropionate (203). According to the procedure given for the synthesis of 202, ethyl p-tolylacetate (2.72 g, 15.2 mmol) was reacted with LDA (7.6 mL, 15.25 mmol) and methyl iodide (3.03 g, 21.30 mmol) in anhydrous THF (70 mL) and DMPU (1 mL). After aqueous workup and extraction, the residue was distilled in high vacuo to give 203 (2.5 g, 86.0%) as an oil. Bp 59-63° C./0.2 mmHg. ¹H NMR (CDCl₃): δ (ppm) 7.18 (d, 2H, J=8.1), 7.10 (d, 2H, J=8.1), 4.09 (m, 2H), 3.67 (q, 1H, J=7.2), 2.29 (s, 3H), 1.47 (d, J=7.2 Hz, 3H), 1.20 (t, J=5.7 Hz, 3H). ¹³C NMR (75 MHz, CDCl₃/TMS): δ (ppm) 174.71, 137.80, 136.63, 129.33, 129.14, 127.36, 60.66, 45.18, 21.05, 18.70, 14.15.

2-(4-Isobutylphenyl)-propionic acid ethyl ester (204). A solution of 2-(4-isobutylphenyl)-propionoic acid (Ibuprofen, 9.6 g, 46.5 mmol) and p-toluenesulfonic acid monohydrate (1.52 g, 7.9 mmol) in benzene (100 mL) and ethanol (75 mL) was heated to reflux using a Dean-Stark apparatus for 4 h. The solvent was removed under reduced pressure and the residue was taken up in Et₂O (100 mL). The solution was extracted with saturated aqueous NaHCO₃ solution (2×100 mL) and water (2×100 mL). The organic layer was dried over anhydrous Na₂SO₄, filtered and concentrated, affording 204 (10.44 g, 96%) as a clear oil. ¹H NMR (CDCl₃): δ 7.19 (d, 2H, J=8.0), 7.08 (d, 2H, J=8.0), 4.10 (m, 2H), 3.66 (q, 1H, J=7.0), 2.44 (d, 2H, J=7.0), 1.84 (m, 1H), 1.47 (d, 3H, J=7.0), 1.19 (t, 3H, J=7.3), 0.89 (d, 6H, J=7.0). ¹³C NMR (CDCl₃): δ 174.92, 140.59, 138.07, 129.45, 127.29, 60.79, 45.32, 45.21, 30.35, 22.55, 18.78, 14.29. HRMS (LSIMS, nba): Calcd for C₁₅H₂₃O₂ (MH⁺): 235.1698. found: 235.1688.

Ethyl 5-Bromo-2,2-dimethylpentanoate (205a). Described in lit. (Kuwahara, M. et al. *Chem. Pharm. Bull.* 1997, 45, 1447-1457) Bp 65.0-66.5° C./0.4 mm Hg (lit. 71-73° C./0.25 mm Hg). ¹H NMR (CDCl₃): 4.12 (q, 2H, J=7.1), 3.38 (t, 2H, J=6.4), 1.88-1.75 (m, 2H), 1.69-1.61 (m, 2H), 1.25 (t, 3H, J=7.1), 1.18 (s, 6H). ¹³C NMR (CDCl₃): 177.54, 60.49, 41.87, 39.22, 33.97, 28.63, 25.26, 14.34.

Ethyl 5-Bromo-2-methyl-2-phenyl-pentanoate (205b). Under Ar-atmosphere, to a solution of ethyl phenylacetate (42.4 g, 0.26 mol) and DMPU (5 mL) in THF (250 mL) was added dropwise a solution of LDA (2 M, 135 mL, 0.27 mol) at −78° C. The mixture was stirred for 2 h, before methyl iodide (41.40 g, 0.29 mol) was added in a single portion. The mixture was stirred overnight and allowed to warm to room temperature. After cooling to −78° C., 1,3-dibromopropane (72.7 g, 0.36 mol) was added and the mixture was allowed to stir overnight, gradually warming to room temperature. The mixture was hydrolyzed by consecutive addition of ice (200 g), saturated aqueous NH₄Cl solution (400 mL), and coned HC (100 mL), and extracted with ethyl acetate (2×200 mL). The organic layers were dried over anhydrous MgSO₄, and distilled under vacuum to give 205b as colorless oil (88.6 g, 59%). Bp 123-128° C./0.25 mmHg. ¹H NMR (CDCl₃): 7.20-7.10 (m, 5H), 4.12 (q, 2H, J=7.2), 3.35 (t, 2H, J=6.9), 2.18-2.00 (m, 2H), 1.77-1.72 (m, 2H), 1.56 (s, 3H), 1.18 (t, 3H, J=6.9). ¹³C NMR (CDCl₃): 175.9, 143.4, 128.5, 126.9, 126.0, 61.0, 49.8, 38.2, 34.0, 28.5, 22.8, 14.2.

Ethyl 6-Bromo-2,2-dimethylhexanoate (205e). This compound was prepared as described in lit. (Ackerley, N. et al. *J. Med. Chem.* 1995, 38, 1608-1628; Manley, P. W. et al. *J. Med. Chem.* 1987, 30, 1812-1818). Bp 65° C./0.15 mmHg (lit. 86° C./0.2 mmHg; lit. 62-64° C./0.40 mmHg). ¹H NMR (CDCl₃):

4.15 (q, 2H, J=7.1), 3.41 (t, 2H, J=6.7), 1.85 (qv, 2H, J=6.7), 1.60-1.45 (m, 2H), 1.40-1.30 (m, 2H), 1.28 (t, 3H, J=7.1), 1.20 (s, 6H). $^{13}$C NMR (CDCl$_3$): 177.3, 60.0, 41.8, 39.4, 33.2, 32.9, 24.9, 23.34, 14.02.

Ethyl 6-Bromo-2-methyl-2-phenylhexanoate (205d). A solution of LDA (14 mL, 28 mmol, 2.0 M in heptane) was added dropwise to a stirred solution of 202 (5.0 g, 28.06 mmol) in anhydrous THF (50 mL) at −78° C. After 1 h, the reaction mixture was added to a −78° C. cold solution of 1,4-dibromobutane (10.06 g, 23.1 mmol) in THF. After the addition of DMPU (5 mL), the reaction mixture was stirred for 1 h, then warmed to room temperature and stirred overnight. The mixture was poured into saturated aqueous NH$_4$Cl solution (500 mL) and extracted with ethyl acetate (4×100 mL). The combined organic phases were washed with brine (100 mL), 1 M HCl (50 mL), saturated aqueous NaHCO$_3$ solution (50 mL), and brine (100 mL). The solution was dried over anhydrous MgSO$_4$ and concentrated in vacuo. The residue was distilled to give 205d as an oil (7.16 g, 99%). Bp 130-131° C./0.2 mm Hg. $^1$H NMR (CDCl$_3$), δ (ppm): 7.40-7.15 (m, 5H), 4.13 (q, 2H, J=6.7), 3.36 (t, 2H, J=6.7), 2.02 (m, 2H), 1.86 (m, 2H), 1.56 (s, 3H), 1.34 (m, 2H), 1.18 (t, 3H, J=6.7). $^{13}$C NMR (CDCl$_3$), δ (ppm): 176.13, 143.91, 128.51, 126.81, 126.03, 60.93, 50.22, 38.53, 33.56, 33.30, 23.58, 22.77, 14.22. HRMS (FAB): Calcd for C$_{15}$H$_{21}$$^{79}$BrO$_2$ (MH$^+$): 313.0803. found 313.0786.

Ethyl 6-Bromo-2-methyl-2-p-tolylhexanoate (205e). This compound was prepared according to the procedure for 205d to give 205e (22.0 g, 90%) as an oil. Bp 128-130° C./0.2 mmHg). $^1$H NMR (CDCl$_3$): δ (ppm) 7.19 (d, 2H, J=8.2 Hz); 7.12 (d, 2H, J=8.2 Hz), 4.13 (q, 2H, J=7.2 Hz), 3.37 (t, J=6.6 Hz, 2H), 2.32 (s, 3H), 2.10-1.80 (m, 4H), 1.54 (s, 3H), 1.36 (m, 2H), 1.19 (t, J=7.2 Hz, 3H). $^{13}$C NMR (CDCl$_3$): δ (ppm) 176.26, 140.92, 136.35, 129.21, 125.89, 60.88, 49.82, 38.53, 33.61, 33.33, 23.59, 22.78, 21.07, 14.25. HRMS (FAB, nba): Calcd for (C$_{16}$H$_{23}$BrO$_2$) 327.0959. found 327.0975.

6-Bromo-2-(4-isobutylphenyl)-2-methylhexanoic acid ethyl ester (205f). Under nitrogen atmosphere and at −78° C., to a solution of 204 (10.5 g, 44.8 mmol) in anhydrous THF (150 mL) was added a solution of LDA (2.0 M, 28 mL, 56 mmol) and the mixture was stirred for 1 h. 1,4-Dibromobutane (25 mL, 37.5 g, 175 mmol) was then added dropwise over 30 min and the solution allowed to warm to room temperature over 5 h. After stirring at room temperature for an additional 16 h, the reaction was hydrolyzed with water (100 mL) and extracted with Et$_2$O (2×100 mL). The combined organic layers were washed with 10% HCl (2×100 mL), saturated aqueous NaHCO$_3$ solution (100 mL) and water (100 mL). After drying with Na$_2$SO$_4$ (5 g), filtration and concentration, the crude product was purified by flash chromatography (silica gel; ethyl acetate/hexanes=5/95) and dried in high vacuo (0.5 mmHg) at 150° C. for 30 min, affording 205f (14.49 g, 88%) as a clear, viscous oil. $^1$H NMR (CDCl$_3$): δ 7.19 (d, 2H, J=8.0), 7.08 (d, 2H, J=8.0), 4.11 (q, 2H, J=7.0), 3.35 (t, 2H, J=6.8), 2.43 (d, 2H, J=7.3), 2.10-1.92 (m, 1H), 1.92-1.78 (m, 4H), 1.53 (s, 3H), 1.40-1.28 (m, 2H), 1.17 (t, 3H, J=7.0), 0.88 (d, 6H, J=6.8). $^{13}$C NMR (CDCl$_3$): δ 176.17, 141.12, 140.04, 129.14, 125.64, 60.77, 49.80, 44.99, 38.52, 33.51, 33.26, 30.22, 23.55, 22.69, 22.50, 14.19. HRMS (LSIMS, nba): Calcd for C$_{19}$H$_{30}$O$_2$Br (MH$^+$): 369.1429. found: 369.1445.

Ethyl 7-Bromo-2,2-dimethylheptanoate (205g). Under argon atmosphere, a solution of 1,5-dibromopentane (500 g, 2.2 mol) and ethyl isobutyrate (221 g, 1.9 mol) in anhydrous THF (4 L) was chilled in a dry ice/acetone bath to −78° C. Over a 40 min period, LDA solution in THF (1.8 M, 1 L, 1.8 mol) was added dropwise. After the addition, the solution was allowed to stir overnight and gradually warm to room temperature. Careful quenching of the excess base by slow addition of saturated aqueous NH$_4$Cl solution (3 L) furnished a two-phase mixture. The organic layer was separated and evaporated under vacuum to a minimum volume (ca. 1 L). The organic residue was recombined with the aqueous layer and the resulting mixture was extracted with ethyl acetate (3×1 L). The combined ethyl acetate layers were then washed with 1 N HCl (5 L), water (3 L) and saturated aqueous NaHCO$_3$ solution (4 L) before drying over anhydrous MgSO$_4$. Concentration in vacuo gave crude material (468.7 g), which was then purified by distillation affording 205g (208.7 g, 44%) as a colorless oil. Bp 106-108° C./0.01 mm Hg. $^1$H NMR (CDCl$_3$): δ 4.11 (q, 2H, J=7.2), 3.39 (t, 2H, J=6.8), 1.85 (m, 2H), 1.56-1.35 (m, 4H), 1.24 (t, 3H, J=7.2), 1.31-1.19 (m, 2H), 1.16 (s, 6H). $^{13}$C NMR (CDCl$_3$): δ 177.9, 60.2, 42.1, 40.5, 33.8, 32.6, 28.6, 25.2, 24.2, 14.3. HRMS (EI): Calcd for C$_{11}$H$_{22}$BrO$_2$ (MH$^+$) 265.0803. found 265.0810.

Ethyl 7-Bromo-2-methyl-2-phenylheptanoate (205h). Under N$_2$ atmosphere, a solution of LDA (2.0 M in heptane/ THF/ethylbenzene, 1.85 mL, 3.70 mol) was added dropwise to a stirred solution of 202 (660 g, 3.70 mol) in anhydrous THF (6.6 L) over 30 min at −78° C. After 1 h, 1,5-dibromopentane (1390 g, 6.05 mol) was added, followed by the addition of DMPU (660 mL). The reaction mixture was stirred for 1 h, then warmed to room temperature and stirred overnight. The mixture was poured into saturated aqueous NH$_4$Cl solution (24 L) and extracted with ethyl acetate (4×6.7 L). The combined organic layers were washed with brine (9 L), 1 N HCl (6 L), saturated aqueous NaHCO$_3$ solution (6 L), and brine (6 L). The solution was dried over MgSO$_4$ and concentrated in vacuo. The residue was distilled in high vacuo to yield 205h (700 g, 58%) as a yellowish oil. Bp 140-145° C./0.3 mmHg. $^1$H NMR (CDCl$_3$): δ 7.30-7.20 (m, 5H), 4.09 (m, 2H), 3.34 (t, 2H, J=6.9), 2.05-1.80 (m, 4H), 1.53 (s, 3H), 1.43-1.14 (m, 4H), 1.16 (t, 3H, J=6.6). $^{13}$C NMR (CDCl$_3$): δ 176.03, 143.99, 128.33, 126.60, 125.89, 60.68, 50.11, 39.03, 33.75, 32.51, 28.59, 23.93, 22.78, 14.10. HRMS (LSIMS, nba): Calcd for C$_{16}$H$_{24}$BrO$_2$ (MH$^+$): 327.0960. found: 327.0952. HPLC: 91.2% pure.

Ethyl 8-bromo-2,2-dimethyloctanoate (205i). Under N$_2$ atmosphere, a solution of LDA (2.0 M in heptane/THF/ethylbenzene, 2.94 L, 5.9 mol) was added dropwise to a stirred solution of ethyl isobutyrate (720 g, 6.2 mol) in anhydrous THF (4.7 L) at −45° C. After 1 h, 1,6-dibromohexane (2400 g, 9.8 mol) was added dropwise, followed by the addition of DMPU (320 mL). The reaction mixture was stirred for 1 h and then allowed to warm to room temperature overnight. Saturated NH$_4$Cl solution (3 L) was added and the mixture was extracted with ethyl acetate (3×6 L). The combined organic layers were washed with brine (4.5 L), 1 M aqueous HCl (6 L), saturated NaHCO$_3$ solution (6 L), and brine (4.5 L). The solution was dried over anhydrous MgSO$_4$ and concentrated in vacuo. The residue was distilled under high vacuo to furnish 205i (856 g, 52%) as a light yellowish oil. Bp 95-100° C./0.2 mmHg. $^1$H NMR (CDCl$_3$): δ (ppm): 4.13 (q, J=7.1, 2H), 3.39 (t, J=6.9, 2H), 1.92-1.75 (m, 2H), 1.58-1.25 (m, 8H), 1.25 (t, J=7.1, 3H), 1.12 (s, 6H). $^{13}$C NMR (CDCl$_3$=77.52 ppm): δ (ppm): 177.62, 60.01, 42.08, 40.50, 33.63, 32.68, 29.13, 27.93, 25.00, 24.66, 14.22. HRMS (LSIMS, nba): Calcd for C$_{12}$H$_{24}$BrO$_2$ (MH$^+$): 279.0960. found: 279.0957. GC: 76.4% pure.

Ethyl 9-bromo-2,2-dimethylnonanoate (205j). Under N$_2$ atmosphere at 0° C., LDA (2 M solution in THF/heptane/ ethylbenzene, 13.0 mL, 26.0 mmol) was added dropwise to a mixture of ethyl isobutyrate (3.5 mL, 3.0 g, 25.9 mmol) and 1,7-dibromoheptane (9.84 g, 38.2 mmol) in dry THF (50 mL) over 1.5 h, while keeping the temperature below 5° C. After 3 h, the mixture was poured into ice-cold saturated aqueous NH$_4$Cl solution (150 mL). The layers were separated and the aqueous phase was extracted with Et$_2$O (3×100 mL). The combined organic layers were washed with aqueous HCl (1 M, 100 mL), saturated aqueous NaHCO$_3$ solution (100 mL) and brine (100 mL), dried over anhydrous Na$_2$SO$_4$ and concentrated in vacuo. The residue (12.4 g) was purified twice by column chromatography (heptane:ethyl acetate=40:1) to give 205j (3.42 g, 45%) as a colorless liquid. $^1$H NMR (CDCl$_3$): δ (ppm): 4.11 (q, J=7.2, 2H), 3.40 (t, J=6.9, 2H), 1.85 (quintet, J=6.9, 2H), 1.52-1.47 (m, 2H), 1.45-1.36 (m, 2H), 1.35-1.20 (m, 6H), 1.24 (t, J=7.2, 3H), 1.15 (s, 6H). $^{13}$C-NMR (CDCl$_3$): δ (ppm): 177.8, 60.0, 42.0, 40.5, 33.7, 32.7, 29.7, 28.5, 28.0, 25.0 (2×), 24.7, 14.1. HRMS: Calcd for C$_{13}$H$_{25}$BrO$_2$ (M$^+$): 292.1038. found: 292.1034.

Representative Procedure for the Reduction of Ethyl m-Bromoalkanoates with Lithium Borohydride and Methanol: 6-Bromo-2-methyl-2-p-tolylhexan-1-ol (206e). Methanol (3.14 g, 98.0 mmol) was added dropwise to a stirred suspension of LiBH$_4$ (2.19 g, 100.6 mmol) in anhydrous CH$_2$Cl$_2$ (50 mL) under N$_2$ atmosphere. After the addition of 5e (22.0 g, 67.2 mmol), the reaction mixture was heated to reflux overnight. The reaction mixture was cooled to 5° C. and hydrolyzed with ice (ca. 40 g) and saturated aqueous NH$_4$Cl solution (150 mL) for 1 h. The layers were separated and the aqueous layer was extracted with CH$_2$Cl$_2$ (3×200 mL). The combined organic layers were washed with saturated aqueous NH$_4$Cl solution (3×150 mL), dried over MgSO$_4$ and concentrated in vacuo to give 206e (18.44 g, 96%) as an oil, which was used without further purification for the next step. $^1$H NMR (CDCl$_3$): δ 7.25-7.00 (m, 4H), 3.68-3.50 (m, 1H), 3.49-3.35 (m, 1H), 3.34-3.21 (t, 2H, J=6.9), 2.31 (s, 3H), 1.88-1.51 (m, 4H), 1.51-1.40 (m, 2H), 1.31 (s, 3H), 1.20-1.00 (m, 1H). $^{13}$C NMR (CDCl$_3$): δ 141.49, 135.74, 129.47, 126.63, 72.54, 43.03, 37.53, 33.69, 33.51, 22.66, 21.58, 20.98. HRMS (LSIMS, nba): Calcd for C$_{14}$H$_{20}$Br (MH$^+$—H$_2$O): 267.0748. found: 267.0750.

5-Bromo-2,2-dimethylpentan-1-ol (206a). According to the procedure given for the synthesis of 206e, 205a (94.0 g, 0.37 mol) was reduced with LiBH$_4$ (12.97 g, 0.60 mol) and methanol (19.04 g, 0.60 mol) in CH$_2$Cl$_2$ (400 mL) to give 206a (78.0 g, 100%) as an oil. $^1$H NMR (DMSO-d$_6$): δ 4.42 (s, 1H), 3.45 (t, 2H, J=6.6), 3.08 (s, 2H), 1.84-1.69 (m, 2H), 1.27 (t, 2H, J=8.3), 0.78 (s, 6H). $^{13}$C NMR (DMSO-d$_6$): δ 69.7, 36.9, 35.7, 34.5, 27.4, 24.0.

5-Bromo-2-methyl-2-phenylpentan-1-ol (206b). According to the procedure given for the synthesis of 206e, 205b (23.70 g, 79.21 mmol) was reduced with LiBH$_4$ (3.45 g, 158.4 mmol) and methanol (5.24 g, 163.5 mmol) in anhydrous CH$_2$Cl$_2$ (150 mL) to give 206b (20.0 g, 98%) as an oil. $^1$H NMR (CDCl$_3$): δ 7.34-7.14 (m, 5H), 3.60 (m, 1H), 3.48 (m, 1H), 3.29 (t, 2H, J=6.0), 1.96-1.44 (m, 5H), 1.32 (s, 3H). $^{13}$C NMR (CDCl$_3$): δ 144.25, 128.59, 126.71, 126.41, 72.44, 43.15, 37.06, 34.64, 27.58, 21.61. HRMS (LSIMS, nba): Calcd for C$_{12}$H$_{16}$Br (MH$^+$—H$_2$O): 239.0435. found: 239.0444.

6-Bromo-2,2-dimethylhexanol (206c). According to the procedure described for the synthesis of 206e (Ackerley, N. et al. *J. Med. Chem.* 1995, 38, 1608-1628; Manley, P. W. et al. *J. Med. Chem.* 1987, 30, 1812-1818), 205c (500.0 g, 2.0 mol) was reacted with LiBH$_4$ (65.0 g, 3.0 mol) and methanol (95.0 g, 3.0 mol) in CH$_2$Cl$_2$ (6.0 L) to afford 206c (417.0 g, 99%) as an oil. $^1$H NMR (CDCl$_3$): δ 3.38 (t, 2H, J=7.4), 3.50-3.40 (br. s, 1H, OH), 3.22 (d, 2H, J=5.6), 1.85 (qv, 2H, J=7.4), 1.50-1.35 (m, 2H), 1.30-1.20 (m, 2H), 0.85 (s, 6H). $^{13}$C NMR (CDCl$_3$) δ 71.4, 37.5, 34.9, 33.9, 33.4, 23.7, 22.4.

6-Bromo-2-methyl-2-phenylhexan-1-ol (206d). According to the procedure given for the synthesis of 206e, 205d (52.0 g, 166.0 mmol) was reacted with LiBH$_4$ (5.4 g, 247.9 mmol) and methanol (8.2 g, 255.9 mmol) in CH$_2$Cl$_2$ (180 mL) to afford 206d (38.0 g, 84%) as an oil. $^1$H NMR (CDCl$_3$): δ 7.5-7.1 (m, 5H), 3.60 (d, 1H, J=10.8), 3.53 (d, 1H, J=10.8), 3.34 (t, 2H, J=7.0), 1.90-1.78 (m, 3H), 1.62-1.26 (m, 3H), 1.35 (s, 3H), 1.14 (m, 1H). $^{13}$C NMR (CDCl$_3$): δ 144.4, 128.4, 126.5, 126.1, 72.4, 43.2, 37.4, 33.5, 33.3, 22.5, 21.4.

7-Bromo-2,2-dimethylheptan-1-ol (206g). According to the method for the synthesis of 206e, 205g (43.0 g, 0.16 mol) was treated with LiBH$_4$ (5.55 g; 0.25 mol) and methanol (7.75 g, 0.24 mol) in CH$_2$Cl$_2$ (200 mL) to give 206g (36.2 g, 98%) as a colorless, viscous oil. $^1$H NMR (CDCl$_3$): δ 3.41 (t, 2H, J=6.9), 3.30 (br. s, 2H), 1.90-1.84 (m, 3H), 1.42-1.22 (m, 6H), 0.86 (s, 6H). $^{13}$C NMR (CDCl$_3$): δ 71.9, 38.6, 35.1, 34.1, 32.9, 29.2, 24.0, 23.2. HRMS (LSIMS, nba): Calcd for C$_9$H$_{18}$Br (MH$^+$—H$_2$O): 205.0592. found: 205.0563.

7-Bromo-2-methyl-2-phenylheptan-1-ol (206h). According to the procedure given for the synthesis of 206e, 205h (60.0 g, 183 mmol) was reduced with LiBH$_4$ (5.96 g, 274 mmol) and methanol (8.55 g, 269 mmol) in anhydrous CH$_2$Cl$_2$ (390 mL). After the typical workup, crude 206h (51.0 g, 98%) was obtained as a yellowish oil, which was used without further purification for the next step. $^1$H NMR (CDCl$_3$): δ 7.25-7.08 (m, 5H), 3.64 (d, 1H, J=7.2), 3.50 (d, 1H, J=7.2), 3.35 (t, 2H, J=6 Hz), 1.92-0.95 (m, 9H), 1.28 (s, 3H). $^{13}$C NMR (CDCl$_3$): δ 144.77, 128.51, 126.76, 126.21, 72.63, 43.45, 38.37, 34.06, 32.73, 28.96, 23.12, 21.59. HRMS (EI): Calcd for C$_{14}$H$_{21}$BrO (M$^+$): 284.0776. found: 284.0787.

Representative Procedure for the THP-Protection of ω-Bromoalkanols: 2-(6-Bromo-2-methyl-2-phenylhexyloxy)-tetrahydropyran (207d). Under N$_2$ atmosphere and cooling with an ice bath, 3,4-dihydro-2H-pyran (33.86 g, 0.40 mol) was added dropwise to a stirred solution of 206d (88.0 g, 0.32 mol) and p-toluenesulfonic acid hydrate (0.05 g, 0.03 mmol) in CH$_2$Cl$_2$ (700 mL). After the addition, the reaction mixture was allowed to warm to room temperature and stirred overnight. The solution was filtered through aluminum oxide (160 g) and the aluminum oxide was washed with CH$_2$Cl$_2$ (800 mL). The filtrate was concentrated in vacuo and purified by flash chromatography on silica gel (hexanes/ethyl acetate=10/1) to give 207d (80.0 g, 70%) as an oil. $^1$H NMR (CDCl$_3$): δ 7.40-7.14 (m 10H), 4.53 (t, 1H, J=3.4), 4.49 (t, 1H, J=3.4), 3.82 (d, 1H, J=9.4), 3.81 (t, 1H, J=9.4), 3.76-3.60 (m, 2H), 3.44 (m, 2H), 3.36 (d, 2H, J=9.4), 3.33 (t, 4H, J=7.0), 1.90-1.42 (m, 14H), 1.79 (t, 4H, J=6.8), 1.37 (s, 6H), 1.34-1.10 (m, 6H). $^{13}$C NMR (CDCl$_3$=77.0 ppm): δ 145.67, 127.91, 127.91, 126.39, 126.37, 125.7, 98.95, 98.81, 76.11, 76.07, 62.78, 61.77, 61.66, 41.88, 41.78, 37.93, 37.75, 33.50, 33.44, 30.59, 30.44, 25.41, 25.37, 22.77, 22.71, 22.62, 19.65, 19.23, 19.15. HRMS (LSIMS, nba): Calcd for C$_{18}$H$_{28}$BrO$_2$ (MH$^+$): 355.1272. found: 355.1272.

2-(5-Bromo-2,2-dimethylpentyloxy)-tetrahydropyran (207a). According to the procedure for the preparation of 207d, 206a (78.0 g, 0.40 mol) was reacted with 3,4-dihydro-2H-pyran (41.5 g, 0.49 mol) and p-toluenesulfonic acid hydrate (0.42 g, 2.2 mmol) in CH$_2$Cl$_2$ (0.5 L) to yield 207a (101.0 g, 90%) as a pale-yellow oil, which was used without further purification. $^1$H NMR (CDCl$_3$): δ 4.55 (t, 1H, J=2.9), 3.83 (m, 1H), 3.51 (m, 1H), 3.47 (d, 1H, J=9.0), 3.38 (t, 2H, J=6.8), 2.98 (d, 1H, J=9.0), 1.94-1.75 (m, 2H), 1.75-1.44 (m, 6H), 1.40 (t, 2H, J=8.5), 0.91 (s, 3H), 0.90 (s, 3H). $^{13}$C NMR (CDCl$_3$): δ 99.01, 76.17, 61.85, 37.89, 34.66, 34.04, 30.62, 27.92, 25.60, 24.64, 24.56, 19.41. HRMS (LSIMS, nba): Calcd for C$_{12}$H$_{24}$BrO$_2$ (MH$^+$): 279.0960. found: 279.0955.

2-(5-Bromo-2-methyl-2-phenylpentyloxy)-tetrahydropyran (207b). According to the method described for the synthesis of 207d, 206b (20.0 g, 77.8 mmol) was treated with 3,4-dihydro-2H-pyran (8.2 g, 96.5 mmol) and p-toluenesulfonic acid hydrate (0.57 g, 3.0 mmol) in $CH_2Cl_2$ (350 mL) to afford 207b (25.2 g, 95%) as an oil, which was used without further purification. $^1H$ NMR ($CDCl_3$): 7.26-7.08 (m, 5H), 4.45 (m, 1H), 3.72 (m, 1H), 3.58 (m, 1H), 3.35-3.05 (m, 2H), 3.28 (t, 2H, J=6.6), 1.95-1.39 (m, 10H), 1.25 (s, 3H). $^{13}C$ NMR ($CDCl_3$): δ 145.38, 128.15, 126.51, 126.03, 99.06, 98.92, 76.20, 61.91, 61.80, 41.82, 41.74, 37.58, 37.43, 34.65, 30.61, 27.88, 25.58, 23.03, 22.90, 19.39, 19.32. HRMS (LSIMS, nba): Calcd for $C_{17}H_{26}O_2Br$ ($MH^+$): 341.1116. found: 341.1127.

2-(6-Bromo-2,2-dimethylhexyloxy)-tetrahydropyran (207c). According to the procedure for the preparation of 207d, (Ackerley, N. et al. *J. Med. Chem.* 1995, 38, 1608-1628; Manley, P. W. et al. *J. Med. Chem.* 1987, 30, 1812-1818) 206c (521.0 g, 2.49 mol) was reacted with 3,4-dihydro-2H-pyran (278.0 g, 3.30 mol) and p-toluenesulfonic acid hydrate (3.13 g, 16 mmol) in $CH_2Cl_2$ (2.2 L) to yield 207c (603.0 g, 83%) as a pale-yellow oil, which was used without further purification. $^1H$ NMR ($CDCl_3$): δ 4.55 (t, 1H, J=3.3), 3.84 (m, 1H), 3.50 (m, 1H), 3.47 (d, 1H, J=9.0), 3.42 (t, 2H, J=6.7), 2.99 (d, 1H, J=9.0), 1.88 (m, 2H), 1.75-1.33 (m, 10H), 0.91 (s, 3H), 0.90 (s, 3H). $^{13}C$ NMR ($CDCl_3$): δ 99.37, 76.58, 62.17, 38.56, 34.43, 34.19, 33.90, 30.88, 25.79, 24.80, 24.71, 22.89, 19.67. HRMS (LSIMS, nba): Calcd for $C_{13}H_{25}BrO_2$ ($MH^+$): 293.1116. found: 293.1128.

2-(6-Bromo-2-methyl-2-p-tolylhexyloxy)-tetrahydropyran (207e). According to the method described for the synthesis of 207d, 206e (18.2 g, 63.8 mmol) was reacted with 3,4-dihydro-2H-pyran (6.4 g, 76.0 mmol) and p-toluenesulfonic acid hydrate (0.43 g, 2.3 mmol) in $CH_2Cl_2$ (300 mL) to give 207e (22.0 g, 93%) as an oil, which was used without further purification. $^1H$ NMR ($CDCl_3$): δ 7.25-7.05 (m, 4H), 4.60-4.48 (m, 1H), 3.82 (m, 2H), 3.48-3.37 (m, 2H), 3.35-3.26 (m, 2H), 2.30 (s, 3H), 1.90-1.40 (m, 11H), 1.34 (s, 3H), 1.40-1.08 (m, 1H). $^{13}C$ NMR ($CDCl_3$): δ 142.78, 135.22, 128.81, 126.39, 99.09, 99.01, 61.93, 61.85, 41.67, 41.56, 38.12, 37.87, 33.68, 33.64, 30.62, 25.96, 22.89, 20.97, 19.41, 19.37. HRMS (LSIMS, nba): Calcd for $C_{19}H_{30}O_2Br$ ($MH^+$): 369.1429. found: 369.1451.

2-(7-Bromo-2,2-dimethylheptyloxy)-tetrahydropyran (207g). According to the method described for the synthesis of 207d, 206g (36.0 g, 161 mmol) was treated with 3,4-dihydro-2H-pyran (18.5 g, 220 mmol) and p-toluenesulfonic acid hydrate (0.28 g, 1.5 mmol) in $CH_2Cl_2$ (60 mL). After filtration through neutral aluminum oxide (200 g) and concentration, the crude product was purified by column chromatography (silica gel; hexanes/ethyl acetate=50/1), affording 207g (23.0 g, 46%) as an oil. $^1H$ NMR ($CDCl_3$): δ 4.54 (t, 1H, J=3.0), 3.84 (m, 1H), 3.51-3.39 (m, 4H), 2.98 (d, 1H, J=9.3), 1.89-1.80 (m, 3H), 1.70-1.40 (m, 7H), 1.29-1.22 (m, 4H), 0.89 (s, 6H). $^{13}C$ NMR ($CDCl_3$): δ 99.3, 76.6, 62.1, 39.3, 34.3, 34.2, 33.0, 30.8, 29.2, 25.7, 24.7, 23.2, 19.6. HRMS (LSIMS, gly): Calcd for $C_{14}H_{28}BrO_2$ ($MH^+$): 307.1272. found: 307.1245.

2-(7-Bromo-2-methyl-2-phenylheptyloxy)-tetrahydropyran (207h). According to the method described for the synthesis of 207d, 206h (51.0 g, 179 mmol) was reacted with 3,4-dihydro-2H-pyran (18.80 g, 223 mmol) and p-toluenesulfonic acid hydrate (1.21 g, 6.36 mmol). Filtration through aluminum oxide (370 g) and concentration in vacuo afforded 207h (48.75 g, 76%) as a yellowish oil. $^1H$ NMR ($CDCl_3$): δ 7.35-7.17 (m, 10H), 4.53 (m, 1H), 4.49 (m, 1H), 3.82 (m, 2H), 3.79 (m, 1H), 3.68-3.60 (m, 2H), 3.45-3.35 (m, 2H), 3.32 (t, 4H, J=6.9), 1.82-1.18 (m, 28H), 1.35 (s, 6H). $^{13}C$ NMR ($CDCl_3$): δ 146.12, 128.11, 126.66, 125.89, 99.18, 99.04, 76.46, 62.02, 61.83, 42.17, 42.07, 38.91, 38.73, 34.12, 32.80, 30.70, 29.04, 25.66, 23.33, 22.97, 22.89, 19.49, 19.39. HRMS (LSIMS, nba): Calcd for $C_{19}H_{30}BrO_2$ ($MH^+$): 369.1429. found: 369.1430.

6. BIOLOGICAL ASSAYS

6.1. Effects of Illustrative Compounds of the Invention on the In Vitro Lipid Synthesis in Isolated Hepatocytes Compounds were tested for inhibition of lipid synthesis in primary cultures of rat hepatocytes. Male Sprague-Dawley rats were anesthetized with intraperitoneal injection of sodium pentobarbital (80 mg/kg). Rat hepatocytes were isolated essentially as described by the method of Seglen (Seglen, P. O. Hepatocyte suspensions and cultures as tools in experimental carcinogenesis. *J. Toxicol. Environ. Health* 1979, 5, 551-560). Hepatocytes were suspended in Dulbecco's Modified Eagles Medium containing 25 mM D-glucose, 14 mM HEPES, 5 mM L-glutamine, 5 mM leucine, 5 mM alanine, 10 mM lactate, 1 mM pyruvate, 0.2% bovine serum albumin, 17.4 mM non-essential amino acids, 20% fetal bovine serum, 100 nM insulin and 20 µg/mL gentamycin) and plated at a density of $1.5 \times 10^5$ cells/$cm^2$ on collagen-coated 96-well plates. Four hours after plating, media was replaced with the same media without serum. Cells were grown overnight to allow formation of monolayer cultures. Lipid synthesis incubation conditions were initially assessed to ensure the linearity of [$1$-$^{14}C$]-acetate incorporation into hepatocyte lipids for up to 4 hours. Hepatocyte lipid synthesis inhibitory activity was assessed during incubations in the presence of 0.25 µCi [$1$-$^{14}C$]-acetate/well (final radiospecific activity in assay is 1 Ci/mol) and 0, 1, 3, 10, 30, 100 or 300 µM of compounds for 4 hours. At the end of the 4-hour incubation period, medium was discarded and cells were washed twice with ice-cold phosphate buffered saline and stored frozen prior to analysis. To determine total lipid synthesis, 170 µl of MicroScint-E® and 50 µl water was added to each well to extract and partition the lipid soluble products to the upper organic phase containing the scintillant. Lipid radioactivity was assessed by scintillation spectroscopy in a Packard TopCount NXT. Lipid synthesis rates were used to determine the $IC_{50}$s of the compounds that are presented in Table 6 and 7.

TABLE 6

Effect of Cyclo-alkyl Ccompounds on Lipid Synthesis in Primary Rat Hepatocytes.

| Compound # | $IC_{50}$ (µm) | 95% Confidence Interval Lower | Upper | $r^{2\,a}$ | m | n | R | R1 | R2 | R3 | R4 | R5 |
|---|---|---|---|---|---|---|---|---|---|---|---|---|
| 107c | 0.6 | 0.3 | 0.9 | 0.98 | 4 | 4 | $CO_2H$ | $CO_2H$ | Me | Me | cyclo-Propyl | |
| 107d | 0.3 | 0.1 | 5 | 0.98 | 4 | 4 | $CO_2H$ | $CO_2H$ | cyclo-Propyl | cyclo-Propyl | | |
| 107e | 6 | 5 | 8 | 0.95 | 4 | 4 | $CO_2H$ | $CO_2H$ | Me | Me | cyclo-Butyl | |
| 107f | 121 | 11 | 1268 | 0.89 | 4 | 4 | $CO_2H$ | $CO_2H$ | cyclo-Butyl | cyclo-Butyl | | |
| 107g | 113 | 7 | 1794 | 0.95 | 4 | 4 | $CO_2H$ | $CO_2H$ | cyclo-Pentyl | cyclo-Pentyl | | |

TABLE 6-continued

Effect of Cyclo-alkyl Ccompounds on Lipid Synthesis in Primary Rat Hepatocytes.

| Compound # | $IC_{50}$ (μm) | 95% Confidence Interval Lower | 95% Confidence Interval Upper | $r^{2\,a}$ | m | n | R | R1 | R2 | R3 | R4 | R5 |
|---|---|---|---|---|---|---|---|---|---|---|---|---|
| 106d | 35 | 26 | 48 | 0.99 | 4 | 4 | $CO_2tBu$ | $CO_2tBu$ | cyclo-Propyl | cyclo-Propyl | | |
| 107k | 1 | 0.7 | 1.4 | 0.94 | 5 | 5 | $CO_2H$ | $CO_2H$ | Me | Me | cyclo-Propyl | |
| 107l | 0.5 | 0.4 | 0.7 | 0.99 | 5 | 5 | $CO_2H$ | $CO_2H$ | cyclo-Propyl | cyclo-Propyl | | |
| 107m | 2 | 2 | 2 | 0.99 | 5 | 5 | $CO_2H$ | $CO_2H$ | cyclo-Pentyl | cyclo-Pentyl | | |
| 107n | 10 | 4 | 21 | 0.97 | 7 | 7 | $CO_2H$ | $CO_2H$ | Me | Me | Me | Me |
| 106n | 13 | 4 | 46 | 0.93 | 7 | 7 | $CO_2Et$ | $CO_2Et$ | Me | Me | Me | Me |

$^a$ $r^2$ is the goodness of fit of the data to the non-linear sigmoidal model.

TABLE 7

Effect of Keto-diacids and -Diols on Lipid Synthesis in Primary Rat Hepatocytes.

| Compound | $IC_{50}$ (μM) | 95% Confidence Interval Lower | 95% Confidence Interval Upper | $r^2$ |
|---|---|---|---|---|
| 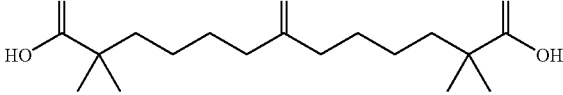 210c | 3 | 2 | 4 | 0.93 |
| 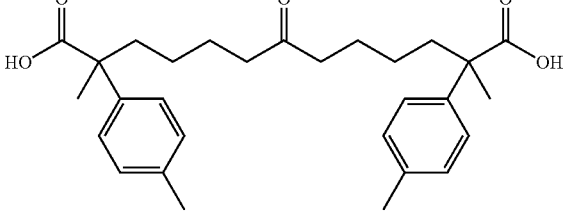 210e | 100-300$^a$ | | | |
| 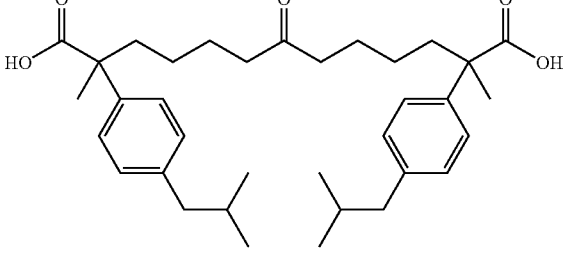 210f | 100-300$^a$ | | | |
| 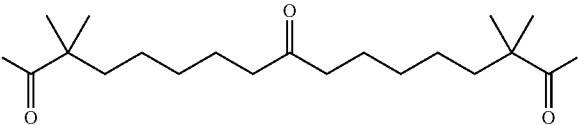 210g | 3 | 3 | 3 | 0.99 |
| 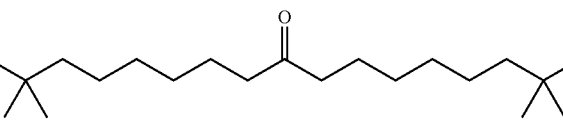 210i | 9 | 8 | 9 | 1 |

US 8,084,498 B2
277                                                                    278
TABLE 7-continued
Effect of Keto-diacids and -Diols on Lipid Synthesis in Primary Rat Hepatocytes.
| Compound | IC$_{50}$ (µM) | 95% Confidence Interval | | r$^2$ |
|---|---|---|---|---|
| | | Lower | Upper | |
| 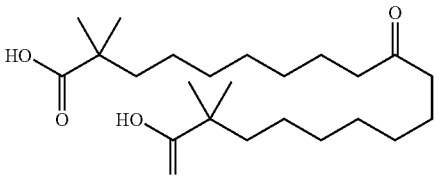 210j | 5 | 2 | 11 | 0.98 |
| 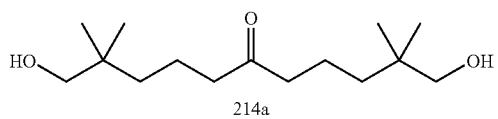 214a | 27 | 21 | 35 | 0.94 |
| 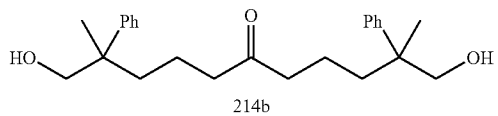 214b | 100-300$^a$ | | | |
| 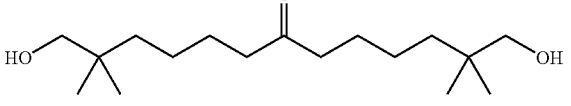 214c | 4 | 3 | 7 | 0.91 |
| 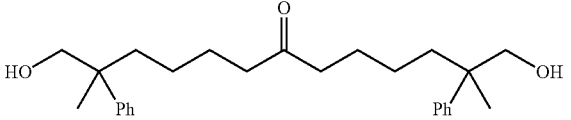 214d | 100-300$^a$ | | | |
| 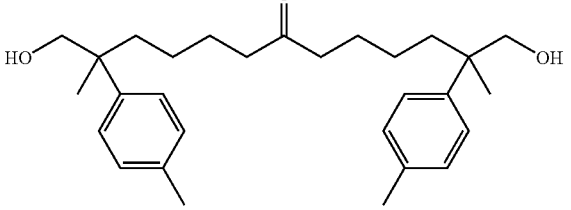 214e | 100-300$^a$ | | | |
| 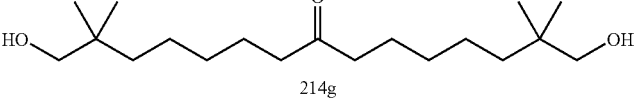 214g | 3 | 3 | 5 | 0.94 |
| 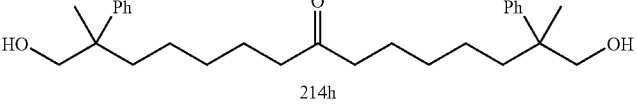 214h | 93 | 60 | 144 | 0.88 |

TABLE 7-continued

Effect of Keto-diacids and -Diols on Lipid Synthesis in Primary Rat Hepatocytes.

| Compound | IC$_{50}$ (µM) | 95% Confidence Interval Lower | 95% Confidence Interval Upper | r$^2$ |
|---|---|---|---|---|
| 214i | 2 | 1 | 8 | 0.97 |
| 217 | 3-10[a] | | | |
| 218 | 1 | 1 | 2 | 0.84 |
| 219 | 2 | 2 | 3 | 0.94 |
| 225 | 8 | 7 | 11 | 0.97 |
| 226 | 3 | 3 | 4 | 0.96 |
| 232 | 52 | 32 | 83 | 0.91 |

[a] The confidence of the IC$_{50}$ estimate is insufficient to assign a value.

6.2. Effects of Illustrative Compounds of the Invention on NonHDL Cholesterol, HDL Cholesterol, Triglyceride Levels, Glycemic Control Indicators and Body Weight Control in Obese Female Zucker Rats Ten- to twelve-week old (400-500 grams) female Zucker fatty rats Crl: (Zuc)-faBR were obtained from Charles River Laboratories. Animals were acclimated to the laboratory environment for seven days. During the acclimation and study period, animals were housed by group in shoebox polycarbonate cages on Cellu-Dri bedding. The temperature and humidity in the animals' quarters (68-78° F.; 30-75% RH) were monitored and the airflow in the room was sufficient to provide several exchanges per hour with 100% fresh filtered air. An automatic timing device provided an alternating 12-hour cycle of light and dark. Rats received pelleted Purina Laboratory Rodent Chow® (5001) prior to and during the drug intervention period except for a 6-hour phase prior to blood sampling. Fresh water was supplied ad libitum via an automatic watering system. Compounds were dissolved, suspended by mixing in a dosing vehicle consisting of 1.5% carboxymethylcellulose/0.2% Tween 20 or 20% ethanol and 80% polyethylene glycol-200 [v/v]. Dose volume of vehicle or vehicle plus each compound was set at 0.25% of body weight in order to deliver the appropriate dose. Doses were administered daily by oral gavage, approximately between 8-10 AM. Regarding blood sampling, animals were fasted for 6 hours prior to all blood collections. Prior to and after 7 days of dosing, a 1.0- to 2.0-mL sample of blood was collected by administering $O_2/CO_2$ anesthesia and bleeding from the orbital venous plexus. Following 14 days of dosing, blood was collected by cardiac puncture after euthanasia with $CO_2$. All blood samples were processed for separation of serum and stored at −80° C. until analysis. Commercially available kits were used to determine serum triglycerides (Roche Diagnostic Corporation, Kit No. 148899 or Boehringer Mannheim, Kit No. 1488872), total cholesterol (Roche Diagnostic Corporation, Kit No. 450061), non-esterified fatty acids (Wako Chemicals, Kit No. 994-75409) and β-hydroxybutyrate (Wako Chemicals, Kit No. 417-73501 or Sigma Kit. No. 310-0) on a Hitachi 912 Automatic Analyzer (Roche Diagnostic Corporation). In some instances, an in-house cholesterol reagent was used to determine total serum cholesterol levels. Serum lipoprotein cholesterol levels were determined by lipoprotein profile analysis. Lipoprotein profiles were analyzed using gel-filtration chromatography on a Superose 6HR (1×30 cm) column equipped with on-line detection of total cholesterol as described by Kieft et al (Kieft, K. A.; Bocan, T. M.; Krause, B. R. Rapid on-line determination of cholesterol distribution among plasma lipoproteins after high-performance gel filtration chromatography. *J. Lipid Res.* 1991, 32, 859-866.). The total cholesterol content of each lipoprotein was calculated by multiplying the independent values determined for serum total cholesterol by the percent area of each lipoprotein in the profile. The percent body weight gain and the ratio of liver to body weight is also determined. Selected data are shown as absolute values or as a percent change of the pretreatment values in Tables 8 and 9.

TABLE 8

Effect of Cyclo-alkyl Compounds in Female Obese Zucker Rats.

Serum Variables (Percent Change from Pre-Treatment)[a]

| Compound # | Dose (mg/kg) | No. animals | NonHDL-Cholesterol 1 wk | 2 wk | HDL-Cholesterol 1 wk | 2 wk | TG 1 wk | 2 wk | m | n | R | R1 | R2 | R3 | R4 | R5 |
|---|---|---|---|---|---|---|---|---|---|---|---|---|---|---|---|---|
| 107c | 100 | 3 | −84 | −20 | 104 | 248 | −93 | −64 | 4 | 4 | $CO_2H$ | $CO_2H$ | Me | Me | cyclo-Propyl | |
| 107d | 100 | 3 | 22 | 63 | 180 | 260 | −51 | −28 | 4 | 4 | $CO_2H$ | $CO_2H$ | cyclo-Propyl | cyclo-Propyl | | |
| 107e | 100 | 4 | 4 | 28 | 30 | 60 | −54 | −51 | 4 | 4 | $CO_2H$ | $CO_2H$ | Me | Me | cyclo-Butyl | |
| 107f | 100 | 4 | −32 | −40 | −1 | 10 | −58 | −59 | 4 | 4 | $CO_2H$ | $CO_2H$ | cyclo-Butyl | cyclo-Butyl | | |
| 107g | 100 | 4 | −68 | −67 | 36 | 40 | −67 | −70 | 4 | 4 | $CO_2H$ | $CO_2H$ | cyclo-Pentyl | cyclo-Pentyl | | |
| 107k | 100 | 4 | −90 | −99 | 43 | 84 | −93 | −98 | 5 | 5 | $CO_2H$ | $CO_2H$ | Me | Me | cyclo-Propyl | |
| 107l | 100 | 4 | −92 | −83 | 136 | 171 | −95 | −94 | 5 | 5 | $CO_2H$ | $CO_2H$ | cyclo-Propyl | cyclo-Propyl | | |
| 107m | 100 | 4 | −54 | −32 | 12 | 27 | −63 | −48 | 5 | 5 | $CO_2H$ | $CO_2H$ | cyclo-Pentyl | cyclo-Pentyl | | |
| 107n | 100 | 3 | −80 | −45 | 44 | 86 | −85 | −64 | 7 | 7 | $CO_2H$ | $CO_2H$ | Me | Me | Me | Me |

[a] 100% represents a 2-fold increase from pre-treatment value

TABLE 9

Effect of Keto-diacids and -Diols in Female Obese Zucker Rats.

| Compound | Dose (mg/kg) | n | NonHDL-Cholesterol 1 wk | 2 wk | HDL Cholestrol 1 wk | 2 wk | TG 1 wk | 2 wk |
|---|---|---|---|---|---|---|---|---|
| 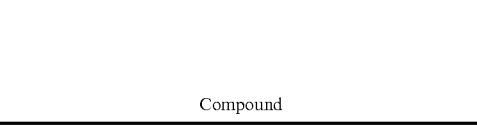 210b | 100 | 3 | 36 | 65 | 4 | 12 | 10 | 26 |
| 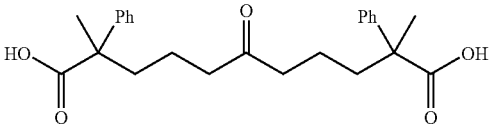 210c | 100 | 5 | −62 | −41 | 54 | 78 | −74 | −69 |

TABLE 9-continued
Effect of Keto-diacids and -Diols in Female Obese Zucker Rats.
| Compound | Dose (mg/kg) | n | NonHDL-Cholesterol 1 wk | NonHDL-Cholesterol 2 wk | HDL Cholestrol 1 wk | HDL Cholestrol 2 wk | TG 1 wk | TG 2 wk |
|---|---|---|---|---|---|---|---|---|
| 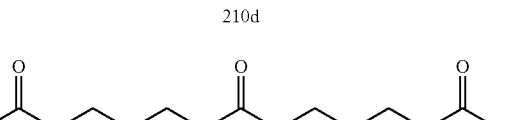 210d | 100 | 3 | 36 | 79 | 43 | 45 | −36 | −8 |
|  210e | 30 | 4 | 0 | 47 | 0 | 10 | −11 | 12 |
| 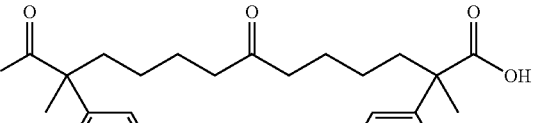 210f | 100 | 3 | −40 | −44 | 11 | 62 | −63 | −66 |
| 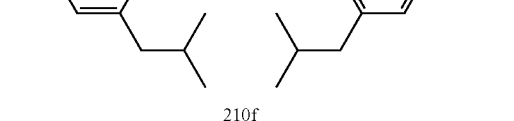 210g | 100 | 4 | −98 | −99 | 72 | 168 | −93 | −94 |
| 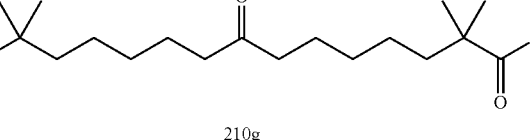 210j | 100 | 3 | −80 | −46 | 44 | 86 | −85 | −63 |
| 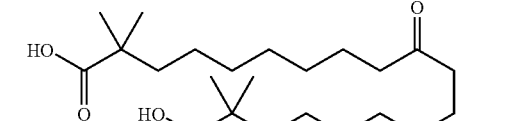 214a | 100 | 3 | −23 | 28 | 24 | 2 | −31 | 0 |
| 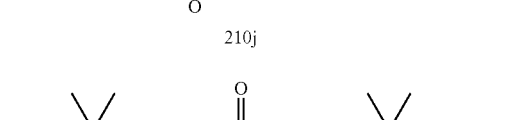 214b | 100 | 4 | −18 | −32 | −14 | −11 | −20 | −17 |

TABLE 9-continued

Effect of Keto-diacids and -Diols in Female Obese Zucker Rats.

| Compound | Dose (mg/kg) | n | NonHDL-Cholesterol 1 wk | NonHDL-Cholesterol 2 wk | HDL Cholestrol 1 wk | HDL Cholestrol 2 wk | TG 1 wk | TG 2 wk |
|---|---|---|---|---|---|---|---|---|
| 214c | 100 | 4 | −23 | −10 | 110 | 126 | −54 | −29 |
| 214d | 30 | 2 | −30 | 30 | −1 | −27 | −24 | 20 |
| 214f | 100 | 3 | 28 | 34 | −5 | 6 | −11 | −15 |
| 214g | 100 | 3 | −91 | −88 | 76 | 135 | −92 | −92 |
| 214h | 100 | 5 | 29 | 9 | 2 | 10 | 24 | 1 |
| 214i | 30 | 4 | −50 | −32 | 85 | 61 | −58 | −33 |
| 217 | 100 | 2 | −26 | 4 | 46 | 48 | −40 | −11 |
| 218 | 30 | 4 | 17 | −8 | −18 | −5 | 18 | −7 |

TABLE 9-continued

Effect of Keto-diacids and -Diols in Female Obese Zucker Rats.

| Compound | Dose (mg/kg) | n | NonHDL-Cholesterol 1 wk | NonHDL-Cholesterol 2 wk | HDL Cholestrol 1 wk | HDL Cholestrol 2 wk | TG 1 wk | TG 2 wk |
|---|---|---|---|---|---|---|---|---|
| 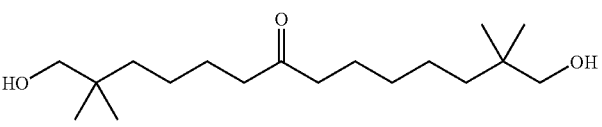 219 | 100 | 2 | −70 | −78 | 78 | 78 | −85 | −87 |
| 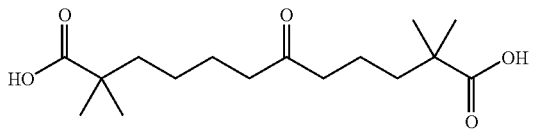 225 | 30 | 4 | −17 | 92 | 7 | 4 | −2 | −22 |
| 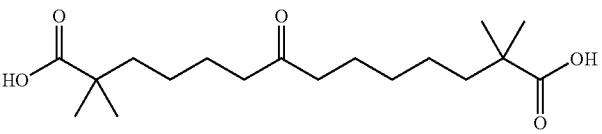 226 | 100 | 3 | −30 | −51 | 240 | 72 | −65 | −62 |
| 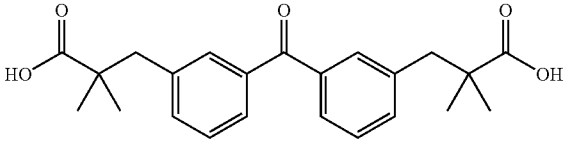 231 | 59 | 3 | −43 | 34 | 2 | 7 | −24 | 7 |
| 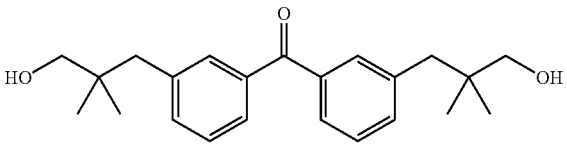 232 | 100 | 4 | −15 | −5 | 1 | −11 | −29 | −8 |

Select compounds (214c, 210c, and 210g) were further evaluated in the Zucker rat by performing a full dose response and measuring additional serum variables including markers for diabetes (Tables 10-12).

TABLE 10

Effect of daily 214c oral treatment on serum lipid and glycemic control variables in female obese Zucker rats.

| Dose mg/kg | n | Non-HDL-C (mg/dl) Pre | Non-HDL-C (mg/dl) 1 wk | Non-HDL-C (mg/dl) 2 wk | HDL-C (mg/dl) Pre | HDL-C (mg/dl) 1 wk | HDL-C (mg/dl) 2 wk | TG (mg/dl) Pre | TG (mg/dl) 1 wk | TG (mg/dl) 2 wk | NEFA (mg/dl) Pre |
|---|---|---|---|---|---|---|---|---|---|---|---|
| 0 | 32 | 25 ± 3 | 36 ± 5$^a$ (+144) | 30 ± 4$^a$ (+120) | 48 ± 2 | 39 ± 2$^a$ (−19) | 41 ± 2$^a$ (−15) | 933 ± 69 | 1114 ± 97$^a$ (+119) | 1099 ± 86$^a$ (+118) | 1.2 ± 0.08 |
| 3 | 9 | 24 ± 3 | 25 ± 3 | 22 ± 2 | 48 ± 3 | 43 ± 4$^a$ (−10) | 39 ± 4$^a$ (−19) | 755 ± 89 | 800 ± 75 | 781 ± 65 | 1.1 ± 0.08 |
| 10 | 18 | 25 ± 3 | 21 ± 2 | 25 ± 2 | 46 ± 3 | 52 ± 3$^a$ (+113) | 53 ± 4$^a$ (+115) | 777 ± 70 | 602 ± 37$^a$ (−23) | 730 ± 52 | 1.2 ± 0.05 |

TABLE 10-continued

Effect of daily 214c oral treatment on serum lipid and glycemic control variables in female obese Zucker rats.

| | | | | | | | | | | | | |
|---|---|---|---|---|---|---|---|---|---|---|---|---|
| 30 | 26 | 30 ± 3 | 28 ± 2 | 38 ± 5$^a$ (+127) | 43 ± 2 | 60 ± 3$^a$ (+140) | 61 ± 4$^a$ (+142) | 998 ± 85 | 726 ± 49$^a$ (−27) | 985 ± 110 | 1.4 ± 0.06 | |
| 100 | 29 | 31 ± 3 | 23 ± 1 | 32 ± 2 | 45 ± 3 | 78 ± 5$^a$ (+173) | 79 ± 6$^a$ (+176) | 1051 ± 80 | 485 ± 29$^a$ (−54) | 702 ± 53$^a$ (−33) | 1.4 ± 0.10 | |

| | | NEFA (mg/dl) | | Glucose (mg/dl) | | | Insulin (ng/ml) | | |
|---|---|---|---|---|---|---|---|---|---|
| mg/kg | n | 1 wk | 2 wk | Pre | 1 wk | 2 wk | Pre | 1 wk | 2 wk |
| 0 | 32 | 1.3 ± 0.06 | 1.6 ± 0.12$^a$ (+133) | 125 ± 2 | 118 ± 3 | 116 ± 3 | 9.1 ± 0.6 | 8.7 ± 0.5 | 7.7 ± 0.5 |
| 3 | 9 | 1.2 ± 0.05 | 1.6 ± 0.13$^a$ (+145) | 118 ± 4 | 106 ± 2 | 103 ± 3 | 8.8 ± 1.5 | 7.5 ± 0.8 | 7.8 ± 0.6 |
| 10 | 18 | 0.98 ± 0.08$^a$ (−18) | 1.0 ± 0.10 | 112 ± 3 | 110 ± 2 | 110 ± 3 | 8.4 ± 0.6 | 7.5 ± 0.4 | 7.8 ± 0.5 |
| 30 | 26 | 1.1 ± 0.05$^a$ (−21) | 1.2 ± 0.10 | 111 ± 1 | 112 ± 13 | 120 ± 3 | 9.3 ± 0.8 | 9.1 ± 0.6 | 9.8 ± 0.7 |
| 100 | 29 | 0.98 ± 0.04$^a$ (−30) | 0.94 ± 0.04$^a$ (−33) | 114 ± 2 | 120 ± 5 | 118 ± 3 | 9.6 ± 0.8 | 10.9 ± 1.0 | 11.0 ± 0.9 |

$^a$ p < 0.05 compared to pretreatment. Data are represented as mean ± SEM. Numbers in parentheses are the percent increases (+) or decreases (−) of the pretreatment control values.

TABLE 11

Effect of daily 210c oral treatment on serum lipid and glycemic control variables in female obese Zucker rats.

| Dose | | Non-HDL-C (mg/dl) | | | HDL-C (mg/dl) | | | TG (mg/dl) | | | NEFA (mg/dl) |
|---|---|---|---|---|---|---|---|---|---|---|---|
| mg/kg | n | Pre | 1 wk | 2 wk | Pre | 1 wk | 2 wk | Pre | 1 wk | 2 wk | Pre |
| 0 | 12 | 40 ± 11 | 43 ± 10 | 29 ± 3 | 39 ± 3 | 39 ± 5 | 38 ± 4 | 1303 ± 261 | 1333 ± 231 | 1140 ± 124 | 1.5 ± 0.12 |
| 3 | 4 | 32 ± 4 | 24 ± 2 | 24 ± 3 | 31 ± 3 | 36 ± 1 | 33 ± 1 | 996 ± 188 | 775 ± 92 | 857 ± 103 | 1.5 ± 0.14 |
| 10 | 4 | 40 ± 8 | 26 ± 4$^a$ (−35) | 27 ± 4 | 37 ± 10 | 47 ± 7 | 39 ± 5 | 1143 ± 373 | 692 ± 180 | 814 ± 205 | 1.6 ± 0.15 |
| 30 | 4 | 48 ± 4 | 37 ± 4$^a$ (−23) | 43 ± 5 | 34 ± 5 | 53 ± 8$^a$ (+156) | 50 ± 9$^a$ (+147) | 1242 ± 144 | 826 ± 92$^a$ (−33) | 962 ± 118 | 1.4 ± 0.15 |
| 100 | 11 | 31 ± 4 | 18 ± 3$^a$ (−42) | 22 ± 3$^a$ (−29) | 38 ± 3 | 66 ± 9$^a$ (+174) | 68 ± 10$^a$ (+179) | 964 ± 90 | 383 ± 49$^a$ (−60) | 440 ± 58$^a$ (−54) | 1.2 ± 0.06 |

| Dose | | NEFA (mg/dl) | | Glucose (mg/dl) | | | Insulin (ng/ml) | | |
|---|---|---|---|---|---|---|---|---|---|
| mg/kg | n | 1 wk | 2 wk | Pre | 1 wk | 2 wk | Pre | 1 wk | 2 wk |
| 0 | 12 | 1.5 ± 0.09 | 1.4 ± 0.10 | 134 ± 6 | 124 ± 7 | 118 ± 3 | 9.8 ± 0.9 | 8.4 ± 0.6 | 6.8 ± 0.7$^a$ (−31) |
| 3 | 4 | 1.2 ± 0.16 | 1.5 ± 0.27 | 108 ± 6 | 99 ± 4 | 103 ± 3 | 10.4 ± 1.3 | 10.7 ± 0.8 | 8.6 ± 0.5 |
| 10 | 4 | 0.92 ± 0.09$^a$ | 1.5 ± 0.28 | 113 ± 7 | 105 ± 3 | 113 ± 3 | 10.6 ± 1.5 | 7.7 ± 1.0$^a$ (−27) | 8.9 ± 1.3 |
| 30 | 4 | 1.0 ± 0.11$^a$ (−29) | 1.1 ± 0.20 | 103 ± 2 | 115 ± 4 | 118 ± 8 | 7.7 ± 1.6 | 9.2 ± 1.3 | 8.5 ± 1.8 |
| 100 | 11 | 0.81 ± 0.07$^a$ (−33) | 0.66 ± 0.06$^a$ (−45) | 110 ± 3 | 113 ± 6 | 122 ± 7 | 8.1 ± 0.9 | 9.0 ± 1.0 | 9.5 ± 0.9 |

$^a$ p < 0.05 compared to pretreatment. Data are represented as mean ± SEM. Numbers in parentheses are the percent increases (+) or decreases (−) of the pretreatment control values.

TABLE 12

Effect of daily 210g oral treatment on serum lipid and glycemic control variables in female obese Zucker rats.

| Dose | | Non-HDL-C (mg/dl) | | | HDL-C (mg/dl) | | | TG (mg/dl) | | | NEFA (mg/dl) |
|---|---|---|---|---|---|---|---|---|---|---|---|
| mg/kg | n | Pre | 1 wk | 2 wk | Pre | 1 wk | 2 wk | Pre | 1 wk | 2 wk | Pre |
| 0 | 27 | 20 ± 2 | 29 ± 3$^a$ (+145) | 28 ± 3$^a$ (+140) | 76 ± 5 | 66 ± 5$^a$ (−13) | 69 ± 5$^a$ (−9) | 950 ± 55 | 1119 ± 82$^a$ (+118) | 1189 ± 92$^a$ (+125) | 1.3 ± 0.06 |
| 3 | 18 | 22 ± 2 | 23 ± 2 | 25 ± 2 | 77 ± 5 | 75 ± 6 | 77 ± 8 | 905 ± 57 | 995 ± 50 | 833 ± 57 | 1.3 ± 0.09 |
| 10 | 22 | 22 ± 1 | 22 ± 2 | 34 ± 3$^a$ (+155) | 86 ± 10 | 136 ± 11$^a$ (+158) | 138 ± 8$^a$ (+160) | 863 ± 63 | 553 ± 35$^a$ (−36) | 865 ± 69 | 1.2 ± 0.08 |

TABLE 12-continued

Effect of daily 210g oral treatment on serum lipid and glycemic control variables in female obese Zucker rats.

| 30 | 18 | 27 ± 3 | 14 ± 2$^a$ (−48) | 30 ± 2 | 62 ± 5 | 159 ± 12$^a$ (+256) | 208 ± 14$^a$ (+335) | 982 ± 75 | 213 ± 19$^a$ (−78) | 473 ± 38$^a$ (−52) | 1.3 ± 0.07 |
|---|---|---|---|---|---|---|---|---|---|---|---|
| 100 | 15 | 26 ± 2 | 2 ± 1$^a$ (−92) | 3 ± 1$^a$ (−88) | 66 ± 5 | 100 ± 8$^a$ (+151) | 141 ± 12$^a$ (+213) | 937 ± 77 | 69 ± 5$^a$ (−93) | 78 ± 10$^a$ (−92) | 1.4 ± 0.06 |

| Dose | | NEFA (mg/dl) | | Glucose (mg/dl) | | | Insulin (ng/ml) | | |
|---|---|---|---|---|---|---|---|---|---|
| mg/kg | n | 1 wk | 2 wk | Pre | 1 wk | 2 wk | Pre | 1 wk | 2 wk |
| 0 | 27 | 1.3 ± 0.07 | 1.3 ± 0.07 | 129 ± 4 | 123 ± 2 | 120 ± 2 | 9.1 ± 0.5 | 10.1 ± 0.6 | 8.1 ± 0.6 |
| 3 | 18 | 1.1 ± 0.07$^a$ (−15) | 1.0 ± 0.10$^a$ (−23) | 114 ± 3 | 117 ± 4 | 124 ± 4$^a$ (+108) | 8.6 ± 0.9 | 10.0 ± 1.0 | 7.3 ± 0.5 |
| 10 | 22 | 1.0 ± 0.07$^a$ (−17) | 0.95 ± 0.08$^a$ (−21) | 120 ± 4 | 122 ± 3 | 125 ± 4 | 9.9 ± 0.9 | 10.5 ± 1.1 | 9.1 ± 0.7 |
| 30 | 18 | 0.88 ± 0.06$^a$ (−32) | 0.66 ± 0.03$^a$ (−49) | 119 ± 5 | 108 ± 4 | 130 ± 4 | 9.8 ± 0.9 | 6.4 ± 0.6$^a$ (−35) | 7.7 ± 0.9$^a$ (−21) |
| 100 | 15 | 0.98 ± 0.08$^a$ (−30) | 0.66 ± 0.06$^a$ (−52) | 117 ± 3 | 92 ± 4$^a$ (−21) | 105 ± 3$^a$ (−10) | 11.9 ± 1.0 | 6.4 ± 1.3$^a$ (−46) | 6.0 ± 0.8$^a$ (−50) |

$^a$p < 0.05 compared to pretreatment. Data are represented as mean ± SEM. Numbers in parentheses are the percent increases (+) or decreases (−) of the pretreatment control values.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

What is claimed is:

1. A method for treating diabetic nephropathy, diabetic retinopathy, a disorder of glucose metabolism, or insulin resistance, relating to diabetes, comprising administering to a patient in need of such treatment a therapeutically effective amount of a compound selected from a group consisting of:
   t-butyl-1-[9-[1-(tert-butyoxycarbonyl)cyclopropyl]-5-oxononyl]-1-cyclopropanecarboxylate;
   11-(1-carboxycyclopropyl)-2,2-dimethyl-7-oxoundecanoic acid;
   1-[9-(1-carboxycyclopropyl)-5-oxononyl]-1-cyclopropanecarboxylic acid;
   11-(1-carboxycyclobutyl)-2,2-dimethyl-7-oxoundecanoic acid;
   1-[9-(1-carboxycyclobutyl)-5-oxononyl]-1-cyclobutanecarboxylic acid;
   1-[9-(1-carboxycyclopentyl)-5-oxononyl]-1-cyclopentylcarboxylic acid;
   13-(1-carboxycyclopropyl)-2,2-dimethyl-8-oxotridecanoic acid;
   1-[11-(1-carboxycyclopropyl)-6-oxoundecyl]-1-cyclopropanecarboxylic acid; and
   1-[11-(1-carboxycyclopentyl)-6-oxoundecyl]-1-cyclopentanecarboxylic acid;
   or a pharmaceutically acceptable salt thereof.

2. The method of claim 1, wherein the compound is selected from a group consisting of:
   t-butyl-1-[9-[1-(tert-butyoxycarbonyl)cyclopropyl]-5-oxononyl]-1-cyclopropanecarboxylate;
   1-[9-(1-carboxycyclopropyl)-5-oxononyl]-1-cyclopropanecarboxylic acid;
   1-[9-(1-carboxycyclobutyl)-5-oxononyl]-1-cyclobutanecarboxylic acid;
   1-[9-(1-carboxycyclopentyl)-5-oxononyl]-1-cyclopentylcarboxylic acid;
   1-[11-(1-carboxycyclopropyl)-6-oxoundecyl]-1-cyclopropanecarboxylic acid; and
   1-[11-(1-carboxycyclopentyl)-6-oxoundecyl]-1-cyclopentanecarboxylic acid;
   or a pharmaceutically acceptable salt thereof.

3. The method of claim 2, wherein the compound is t-butyl-1-[9-[1-(tert-butyoxycarbonyl)cyclopropyl]-5-oxononyl]-1-cyclopropanecarboxylate, or a pharmaceutically acceptable salt thereof.

4. The method of claim 2, wherein the compound is 1-[9-(1-carboxycyclopropyl)-5-oxononyl]-1-cyclopropanecarboxylic acid, or a pharmaceutically acceptable salt thereof.

5. The method of claim 2, wherein the compound is 1-[9-(1-carboxycyclobutyl)-5-oxononyl]-1-cyclobutanecarboxylic acid, or a pharmaceutically acceptable salt thereof.

6. The method of claim 2, wherein the compound is 1-[9-(1-carboxycyclopentyl)-5-oxononyl]-1-cyclopentylcarboxylic acid, or a pharmaceutically acceptable salt thereof.

7. The method of claim 2, wherein the compound is 1-[11-(1-carboxycyclopropyl)-6-oxoundecyl]-1-cyclopropanecarboxylic acid, or a pharmaceutically acceptable salt thereof.

8. The method of claim 2, wherein the compound is 1-[11-(1-carboxycyclopentyl)-6-oxoundecyl]-1-cyclopentanecarboxylic acid, or a pharmaceutically acceptable salt thereof.

9. The method of claim 1, wherein the compound is selected from a group consisting of:
   11-(1-carboxycyclopropyl)-2,2-dimethyl-7-oxoundecanoic acid;
   11-(1-carboxycyclobutyl)-2,2-dimethyl-7-oxoundecanoic acid; and
   13-(1-carboxycyclopropyl)-2,2-dimethyl-8-oxotridecanoic acid;
   or a pharmaceutically acceptable salt thereof.

10. The method of claim 9, wherein the compound is 11-(1-carboxycyclopropyl)-2,2-dimethyl-7-oxoundecanoic acid, or a pharmaceutically acceptable salt thereof.

11. The method of claim 9, wherein the compound is 11-(1-carboxycyclobutyl)-2,2-dimethyl-7-oxoundecanoic acid, or a pharmaceutically acceptable salt thereof.

12. The method of claim 9, wherein the compound is 13-(1-carboxycyclopropyl)-2,2-dimethyl-8-oxotridecanoic acid, or a pharmaceutically acceptable salt thereof.

13. The method of claim 1, wherein the patient is in need of treatment for or prevention of insulin resistance.

14. The method of claim 1, wherein the patient is in need of treatment for or prevention of a disorder of glucose metabolism.

* * * * *

UNITED STATES PATENT AND TRADEMARK OFFICE
CERTIFICATE OF CORRECTION

PATENT NO.         : 8,084,498 B2                          Page 1 of 1
APPLICATION NO.    : 12/492597
DATED              : December 27, 2011
INVENTOR(S)        : Jean-Louis Henri Dasseux et al.

It is certified that error appears in the above-identified patent and that said Letters Patent is hereby corrected as shown below:

Column 292, claim 13, line 61, before "of insulin resistance" delete "for or prevention".

Column 292, claim 14, line 63, before "of a disorder of glucose" delete "for or prevention".

Signed and Sealed this
Twenty-ninth Day of May, 2012

David J. Kappos
*Director of the United States Patent and Trademark Office*